US007200088B2

(12) United States Patent
Worthington et al.

(10) Patent No.: US 7,200,088 B2
(45) Date of Patent: Apr. 3, 2007

(54) SYSTEM AND METHOD OF DETECTING INVESTIGATIONAL FEATURES RELATED TO A SAMPLE

(75) Inventors: Mark Oscar Worthington, Irvine, CA (US); Stephen Kou-An Shu, Laguna Niguel, CA (US); Kevin Robert McIntyre, Irvine, CA (US)

(73) Assignees: Burstein Technologies, Inc., Irvine, CA (US); Nagaoka & Co., Ltd., Hyogo (JP)

( * ) Notice: Subject to any disclaimer, the term of this patent is extended or adjusted under 35 U.S.C. 154(b) by 609 days.

(21) Appl. No.: 10/043,688

(22) Filed: Jan. 10, 2002

(65) Prior Publication Data

US 2002/0176342 A1 Nov. 28, 2002

Related U.S. Application Data

(63) Continuation-in-part of application No. 10/008,156, filed on Nov. 9, 2001.

(60) Provisional application No. 60/322,863, filed on Sep. 12, 2001, provisional application No. 60/307,487, filed on Jul. 24, 2001, provisional application No. 60/293,093, filed on May 22, 2001, provisional application No. 60/292,108, filed on May 18, 2001, provisional application No. 60/270,095, filed on Feb. 20, 2001, provisional application No. 60/262,532, filed on Jan. 18, 2001, provisional application No. 60/260,761, filed on Jan. 11, 2001.

(51) Int. Cl.
G11B 11/03 (2006.01)

(52) U.S. Cl. .................................. 369/53.31; 369/44.41

(58) Field of Classification Search ............. 369/44.41, 369/47.14, 47.15, 47.23, 47.24, 47.25, 47.35, 369/53.28, 53.31, 53.35, 59.21
See application file for complete search history.

(56) References Cited

U.S. PATENT DOCUMENTS

| 3,901,658 | A | 8/1975 | Burtis, et al. |
|---|---|---|---|
| 3,966,322 | A | 6/1976 | Greaves et al. |
| 4,469,793 | A | 9/1984 | Guigan |
| 4,672,600 | A | 6/1987 | Balston et al. |
| 4,866,688 | A | 9/1989 | Ohtake et al. |
| 4,876,557 | A | 10/1989 | Yabe |
| 4,972,404 | A | 11/1990 | Yamaguchi et al. |
| 5,119,363 | A | 6/1992 | Satoh et al. |
| 5,122,284 | A | 6/1992 | Braynin et al. |
| 5,130,963 | A | 7/1992 | Kusano et al. |

(Continued)

FOREIGN PATENT DOCUMENTS

EP 0 392 475 A2 10/1990

(Continued)

*Primary Examiner*—Paul W. Huber
(74) *Attorney, Agent, or Firm*—Knobbe, Martens, Olson & Bear, LLP

(57) ABSTRACT

An optical disc system includes a photo detector circuit of an optical disc drive and a signal processing system. The photo detector circuit is configured to generate at least one information-carrying signal from an optical disc assembly. The signal processing system is coupled to the photo detector circuit to obtain from the at least one information-carrying signal both operational information used to operate the optical disc system and data indicative of presence and/or characteristics of an investigational feature associated with the optical disc assembly. Methods and discs for imaging a biological or medical investigational feature are also provided.

19 Claims, 76 Drawing Sheets

U.S. PATENT DOCUMENTS

| | | | |
|---|---|---|---|
| 5,173,262 A | 12/1992 | Burtis et al. | |
| 5,310,523 A | 5/1994 | Smethers et al. | |
| 5,329,461 A | 7/1994 | Allen et al. | |
| 5,407,554 A | 4/1995 | Saurer | |
| 5,412,087 A | 5/1995 | McGall et al. | |
| 5,457,053 A | 10/1995 | Burd et al. | |
| 5,506,827 A * | 4/1996 | Tobita | 369/59.22 |
| 5,508,985 A | 4/1996 | Fairchild et al. | |
| 5,510,270 A | 4/1996 | Fodor et al. | |
| 5,513,169 A | 4/1996 | Fite et al. | |
| 5,572,507 A | 11/1996 | Ozaki et al. | |
| 5,585,069 A | 12/1996 | Zanzucchi et al. | |
| 5,629,514 A | 5/1997 | Lee et al. | |
| 5,631,844 A | 5/1997 | Margrey et al. | |
| 5,661,703 A | 8/1997 | Moribe et al. | |
| 5,671,202 A | 9/1997 | Brownstein et al. | |
| 5,696,757 A | 12/1997 | Ozaki et al. | |
| 5,737,478 A | 4/1998 | Yamagishi et al. | |
| 5,768,227 A * | 6/1998 | Baba | 369/44.28 |
| 5,793,969 A | 8/1998 | Kamentsky et al. | |
| 5,834,758 A | 11/1998 | Trulson et al. | |
| 5,837,552 A | 11/1998 | Cotton et al. | |
| 5,863,708 A | 1/1999 | Zanzucchi et al. | |
| 5,878,018 A | 3/1999 | Moriya et al. | |
| 5,879,774 A | 3/1999 | Taylor et al. | |
| 5,882,903 A | 3/1999 | Andrevski et al. | |
| 5,892,577 A | 4/1999 | Gordon | |
| 5,922,617 A | 7/1999 | Wang et al. | |
| 5,994,150 A | 11/1999 | Challener et al. | |
| 6,009,057 A | 12/1999 | Furukawa et al. | |
| 6,013,352 A | 1/2000 | Gallant | |
| 6,030,581 A | 2/2000 | Virtanen | |
| 6,031,815 A | 2/2000 | Heemskerk | |
| 6,121,048 A | 9/2000 | Zaffaroni et al. | |
| 6,147,941 A | 11/2000 | Kumagai | |
| 6,212,158 B1 | 4/2001 | Ha et al. | |
| 6,231,812 B1 | 5/2001 | Rothberg et al. | |
| 6,233,207 B1 * | 5/2001 | Tanaka | 369/44.26 |
| 6,256,088 B1 | 7/2001 | Gordon | |
| 6,327,031 B1 | 12/2001 | Gordon | |
| 6,339,473 B1 | 1/2002 | Gordon | |
| 6,342,395 B1 | 1/2002 | Hammock et al. | |
| 6,395,562 B1 | 5/2002 | Hammock et al. | |
| 6,438,097 B1 | 8/2002 | Kajiyama et al. | |
| 6,476,907 B1 | 11/2002 | Gordon | |
| 6,646,967 B1 | 11/2003 | Garcia | |
| 6,760,298 B2 | 7/2004 | Worthington et al. | |
| 6,813,237 B2 | 11/2004 | Yamaguchi et al. | |
| 6,920,092 B2 | 7/2005 | Kuriuzawa et al. | |
| 2002/0047003 A1 | 4/2002 | Bedingham, et al. | |
| 2002/0076354 A1 | 6/2002 | Cohen | |
| 2002/0097658 A1 | 7/2002 | Worthington, et al. | |
| 2002/0098528 A1 | 7/2002 | Gordon, et al. | |
| 2002/0145960 A1 | 10/2002 | Worthington, et al. | |
| 2002/0168652 A1 | 11/2002 | Werner, et al. | |
| 2002/0168663 A1 | 11/2002 | Phan, et al. | |
| 2002/0171838 A1 | 11/2002 | Pal, et al. | |
| 2003/0104486 A1 | 6/2003 | Selvan | |

FOREIGN PATENT DOCUMENTS

| | | |
|---|---|---|
| EP | 0 417 305 A1 | 3/1991 |
| EP | 0 521 421 A2 | 1/1993 |
| EP | 0 866 449 A2 | 3/1998 |
| GB | 2 337 113 A | 11/1999 |
| WO | WO 96/09548 | 3/1996 |
| WO | WO 98/01857 | 1/1998 |
| WO | WO 98/12559 | 3/1998 |
| WO | WO 98/38510 | 9/1998 |
| WO | WO 00/05582 | 2/2000 |
| WO | WO 00/26677 | 5/2000 |

* cited by examiner

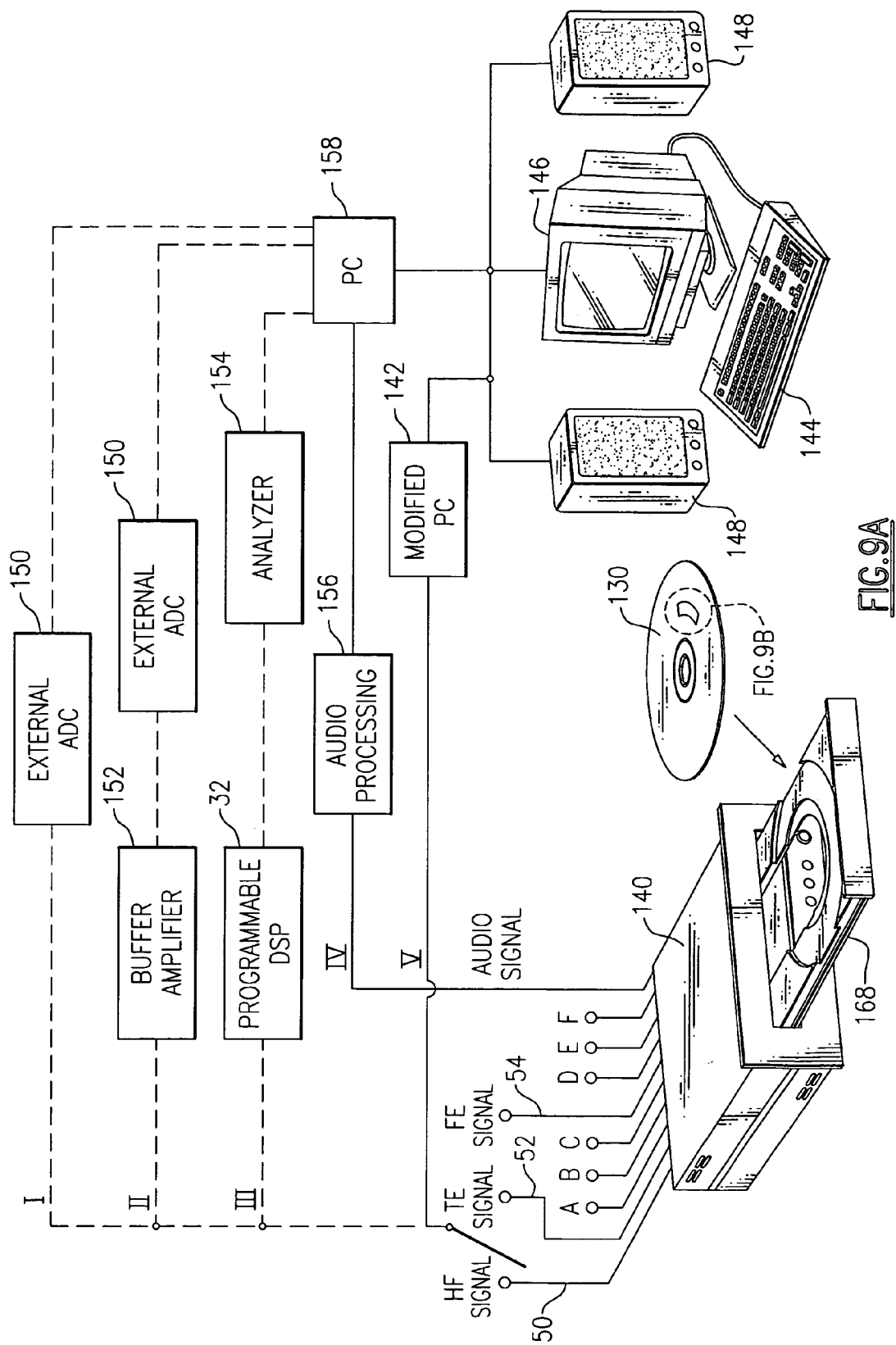

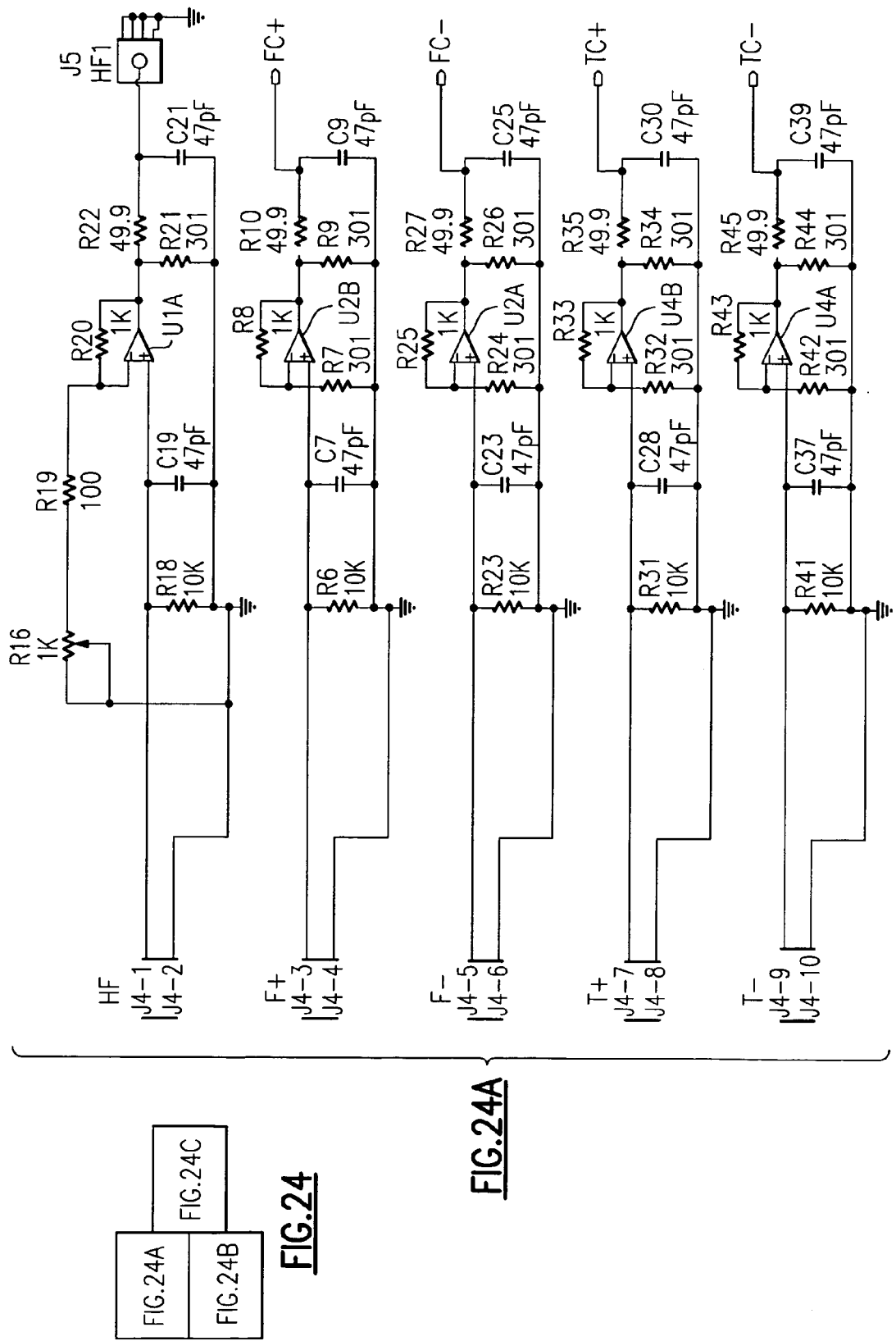

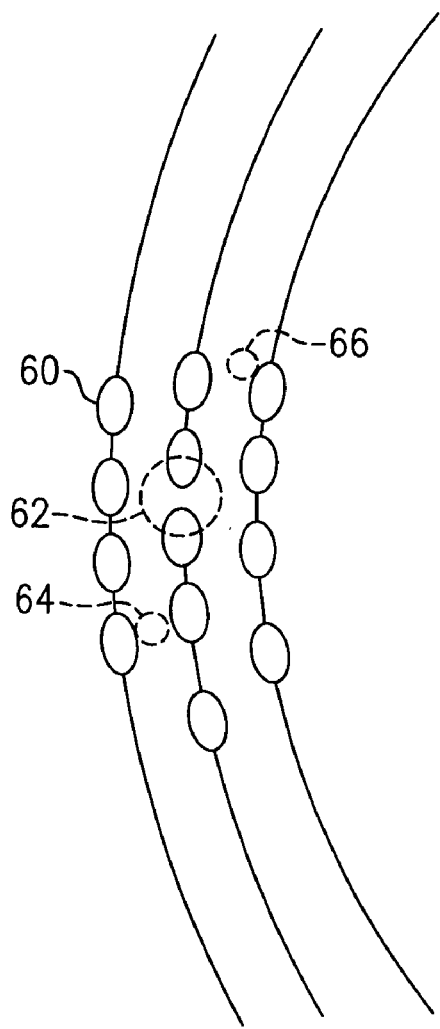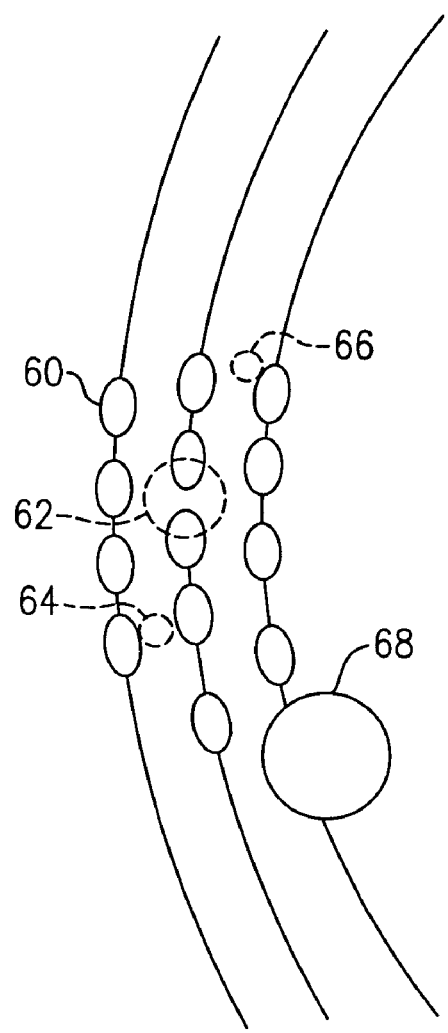
FIG.42
Prior Art
FIG.43

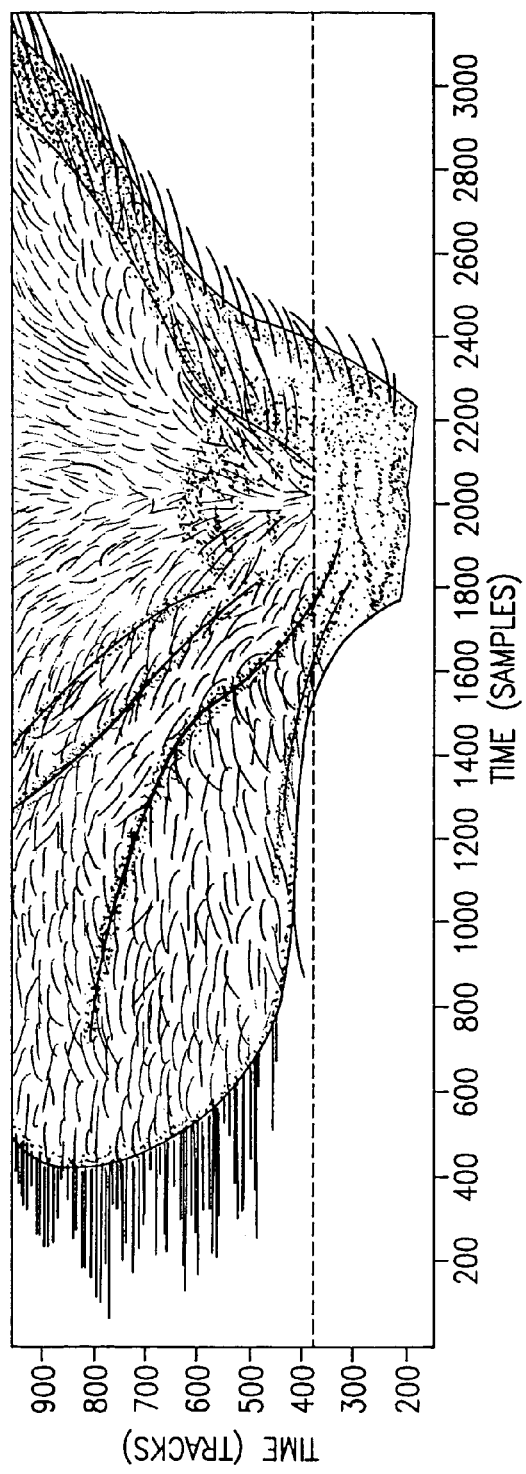
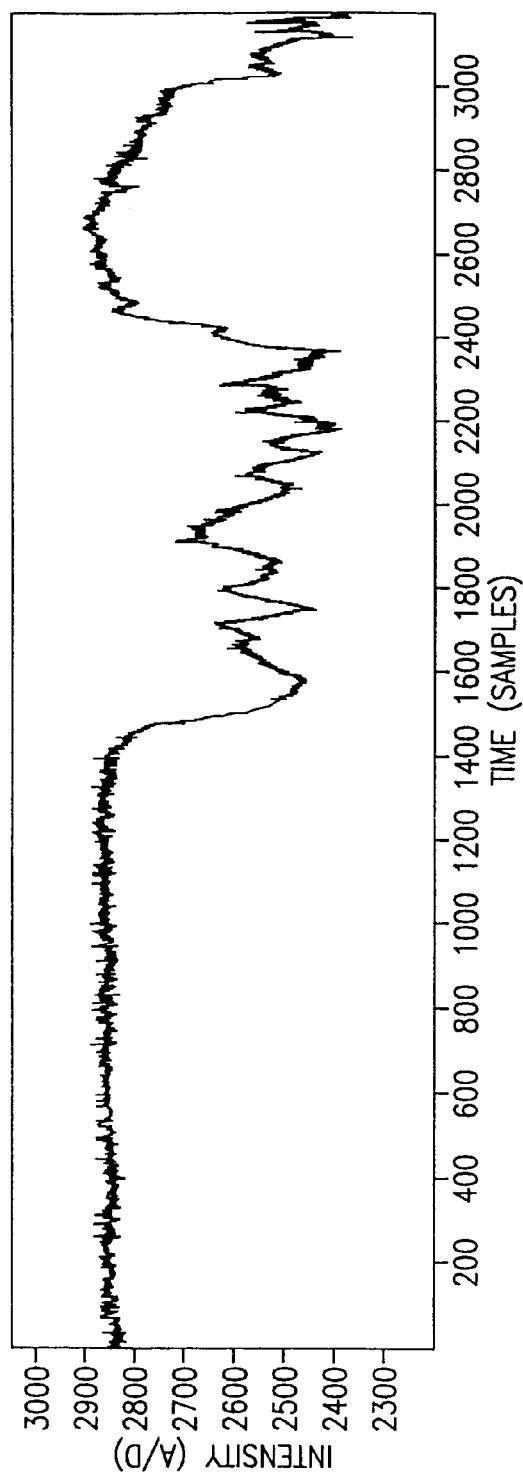
FIG.73A
FIG.73B

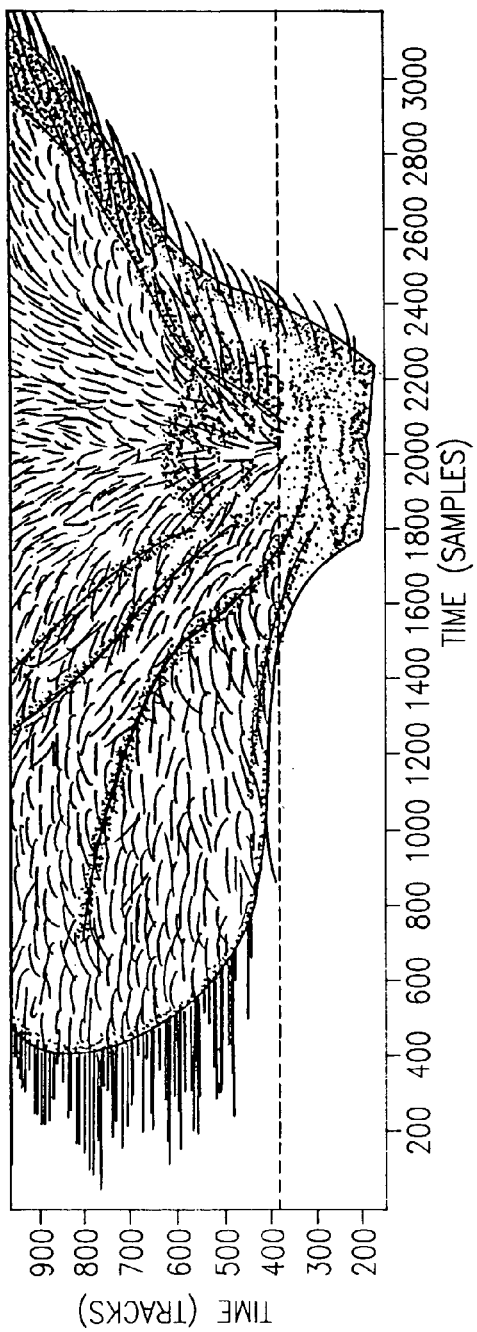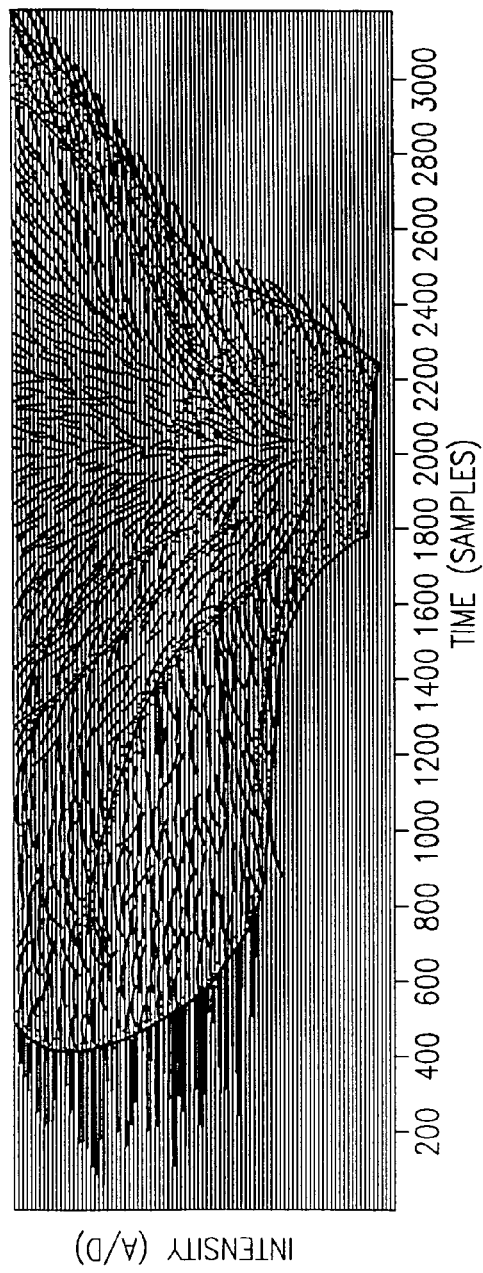
FIG. 76A
FIG. 76B

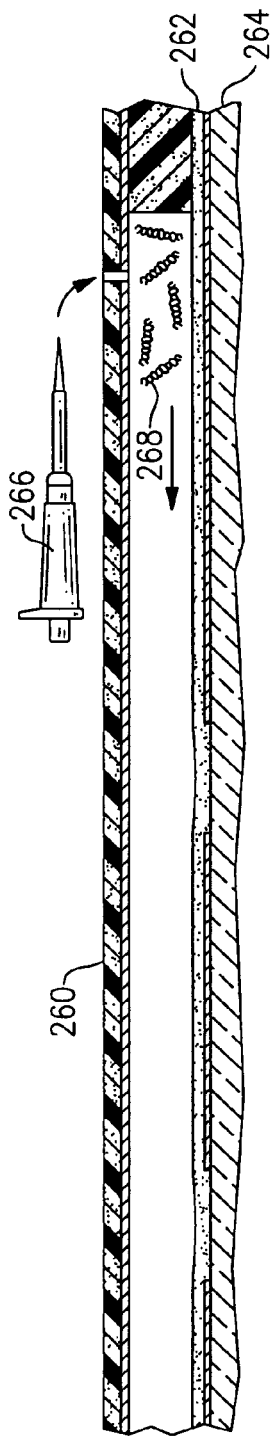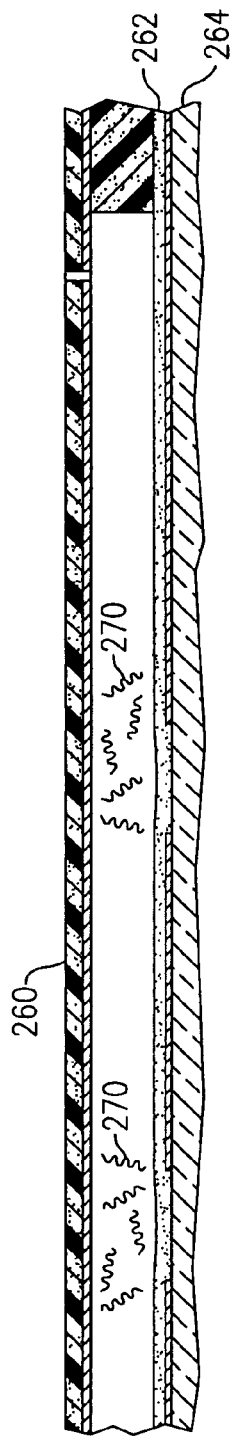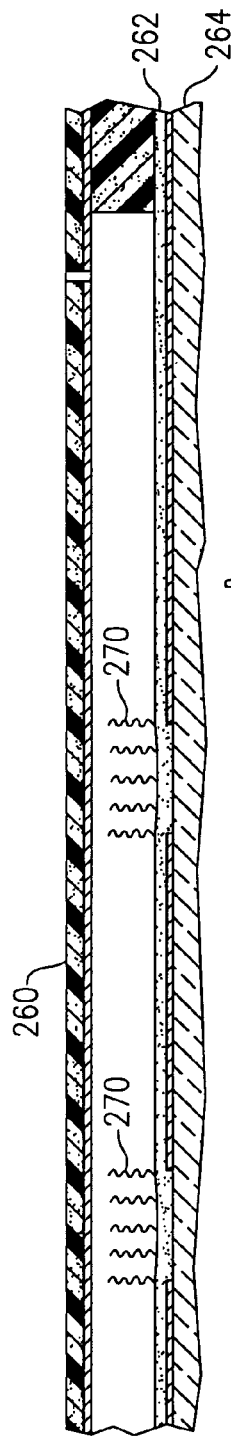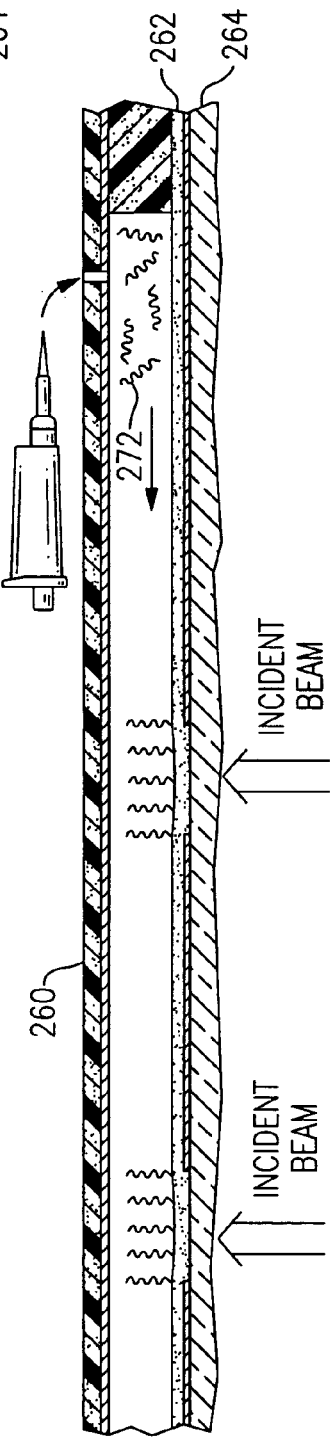

SYSTEM AND METHOD OF DETECTING INVESTIGATIONAL FEATURES RELATED TO A SAMPLE

CROSS-REFERENCE TO RELATED APPLICATIONS

This application is a continuation-in-part of U.S. application Ser. No. 10/008,156 filed Nov. 9, 2001.

This application also claims the benefit of priority from U.S. Provisional Application No. 60/260,761 filed the Jan. 11, 2001; U.S. Provisional Application No. 60/262,532 filed the Jan. 18, 2001; U.S. Provisional Application No. 60/270,095 filed the Feb. 20, 2001; U.S. Provisional Application No. 60/292,108 filed May 18, 2001; U.S. Provisional Application No. 60/293,093 filed May 22, 2001; U.S. Provisional Application No. 60/307,487 filed Jul. 24, 2001; and U.S. Provisional Application No. 60/322,863 filed Sep. 12, 2001. Each of these applications is herein incorporated by reference.

BACKGROUND OF THE INVENTION

1. Field of the Invention

The present invention relates generally to optical discs and optical disc readers. In particular, the invention relates to the use of standard optical disc drives, and slightly modified drives, to permit discriminable acquisition of a variety of different types of signals from an optical disc. The optical discs in such use include optical bio-discs discs having encoded information as well as investigational structures or features that are deposited on external or internal surfaces of the disc.

2. Description of Related Art

Commonly assigned, co-pending U.S. patent application Ser. Nos. 09/183,842 and 09/311,329 describe methods and apparatus for detecting operational and investigational structures on one or more surfaces of an optical disc assembly. Some of the methods and apparatus discussed in these applications detect investigational structures by physically modifying certain processing circuits in the optical disc drives. As an alternative to these and similar approaches, the present invention is directed to utilizing a principal advantage of relying on standard optical disc readers for laser microscopic detection. This advantage includes the ubiquitous distribution of such drives in the current consumer environment. Therefore, it would be desirable to provide methods and apparatus for detecting operational and investigational structures on an optical disc assembly without having to physically modify the processing circuitry herein.

To provide some background for further discussion of the present invention, relevant features of a conventional optical disc reader and optical disc are described briefly in connection with FIGS. 1–7. For purposes of preliminary introduction these figures will be briefly described. FIG. 1 is a cross-sectional view of typical single-layer CD or CD-like disc and a schematic representation of a reader associated therewith. FIG. 2 is a side cross-sectional view of the disc shown in FIG. 1 at greater magnification. FIG. 3 is a perspective view of the surface of a CD-R disc with wobble grooves. FIG. 4 is a schematic representation of an optical disc detector and associated electronics that use three beams for tracking, focusing, and reading. FIG. 5 is a plan view that illustrates the position of beams from a typical three-beam pickup relative to a track on an optical disc. FIG. 6 is a block diagram of a known optical disc reader. And, FIG. 7 is a functional block diagram of a conventional digital signal processing circuit.

More particularly now, FIG. 1 depicts the reader's optical pickup or objective assembly 10 and a conventional CD-type optical disc 11 with a light path indicated as dashed lines. For clarity, FIG. 1 depicts a minimal complement of the optical pickup components. FIG. 2 provides a side cross-sectional enlarged view of disc 11 in the same orientation relative to the incident light.

With reference to FIGS. 1 and 2, the conventional optical pickup 10 includes light source 19, lenses 12, 13, and 14, beam splitter 15, quarter wave plate 20, and detector 18. Light source 19 is placed at a focal point of a collimator lens 12 that normally has a long focal distance. Collimator lens 12 makes the divergent light rays parallel. A monitor diode (not shown) may be used to stabilize the laser's output. Light source 19 may be a laser, LED, or laser diode, although the present invention may be implemented on a non-coherent light system as well.

A conventional optical design used for three-beam pickup typically uses two secondary beams for tracking. To generate these beams, light from source 19 passes through diffraction grating 17, which is a screen with slits spaced only a few laser wavelengths apart. As the beam passes through the grating, the light diffracts; when the resulting collection is again focused, it will appear as a single, bright, centered beam with a series of successively less intense beams on either side. It is this diffraction pattern that actually strikes the disc.

A conventional three-beam pickup uses the center beam for reading data and focusing and two secondary beams for tracking only. In this design, the beams are spatially linked because they are the result of a single diffracted laser beam. By contrast, a one-beam pickup accomplishes all of these tasks using a single beam.

Polarization beam splitter 15 (PBS) directs the light to a disc surface and then directs the reflected light to the photodiode sensor 18. PBS 15 normally includes two prisms with a common 45° face acting as a polarizing prism. Collimator lens 12 preferably follows PBS 15. The light then passes through the quarter-wavelength plate 20, which is an anisotropic material that rotates the plane of polarization of the light beams. Light that has passed through quarter-wavelength plate 20 and that has been reflected from disc 11 back again through quarter-wavelength plate 20 will be polarized in a plane at right angles to that of the incident light. Because PBS 15 passes light in one plane, (e.g., horizontally polarized) but reflects light in the other plane (e.g., vertically polarized), PBS 15 deflects the reflected beam toward sensor 18 to read the digital data.

The final piece of optics in the optical path to disc 11 is objective lens 13, which is used to focus the beams onto the disc data surface, taking into account the refractive index of the light-proximal polycarbonate substrate 112 of disc 11. Objective lens 13 focuses the light into a convergent cone of light, or light spot. The convergence is a function of the numerical aperture of the lens.

The data encoded on disc 11 now determines the fate of the laser light. In a regular CD, when the light spot strikes a land, the smooth interval between two pits, light is almost totally reflected. When it strikes a pit with a depth of about a quarter wavelength of the light, diffraction and cancellation due to interference cause less light to be reflected. All three intensity-modulated light beams return through objective lens 13, quarter-wavelength plate 20, collimator 12, and PBS 15. Finally, these beams pass through singlet lens 14 and an astigmatic element 16, which may be a cylindrical lens, to introduce astigmatism in the reflected light beam en route to photodiode 18.

As shown in greater detail in FIG. 2, CD-type disc 11 includes three layers from the light-proximal surface to the light-distal surface. By convention, disc layers are numbered upwards from the light-proximal surface to the light-distal surface. These layers include the transparent substrate 112, a reflective layer 114, and a protective layer 116. Transparent substrate 112 makes up most of the thickness of a typical CD-type disc, as measured along the optical axis, and provides both optical and structural features necessary for disc operation.

Transparent substrate 112 is typically impressed or embossed with a spiral track that starts at the innermost readable portion of the disc and then spirals out to the outermost readable portion of the disc. In a non-recordable disc (e.g., pre-recorded), this track is made up of a series of embossed pits, each typically having a depth of approximately one-quarter the wavelength of the light that is used to read the disc. The pits have varying lengths. The length and spacing of the pits is employed as the mechanism for encoding the data.

With reference now to FIG. 3, the spiral groove in a recordable disc contains a dye rather than pits. A typical recordable disc includes a spiral groove having a characteristic shape along the length thereof. This type of groove is known as a "wobble groove," and is formed by a bottom portion having undulating or wavy sidewalls. A raised or elevated portion separates adjacent grooves in the spiral. Such a wobble groove may then include embossed portion 110 and groove portion 118 as shown in FIG. 3. Embossed portion 110 and groove portion 118 are similar to the wobble groove found on a standard recordable CD.

Referring now to FIG. 4, the exemplary detector 18 and its associated electronics are described in more detail. Detector 18 typically includes a central detector 25, and can be bordered by additional side detector elements 26 and 27. Central detector 25 may be split into multiple detector elements (e.g., four), represented as A, B, C, and D. Detector elements A, B, C, and D (sometimes collectively referred to as a "quad detector") each provide an electrical signal indicative of the intensity of the reflected light beam striking that element.

The sum of the signals from the quad detector 25, e.g., A+B+C+D, provides a radio frequency (RF) signal 50, also referred to as a high frequency (HF), quad-sum, or sum signal. As used herein the notation "A+B" indicates the sum of the signals from detector elements A and B. The HF signal 50 (i.e., RF, quad-sum, or sum signal) is typically demodulated to recover data recorded on the optical disc.

Various pairs of the signals from detector elements A to F are also combined to provide feedback signals for tracking and focus control. For example, a tracking signal 52 (e.g., tracking error or TE signal) is obtained from the difference between the E and F signals, (i.e., E−F). A focus error (FE) signal 54 may be obtained from the difference between the A+C and B+D signals.

Typically, such processing is performed by analog circuitry in combination with one or more integrated circuit chips. Often, the circuitry takes the form of a special chip set or a single ASIC (application-specific integrated circuit) chip.

The circuitry of FIG. 4 is just one example of circuitry that provides focus and tracking error signals in an optical disc player. Numerous methods are known for providing these signals. For example, a focus error signal may be obtained by the critical angle method, described in U.S. Pat. No. 5,629,514 or the Foucault and astigmatism methods, described in *The Compact Disc Handbook* by Pohlmann, A-R Editions, Inc. (1992) both of which are incorporated herein by reference in their entireties. Similarly, tracking error signals may be obtained using the single beam push-pull or three beam methods described in *The Compact Disc Handbook* or the differential phase method described in U.S. Pat. No. 5,130,963, which is incorporated herein by reference in its entirety, or the single beam high frequency wobble method.

With reference now to FIG. 5, a CD drive typically uses a three-beam pickup, in which the light beam is split into three beams, a main beam 21 and two tracking beams 23. The main beam 21 is focused onto the surface of an optical disc so that it is centered on a tracking structure, whereas the tracking beams 23 fall on opposite sides of the tracking structure. Main beam 21 is shown centered on track 24 (as defined by pits 22), with tracking beams 23 falling on opposite sides of track 24. By design, the three beams are reflected from the optical disc and directed to detector 18 (FIG. 4) so that main beam 21 falls on the quad detector, and tracking beams 23 fall on sensor elements E and F.

FIG. 6 is a generalized block diagram of an illustrative chip set 30 for a typical optical drive system. Although the chip sets for CD, CD-R, and DVD drives can be somewhat different from one another, it will be understood that the system shown in FIG. 6 is meant to generically represent all types of optical drives, and that a detailed understanding of the differences between the chip sets is not necessary to practice the present invention.

The HF signal 50, obtained from summing the signals from detector elements A, B, C, and D, is normally processed to extract whatever data is recorded on the optical disc. First, analog HF signal 50 is conditioned, with normalization and equalization performed. Next, analog signal 50 is converted to a digitized signal including a serial stream of digital data referred to as channel bits. The channel bit stream is then demodulated according to the modulation standard used for the type of optical disc being read. For example, it is common for CD-type discs to use eight-to-fourteen (also denominated "eight-of-fourteen") modulation (EFM) wherein a data byte, or eight data bits, is encoded into fourteen channel bits. There are three merging bits between each group of fourteen channel bits. Thus, when reading a CD-type optical disc, seventeen channel bits are read from the optical disc, the merging bits are discarded, and the remaining fourteen bits are decoded, or demodulated, to obtain the original data byte. The data bytes themselves are grouped into blocks, which are further processed to reduce the effects of disc defects, such as scratches on the disc surface.

HF signal 50 from detector 18 (FIG. 4) may be converted to a square wave signal 51 by comparator 31, which provides a high output when HF signal 50 is above a threshold level, and a low output when HF signal 50 is below the threshold. Digital signal processing circuit (DSP) 32 then samples the resulting square wave signal 51 to determine the value of each channel bit. DSP 32 further demodulates the channel bits to extract the data bytes that are then grouped into blocks and processed to correct errors that may have occurred. Memory 33a provides temporary storage for the data, as it is being processed by DSP 32 and assembled into blocks.

Servo block 34 analyzes the tracking error (TE) signal 52 (or a wobble tracking error (WTE) in a DVD or CD-R system) and provides a tracking control signal to the tracking mechanisms to ensure that the pickup assembly maintains proper tracking. Similarly, a focus control signal 53 is provided based on focus error (FE) signal 54. DSP 32 provides an indication of the data rate of HF signal 50, which is used by servo block 34 to provide a speed control signal 55 to the spindle motor (not shown) of the optical disc drive.

In an audio CD player, after processing by DSP 32, each data block is sent to audio reproduction circuitry not shown in FIG. 6. However, in some data storage applications, each data block may contain additional error detection codes (EDC) and error correction codes (ECC). EDC/ECC circuitry 35 typically uses the EDC and ECC codes to increase the integrity of the data block by detecting and correcting errors not already corrected by DSP 32. Memory 33b, which may be combined with memory 33a, provides temporary storage for data blocks being processed by EDC/ECC circuitry 35. Finally, the data blocks are transferred from the optical disc player to host 37 by means of interface circuitry 36. Although an ATAPI interface is shown, it will be understood that other interfaces, such as SCSI, Firewire, or Universal Serial Bus (USB) and the like could also be used.

A controller 38 coordinates the operation of the various components of chip set 30, for example, by coordinating the transfer of data blocks between DSP 32 and EDC/ECC circuitry 35. Controller 38 also keeps track of which data block is being read and may keep track of various parameters indicative of the operational status of the optical disc reader.

Program memory 39 contains program code for the operation of controller 38. In many optical disc reader chip sets, program memory 39 may also contain program instructions for DSP 32 or EDC/ECC circuitry 35. This is advantageous for manufacturers in that the operation of the disc drive may be changed by altering the program code in program memory 39. For example, a newly developed method of modulating or encoding data on an optical disc may be accommodated by changing program memory 39.

FIG. 7 is a functional block diagram illustrating the signal processing that occurs within DSP chip 32 when configured in a conventional manner. As shown, DSP 32 performs several functions. For example, DSP 32 typically normalizes and/or equalizes the HF signal (block 40); converts the normalized HF signal from the analog-to-digital (block 42); demodulates and decodes the resulting EFM signal (block 44); performs some type of error checking procedure (e.g., using Cross-Interleaved Reed-Solomon Code "CIRC" block 46); and provides the resulting signal to an output interface (block 48) for communication with the host data bus 37 (FIG. 6). Examples of commonly used DSP chips that perform some or all of these functions include the SAA 7210, SAA 7220, and the SAA 7735, available from Philips Electronics Corporation, Eindhoven, Netherlands.

While the foregoing description is sufficient for a basic understanding of the present invention, there are numerous alternative designs and configurations of an optical pickup and associated electronics which may be used in the context of the present invention. Further details and alternative designs are described in *Compact Disc Technology*, by Nakajima and Ogawa, IOS Press, Inc. (1992); *The Compact Disc Handbook, Digital Audio and Compact Disc Technology*, by Baert et al. (eds.), Books Britain (1995); *CD-Rom Professional's CD-Recordable Handbook: The Complete Guide to Practical Desktop CD*, Starrett et al. (eds.), ISBN: 0910965188 (1996); all of which are incorporated herein in their entirety by this reference.

SUMMARY OF THE INVENTION

It is an object of the present invention to overcome limitations in the known art. It is a further object of the present invention to adapt a known optical disc system to read an optical disc assembly and extract both operational information used to operate the optical disc system and indicia data indicative of a presence of an investigational feature associated with the optical disc assembly.

These and other objects and advantages of the present invention are achieved in an optical disc system that includes a photo detector circuit of an optical disc drive and a signal processing system. The photo detector circuit of the optical disc drive is configured to generate at least one information-carrying signal from an optical disc assembly. The signal processing system is coupled to the photo detector circuit to obtain from the at least one information-carrying signal both operational information used to operate the optical disc system, and indicia or characteristic data indicative of a presence of an investigational feature associated with the optical disc assembly.

The present invention is also directed to a method that includes depositing a test sample, spinning the optical disc assembly, directing an incident beam, detecting a return beam, and processing the detected return beam to acquire information about an investigational feature associated with the test sample. The step of depositing a test sample positions the sample at a predetermined location on an optical disc assembly. The step of spinning the optical disc assembly is directed to spinning the disc assembly in an optical disc drive. The step of directing an incident beam directs the beam onto the optical disc assembly. The step of detecting a return beam detects the returned beam formed as a result of the incident beam interacting with the test sample.

Other advantages of the present invention are achieved in an alternative method that includes acquiring a plurality of analog signals, summing a first subset of the plurality of analog signals, combining a second subset of the plurality of analog signals, obtaining information used to operate an optical disc drive, and converting the sum signal to a digitized signal. The step of acquiring a plurality of analog signals includes receiving return light from the optical disc assembly using a plurality of photo detectors. The step of summing a first subset of the plurality of analog signals produces a sum signal. The step of combining a second subset of the plurality of analog signals produces a tracking error signal. The step of obtaining information used to operate the optical disc drive includes processing the tracking error signal.

An alternative method of the present invention includes adapting a portion of a signal processing system, acquiring a plurality on analog signals, converting the analog signals into a digitized signal, and characterizing investigational features on an optical disc assembly based on the digitized signal. The step of adapting a portion of a signal processing system adapts the system to operate as an analog-to-digital converter. The step of acquiring a plurality on analog signals acquires the signals from a photo detector circuit of an optical disc drive. The plurality of analog signals include information that is indicative of the investi-gational features. The step of converting the analog signals into a digitized signal converts the signals using the signal processing system.

A specific implementation of this method includes steps of receiving and converting. The step of receiving includes receiving at least one analog signal at a corresponding input of signal processing circuitry. The at least one analog signal is provided by at least one corresponding photo detector element that detects light returned from a surface of the optical disc assembly. The step of converting includes converting each of the at least one analog signal into a corresponding digitized signal. Each digitized signal is substantially proportional to an intensity of the returned light detected by a corresponding one of the at least one photo detector elements.

More specifically, the present invention is directed to an optical disc system including a photo detector circuit of an optical disc drive configured to generate at least one information-carrying signal from an optical disc assembly. The optical disc system is further provided with a signal processing system coupled to the photo detector circuit to obtain from the at least one information-carrying signal both operational information used to operate the optical disc system and indicia data indicative of a presence of an investigational feature associated with the optical disc assembly.

In one embodiment, the signal processing system includes a PC and analog-to-digital converter coupled between the at least one information carrying signal and the PC. The analog-to-digital converter may advantageously provide a digitized signal and the PC may include a first program module to detect and characterize peaks in the digitized signal. In this embodiment, the PC may further include a second program module to detect and count double peaks in the digitized signal. In addition, the signal processing system may also further include an analyzer coupled between the analog-to-digital converter and the PC. In this embodiment, the analog-to-digital converter provides a digitized signal, and the analyzer includes logic to detect and characterize peaks in the digitized signal. According to one aspect of this embodiment, the analyzer further includes logic to detect and count double peaks in the digitized signal.

Alternatively, the optical disc system may include a signal processing system that has an audio processing module coupled between the at least one information-carrying signal and the analog-to-digital converter. In this alternate implementation, the optical disc system further includes a predetermined sound recorded on the optical disc assembly, and a program module in the PC for detecting the indicia data in a deviation of the at least one information carrying signal from the predetermined sound when the investigational feature is present.

The predetermined sound may be encoded silence.

In another embodiment, the signal processing system further includes a buffer coupled between the at least one information-carrying signal and the analog-to-digital converter. The signal processing system may further advantageously include a trigger detection circuit coupled to the analog-to-digital converter, the trigger detection circuit being operative to detect a particular time in relation to a time when the indicia data is present in the at least one information-carrying signal.

In yet another implementation of the present invention, the signal processing system includes a programmable digital signal processor selectively configurable to extract the operational information from the at least one information-carrying signal while in a first configuration and operate as an analog-to-digital converter to provide the indicia data while in a second configuration. According to an aspect of this implementation of the invention, the signal processing system may include a PC, a programmable digital signal processor coupled to the at least one information-carrying signal, and an analyzer coupled between the programmable digital signal processor and the PC so that the analyzer provides the indicia data.

In many of the specific implementations and embodiments of the present invention, the signal processing system may advantageously be provided with a trigger detection circuit that detects a time period during which the investigational feature associated with the optical disc assembly is scanned by the photo detector circuit, or alternatively a trigger detection circuit that detects a particular trigger time in relation to a respective time duration during which the indicia data is present in the at least one information-carrying signal, and each respective time duration occurs periodically with a respective investigational feature and a corresponding set of indicia data.

According to one aspect of the audio implementation of this invention, the signal processing system includes a PC and an audio processing module coupled between the PC and the at least one information-carrying signal. The audio processing module may be selected one of either an external module independent of the optical disc drive, a drive module that is a part of the optical disc drive, or a modified drive module that is a part of the optical disc drive. The PC may advantageously include a processor coupled to the audio module, and a software module stored in a memory to control the processor to extract the indicia data from audio data.

In one principal embodiment of the present invention, the photo detector circuit includes circuitry to generate an analog signal as the at least one information-carrying signal. The analog signal including one of a high frequency signal from a photo detector, a tracking error signal, a focus error signal, an automatic gain control setting, a push-pull tracking signal, a CD tracking signal, a CDR tracking signal, a focus signal, a differential phase detector signal, a laser power monitor signal, and a sound signal.

According to other aspects of this invention, the optical disc system may include an optical disc assembly having disposed thereon the associated investigational feature in a first disc sector and encoded thereon the operational information used to operate the optical disc drive in a remaining disc sector. The optical disc assembly may include a reflective-type or transmissive-type optical disc. The optical disc assembly may include a trigger mark disposed thereon in a predetermined position relative to the first disc sector. In this embodiment, the signal processing system includes a trigger detection circuit that detects the trigger mark.

In accordance with certain aspects hereof, the trigger detection circuit detects the trigger mark periodically. The trigger detection circuit may detects the trigger mark either at (i) a predetermined time in advance of, (ii) a time at, or (iii) a predetermined time after a time when a respective investigational feature is read by the photo detector circuit based on the predetermined position of the trigger mark relative to the first disc sector.

In alternative designs of one principal embodiment of the optical disc system, one or more additional photo detector circuits are configured to generate at least one information-carrying signal from a respective optical disc assembly. The optical disc assembly may include one or more reporters having an affinity for a respective investigational feature. One or more of the reporters may be individually selected from the group consisting of plastic micro-spheres, colloidal gold beads, silica beads, glass beads, latex beads, polystyrene beads, magnetic beads, and fluorescent beads.

According to another aspect of the present invention, there is provided an assay method which includes the steps of (1) depositing a test sample at a predetermined location on an optical disc assembly, (2) spinning the optical disc assembly in an optical disc drive, (3) directing an incident beam onto the optical disc assembly, (4) detecting a return beam formed as a result of the incident beam interacting with the test sample, and (5) processing the detected return beam to acquire information about an investigational feature associated with the test sample. In this method the optical disc assembly may include one or more reporters having an affinity for investigational features in the test sample. These reporters may be individually selected from the group consisting of plastic micro-spheres, colloidal gold beads, silica beads, glass beads, latex beads, polystyrene beads, magnetic beads, and fluorescent beads.

In this embodiment of the present method, the step of detecting a return beam may form a plurality of analog signals. The step of processing the detected return beam may advantageously include (1) summing a first subset of the plurality of analog signals to produce a sum signal (2) combining one of the first subset and a second subset of the plurality of analog signals to produce a tracking error signal, (3) obtaining information used to operate an optical disc drive from the tracking error signal, and (4) converting the sum signal to a digitized signal. This method may optionally include the additional step of detecting a trigger mark associated with the optical disc assembly.

Another assay method according to certain aspects of this invention includes the steps of (1) depositing a test sample at a predetermined location on an optical disc assembly (2) spinning the optical disc assembly in an optical disc drive, (3) directing an incident beam onto the optical disc assembly, (4) detecting a transmitted beam formed as a result of the incident beam interacting with the test sample and continuing through the disc assembly, and (5) processing the detected transmitted beam to acquire information about an investigational feature associated with the test sample. This method may include the further steps of detecting a reflected beam formed as a result of the incident beam interacting with the test sample, and processing the detected reflected beam to acquire information about an investigational feature associated with the test sample. This method may also include the optical disc assembly having one or more reporters with an affinity for investigational features in the test sample. As with the prior method discussed above, in this method the one or more reporters may be individually selected from the group consisting of plastic micro-spheres, colloidal gold beads, silica beads, glass beads, latex beads, polystyrene beads, magnetic beads, and fluorescent beads.

Also in this method, the step of detecting a transmitted beam forms a plurality of analog signals. Similarly, the step of processing the transmitted beam may include the additional steps of (1) summing a first subset of the plurality of analog signals to produce a sum signal, (2) combining one of the first subset and a second subset of the plurality of analog signals to produce a tracking error signal, (3) obtaining information used to operate an optical disc drive from the tracking error signal, and (4) converting the sum signal to a digitized signal. This method may optionally include the additional step of detecting a trigger mark associated with the optical disc assembly.

Yet another method of this invention includes the steps of (1) acquiring a plurality of analog signals from an optical disc assembly using one or more photo detectors, (2) summing a first subset of the plurality of analog signals to produce a sum signal, (3) combining a second subset of the plurality of analog signals to produce a tracking error signal, (4) obtaining information used to operate an optical disc drive from the tracking error signal, and (5) converting the sum signal to a digitized signal. In this alternative method, the steps of acquiring and summing produce the sum signal, and the sum signal includes perturbations indicative of an investigational feature positioned at a location on the optical disc assembly. This method may include the further step of characterizing the investigational feature based on the digitized signal.

In this method, the step of converting may include configuring a portion of an optical disc drive chip set to operate as an analog-to-digital converter. In one embodiment, this configuring step includes programming a digital signal processing chip within the optical disc drive chip set to operate as an analog-to-digital converter. The digital signal processing chip may advantageously be provided with a normalization function, an analog-to-digital converter function, a demodulation/decode function, and an output interface function. In this specific embodiment, the step of configuring may further include by-passing the sum signal around the demodulation/decode function by creating a path from the analog-to-digital converter function to the output interface function. And, the step of configuring may also include deactivating the demodulation/decode function.

According to one principal aspect of this method, the step of converting includes configuring a digital signal processing chip that includes a normalization function, an analog-to-digital converter function, a demodulation/decode function, and an output interface function. And, the step of configuring includes creating a path from the analog-to-digital converter function to the output interface function so that the sum signal is unprocessed by the demodulation/decode function. Herein, the step of configuring may similarly include deactivating the demodulation/decode function.

In accordance with one aspect of this method, the step of acquiring may include tapping one or more of the plurality of analog signals directly at the one or more photo detectors. And, the step of converting may include directing the signals into an analog-to-digital converter. In a particular embodiment, the step of converting further includes directing the analog signals from the one or more photo detectors into a buffer amplifier before processing by the analog-to-digital converter.

Alternatively, the step of acquiring may include tapping one or more of the plurality of analog signals after processing by an optical disc drive chip set, while the step of converting may then include directing the signals into an analog-to-digital converter. In this alternative embodiment, the step of converting may similarly include directing the analog signals from the optical disc drive chip set into a buffer amplifier before directing the analog signals into the analog-to-digital converter.

According to still another aspect of this invention, there is provided an alternative method including the steps of (1) adapting a portion of a signal processing system to operate as an analog-to-digital converter (2) acquiring a plurality of analog signals from a photo detector circuit of an optical disc drive, the plurality of analog signals including information therein that is indicative of investigational features on an optical disc assembly (3) converting the analog signals into a digitized signal with the signal processing system, and (4) characterizing the investigational features based on the digitized signal. In this embodiment, the step of adapting may include programming a digital signal processing chip within the signal processing system to operate as the analog-to-digital converter.

Still yet a further method according to this invention includes the steps of (1) receiving each of at least one analog signal at a corresponding input of signal processing circuitry, the at least one analog signal having been provided by at least one corresponding photo detector element that detects light returned from a surface of an optical disc assembly, and (2) converting each of the at least one analog signal into a corresponding digitized signal, each digitized signal being substantially proportional to an intensity of the returned light detected by a corresponding one of the at least one photo detector element. In this method, the step of converting may advantageously include operating the signal processing circuitry to bypass any demodulation of a first digitized signal. In this embodiment, the step of converting may further include the steps of (1) operating the signal processing circuitry to bypass any decoding of the first digitized signal, and (2) operating the signal processing circuitry to bypass any checking for errors in the first digitized signal.

Alternatively, the step of converting may include operating the signal processing circuitry to bypass any decoding of a first digitized signal. As an alternative thereto, the converting step may include operating the signal processing circuitry to bypass any checking for errors in a first digitized signal.

The different embodiments of this method may each include the further step of combining at least two of the at least one analog signal when there are two or more such signals. In this embodiment, the step of combining is a step selected from a group consisting of adding, subtracting, dividing, and multiplying, and any combination thereof. The step of combining may be performed before, or alternatively after, the step of converting.

The method of claim 55 wherein the step of receiving includes at least one analog signal provided by at least one corresponding photo detector element that detects light transmitted through an optical disc assembly.

Generally for this method, the step of receiving may include detection of a trigger mark indicative of a time period during which the investigational feature associated with the optical disc assembly is scanned by the at least one photo detector. Also any of these embodiments may further include a step of supplying a first digitized signal of the at least one digitized signal at an output interface of the signal processing circuitry after the step of converting without substantially modifying the first digitized signal between the steps of converting and supplying. In these embodiments, the signal processing circuitry includes a digital signal processor or, alternatively, an external analog-to-digital converter. In the A/D converter implementation, the signal processing circuitry may further include a buffer amplifier before the external analog-to-digital converter.

According to other aspects of this invention, the characteristic signals generated hereby are considered inventive in their own right. Thus the present invention is further directed to a signal characteristic of information about an investigational feature located in an optical disc assembly, the signal being generated by a process including the steps of (1) depositing a test sample at a predetermined location on an optical disc assembly, (2) spinning the optical disc assembly in an optical disc drive, (3) directing an incident beam onto the optical disc assembly, (4) detecting a return beam formed as a result of the incident beam interacting with the test sample, and (5) processing the detected return beam to acquire information about an investigational feature associated with the test sample. The return beam may be formed as a result of the incident beam interacting with one or more reporters having an affinity for investigational features in the test sample. The step of detecting the return beam may form a plurality of analog signals. In this embodiment, the step of processing the detected return beam may include (1) summing a first subset of the plurality of analog signals to produce a sum signal, (2) combining one of the first subset and a second subset of the plurality of analog signals to produce a tracking error signal, (3) obtaining information used to operate an optical disc drive from the tracking error signal, and (4) converting the sum signal to a digitized signal. The signal may then include distinctive perturbations indicative of an investigational feature located at a location of the optical disc assembly. As above, the step of converting may include configuring a portion of an optical disc drive chip set to operate as an analog-to-digital converter. And, the step of configuring may include programming a digital signal processing chip within the optical disc drive chip set to operate as an analog-to-digital converter.

In one specific embodiment of the process employed to generate the desired signal, the digital signal processing chip includes a normalization function, an analog-to-digital converter function, a demodulation/decode function, and an output interface function. In this embodiment, the step of configuring may further comprises passing the sum signal around the demodulation/decode function by creating a path from the analog-to-digital converter function to the output interface function. Also, the step of configuring may further include deactivating the demodulation/decode function.

In another specific embodiment of the process employed to generate the desired signature signals, the step of converting may include directing the sum signal into an external analog-to-digital converter. In this embodiment, the step of converting may further include directing the sum signal into a buffer amplifier prior to the external analog-to-digital converter.

In yet a further specific embodiment of the process employed to generate the desired signal signatures, the step of converting may include configuring a digital signal processing chip that includes a normalization function, an analog-to-digital converter function, a demodulation/decode function, and an output interface function, while the step of configuring includes creating a path from the analog-to-digital converter function to the output interface function so that the sum signal is unprocessed by the demodulation/decode function.

In many of these signal generating processes, the step of detecting may further include detecting a transmitted beam formed as a result of the incident beam interacting with the test sample and passing through the optical disc assembly.

Additionally, the step of detecting the return beam may form a plurality of analog signals and the step of processing the detected return beam may include (1) summing a first subset of the plurality of analog signals to produce a sum signal, (2) combining a second subset of the plurality of analog signals to produce a tracking error signal, (3) obtaining information used to operate an optical disc drive from the tracking error signal, and (4) converting the sum signal to a digitized signal. In these embodiments, the sum signal advantageously includes perturbations indicative of an investigational feature located at a location of the optical disc assembly.

The step of converting may include configuring a portion of an optical disc drive chip set to operate as an analog-to-digital converter. In these embodiments, the step of configuring may include programming a digital signal processing chip within the optical disc drive chip set to operate as an analog-to-digital converter. In a more specific implementation thereof, the digital signal processing chip includes a normalization function, an analog-to-digital converter function, a demodulation/decode function, and an output interface function. In these specific embodiments, the step of configuring may further include passing the sum signal around the demodulation/decode function by creating a path from the analog-to-digital converter function to the output interface function. Also, the step of configuring may further include deactivating the demodulation/decode function.

In certain embodiments of the process for generation the desired signal signatures, the step of converting includes configuring a digital signal processing chip that includes a normalization function, an analog-to-digital converter function, a demodulation/decode function, and an output interface function, while the step of configuring comprises creating a path from the analog-to-digital converter function to the output interface function so that the sum signal is unprocessed by the demodulation/decode function.

The unique signal signatures of the present invention may also be generated by a process including the steps of (1) adapting a portion of a signal processing system to operate as an analog-to-digital converter, (2) acquiring a plurality of analog signals from a photo detector circuit of an optical disc drive, wherein the plurality of analog signals includes information therein that is indicative of investigational features on an optical disc assembly, (3) converting the analog signals into a digitized signal with the signal processing system, and (4) characterizing the investigational features based on the digitized signal. In this process, the step of adapting may include programming a digital signal processing chip within the signal processing system to operate as the analog-to-digital converter. Also, the step of acquiring may include tapping the analog signals prior to an optical drive buffer. And, the step of acquiring may include trigger mark signals indicative of a time period during which the investigational feature associated with the optical disc assembly is scanned by the photo detector circuit.

According to still other aspects of this invention, there is provided a method of detecting a signal within an optical disc system, which method includes the steps of (1) generating an incident beam of known wavelength, (2) directing the beam onto an optical disc containing an investigational feature, and (3) receiving a return beam formed as a result of the incident beam interacting with the investigational feature. In this method the optical disc may comprise one or more reporters having an affinity for the investigational feature, the reporters being capable of interacting with the incident beam. One or more of the reporters may be individually selected from the group consisting of plastic micro-spheres, colloidal gold beads, silica beads, glass beads, latex beads, polystyrene beads, magnetic beads, and fluorescent beads. Also in this method, the step of receiving may further include receiving a transmitted beam formed as a result of the incident beam interacting with the investigational feature, and passing through the optical disc. Generally, the step of receiving may advantageously involve use of one or more photo detectors. The step of receiving may form a plurality of analog signals for processing by a signal processing system. In addition, the signal processing system may include an external analog-to-digital converter and with or without a buffer amplifier associated therewith. In the embodiment utilizing the buffer amplifies, the analog signals may be tapped prior to processing by an internal optical disc drive buffer circuit. In certain implementations of these aspects of the present invention, the signal processing system may include programmable digital signal processing circuitry or audio processing circuitry.

According to yet still additional aspects of the present invention, there is provided a method of imaging an investigational feature including the steps of (1) depositing an investigational feature at a predetermined location on an optical disc assembly, (2) spinning the optical disc assembly in an optical disc drive, (3) directing an incident beam onto the optical disc assembly, (4) detecting a return beam formed as a result of the incident beam interacting with the investigational feature, (5) processing the detected return beam to acquire information about an investigational feature, and (6) imaging the investigational feature based on the information. In this method, the optical disc assembly may be provided with one or more reporters having an affinity for investigational features in the test sample. The one or more reporters may be individually selected from the group consisting of plastic micro-spheres, colloidal gold beads, silica beads, glass beads, latex beads, polystyrene beads, magnetic beads, and fluorescent beads. Also in this method, the step of detecting the return beam may form a plurality of analog signals, and the step of processing comprises converting the analog signals into a digitized signal. In this particular embodiment, the step of processing involves a signal processing system that may include an external analog-to-digital converter with or without a buffer amplifier. Alternatively, the signal processing system may be provided with programmable digital signal processing circuitry and/or related audio processing circuitry.

In many implementations of this particular method, the step of processing the detected return beam may include the further steps of (1) summing a first subset of the plurality of analog signals to produce a sum signal, (2) combining one of the first subset and a second subset of the plurality of analog signals to produce a tracking error signal, (3) obtaining information used to operate an optical disc drive from the tracking error signal, (4) converting the sum signal to a digitized signal, and (4) outputting the digitized signal. In these implementations, the step of outputting may involve displaying the digitized signal on a monitor or playing the digitized signal as sound using speakers.

In accordance with yet still additional aspects of this invention, there is provided a kit for the detection of an investigational feature in a test sample. The kit includes a carrier compartmentalized to receive one or more optical discs. The kit may further include one or more containers, the containers having one or more agents selected from the group consisting of isolated nucleic acids, antibodies, proteins, reagents, and reporters. The kit of may further be provided with at least one optical bio-disc according to the present invention, and/or a setup optical disc.

The kit may further include a buffer amplifier card, the card being adapted to retrofit into an optical disc drive. The kit may alternatively include a modified optical disc drive.

According to still further aspects of this invention, an optical analysis disc for detection of a signal element is provided. This disc includes a substrate layer, an operational layer associated with the substrate layer, the operational layer having operational information encoded therein, and a signal element positioned relative to the operational layer, the signal element and the operational layer having optical or magnetic characteristics selected to provide a predetermined contrast therebetween to thereby provide a return signal indicative of distinctions between information associated with the operation layer and characteristics of the signal element. The optical or magnetic characteristics include but are not limited to, electrical or magnetic polarization state or irradiance of the signal element and/or the operational layer.

In accordance with yet still additional aspects of the present invention, there is provided an optical analysis disc for use in imaging a biological or medical investigational feature. This disc includes a substrate, an operational layer associated with the substrate, the operational layer having encoded operational features positioned relative to each other at a specified track pitch, and an investigational feature positioned relative to the operational layer, the investigational feature selected to be larger in size than a corresponding operational feature and at least as large in size as one-half of the track pitch to thereby provide at least one scan of the investigational feature as an incident beam tracks along the operational features. In this embodiment, rotational speed of the disc may be controlled to produce a higher quantized resolution in the digitization of a return signal generated by the disc. This disc may also advantageously include logic to provide random access to preaddressed locations on the disc.

BRIEF DESCRIPTION OF DRAWING FIGURES

Further objects of the present invention together with additional features contributing thereto and advantages accruing therefrom will be apparent from the following description of the preferred embodiments of the invention which are shown in the accompanying drawing with like reference numerals indicating like components throughout, wherein:

FIG. 9A is a pictorial representation and block diagram illustrating alternative embodiments of the present invention directed to processing the high frequency, tracking, focusing, audio, or other signals of a disc drive and displaying or outputting results relating thereto;

Figure 22:
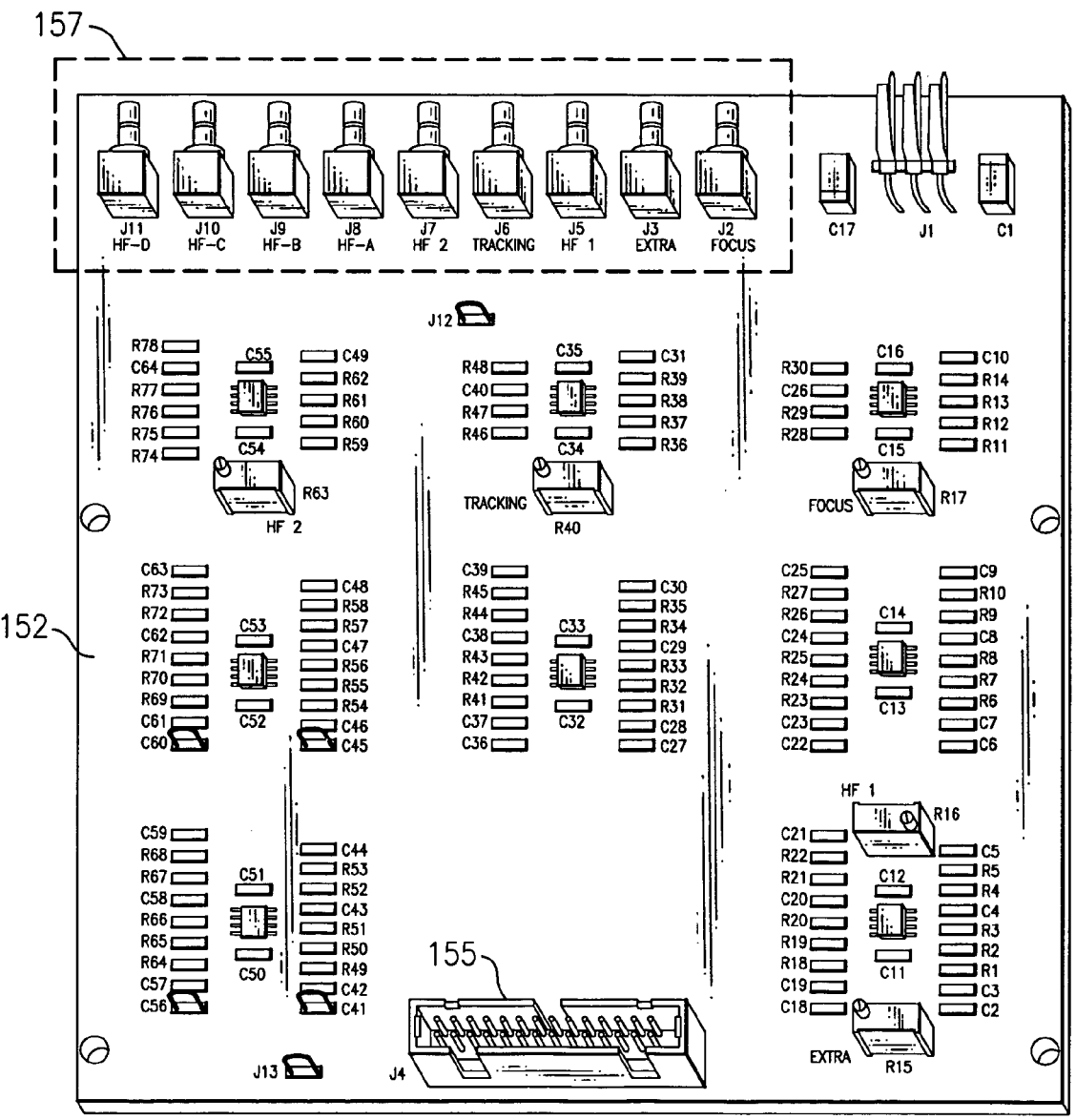
FIG. 22 is a top perspective view of an external buffer amplifier card adapted to receive signals from the head assembly of the drive buffer according to a first embodiment of the present invention.
Figure 23:
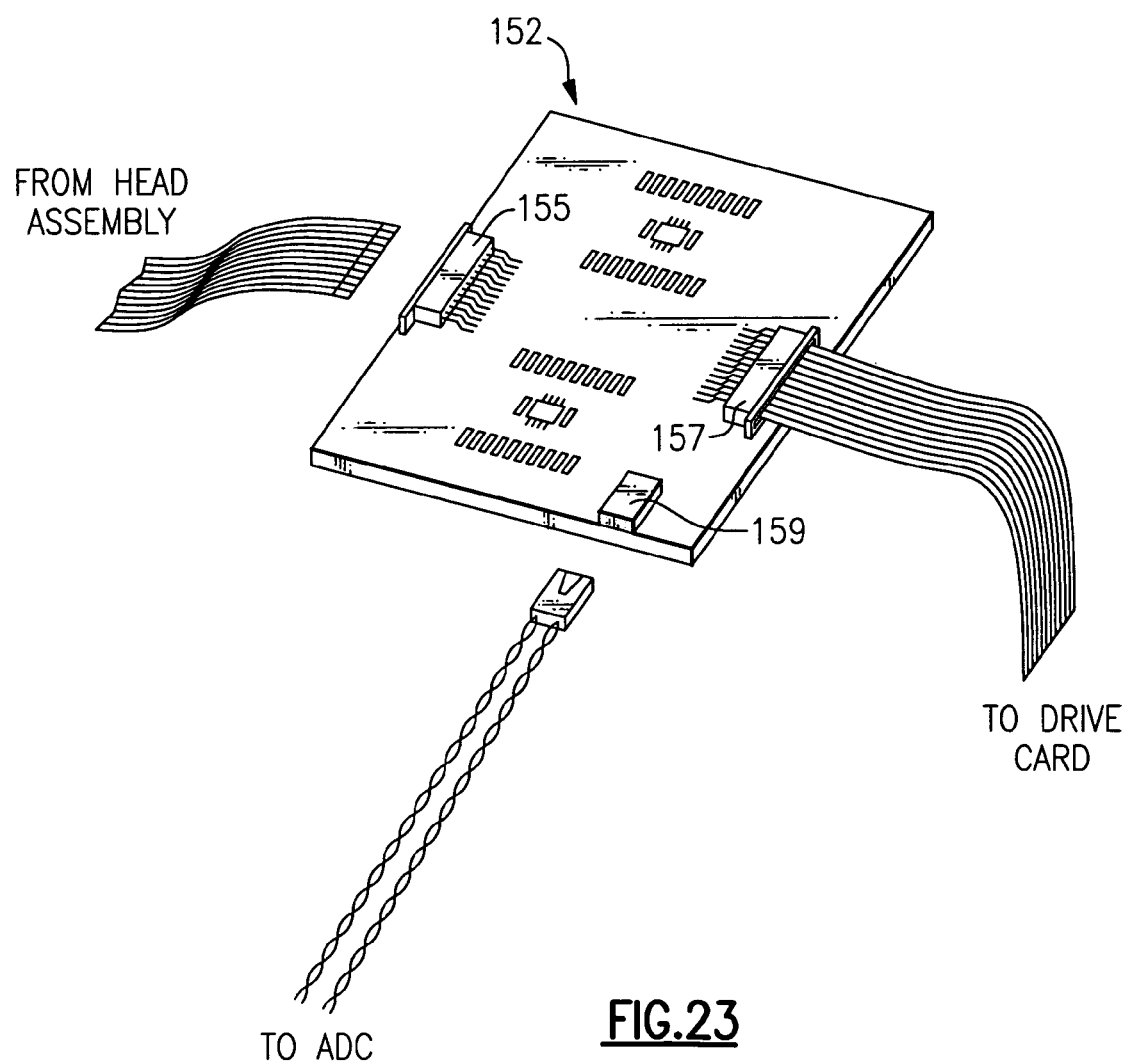
FIG. 23 is a perspective view of an alternative embodiment of the external buffer amplifier card illustrated in FIG. 22.
Figure 24B:
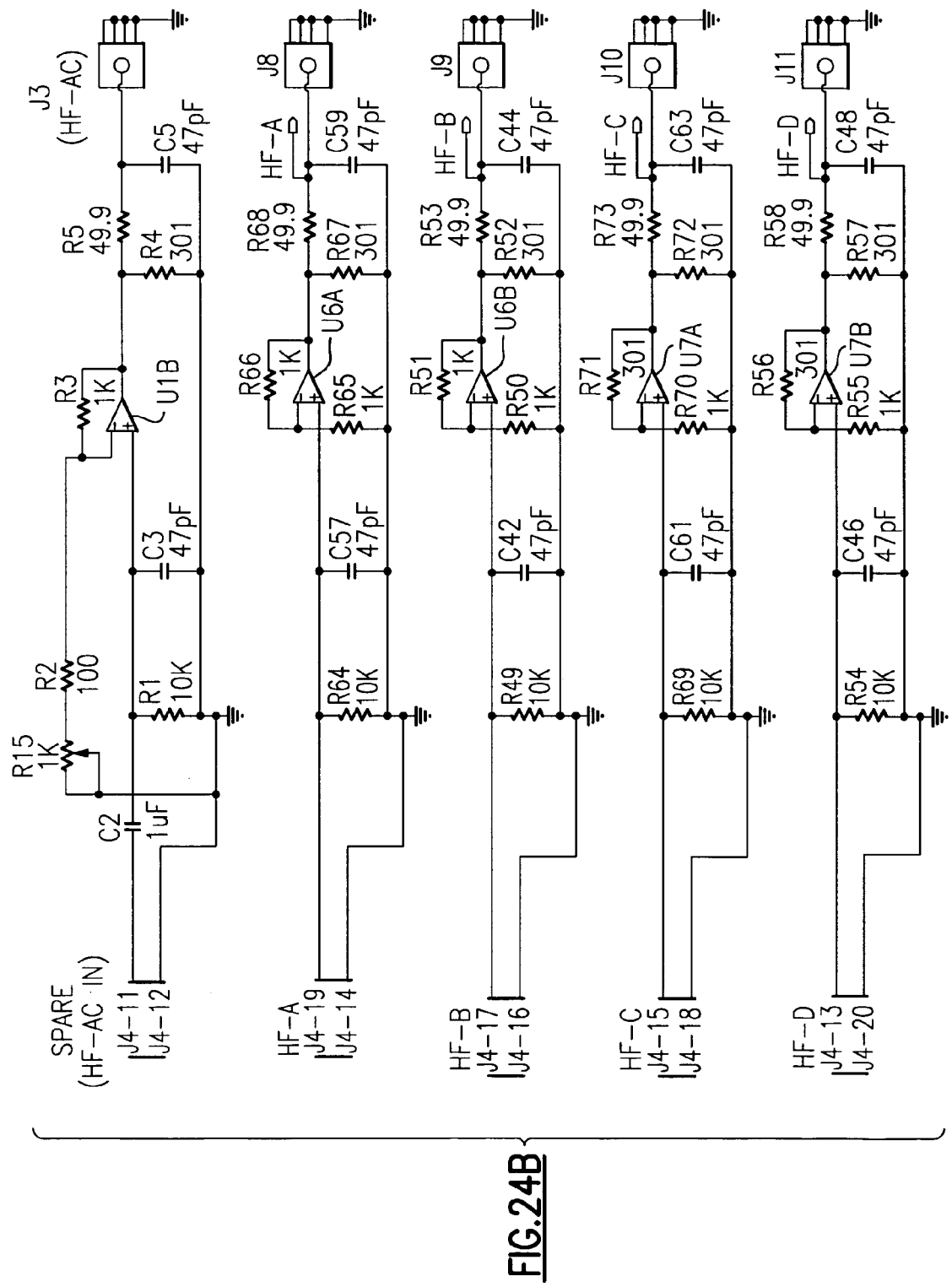
FIG. 24 is a graphical representation illustrating the relationship between FIGS. 24A, 24B, and 24C.
Figure 24C:
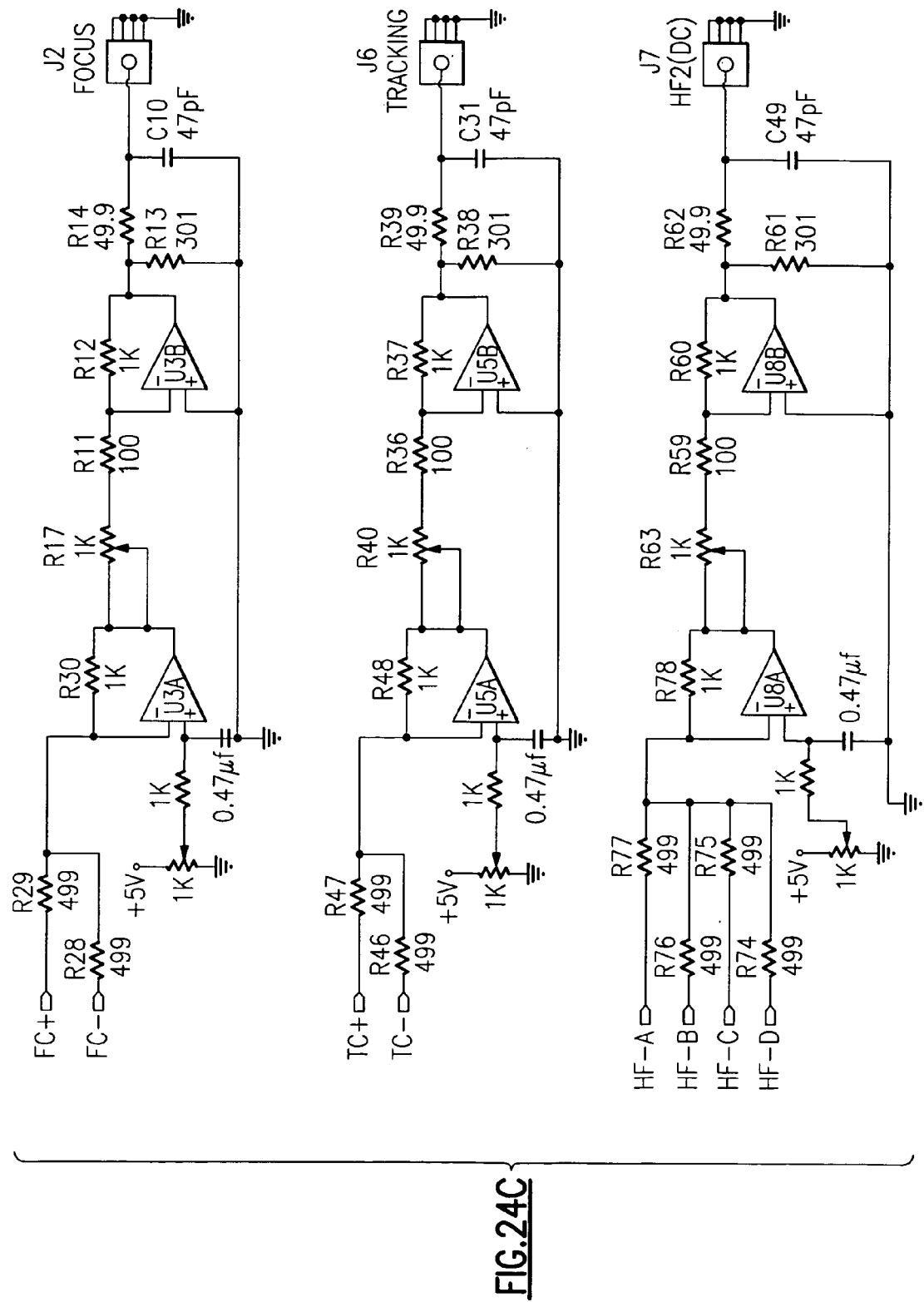
Figure 25:
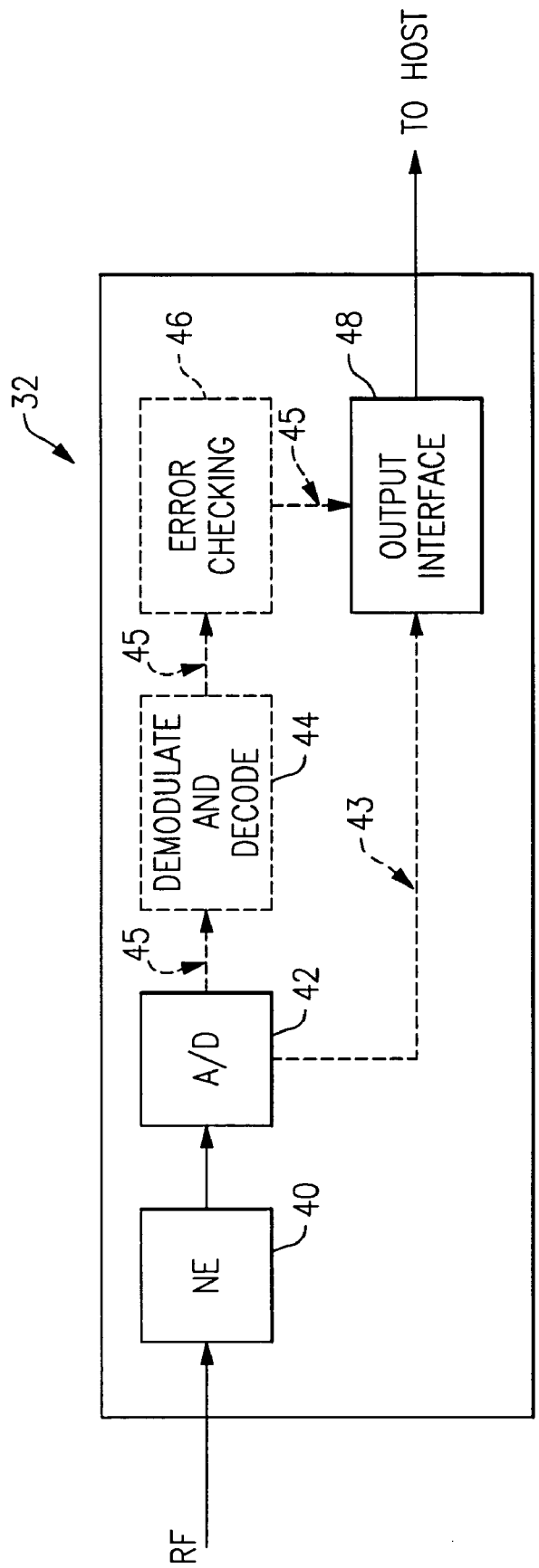
Figure 26:
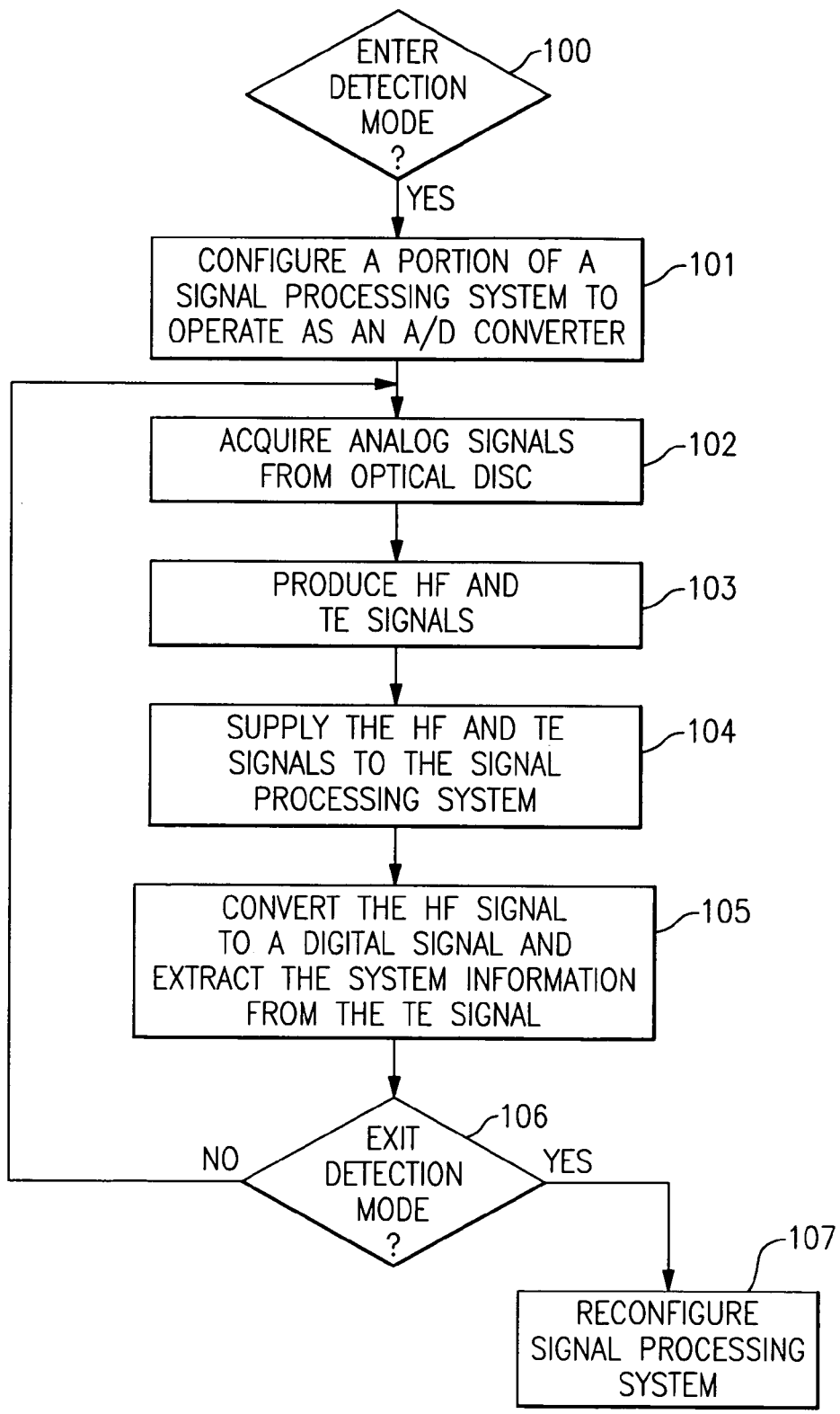
Figure 27:
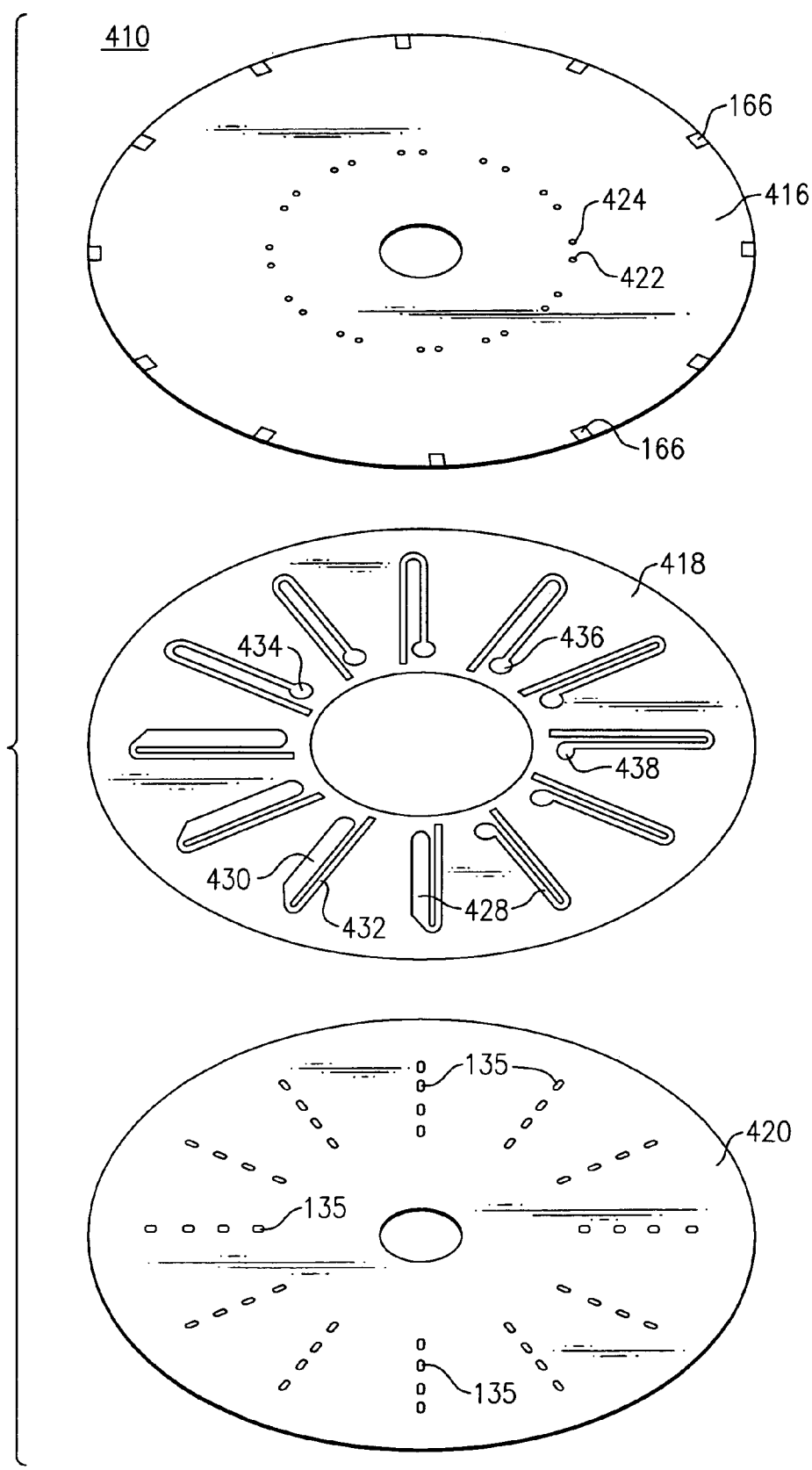
Figure 28:
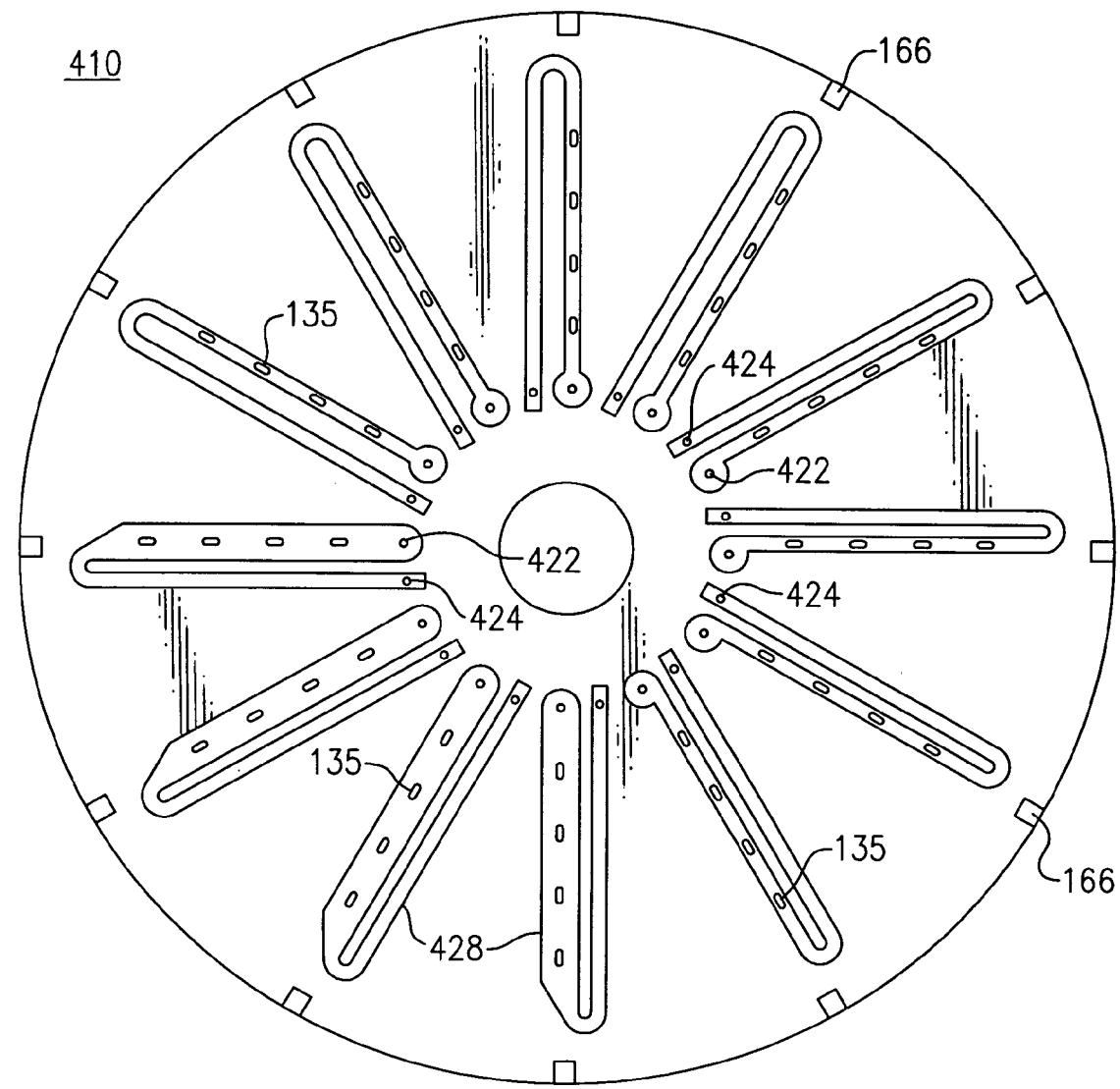
Figure 29:
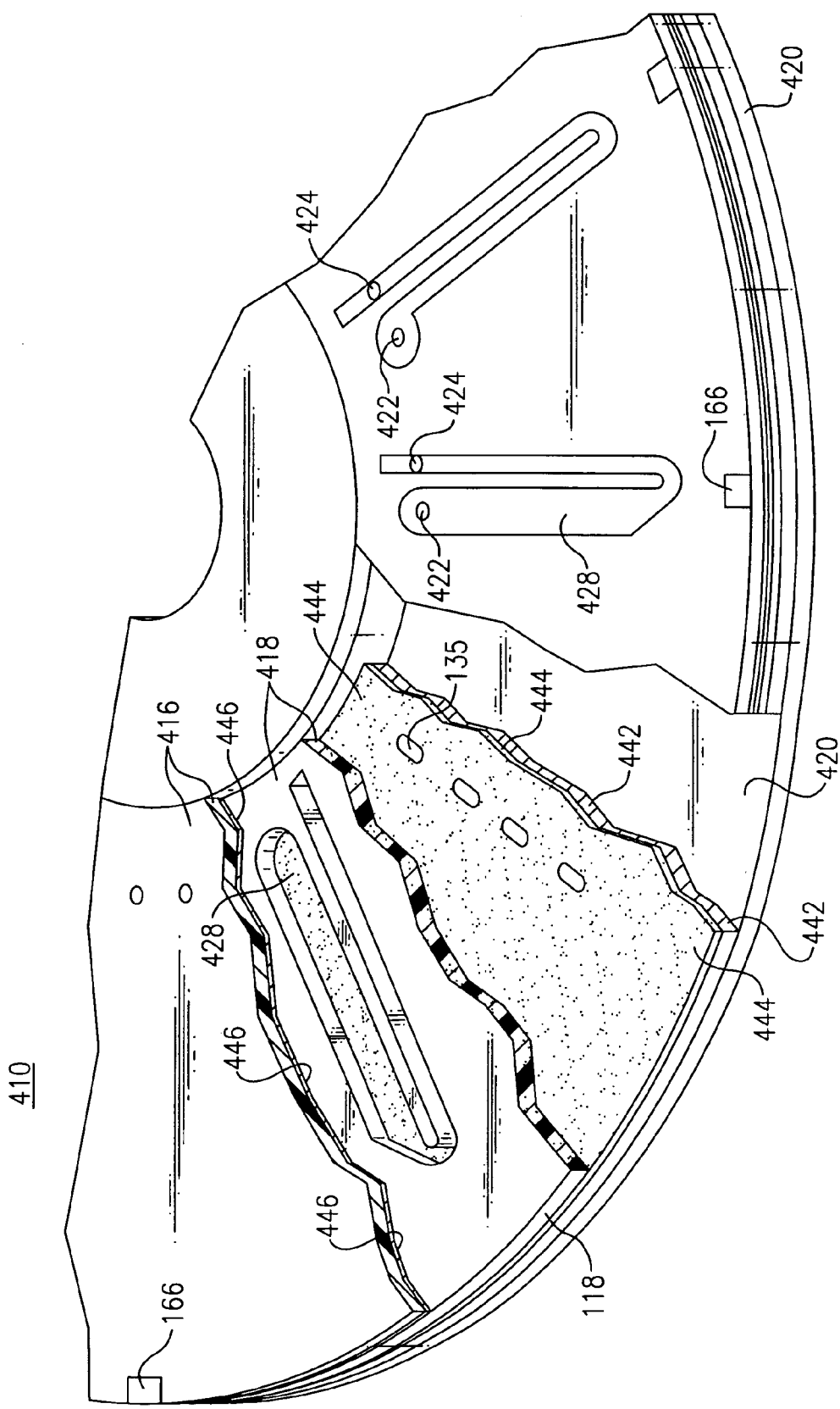
Figure 30:
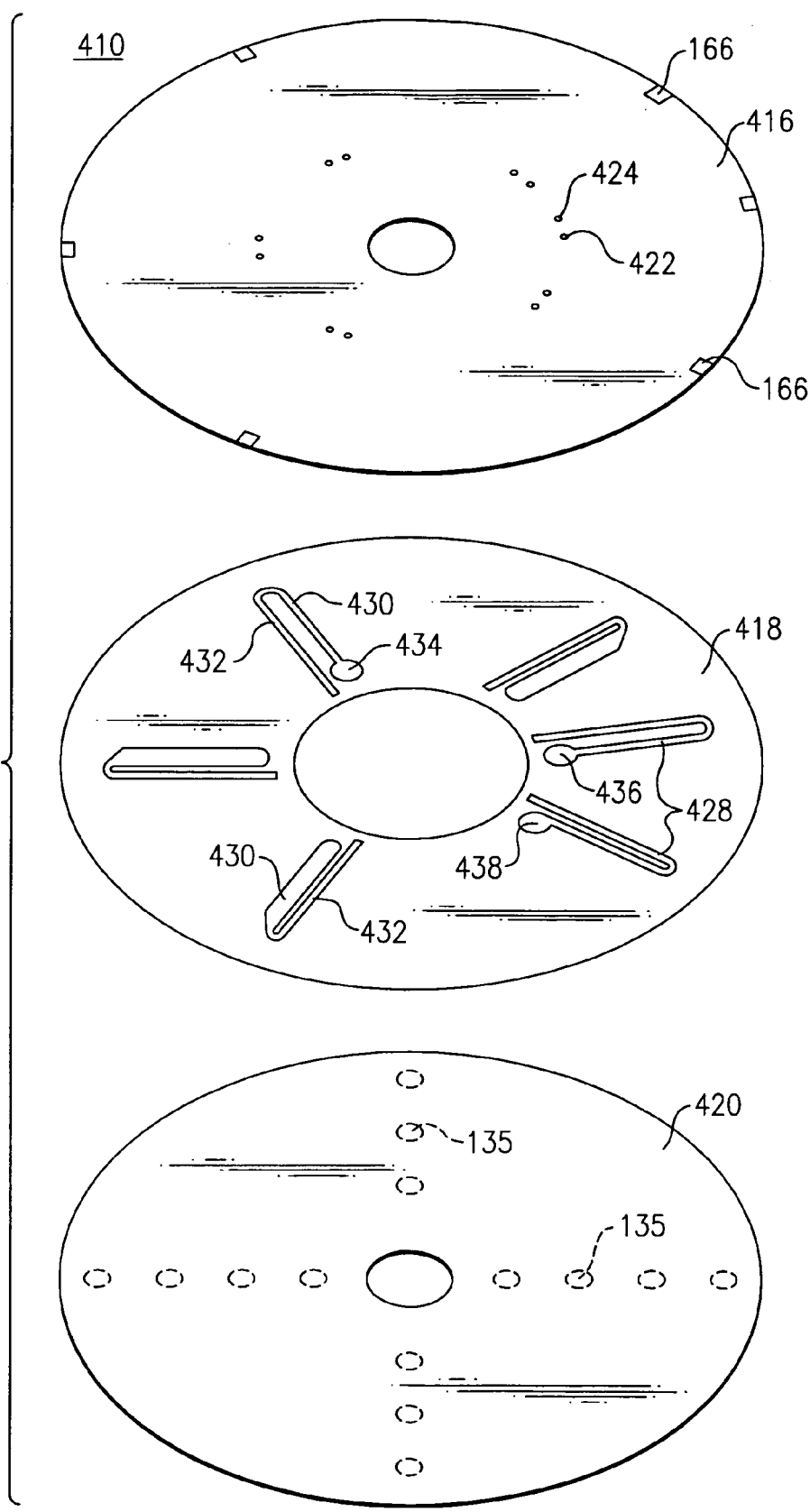
Figure 31:
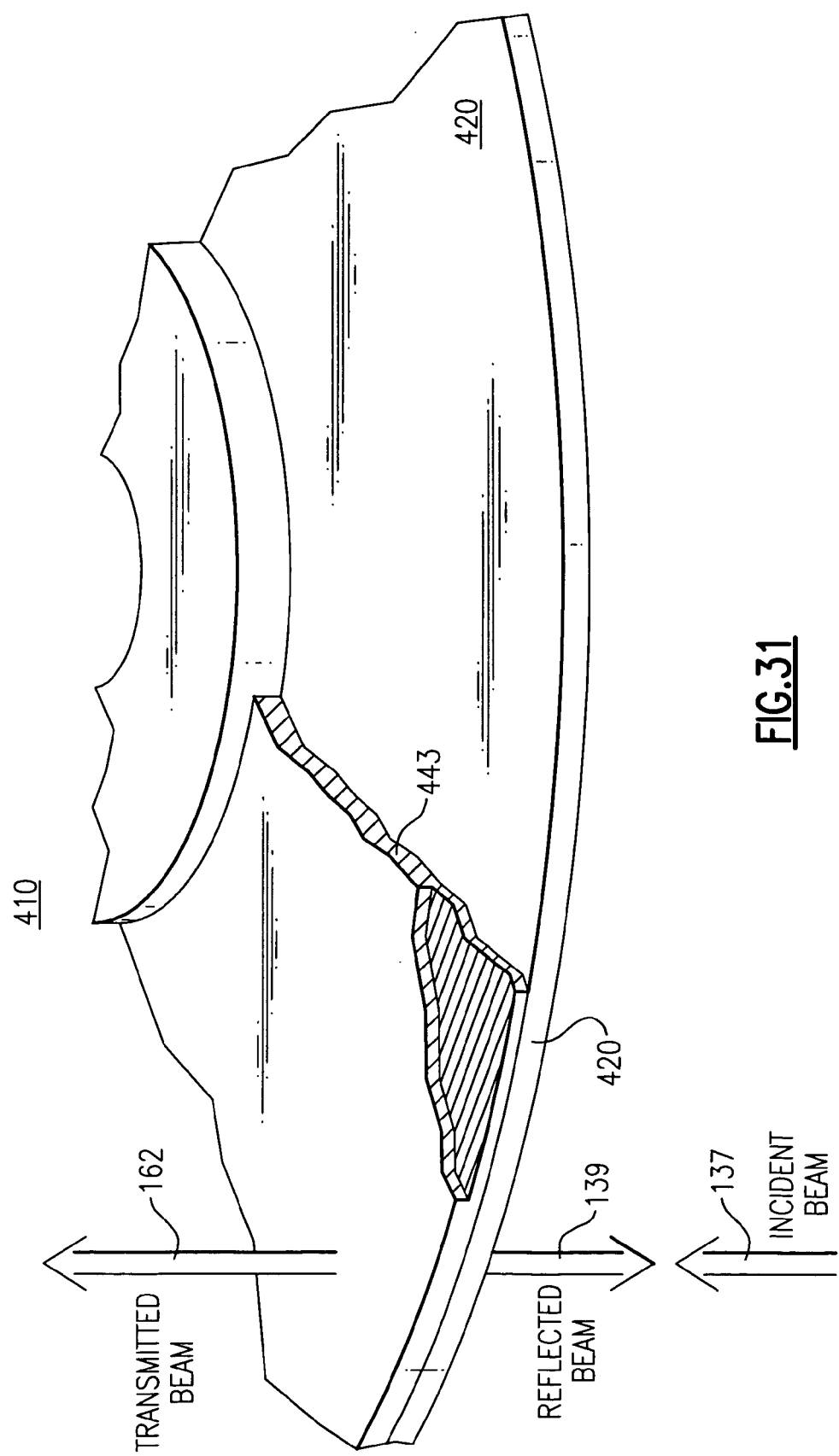
Figure 32:
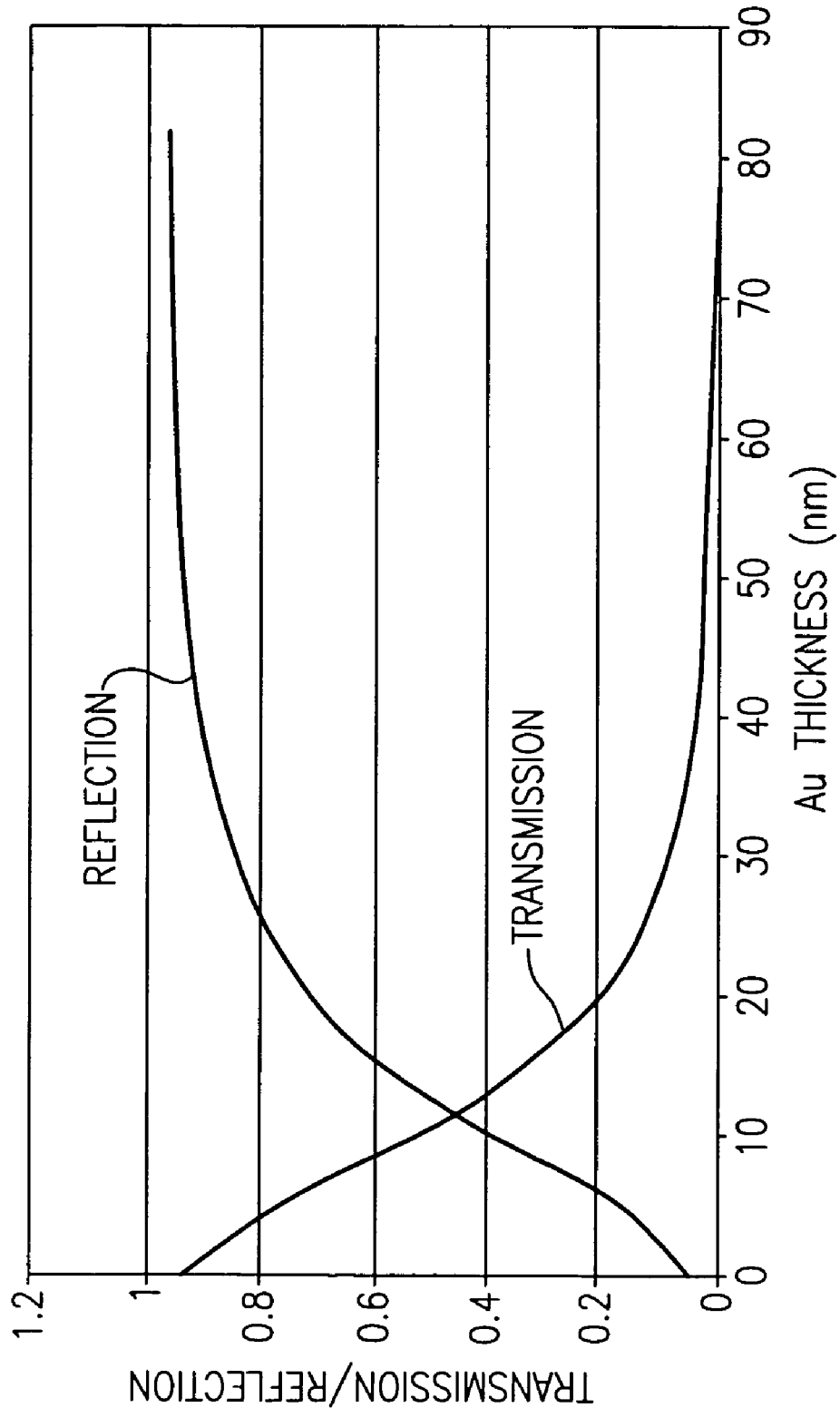
Figure 33:
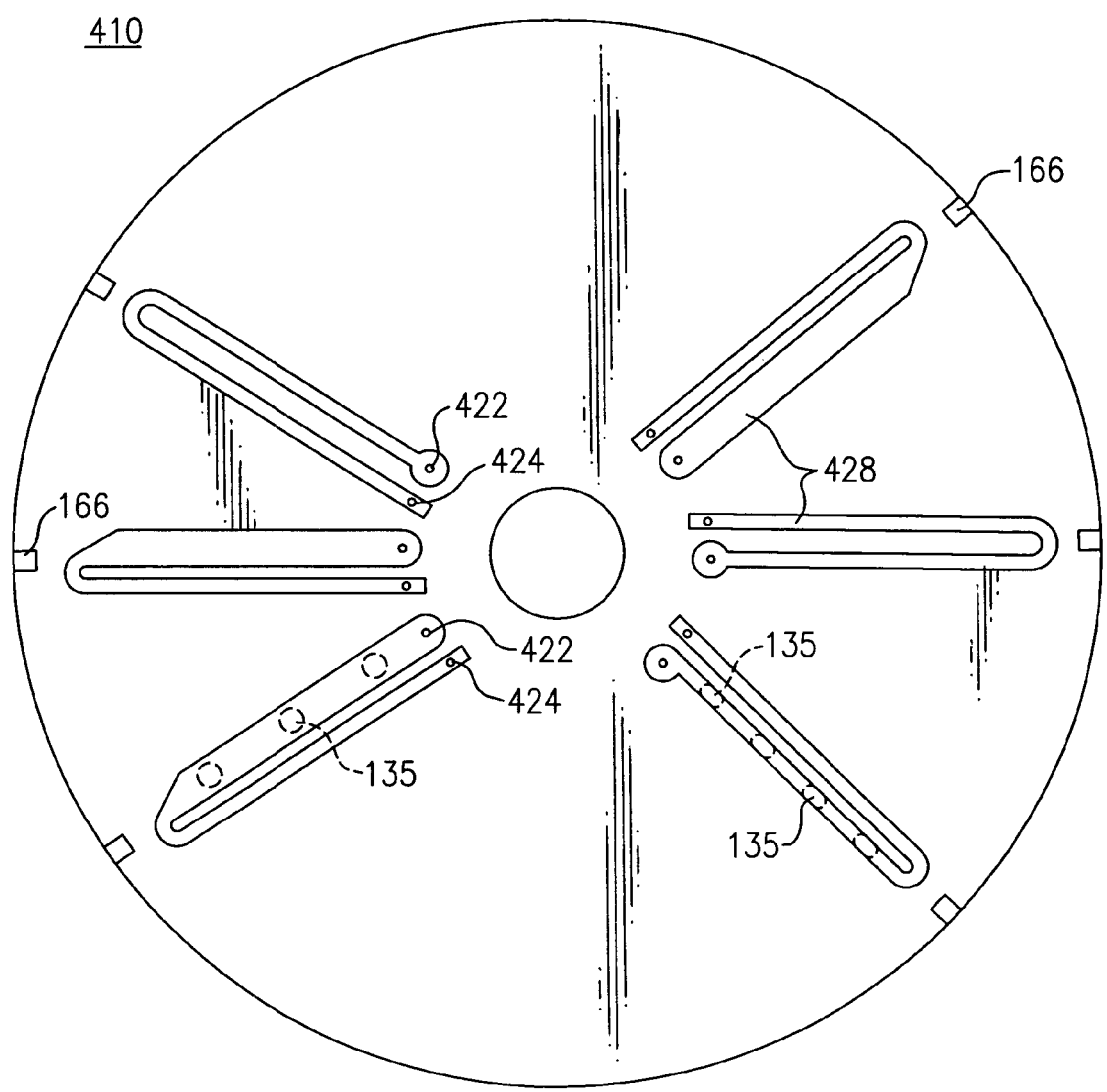
Figure 34:
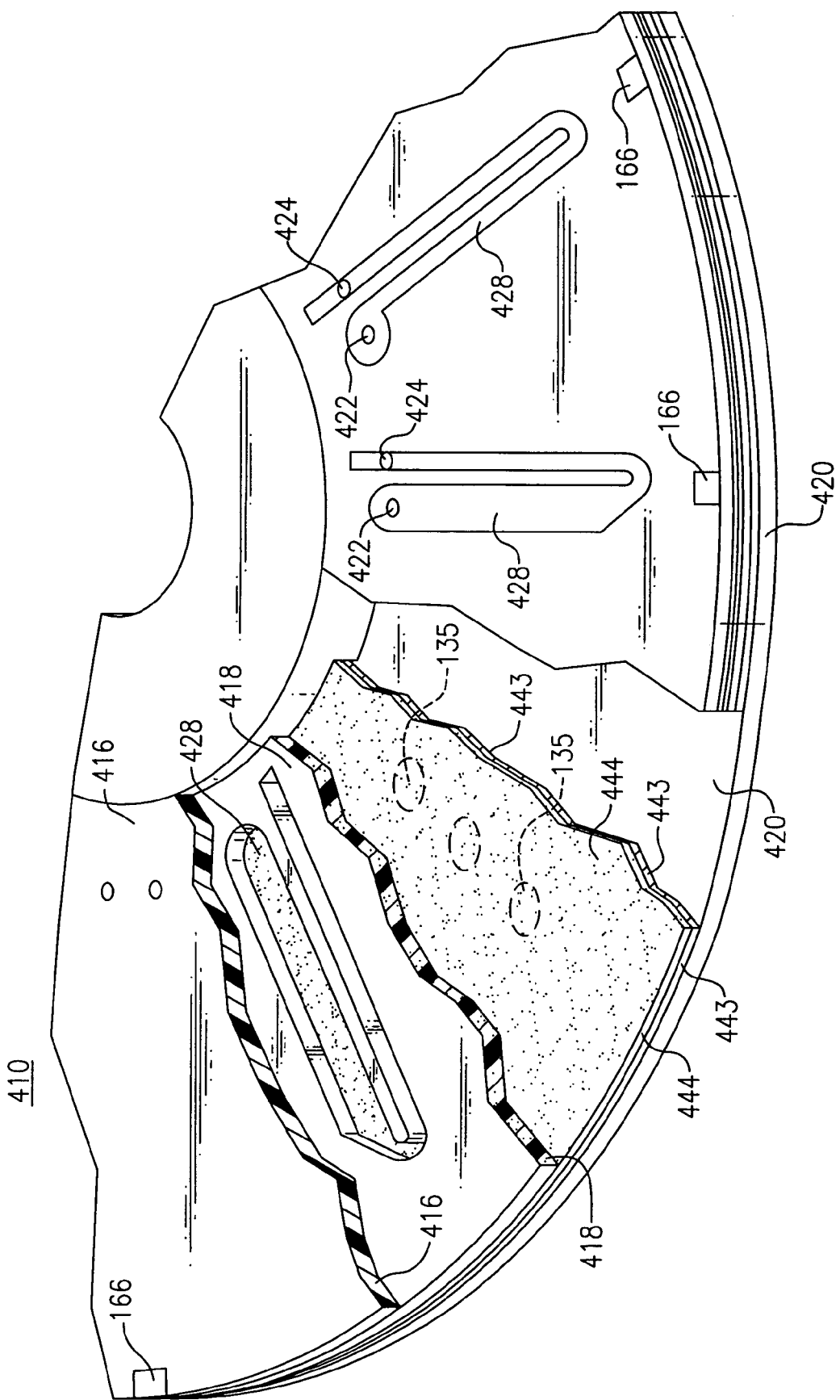
Figure 35:
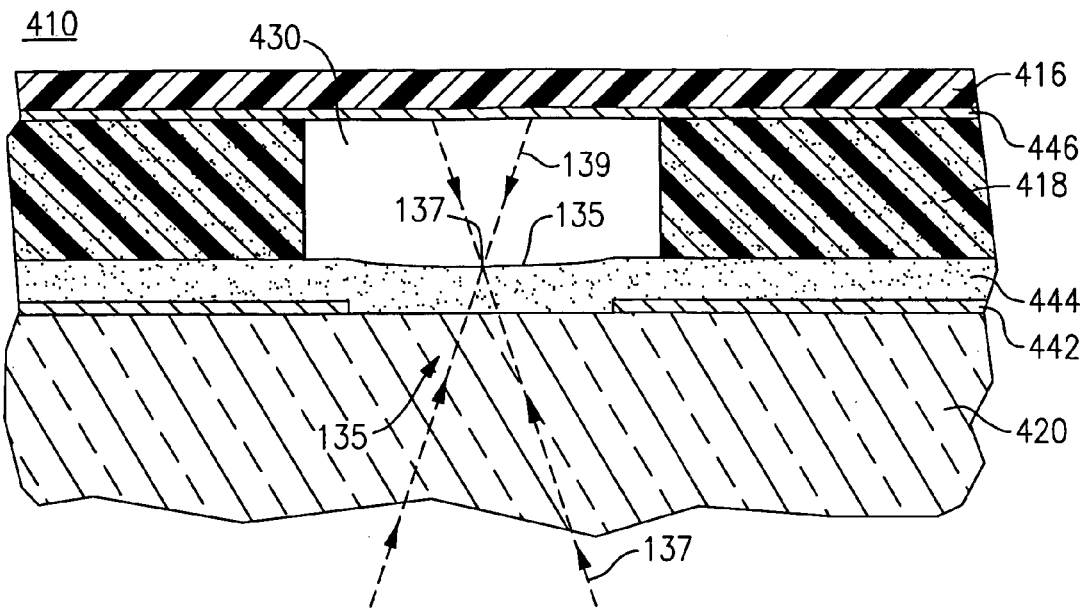
Figure 36:
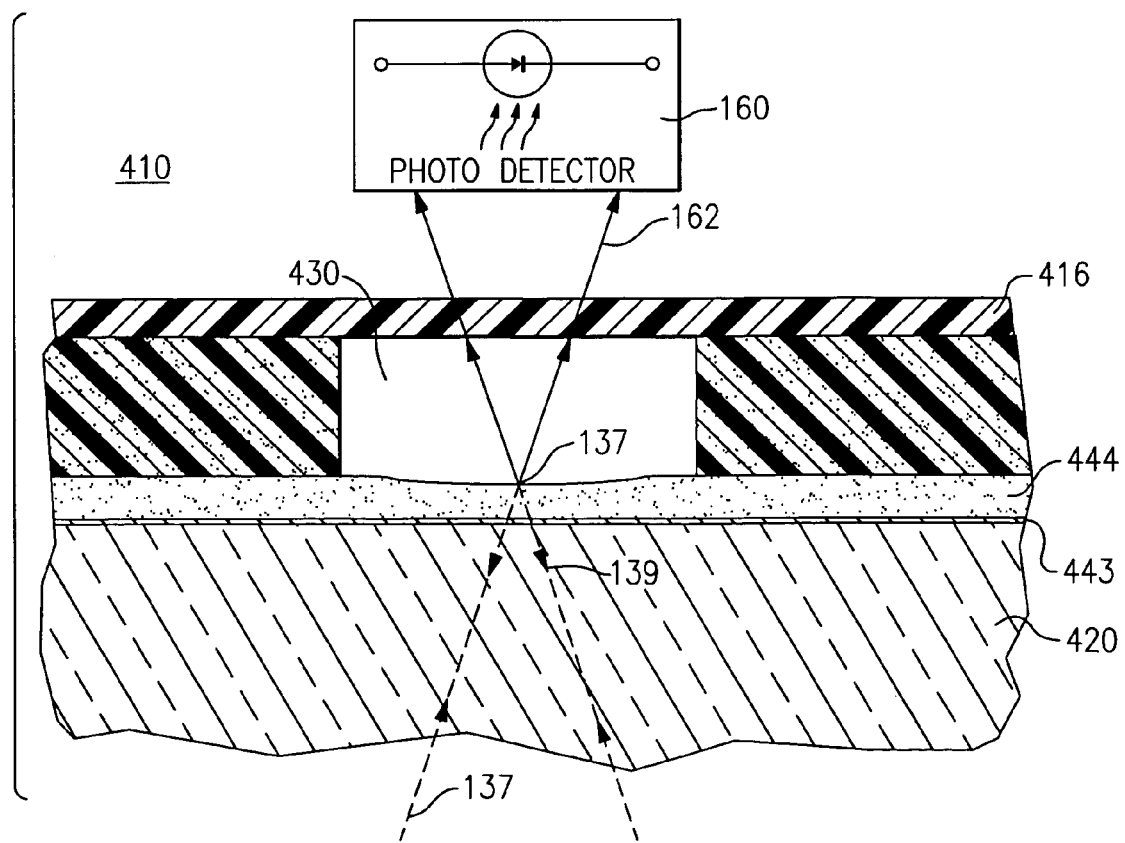
Figure 38:
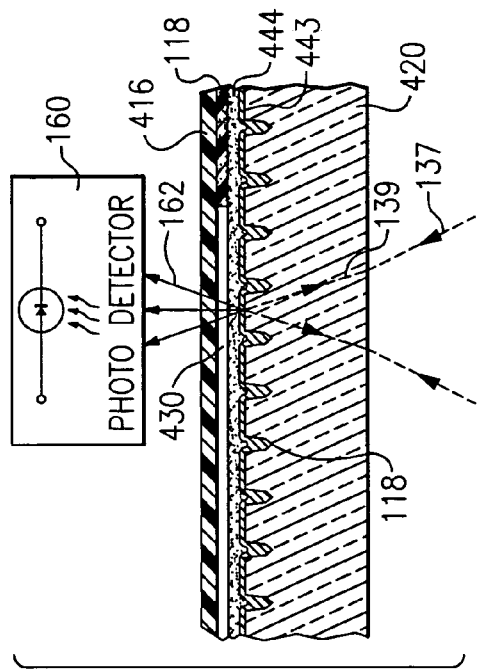
Figure 40:
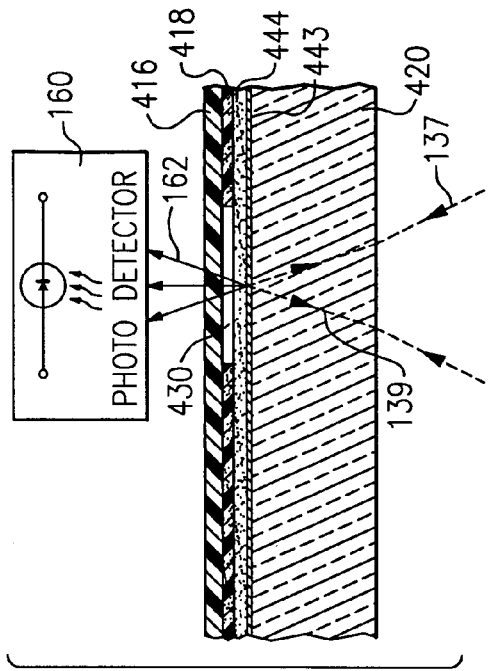
Figure 37:
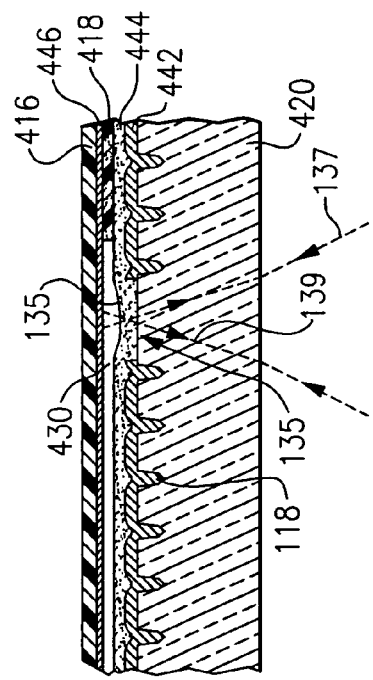
Figure 39:
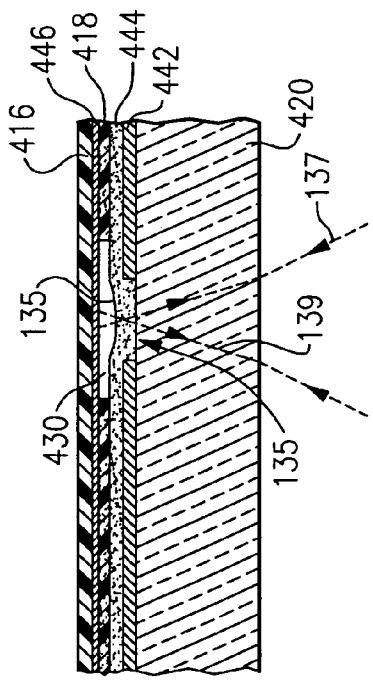
Figure 41:
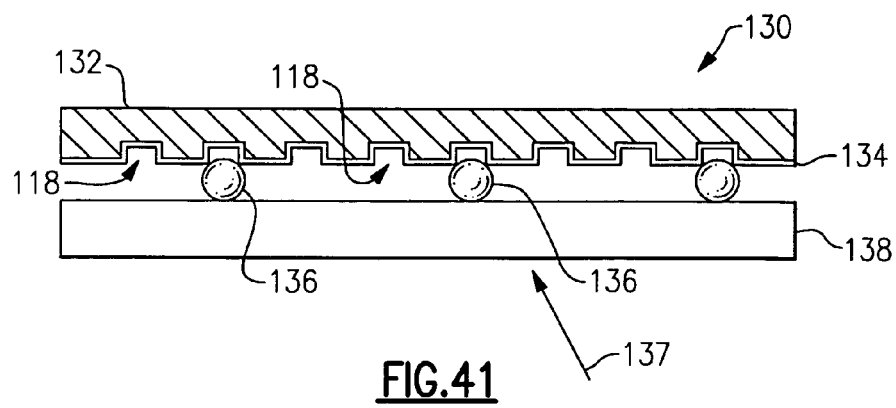
Figure 50:
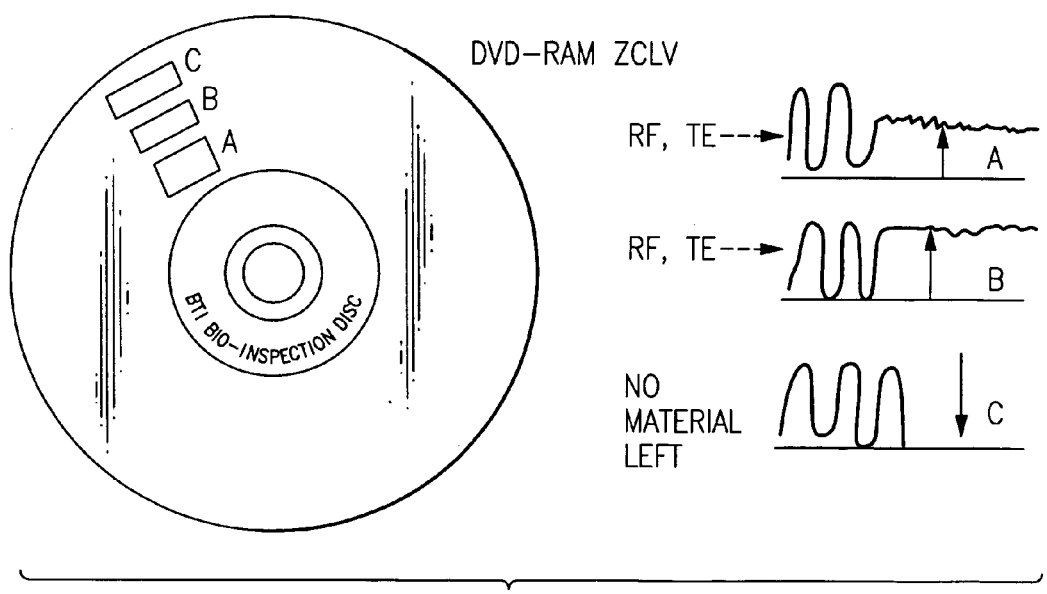
Figure 44:
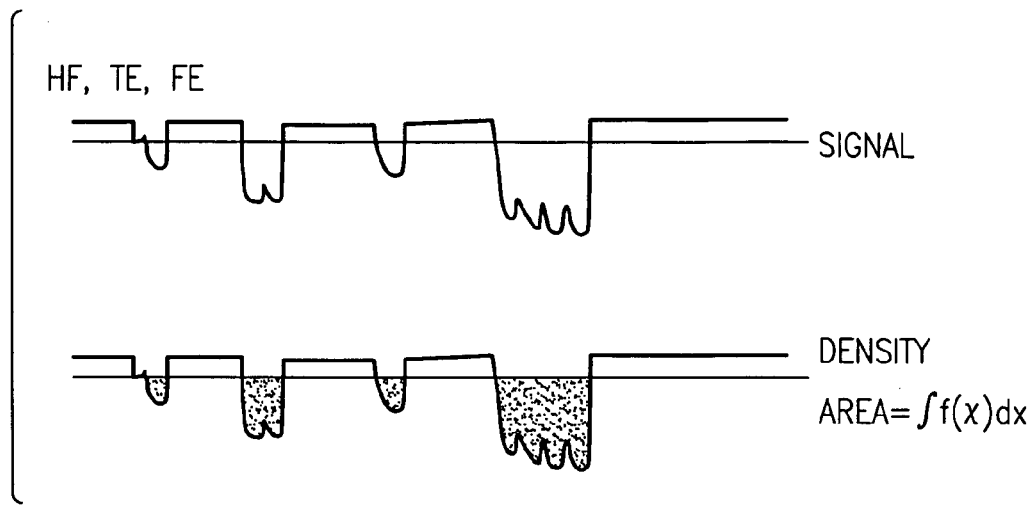
Figure 45:
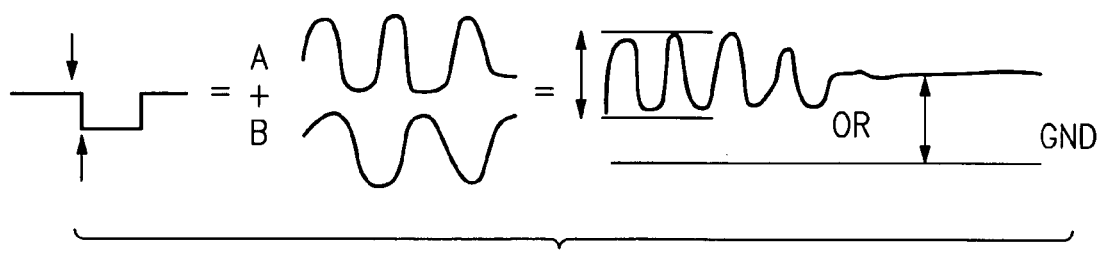
Figure 46:
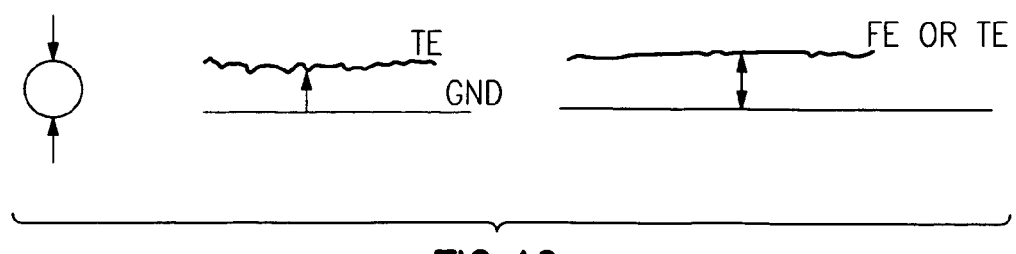
Figure 47:
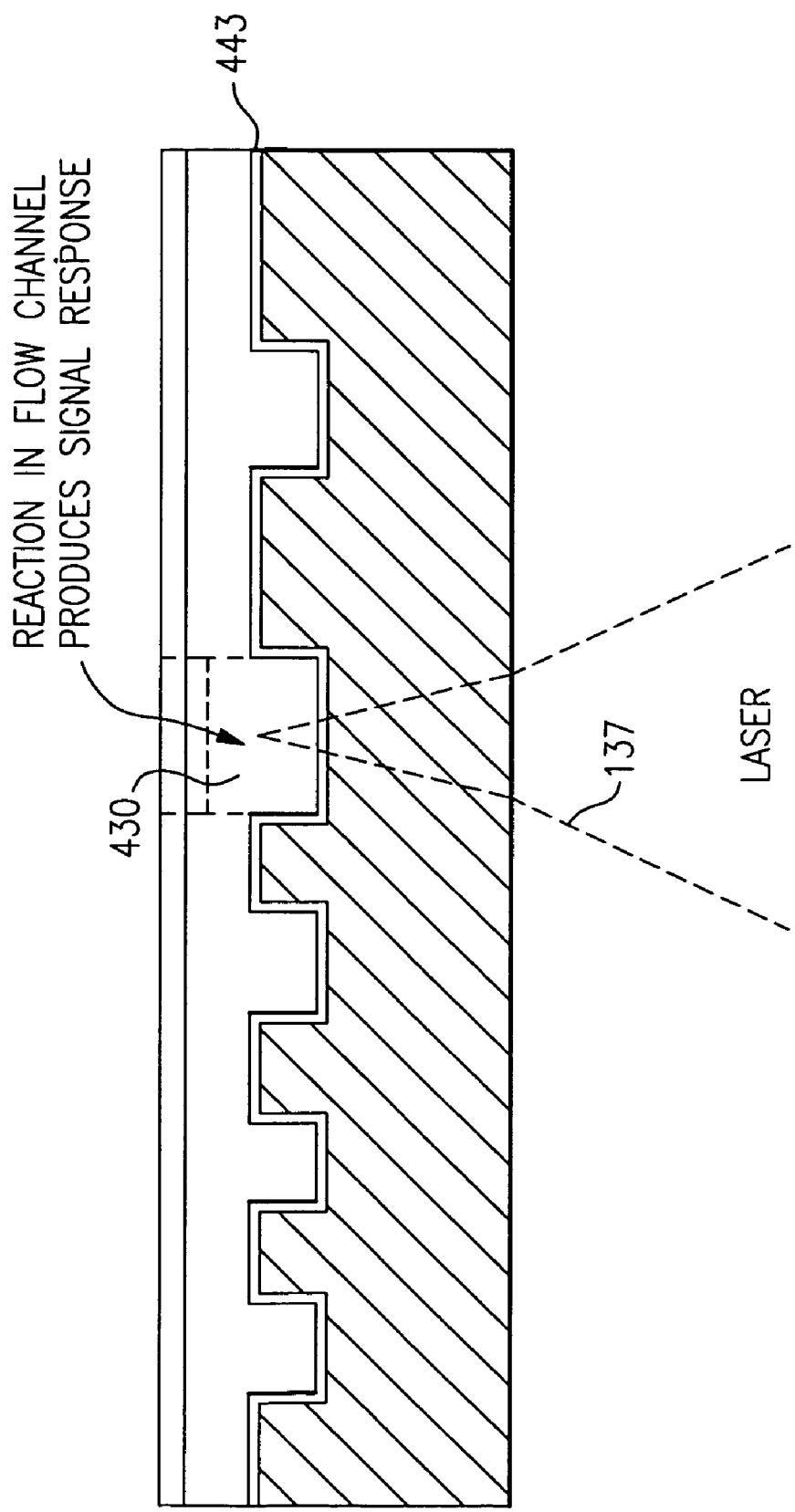
Figure 48:
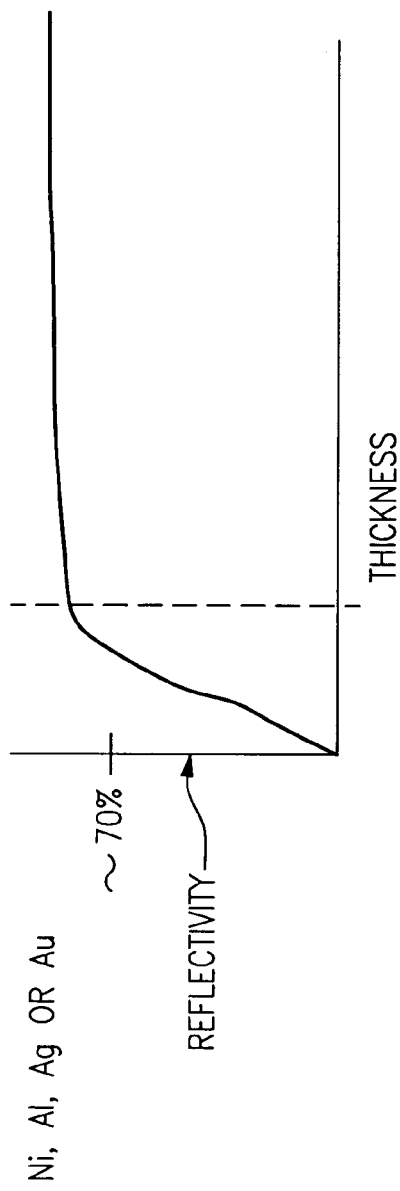
Figure 49:
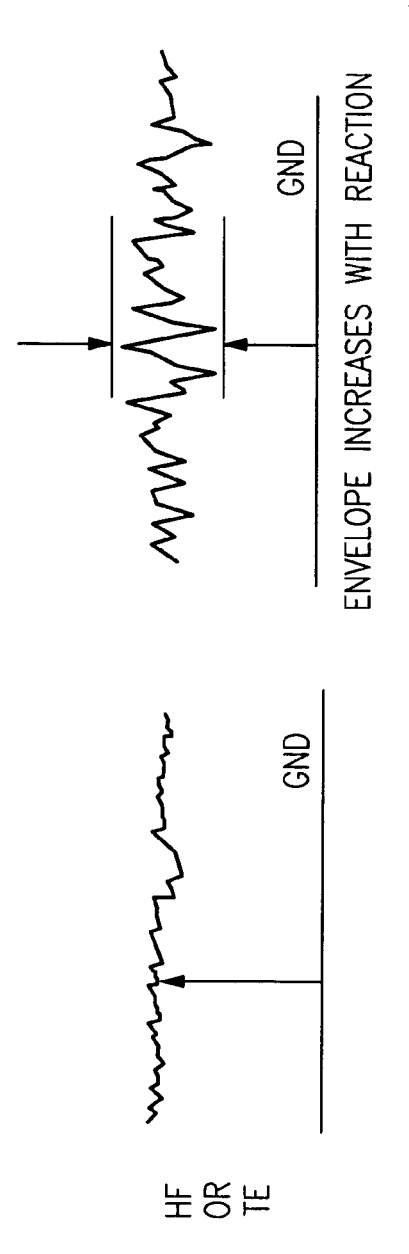
Figure 51:
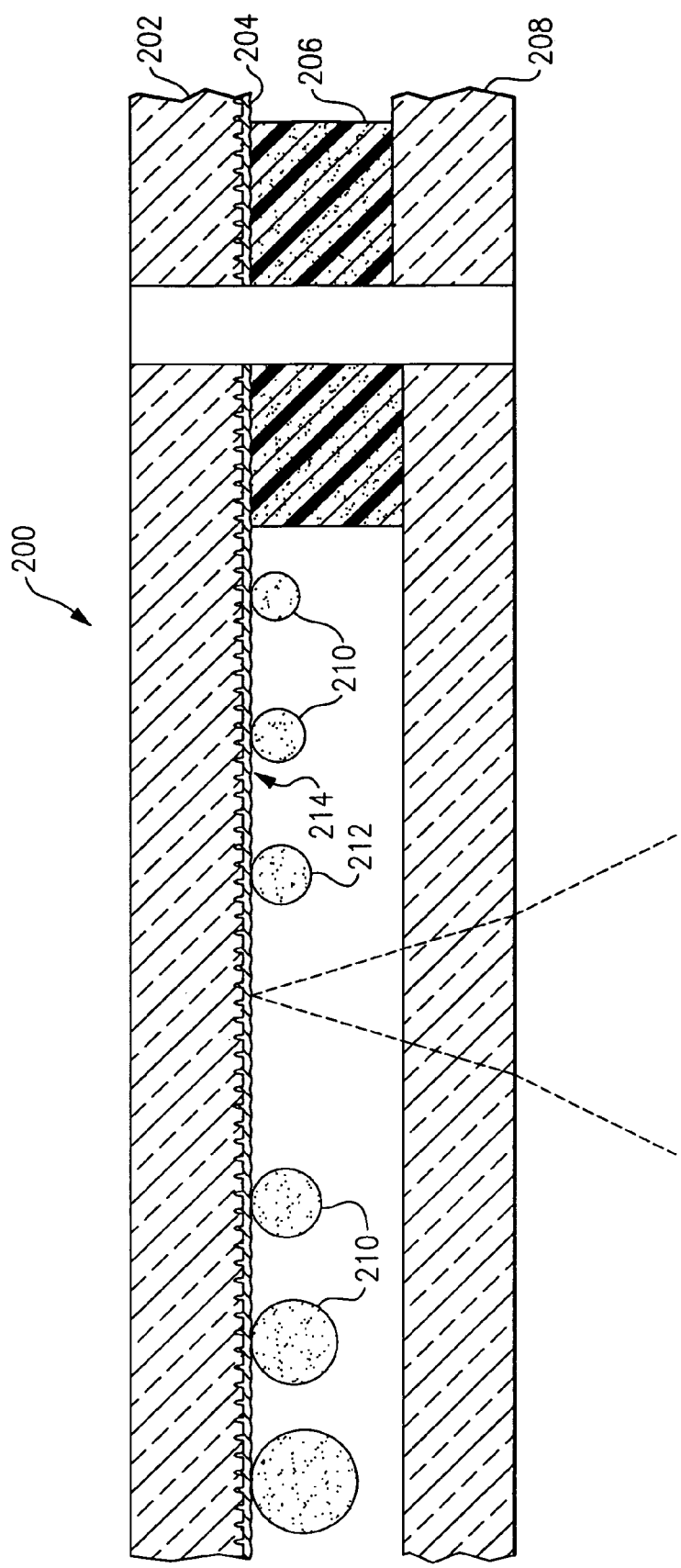
Figure 52A:
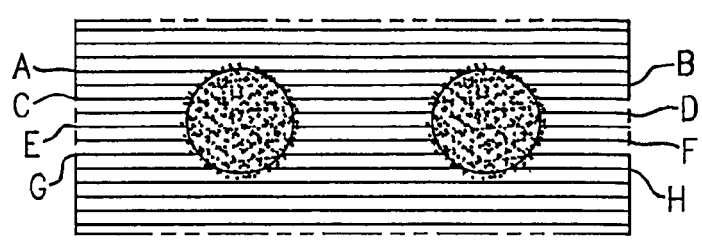
Figure 52B:
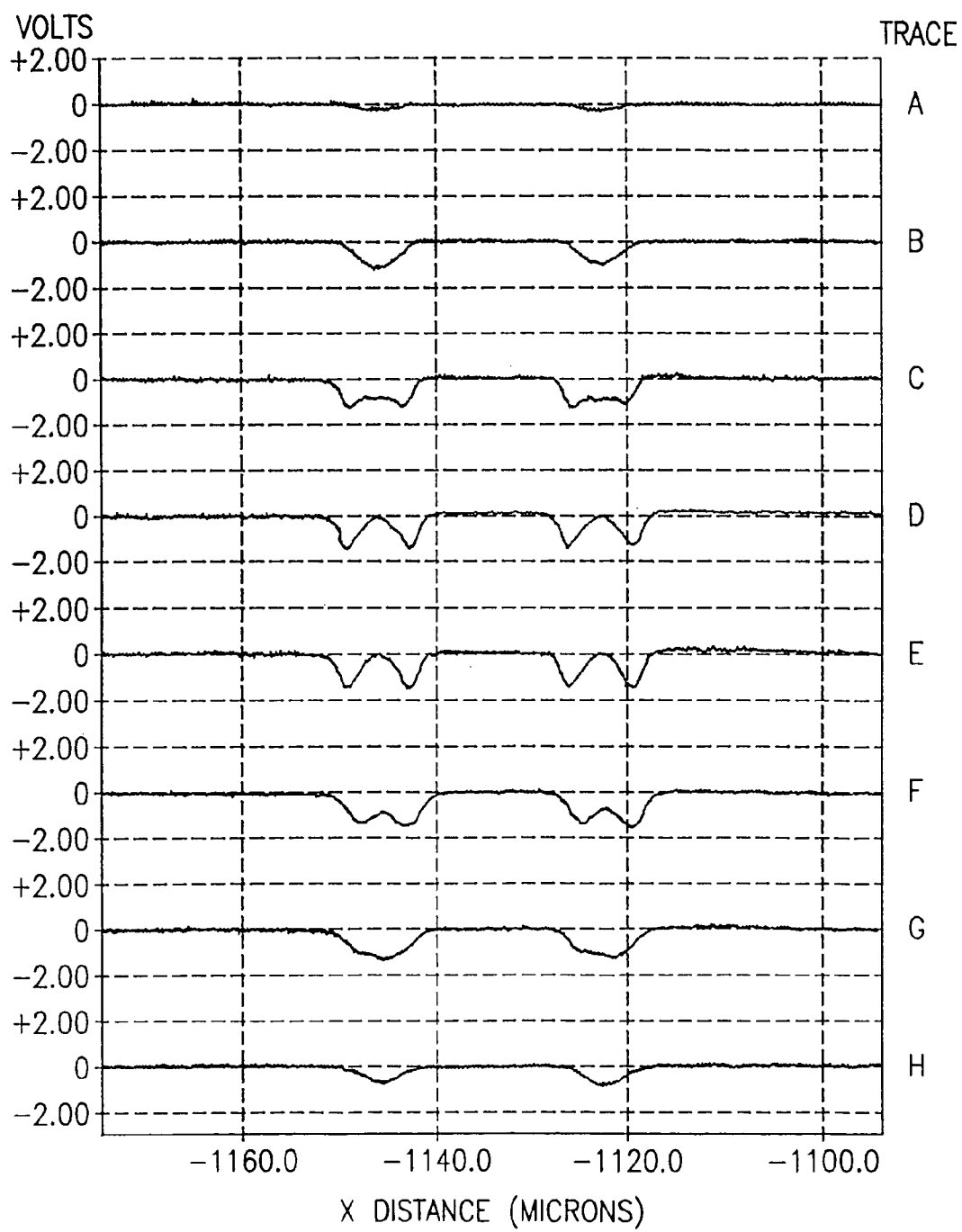
Figure 53A:
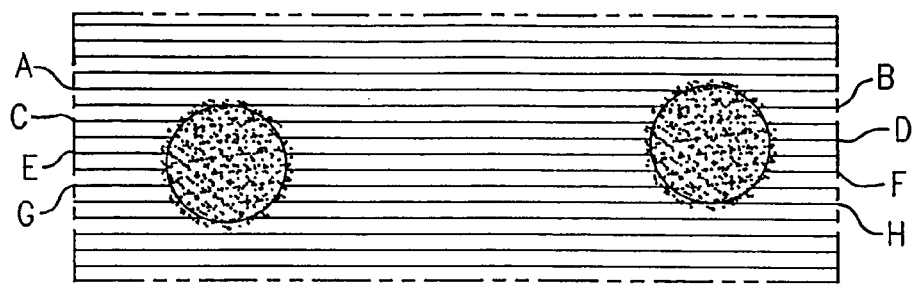
Figure 53B:
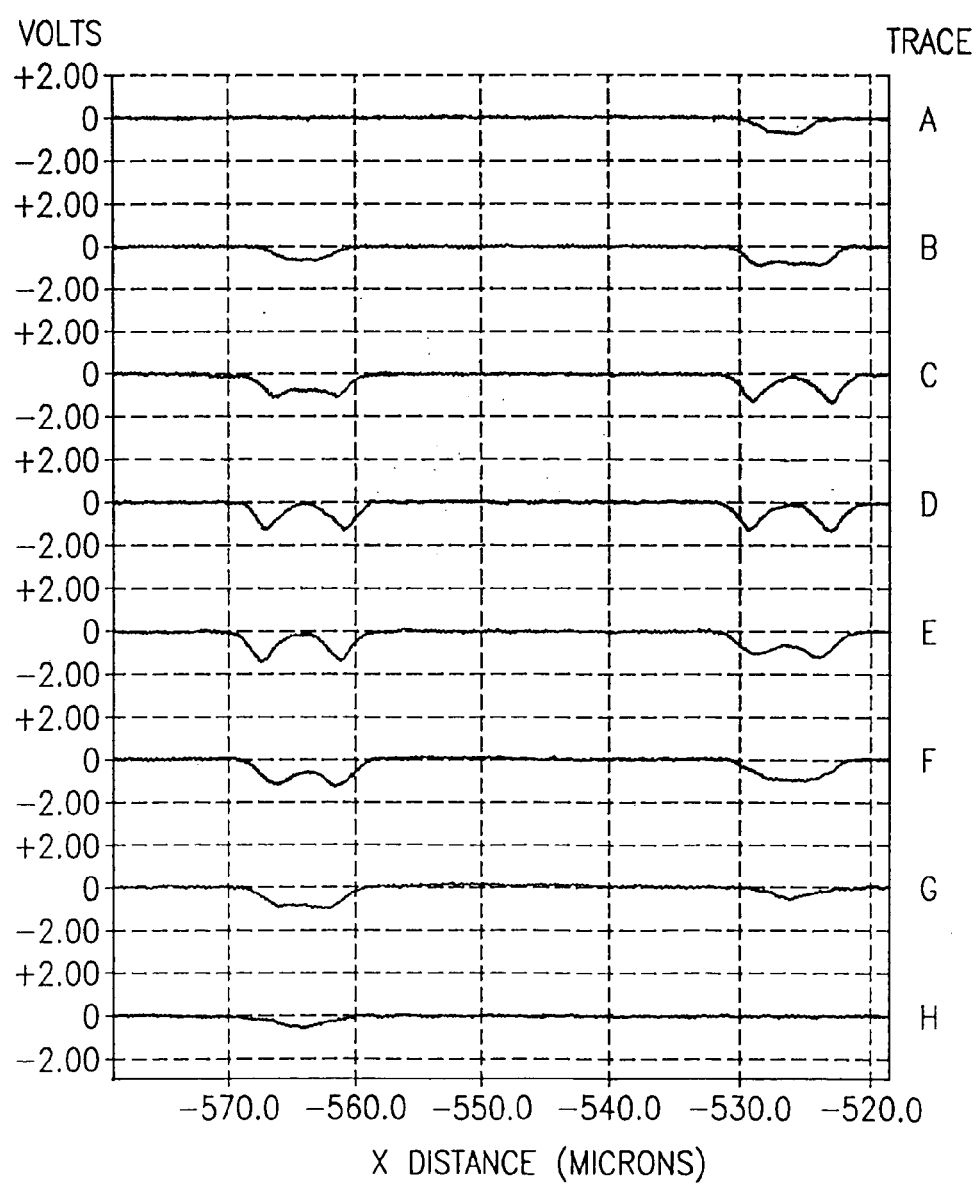
Figure 54A:
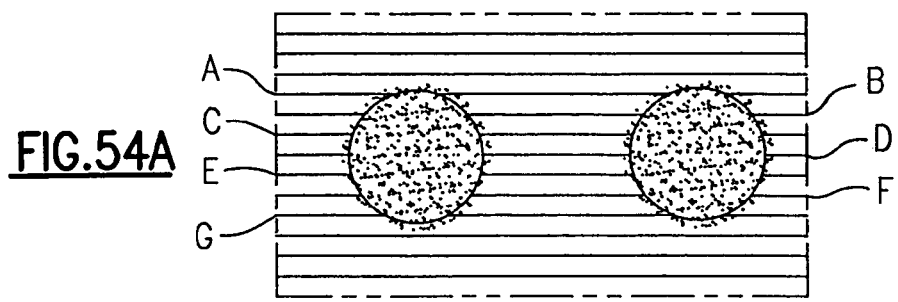
Figure 54B:
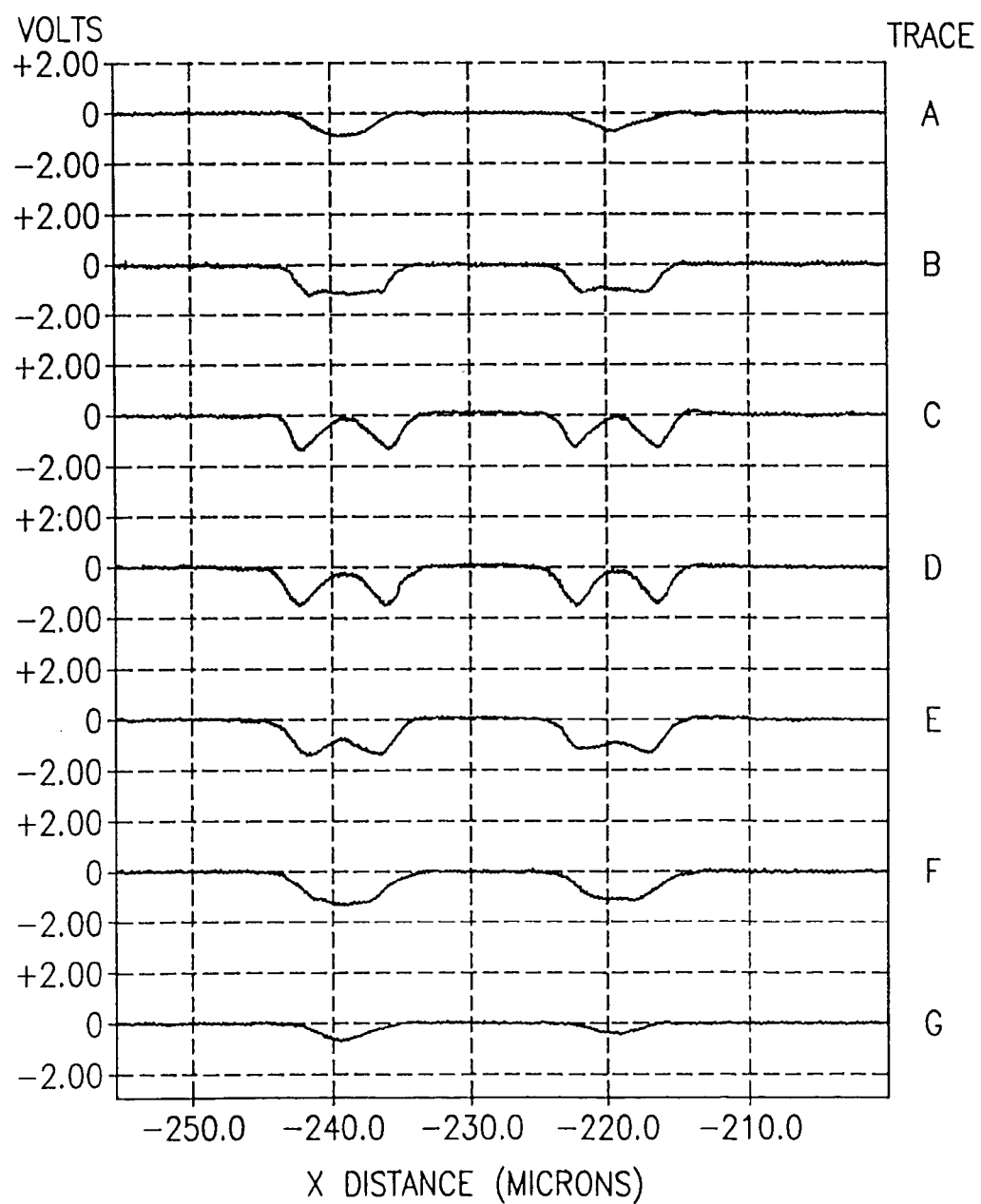
Figure 55A:
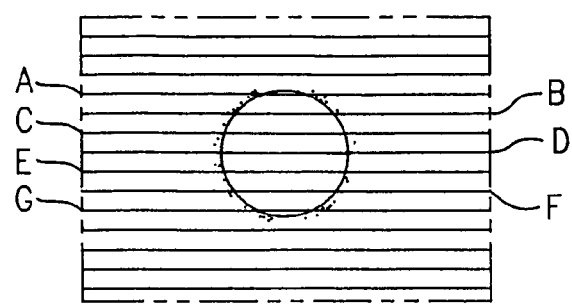
Figure 55B:
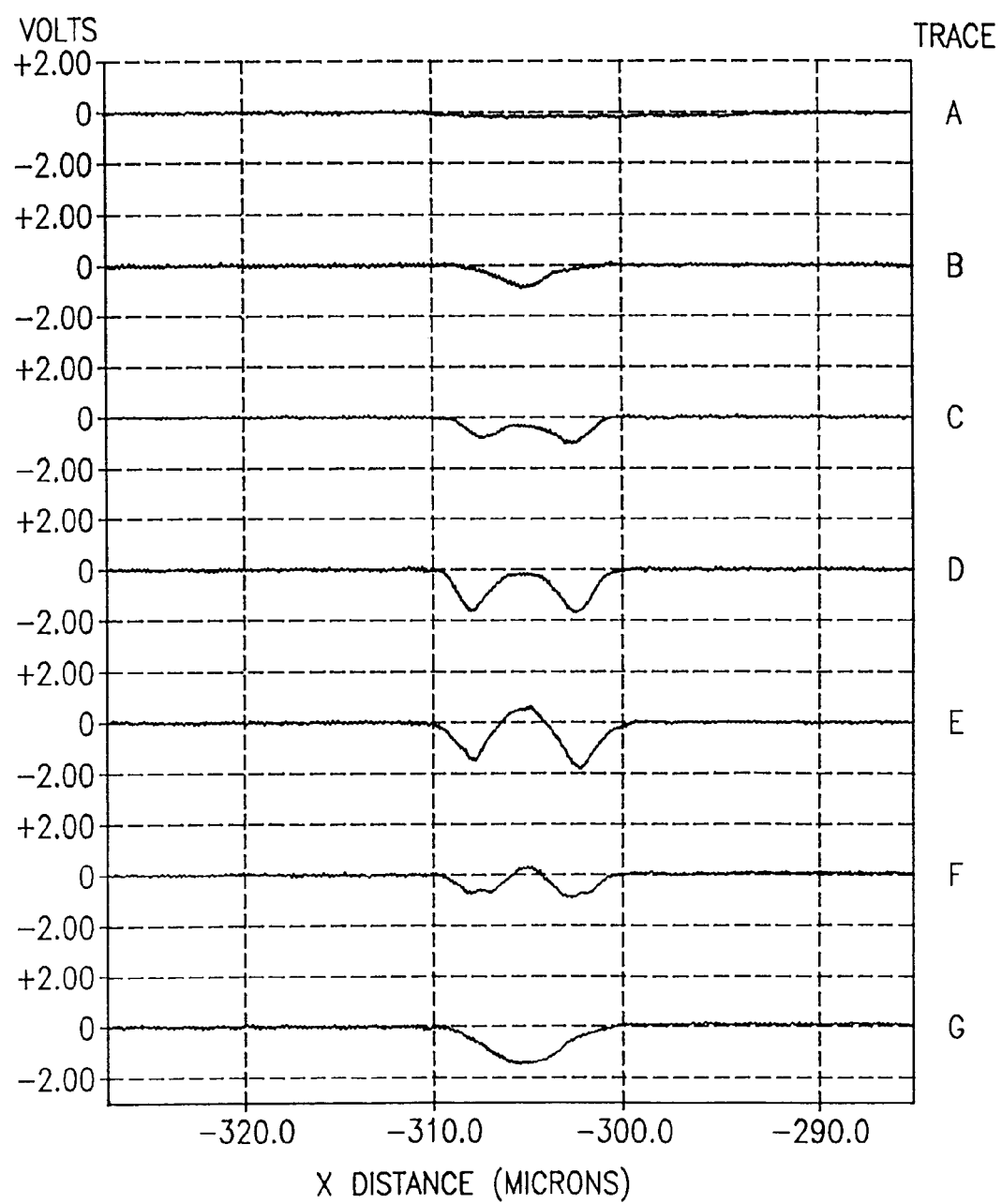
Figure 56A:
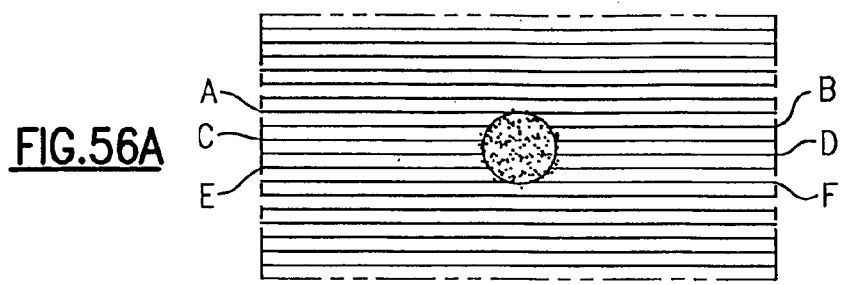
Figure 56B:
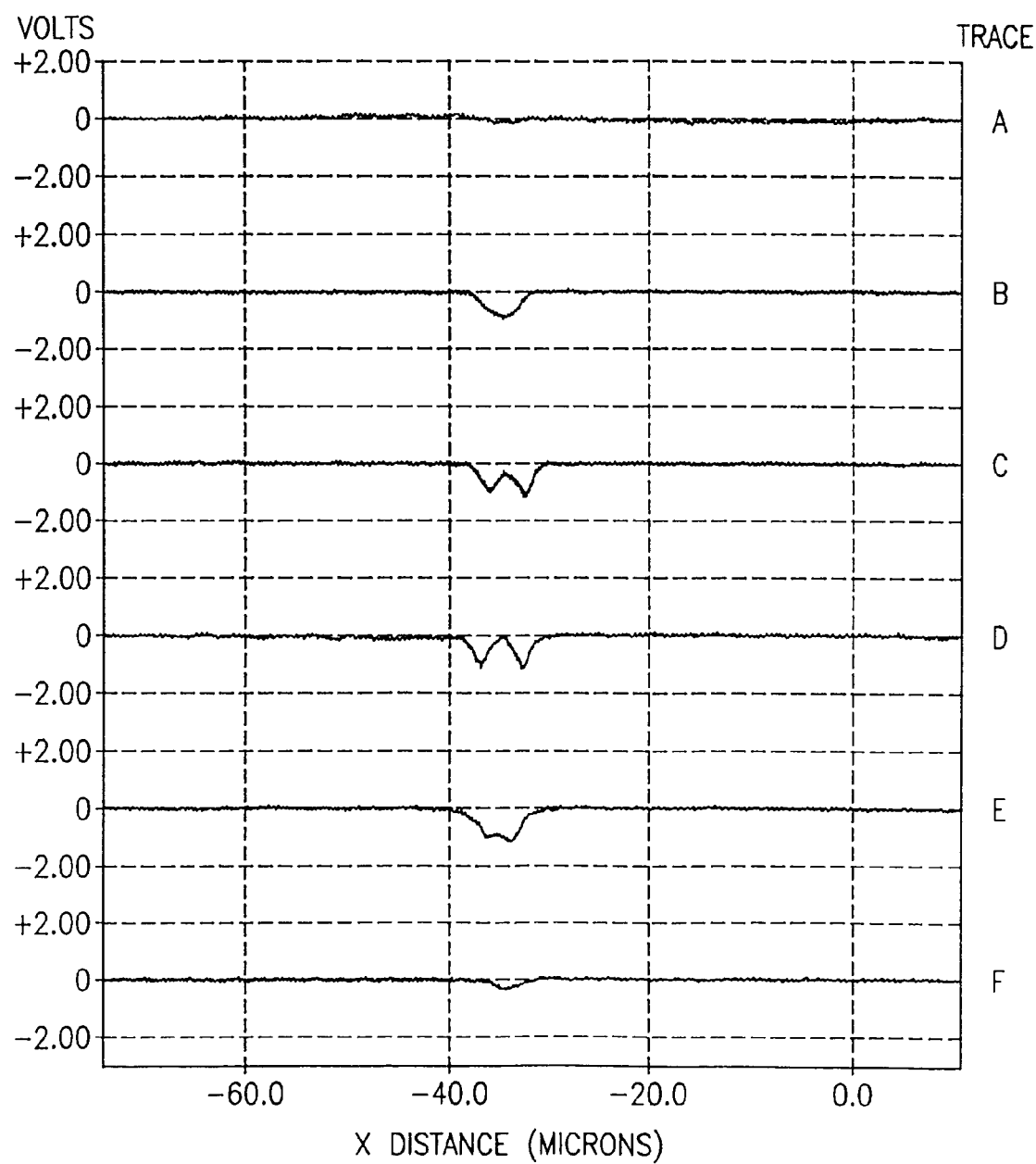
Figure 57A:
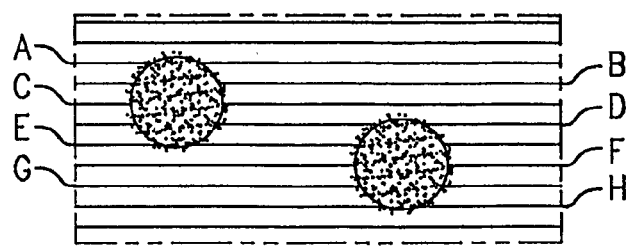
Figure 57B:
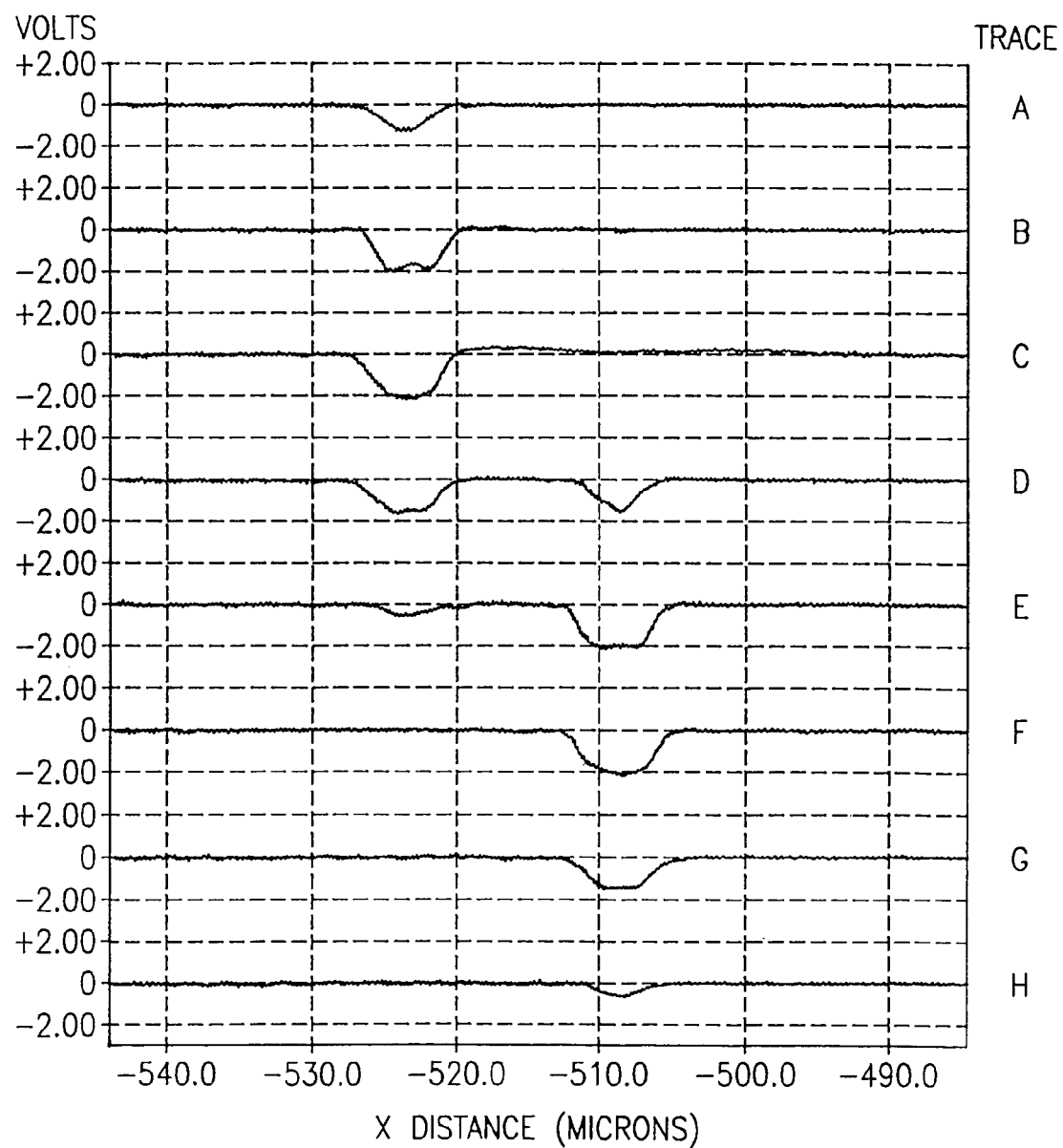
Figure 58A:
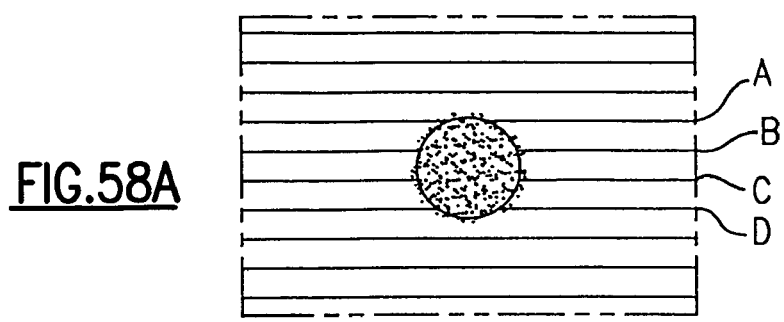
Figure 58B:
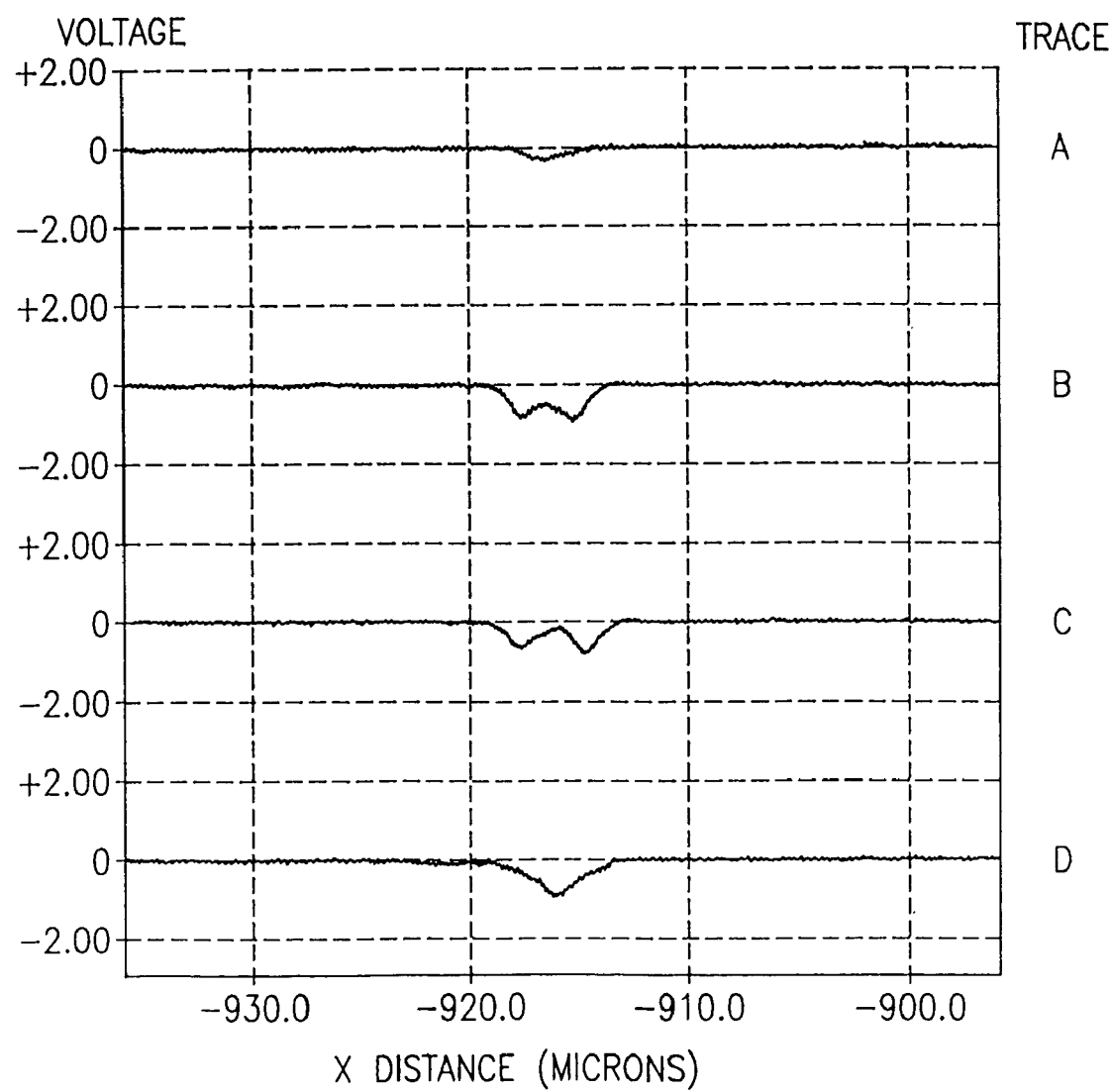
Figure 59A:
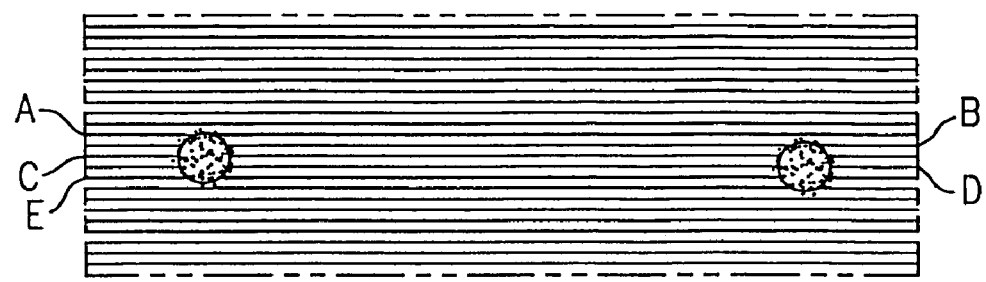
Figure 59B:
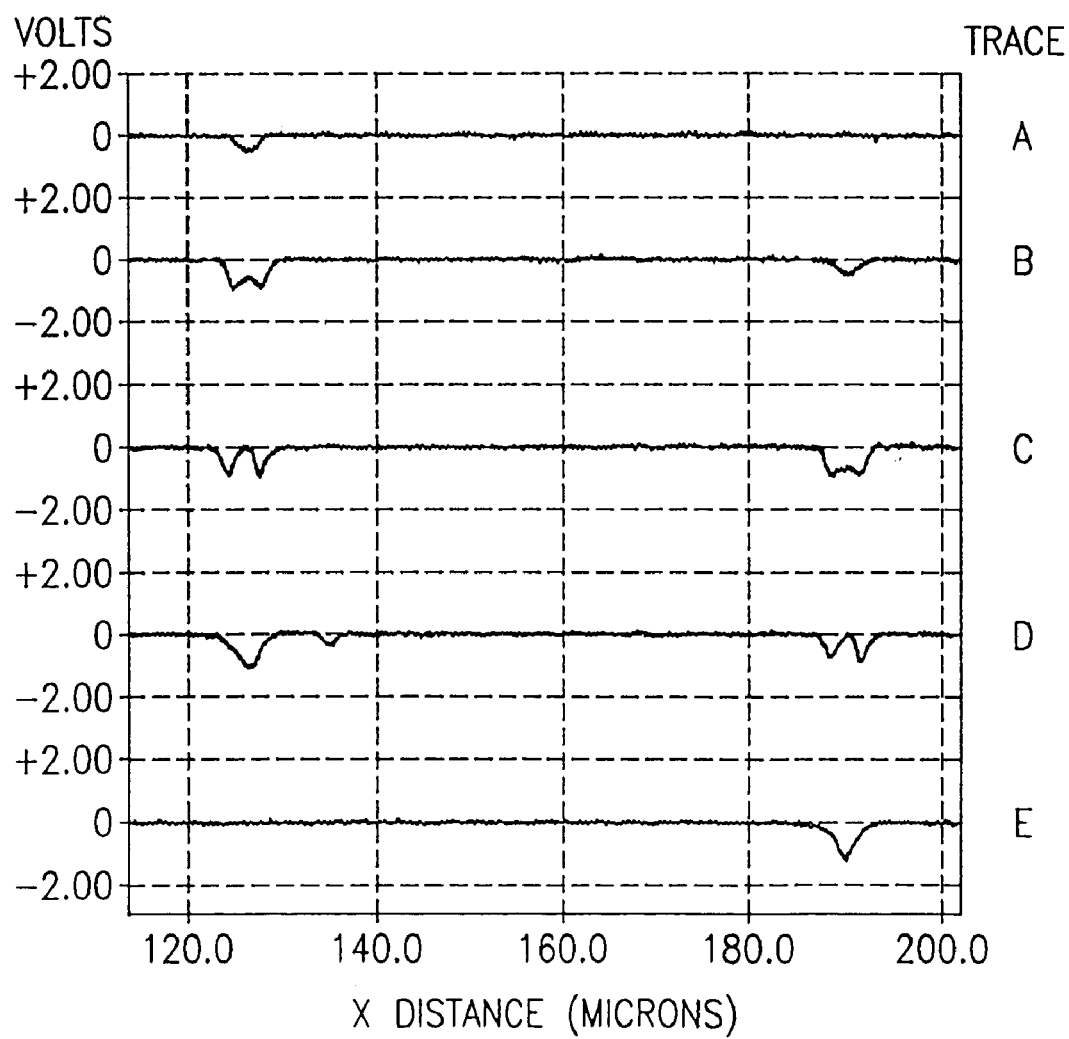
Figure 60A:
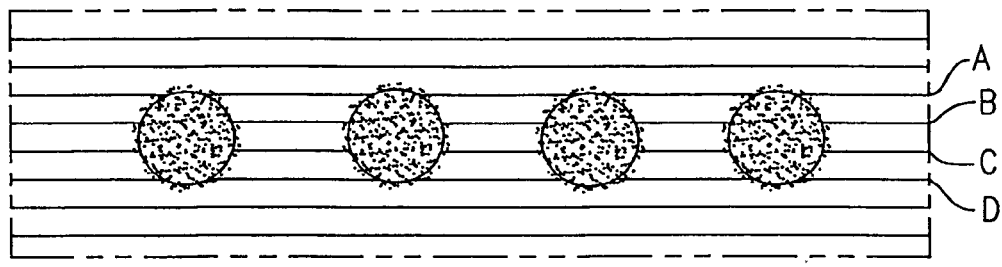
Figure 60B:
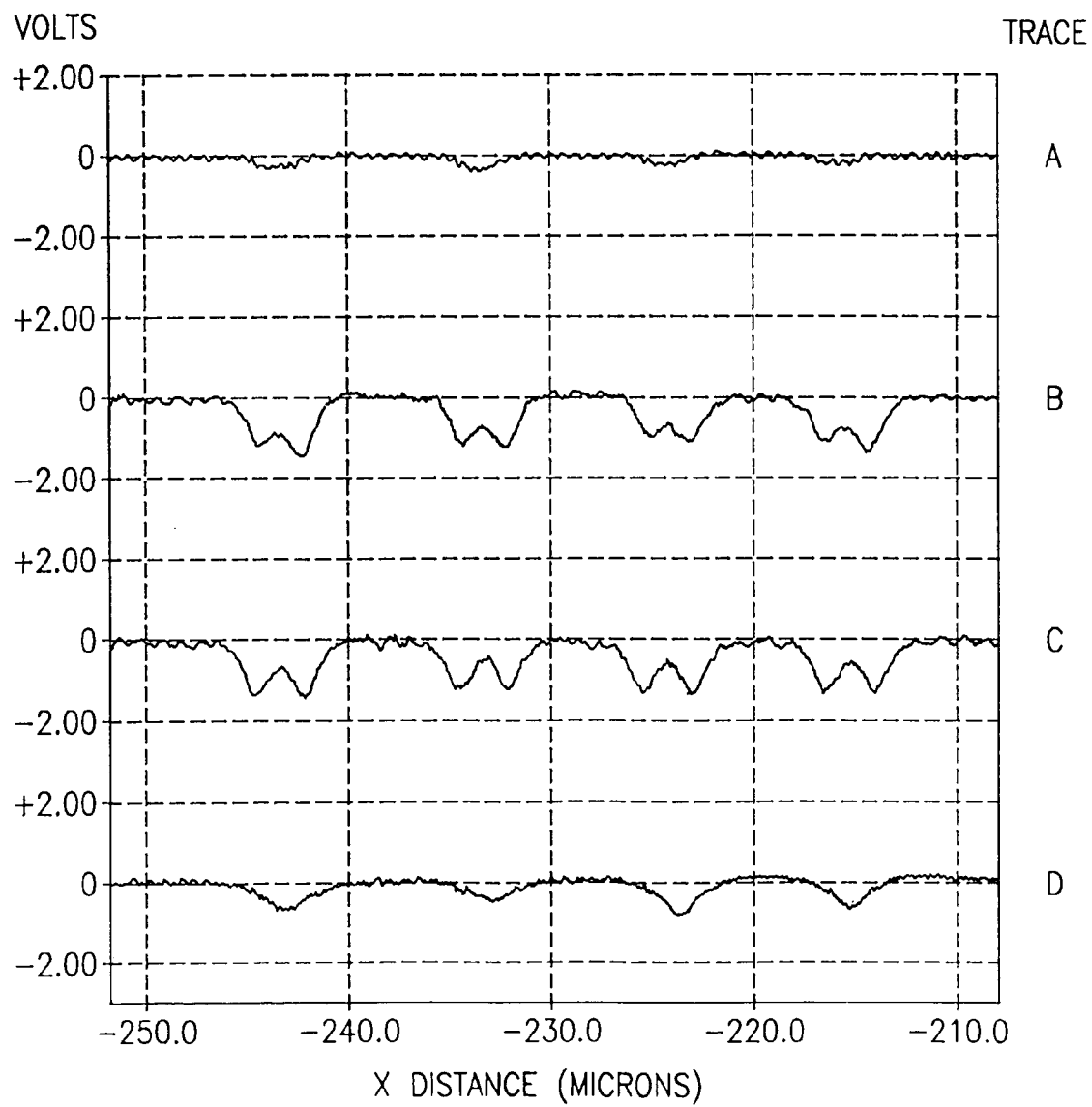
Figure 61A:
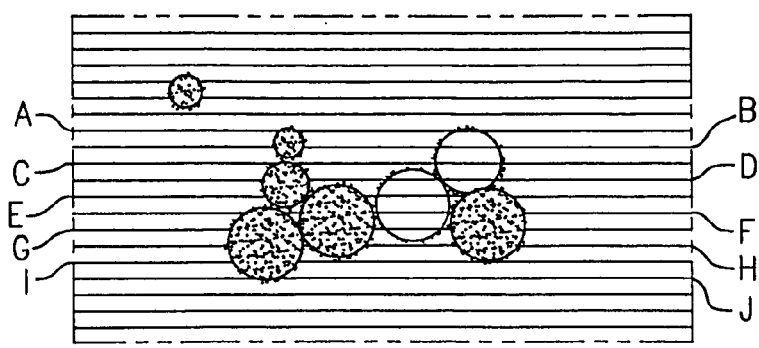
Figure 61B:
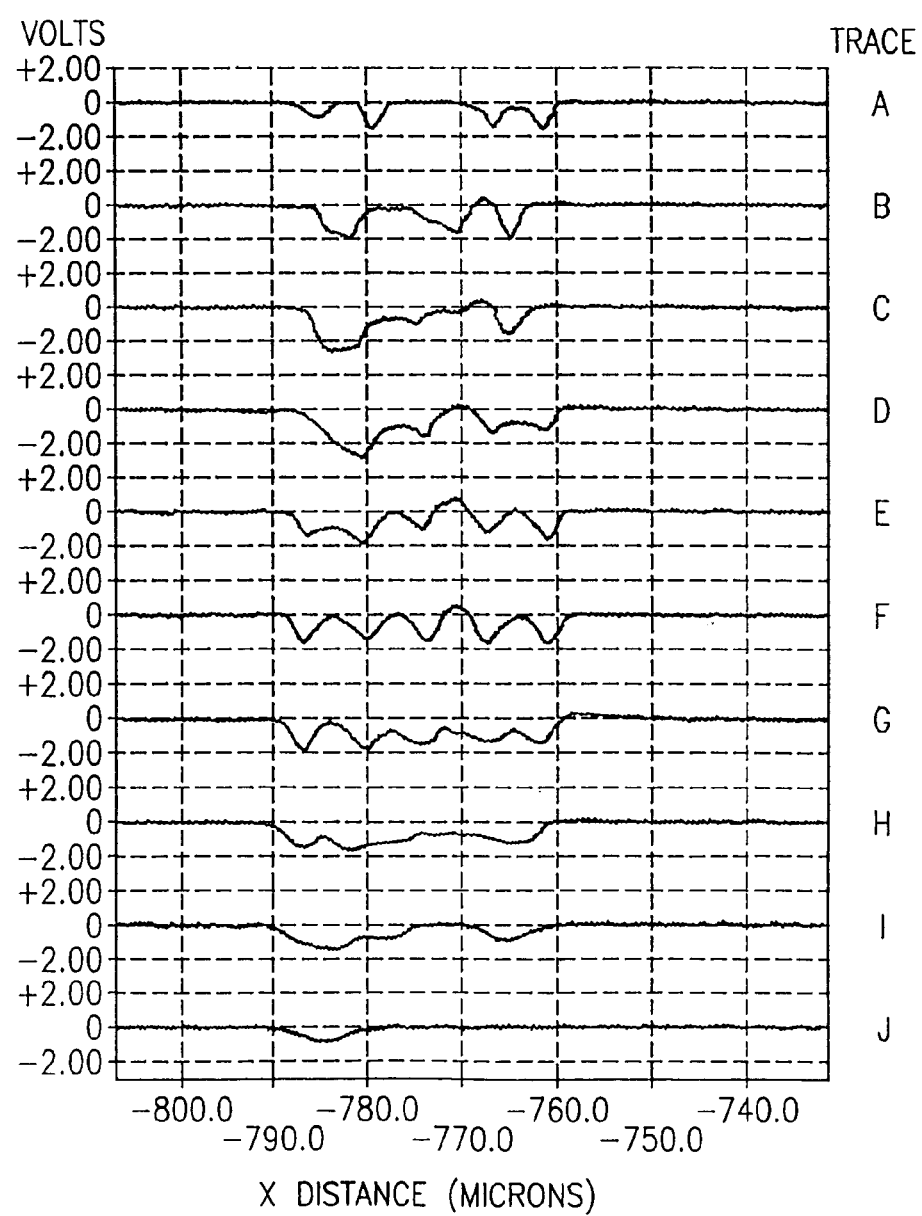
Figure 62A:
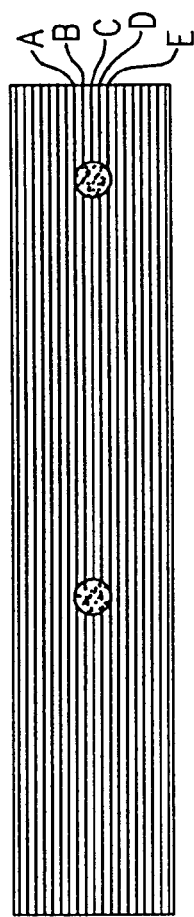
Figure 62B:
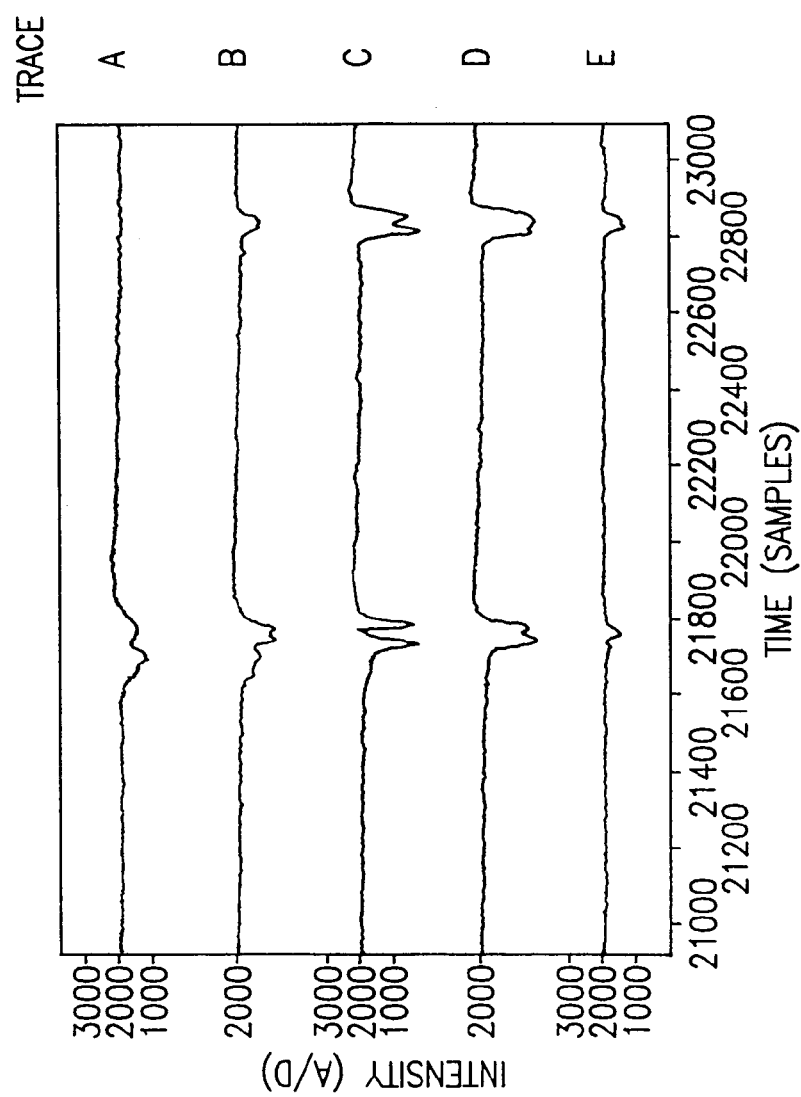
Figure 63A:
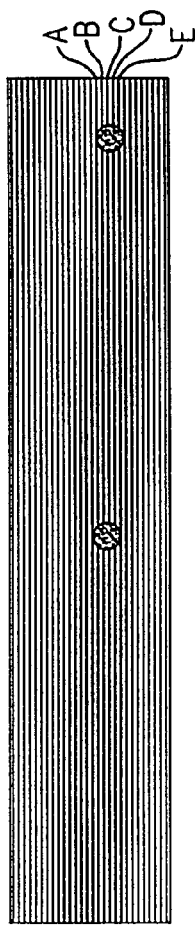
Figure 63B:
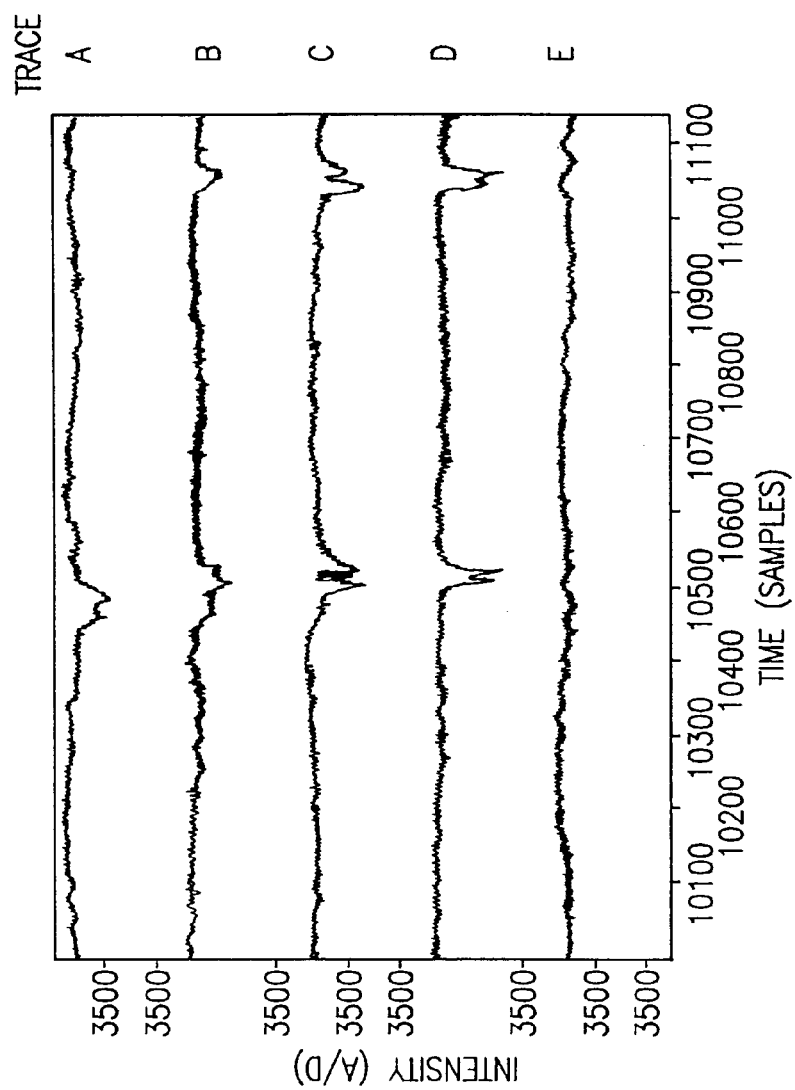
Figure 64A:
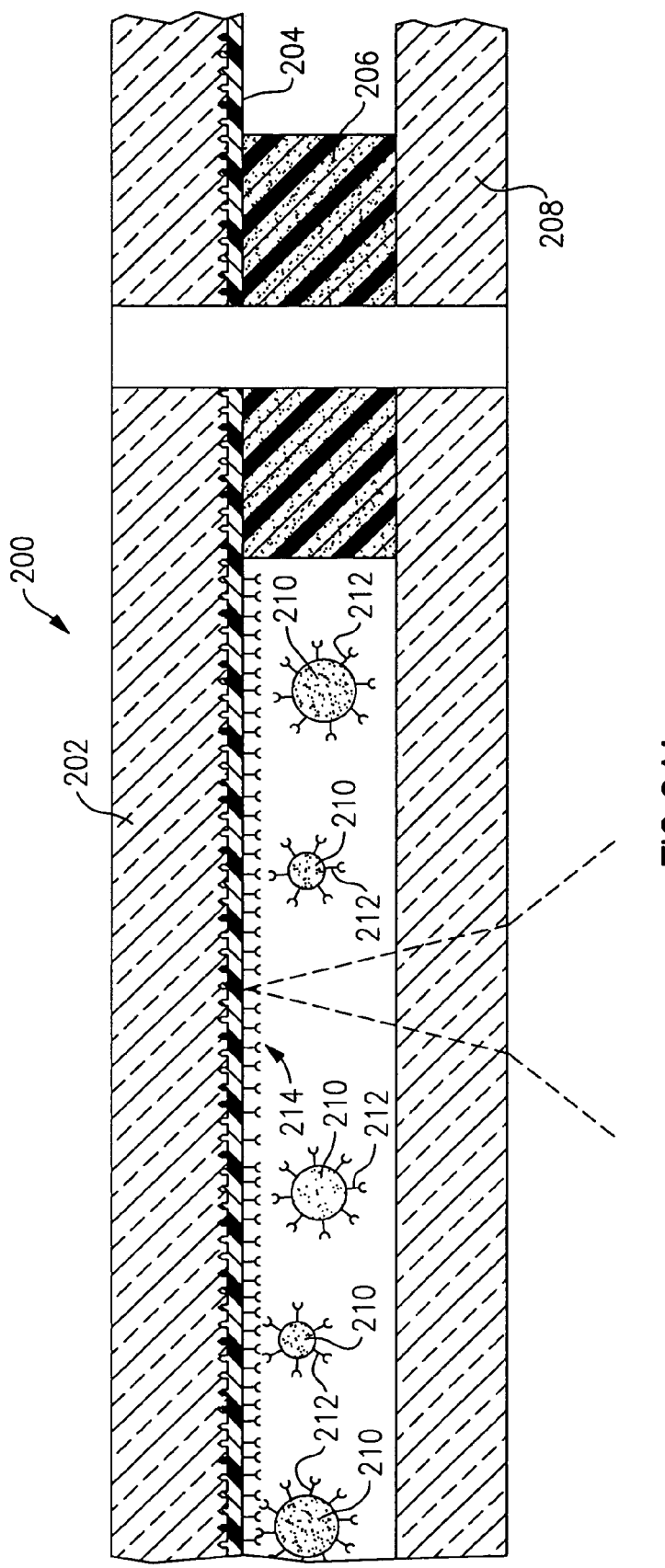
Figure 64B:
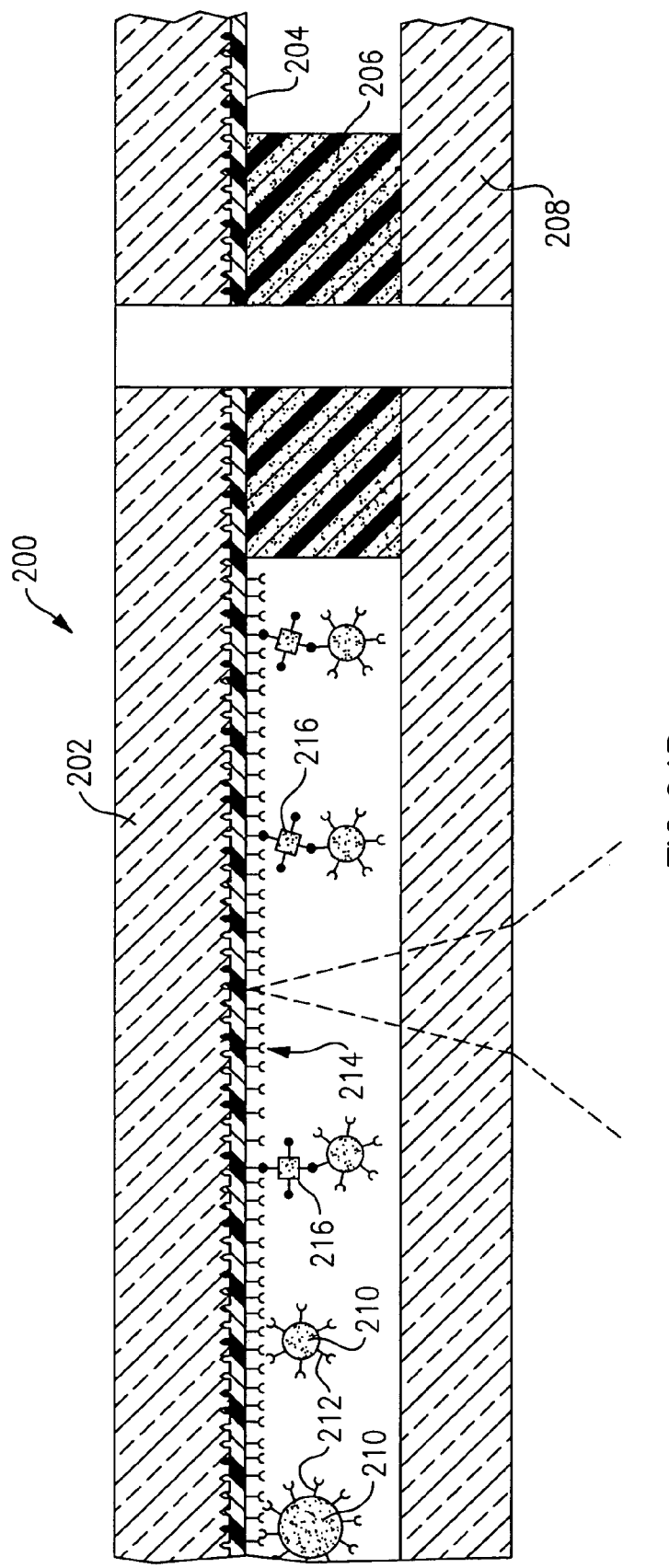
Figure 65:
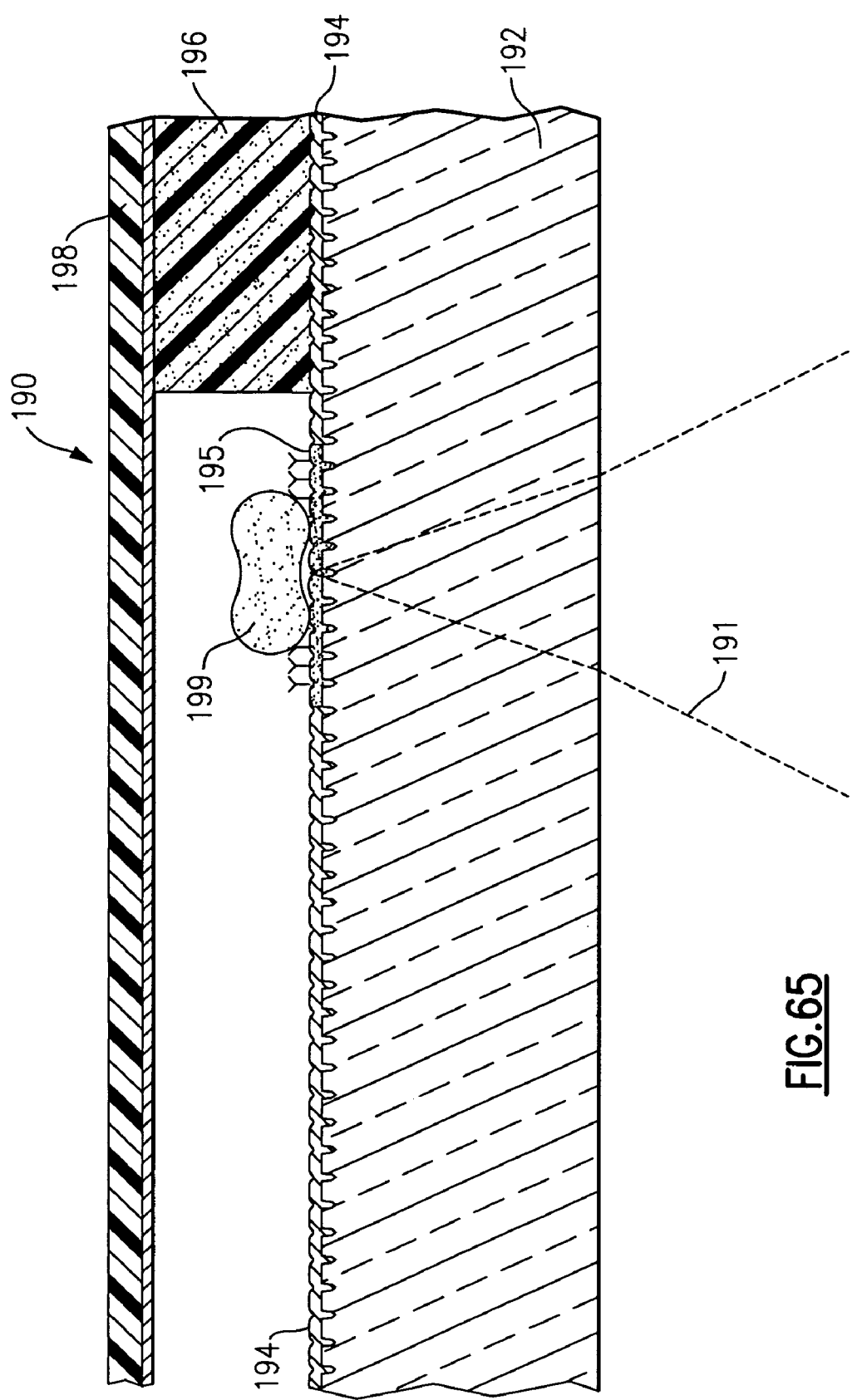
Figure 66A:
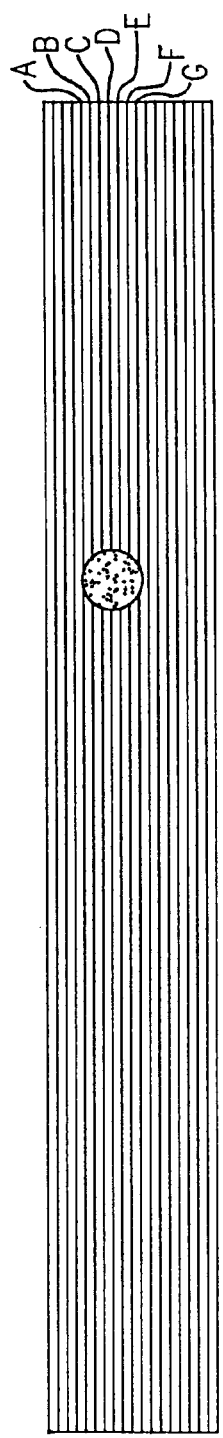
Figure 66B:
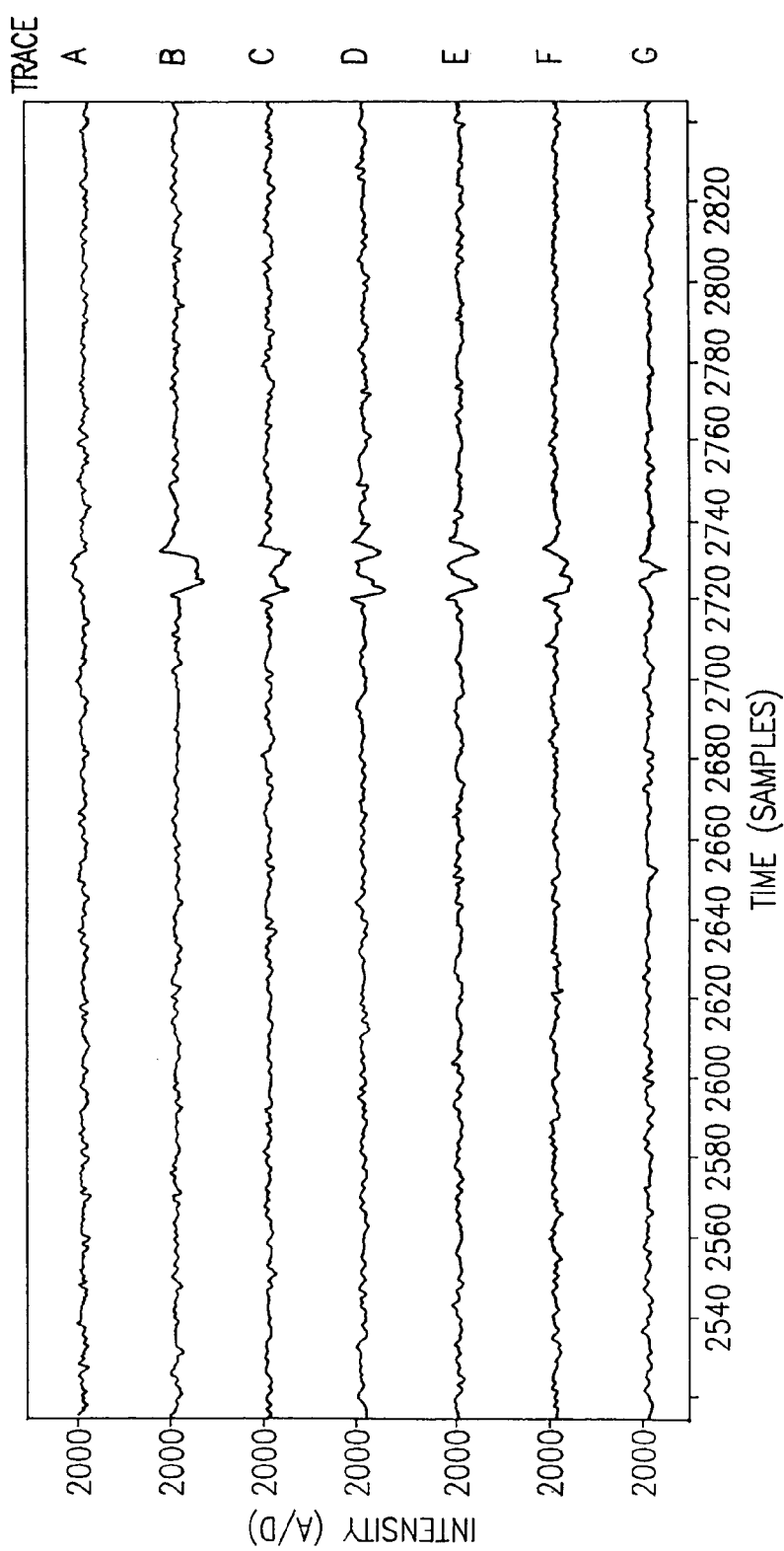
Figure 67A:
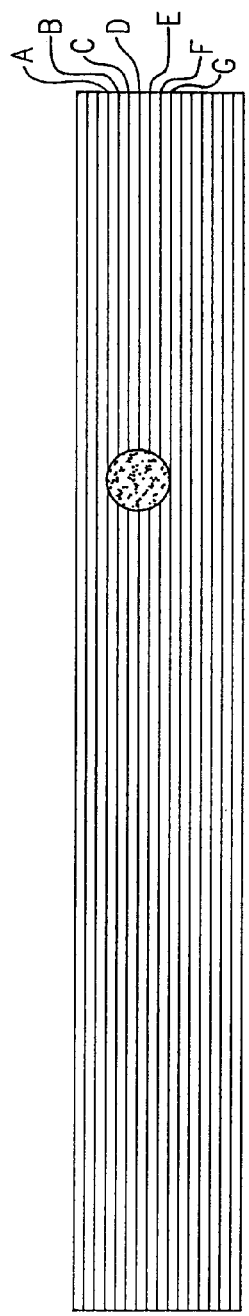
Figure 67B:
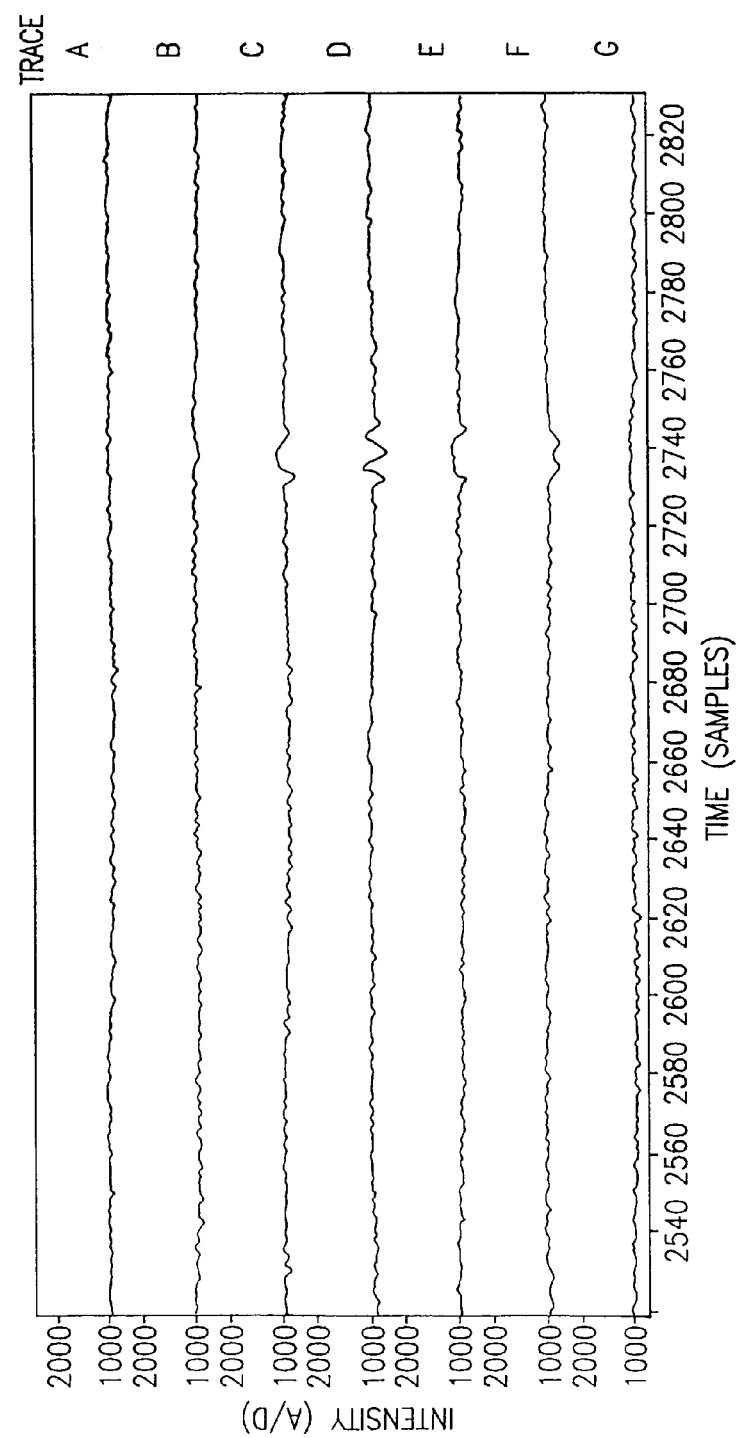
Figure 68:
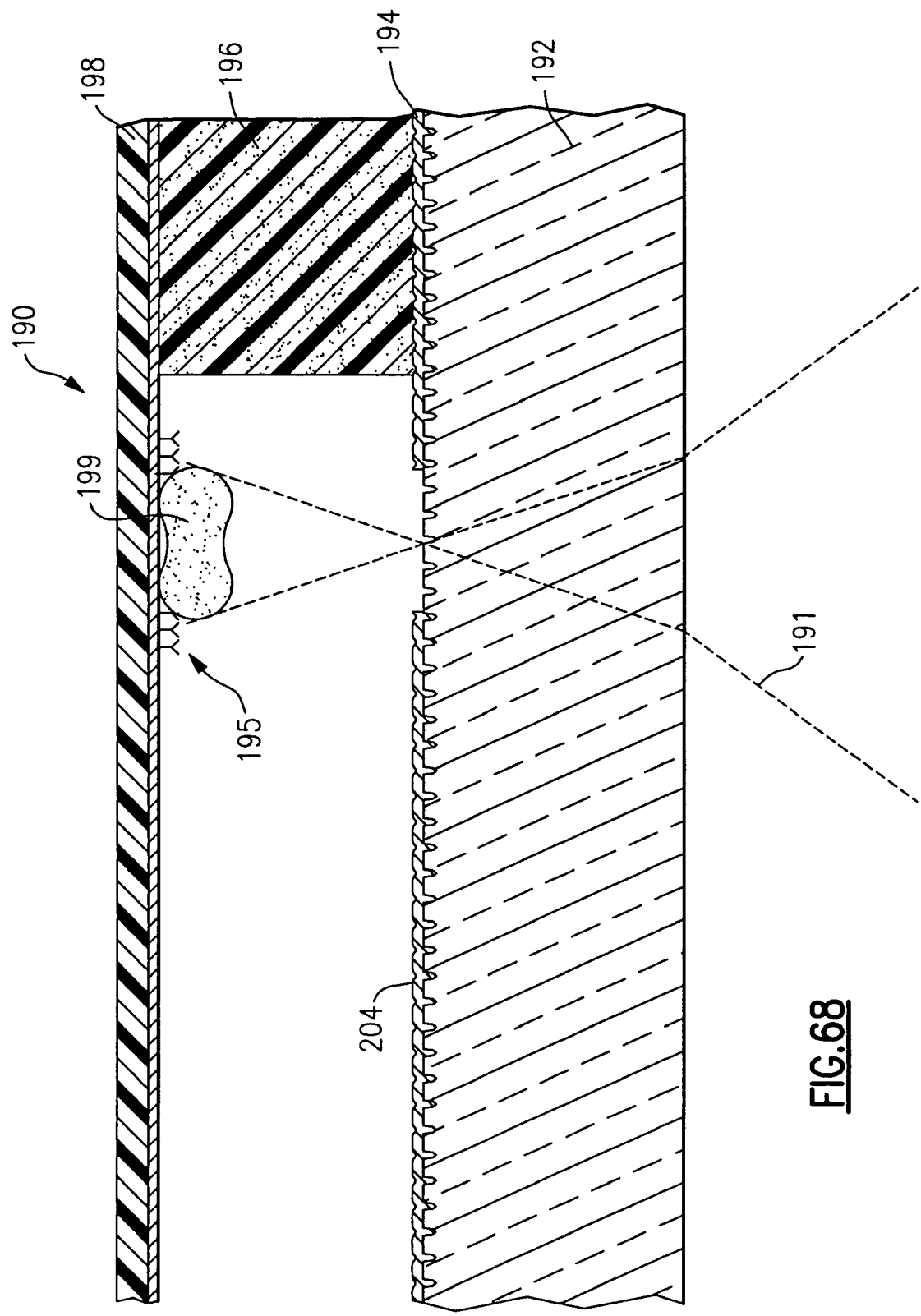
Figure 69A:
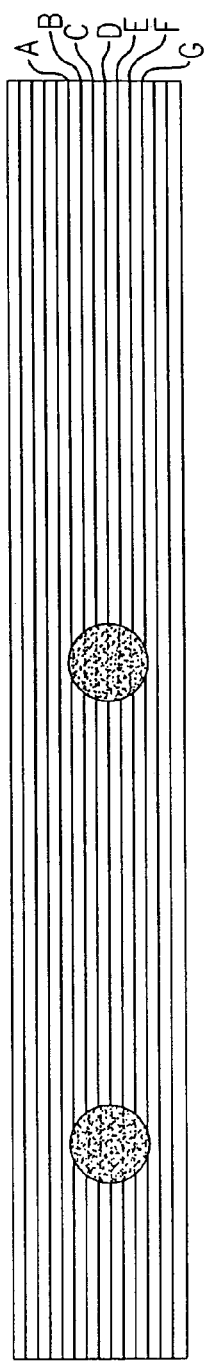
Figure 69B:
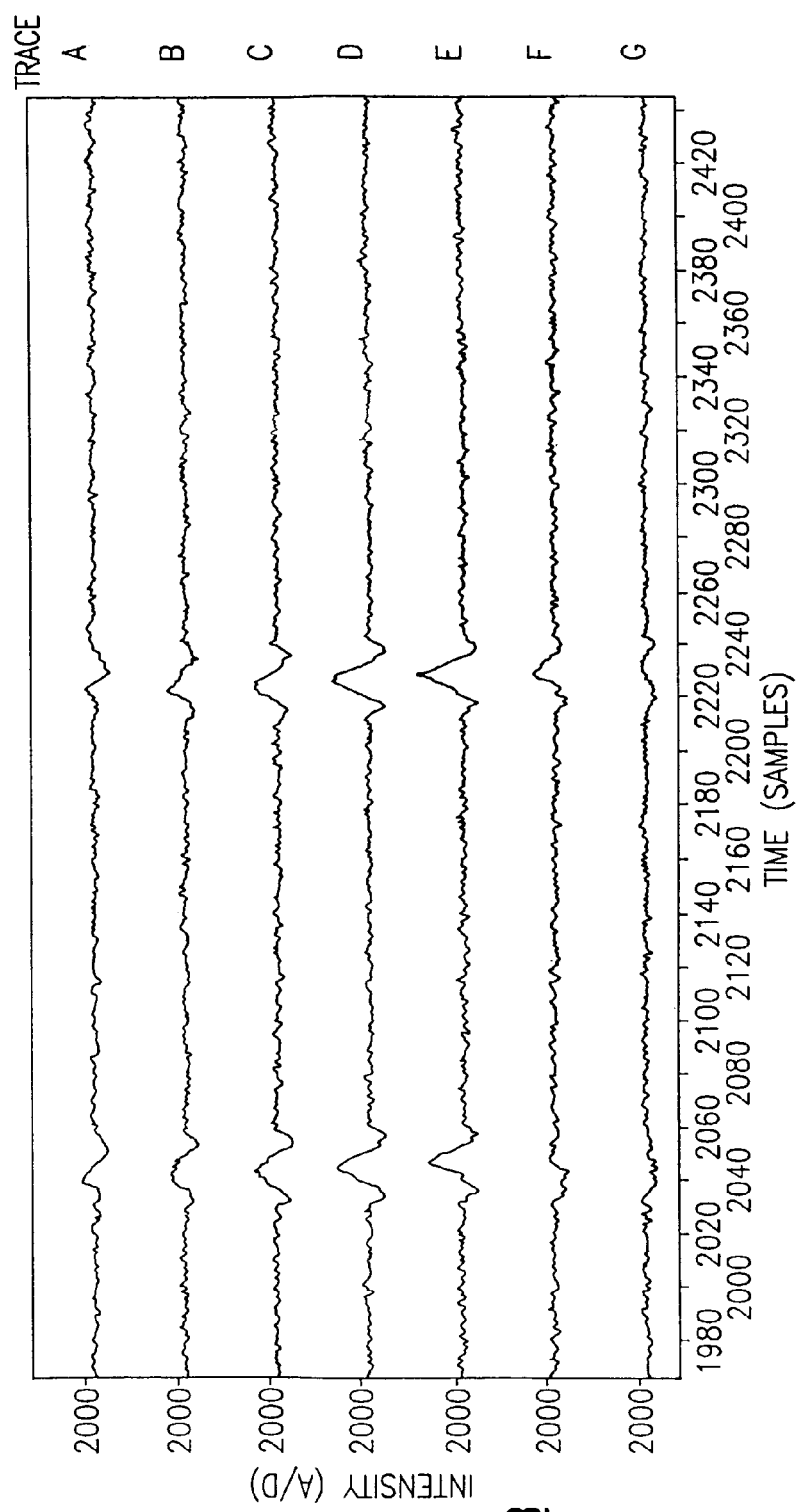
Figure 70A:
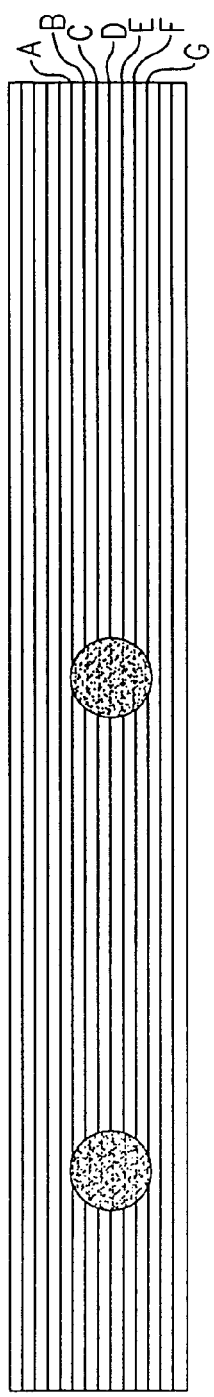
Figure 70B:
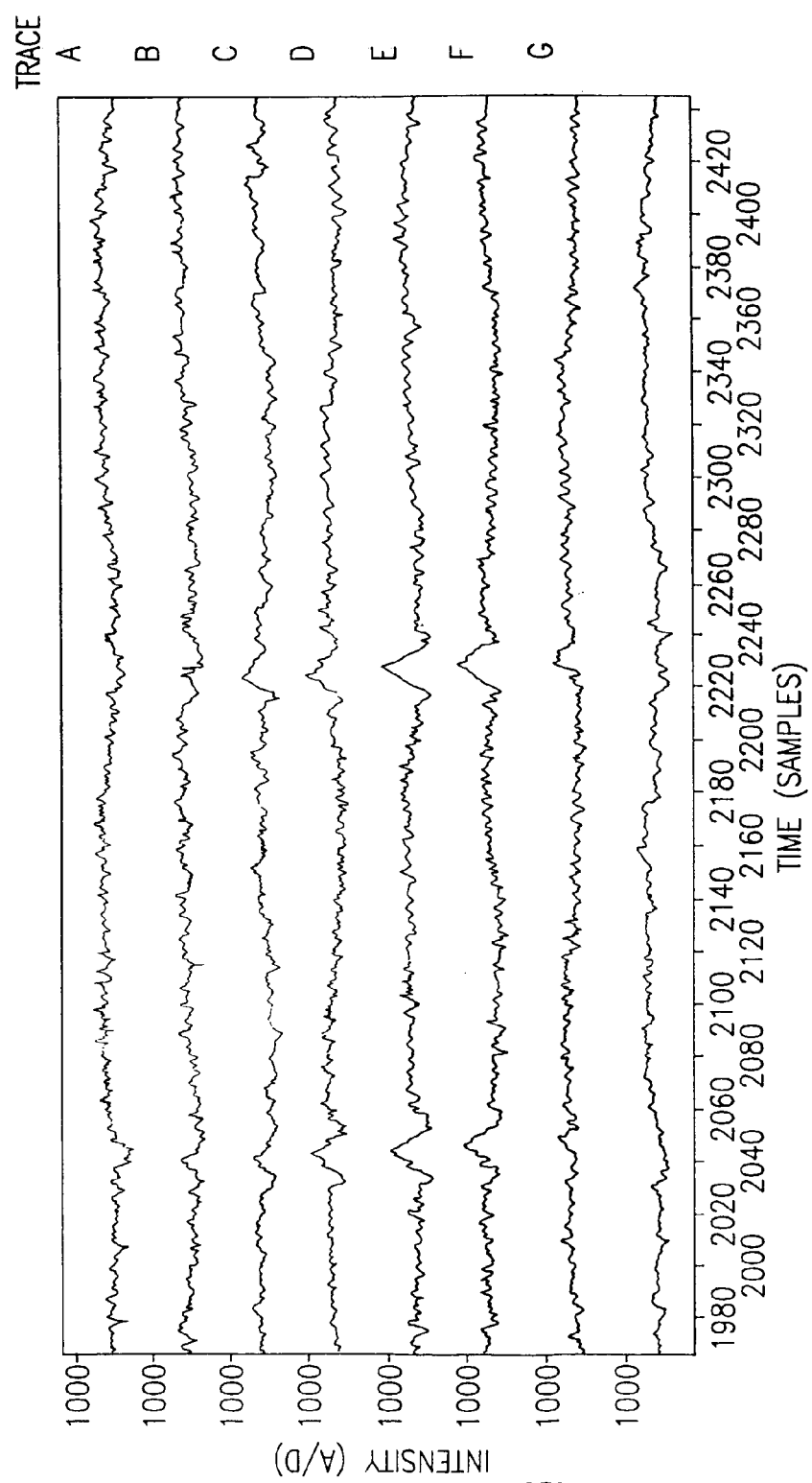
Figure 71:
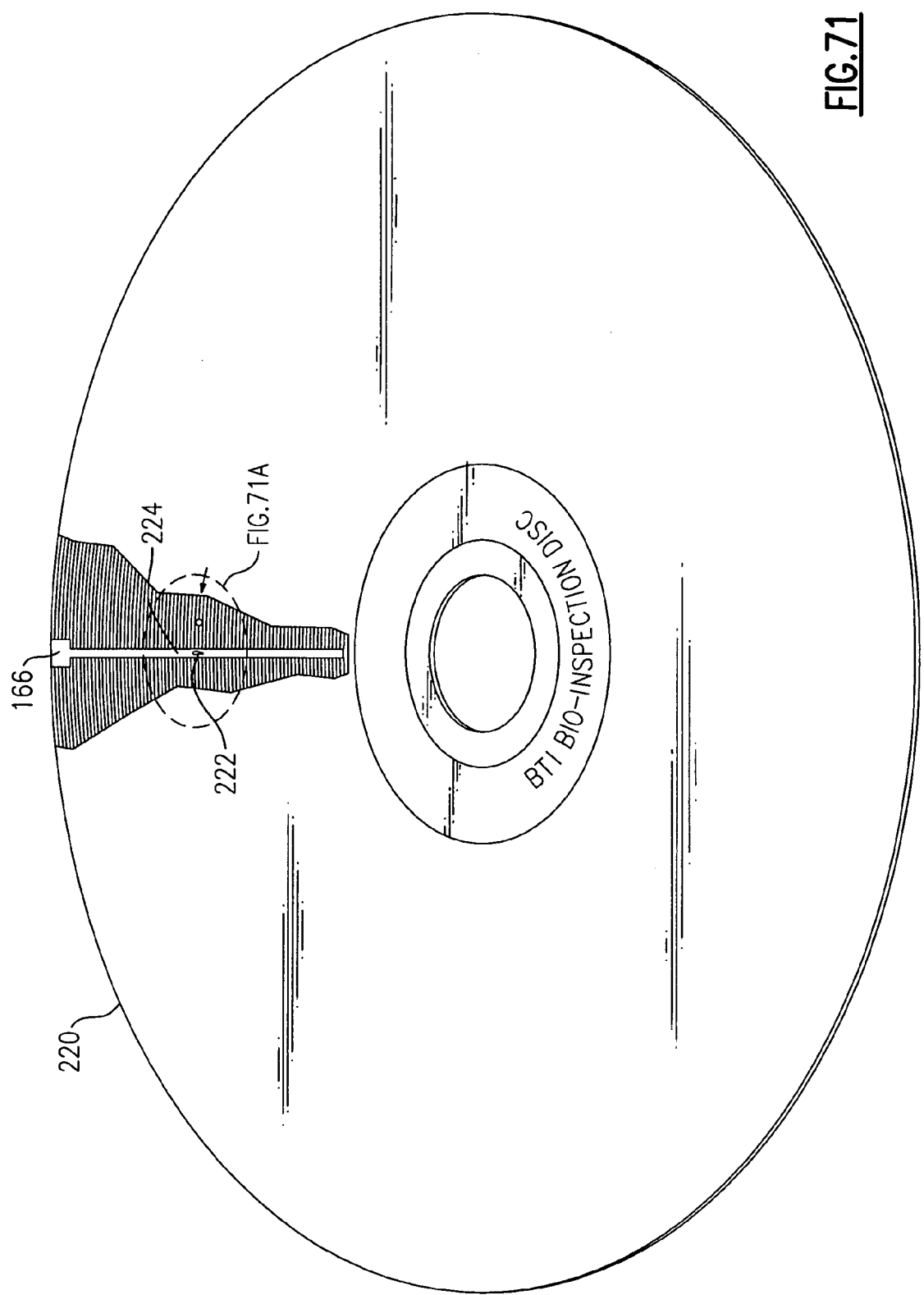
Figure 71A:
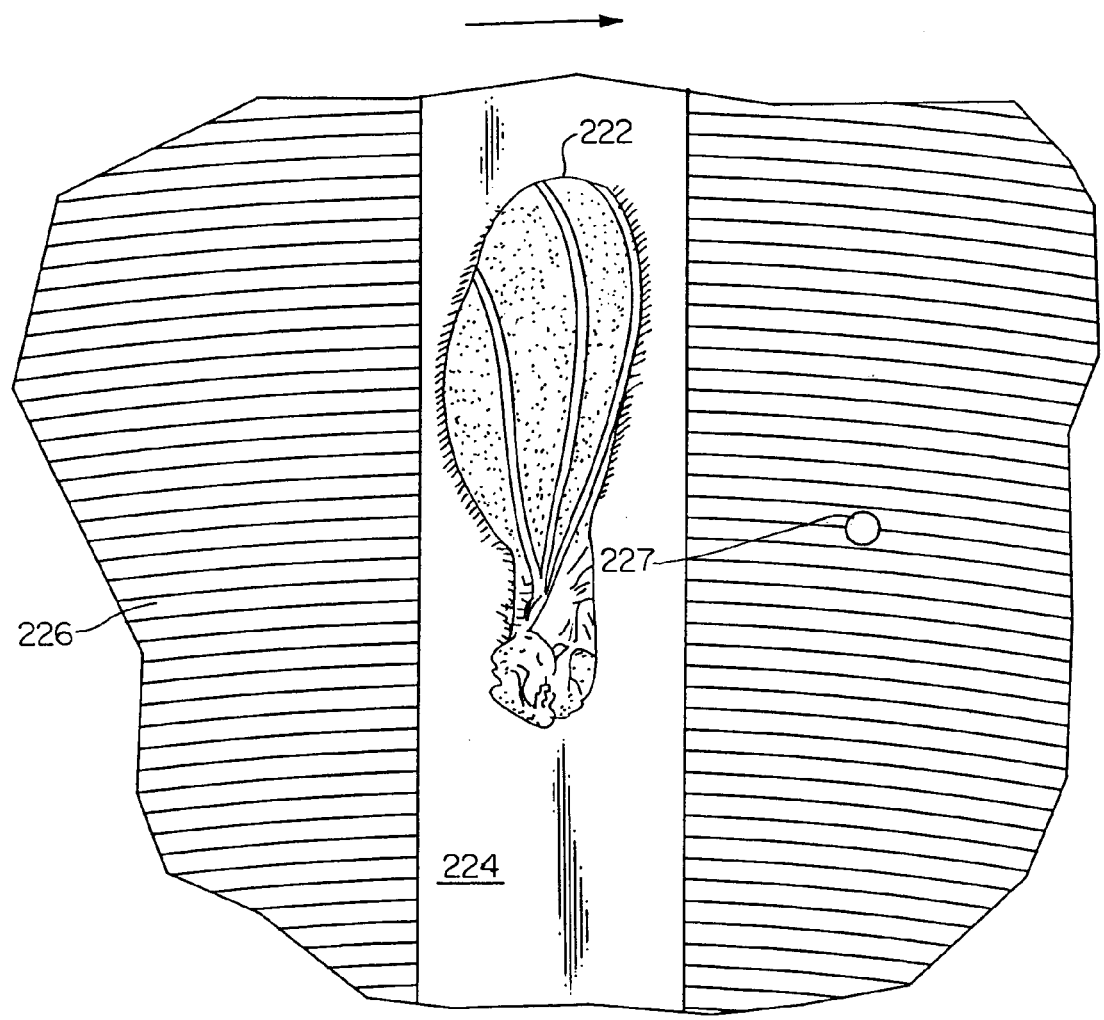
Figure 72:
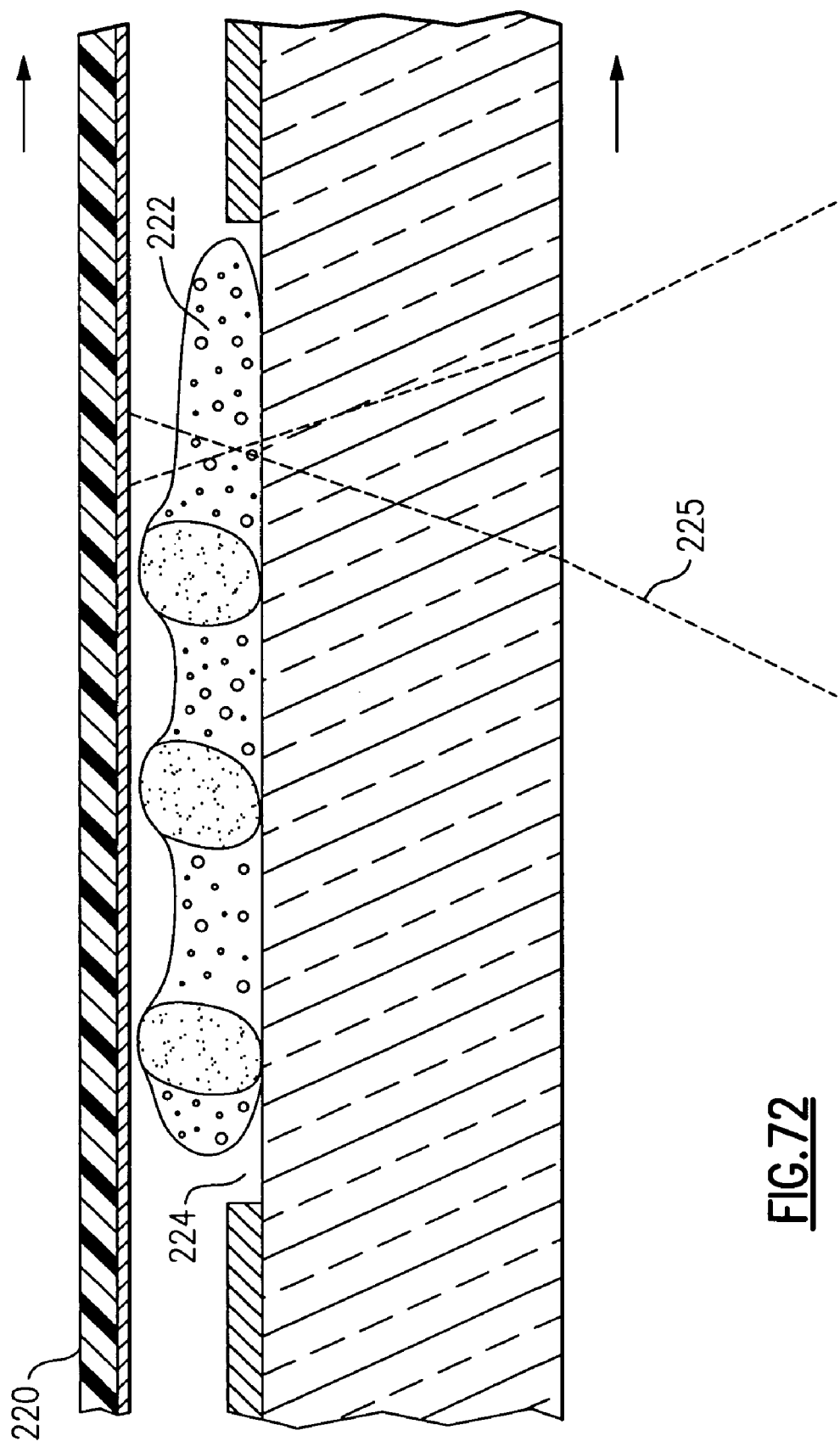
Figure 74A:
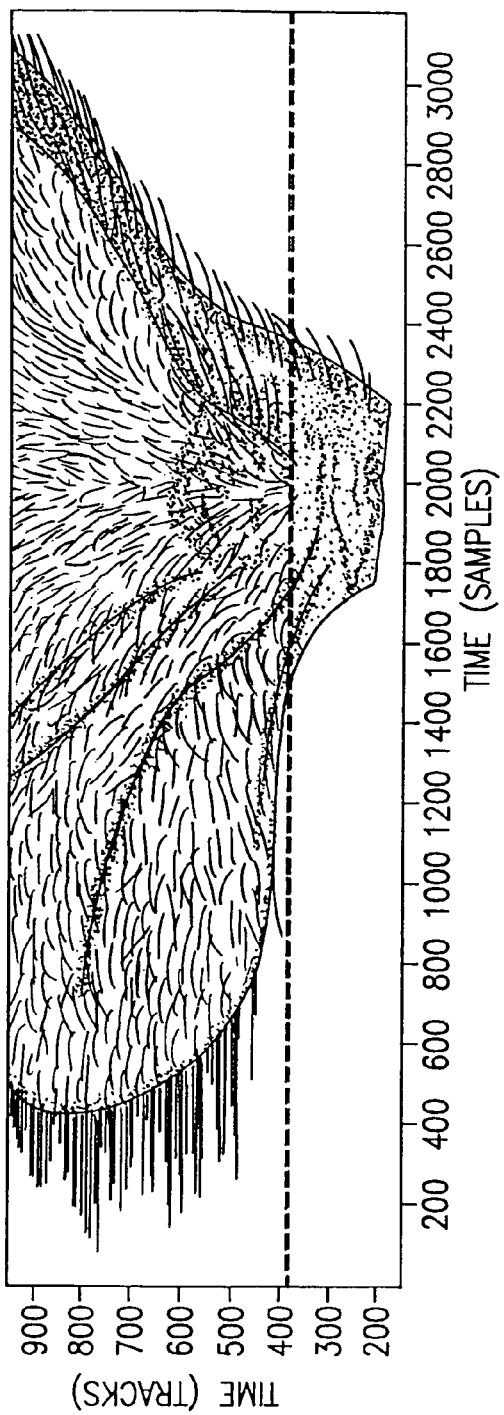
Figure 74B:
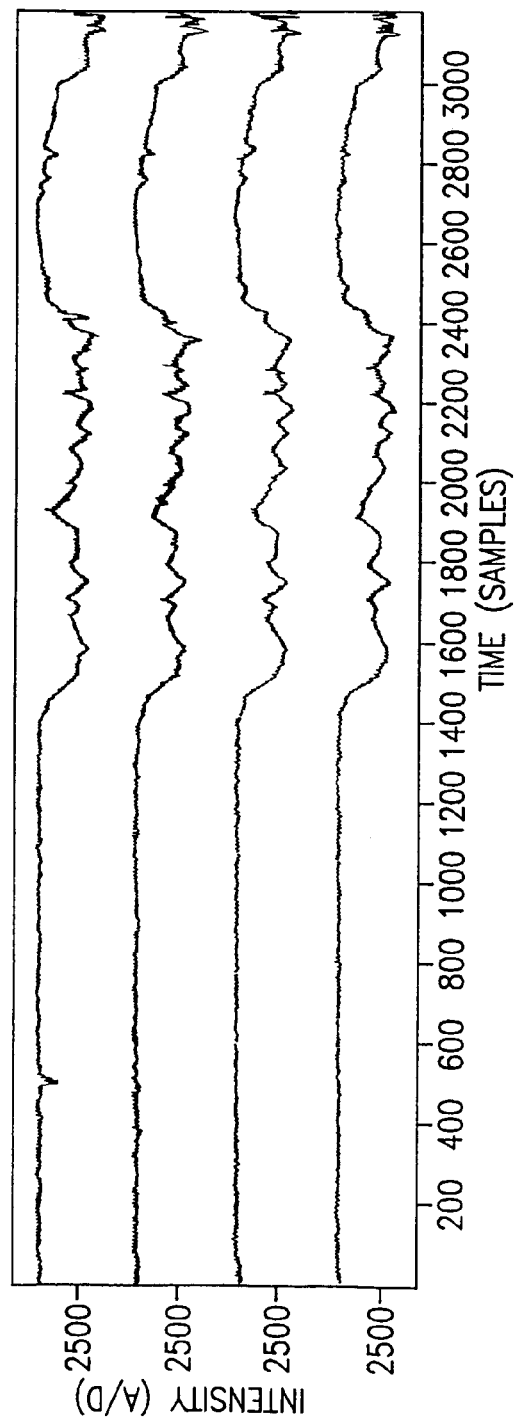
Figure 75A:
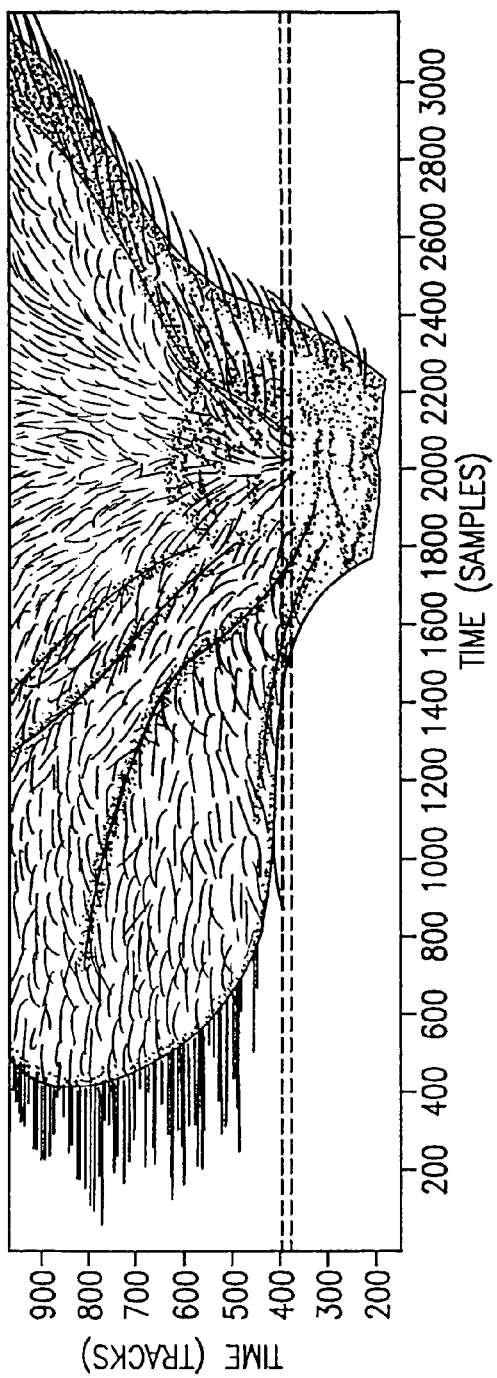
Figure 75B:
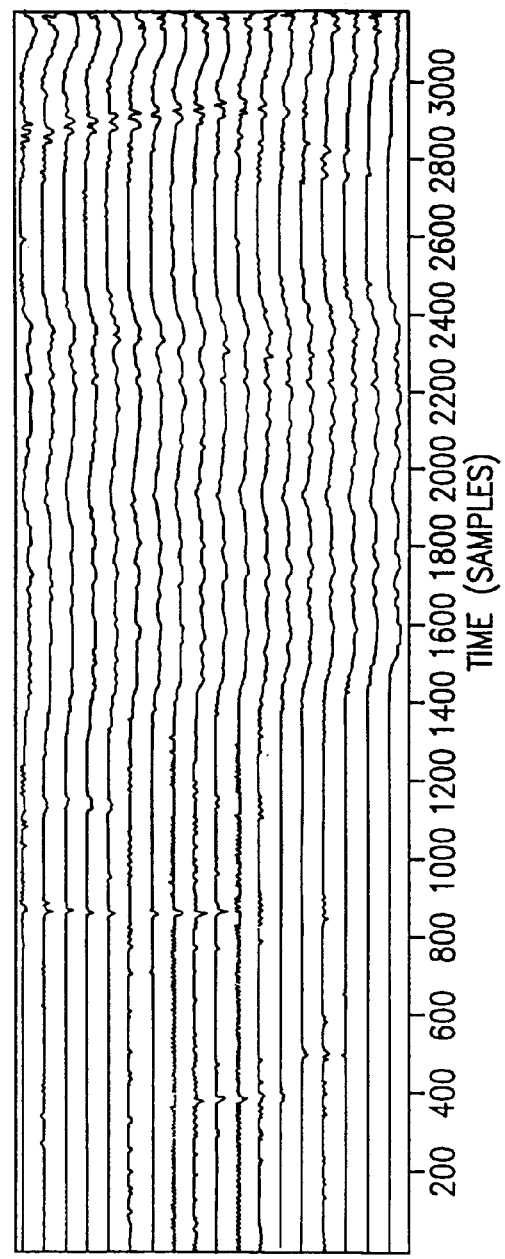
Figure 77C:
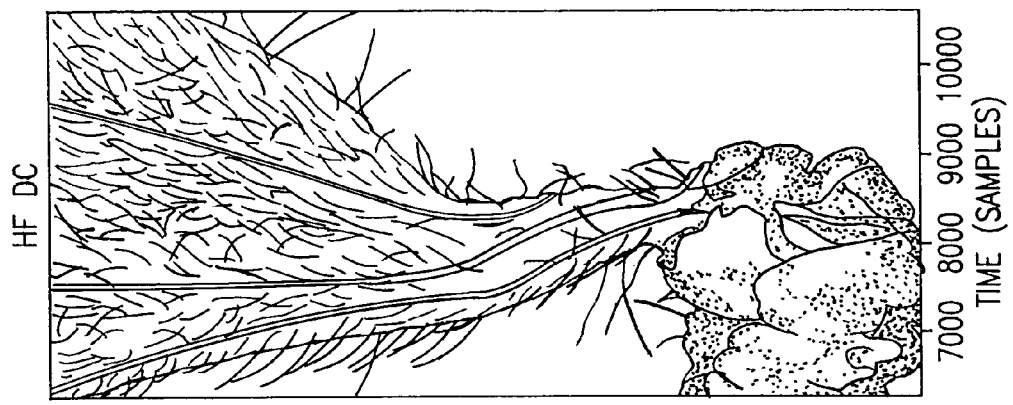
Figure 77B:
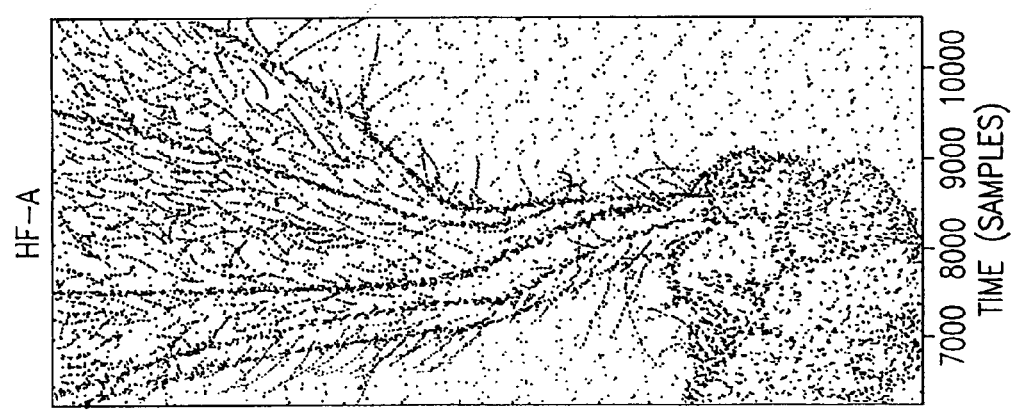
Figure 77A:
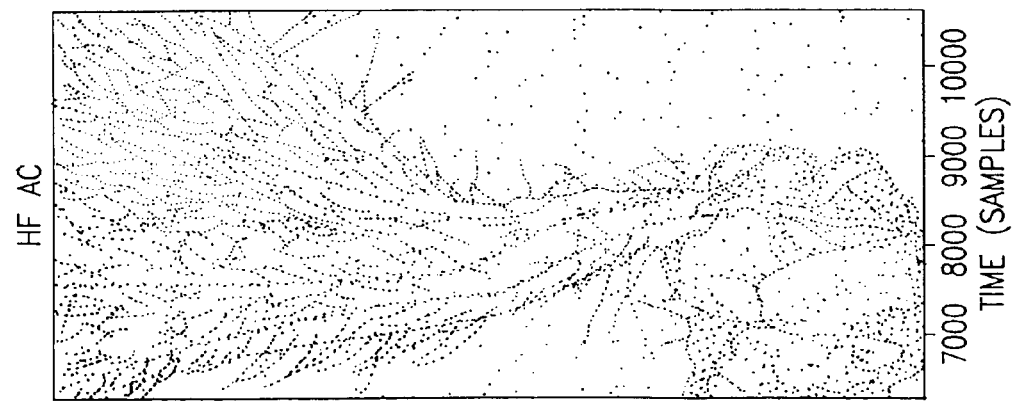
Figure 78A:
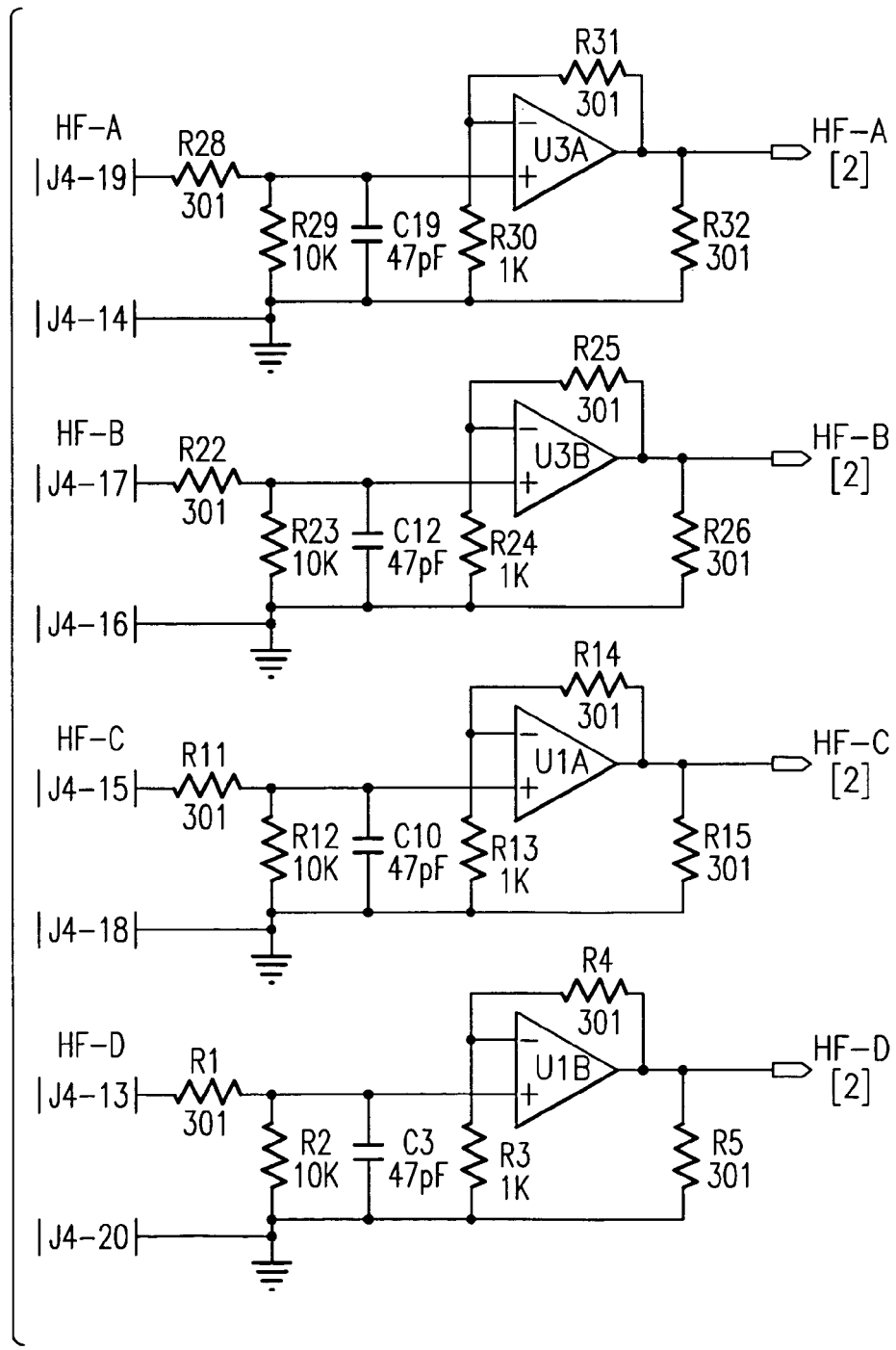
Figure 78B:
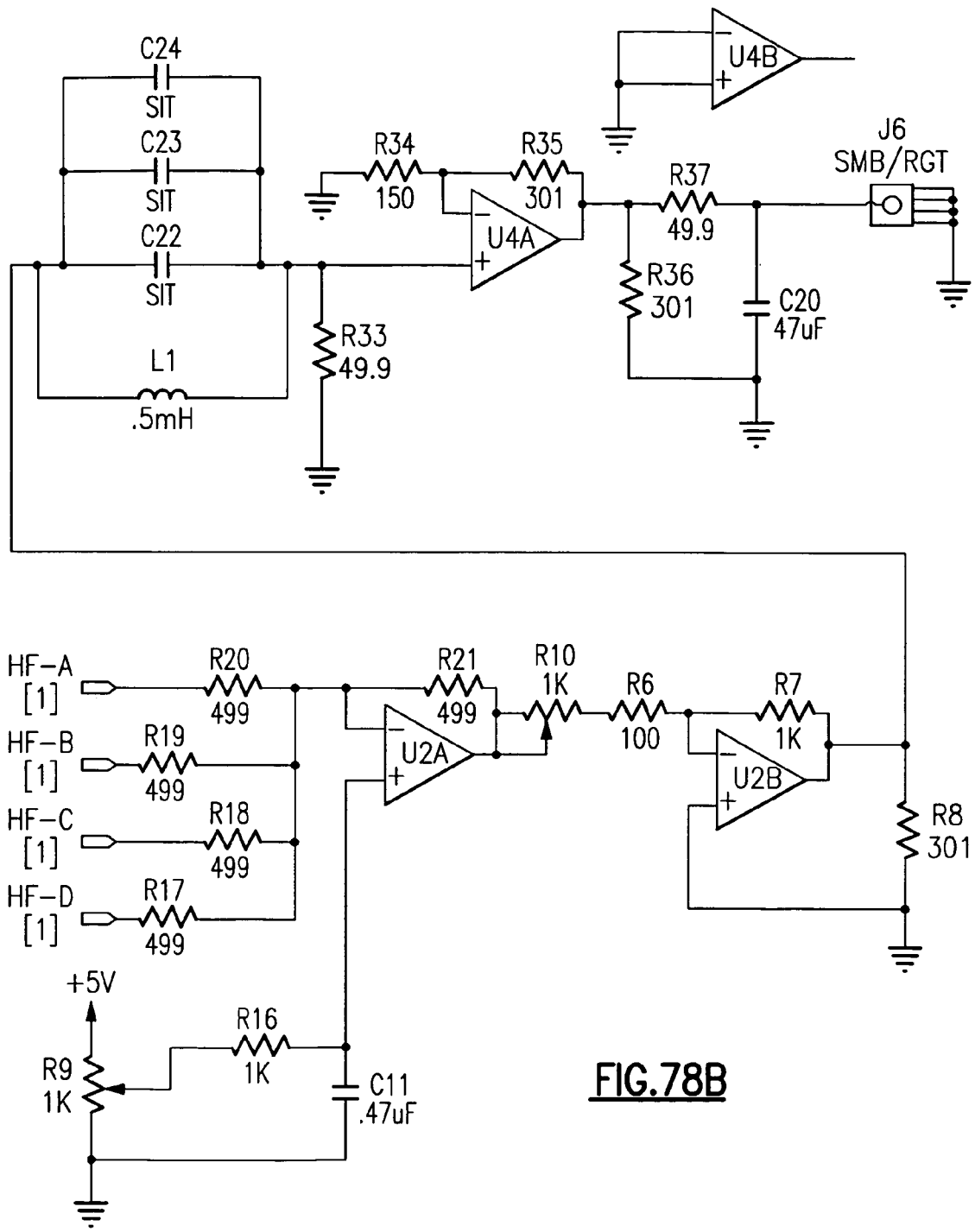
Figure 79A:
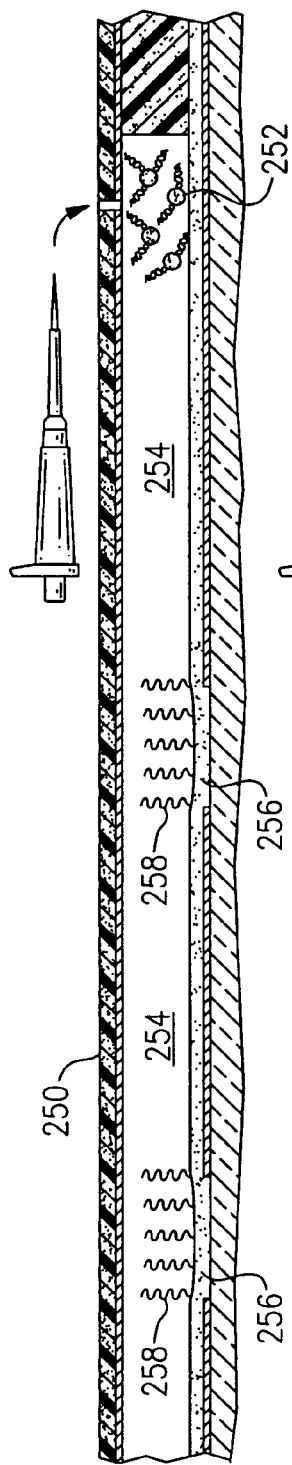
Figure 79B:
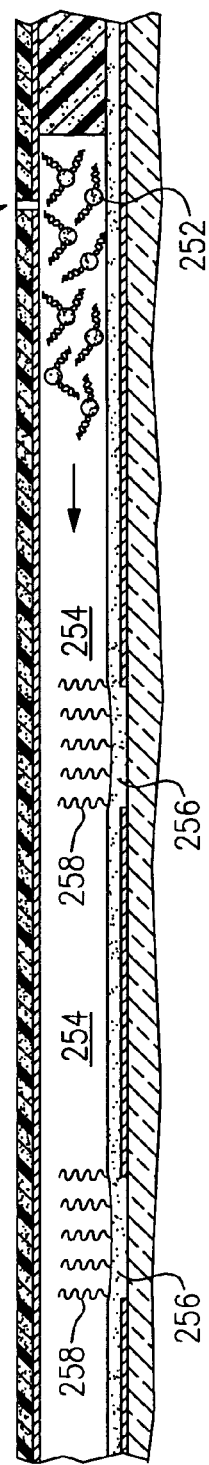
Figure 79C:
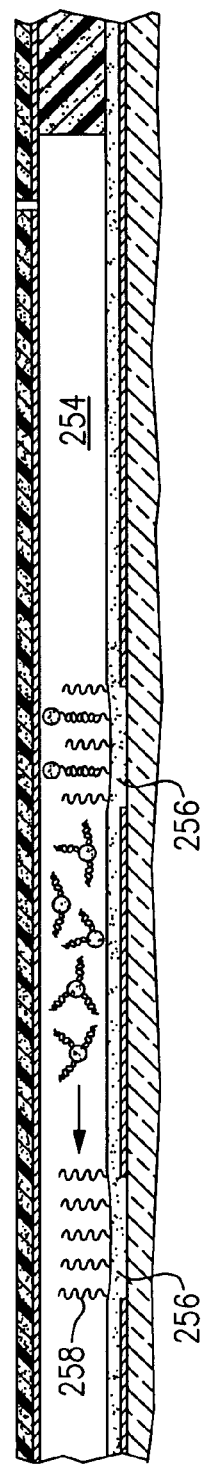
Figure 79D:
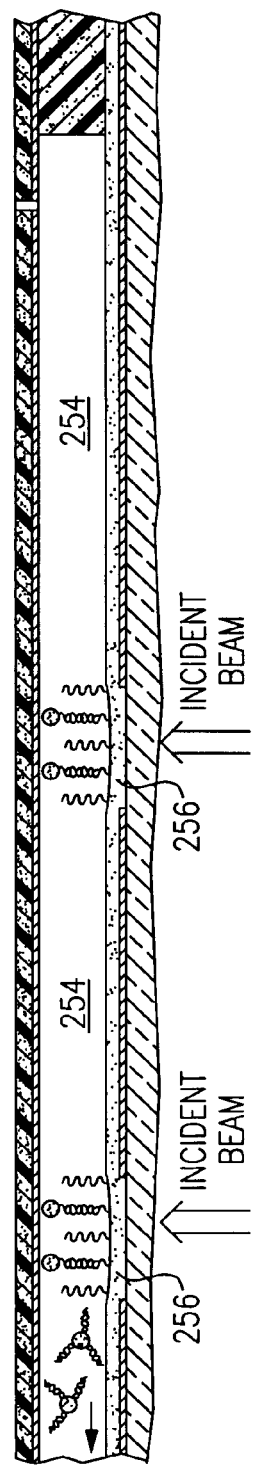
Figure 81A:
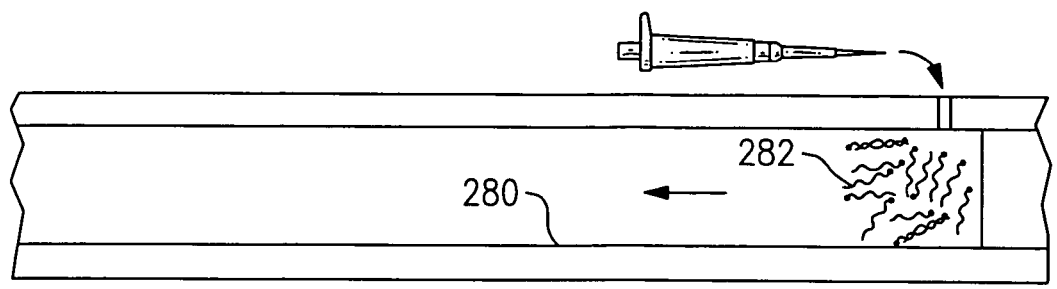
Figure 81B:
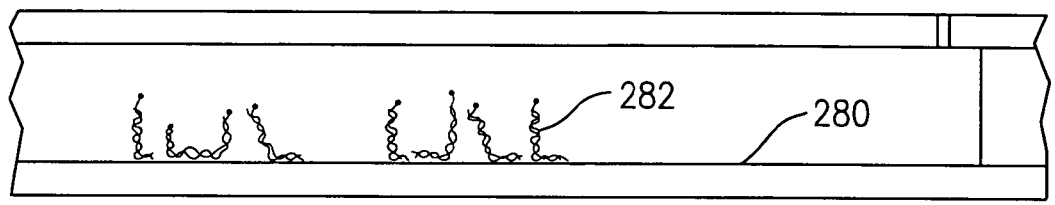
Figure 81C:
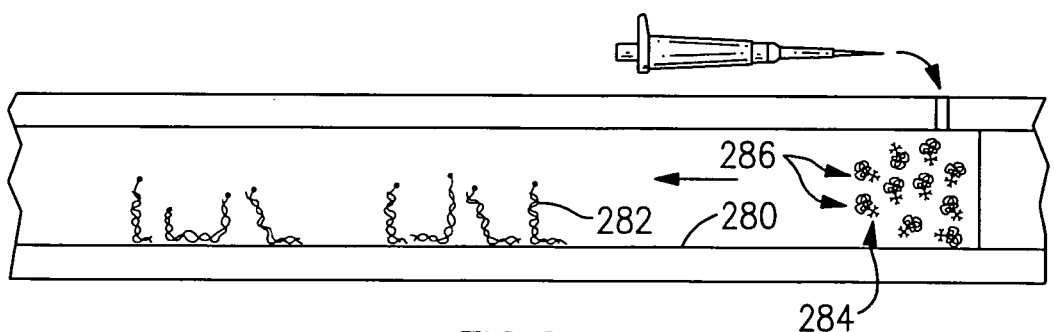
Figure 81D:
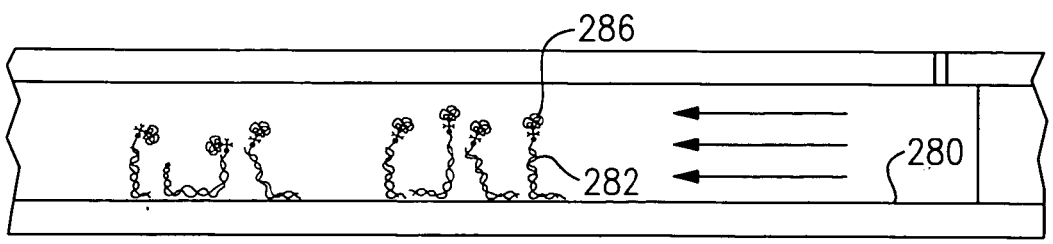
Figure 81E:
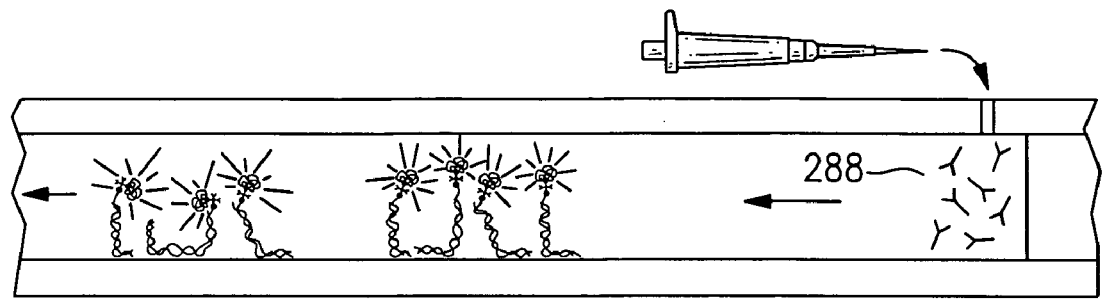
Figure 81F:
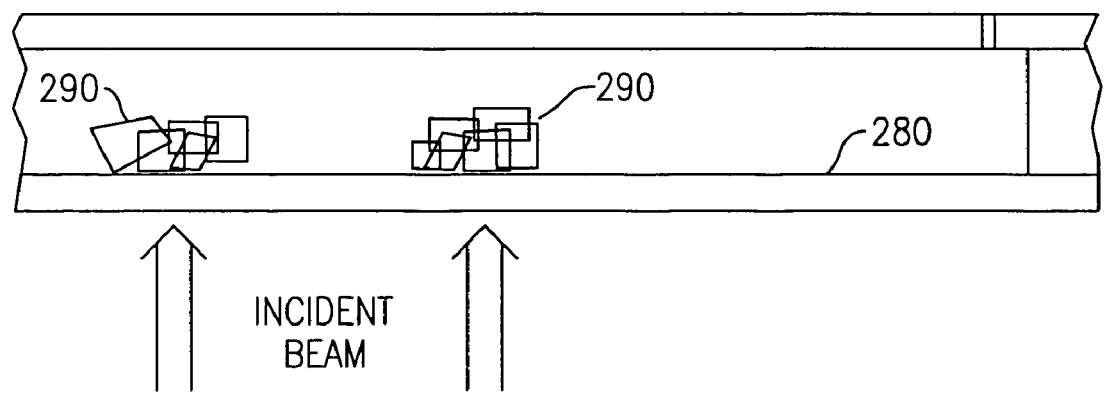

FIGS. 24A, 24B, and 24C are electrical schematics of the amplifier stages according to a first embodiment of the buffer cards shown in FIGS. 22 and 23;

FIG. 25 is a functional block diagram of a digital signal processing circuit programmably configured as an analog-to-digital converter in accordance with the principles of an alternate embodiment of the present invention as represented in FIG. 9;

FIG. 26 is a flow chart illustrating some of the steps involved in detecting investigational elements in accordance with the second embodiment of the present invention illustrated in FIG. 25;

FIG. 27 is an exploded perspective view of a reflective bio-disc as utilized in conjunction with the present invention;

FIG. 28 is a top plan view of the disc shown in FIG. 27;

FIG. 29 is a perspective view of the disc illustrated in FIG. 27 with cut-away sections showing the different layers of the disc;

FIG. 30 is an exploded perspective view of a transmissive bio-disc as employed in conjunction with the present invention;

FIG. 31 is a perspective view representing the disc shown in FIG. 30 with a cut-away section illustrating the functional aspects of a semi-reflective layer of the disc;

FIG. 32 is a graphical representation showing the relationship between thickness and transmission of a thin gold film;

FIG. 33 is a top plan view of the disc shown in FIG. 30;

FIG. 34 is a perspective view of the disc illustrated in FIG. 30 with cut-away sections showing the different layers of the disc including the type of semi-reflective layer shown in FIG. 31;

FIG. 35 is a partial cross sectional view taken perpendicular to a radius of the reflective optical bio-disc illustrated in FIGS. 27, 28, and 29 showing a flow channel formed therein;

FIG. 36 is a partial cross sectional view taken perpendicular to a radius of the transmissive optical bio-disc illustrated in FIGS. 30, 33, and 34 showing a flow channel formed therein and a top detector;

FIG. 37 is a partial longitudinal cross sectional view of the reflective optical bio-discs shown in FIGS. 27, 28, and 29 illustrating a wobble groove formed therein;

FIG. 38 is a partial longitudinal cross sectional view of the transmissive optical bio-disc illustrated in FIGS. 30, 33, and 34 showing a wobble groove formed therein and a top detector;

FIG. 39 is a view similar to FIG. 35 showing the entire thickness of the reflective disc and the initial refractive property thereof;

FIG. 40 is a view similar to FIG. 36 showing the entire thickness of the transmissive disc and the initial refractive property thereof;

FIG. 41 is a cross sectional side view of an optical disc assembly including a light refractive cover and investigational features according to the present invention;

FIG. 42 is a plan view showing a typical three-beam system projecting onto three tracks of the disc;

FIG. 43 is a plan view of three beams relative to three tracks, one of which has an investigational feature positioned thereon according to the present invention;

FIG. 44 is a graph depicting a signal that corresponds to an operation feature such as a pit or land including discernable changes as exploited by the present invention;

FIGS. 45 and 46 are graphs depicting changes in signals produced by operational features encountered on the disc;

FIG. 47 is a section view of a bio-disc according to the present invention that shows a micro-fluidic channel;

FIG. 48 is a representative graph of the change in reflectivity of materials with thickness that is exploited according to the present invention;

FIG. 49 is pair of graphs depicting an envelope of fluctuations of an analog readout signal that has been enlarged by reaction in a micro-fluidic channel according to the present invention;

FIG. 50 is a plan view of a bio-disc and corresponding readout of test sample signals according to the present invention;

FIG. 51 is a cross-sectional side view of an optical bio-disc including bead reporters as utilized in conjunction with the present invention;

FIG. 52A is a graphical representation of two 6.8 µm blue beads positioned relative to the tracks of an optical bio-disc according to the present invention;

FIG. 52B is a series of signature traces derived from the beads of FIG. 52A utilizing an AC coupled and buffered HF signal from the optical drive according to the present invention;

FIG. 53A is a graphical representation of two 6.42 µm red beads positioned relative to the tracks of an optical bio-disc according to the present invention;

FIG. 53B is a series of signature traces derived from the beads of FIG. 53A utilizing an AC coupled and buffered HF signal from the optical drive according to the present invention;

FIG. 54A is a graphical representation of two 6.33 µm polystyrene beads positioned relative to the tracks of an optical bio-disc according to the present invention;

FIG. 54B is a series of signature traces derived from the beads of FIG. 54A utilizing an AC coupled and buffered HF signal from the optical drive according to the present invention;

FIG. 55A is a graphical representation of a 5.5 µm glass bead positioned relative to the tracks of an optical bio-disc according to the present invention;

FIG. 55B is a series of signature traces derived from the bead illustrated in FIG. 55A utilizing an AC coupled and buffered HF signal from the optical drive according to the present invention;

FIG. 56A is a graphical representation of a 4.5 µm magnetic bead positioned relative to the tracks of an optical bio-disc according to the present invention;

FIG. 56B is a series of signature traces derived from the bead of FIG. 56A utilizing an AC coupled and buffered HF signal from the optical drive according to the present invention;

FIG. 57A is a graphical representation of two 4.0 µm blue beads positioned relative to the tracks of an optical bio-disc according to the present invention;

FIG. 57B is a series of signature traces derived from the beads of FIG. 57A utilizing an AC coupled and buffered HF signal from the optical drive according to the present invention;

FIG. 58A is a graphical representation of a 2.986 µm polystyrene bead positioned relative to the tracks of an optical bio-disc according to the present invention;

FIG. 58B is a series of signature traces derived from the bead illustrated in FIG. 58A utilizing an AC coupled and buffered HF signal from the optical drive according to the present invention;

FIG. 59A is a graphical representation of two 2.9 µm white beads positioned relative to the tracks of an optical bio-disc according to the present invention;

FIG. 59B is a series of signature traces derived from the beads of FIG. 59A utilizing an AC coupled and buffered HF signal from the optical drive according to the present invention;

FIG. 60A is a graphical representation of four 2.8 µm magnetic beads positioned relative to the tracks of an optical bio-disc according to the present invention;

FIG. 60B is a series of signature traces derived from the beads of FIG. 60A utilizing an AC coupled and buffered HF signal from the optical drive according to the present invention;

FIG. 61A is a graphical representation of a mixture of beads including 2.8 µm magnetic beads, 4.0 and 6.8 µm blue polystyrene beads, and different sized silica beads positioned relative to the tracks of an optical bio-disc according to the present invention;

FIG. 61B is a series of signature traces derived from the cluster of beads illustrated in FIG. 61A, the traces being derived from an AC coupled and buffered HF signal from the optical drive according to the present invention;

FIG. 62A is a graphical representation of two 2.9 µm white fluorescent polystyrene beads positioned relative to the tracks of an optical bio-disc according to the present invention;

FIG. 62B is a series of signature traces derived from the beads of FIG. 62A utilizing a DC coupled and buffered HF signal from the optical drive according to the present invention;

FIG. 63A is a graphical representation of two 2.9 μm white fluorescent polystyrene beads positioned relative to the tracks of an optical bio-disc according to the present invention;

FIG. 63B is a series of signature traces derived from the beads of FIG. 63A utilizing a DC coupled and buffered "A" signal from the optical drive according to the present invention;

FIGS. 64A and 64B are cross-sectional side views similar to FIG. 51 showing the biochemical interaction between the bio-disc and the reporter beads in greater detail;

FIG. 65 is a cross-sectional side view of an optical bio-disc including a proximally positioned red blood cell as the investigational feature interrogated by the read beam of the optical disc drive assembly according to the present invention;

FIG. 66A is a graphical representation of a proximally positioned red blood cell approximately 6.0 μm in diameter positioned relative to the tracks of an optical bio-discs according to the present invention;

FIG. 66B is a series of signature traces derived from the red blood cell of FIG. 66A utilizing an AC coupled and buffered HF signal from the optical drive according to the present invention;

FIG. 67A is a graphical representation of a proximally positioned red blood cell approximately 6.0 μm in diameter positioned relative to the tracks of an optical bio-disc according to the present invention;

FIG. 67B is a series of signature traces derived from the red blood cell of FIG. 67A utilizing a DC coupled and buffered HF signal from the optical drive according to the present invention;

FIG. 68 is a cross-sectional side view of an optical bio-disc including a distally positioned red blood cell as the investigational feature interrogated by the read beam of the optical disc drive assembly according to the present invention;

FIG. 69A is a graphical representation of two distally positioned red blood cells approximately 6.0 μm in diameter positioned relative to the tracks of an optical bio-disc according to the present invention;

FIG. 69B is a series of signature traces derived from the red blood cells of FIG. 69A utilizing an AC coupled and buffered HF signal from the optical drive according to the present invention;

FIG. 70A is a graphical representation of two distally positioned red blood cells approximately 6.0 μm in diameter positioned relative to the tracks of an optical bio-disc according to the present invention;

FIG. 70B is a series of signature traces derived from the red blood cells of FIG. 70A utilizing a DC coupled and buffered HF signal from the optical drive according to the present invention;

FIG. 71 is a perspective top view an optical inspection disc with a portion of the top cap cut away to illustrate a gnat's wing positioned in an inspection channel according to the present invention;

FIG. 71A is an enlarged top view of the indicated portion of FIG. 71 showing in greater detail the gnat's wing, inspection channel, information storage tracks of the disc, and a focused spot of an incident beam on the tracks of the optical inspection disc according to this embodiment of the present invention;

FIG. 72 is a cross-sectional side view taken perpendicular to a radius of the optical inspection disc of FIG. 71 including the gnat's wing as the investigational feature interrogated according to the present invention by the read beam of an optical disc drive assembly;

FIG. 73A is a graphical representation of a lateral section of the gnat's wing of FIGS. 71A and 72 as positioned in the inspection channel relative to the tracks of an optical inspection disc according to the present invention;

FIG. 73B is a single signature trace derived from the section of the gnat's wing of FIG. 73A utilizing an AC coupled and buffered HF signal from the optical drive according to the present invention;

FIG. 74A is a graphical representation similar to that shown in FIG. 73A;

FIG. 74B is a series of four consecutive signature traces derived from the section of the gnat's wing of FIG. 74A utilizing an AC coupled and buffered HF signal from the optical drive according to the present invention;

FIG. 75A is a graphical representation similar to that shown in FIG. 73A;

FIG. 75B is a series of consecutive signature traces at moderate density derived from the section of the gnat's wing of FIG. 75A utilizing an AC coupled and buffered HF signal from the optical drive according to the present invention;

FIG. 76A is a graphical representation similar to that shown in FIG. 73A;

FIG. 76B is a series of consecutive signature traces at higher density derived from the section of the gnat's wing of FIG. 76A utilizing an AC coupled and buffered HF signal from the optical drive according to the present invention;

FIGS. 77A, 77B, and 77C are pictorial representations of the gnat's wing of FIGS. 71A and 72 as rendered by methods according to the present invention respectively utilizing either an AC coupled and buffered HF signal, a DC coupled and buffered "A" signal, or a DC coupled and buffered HF signal from an optical drive assembly;

FIG. 78 is a graphical representation illustrating the relationship between FIGS. 78A and 78B;

FIGS. 78A and 78B are electrical schematics of a second embodiment of the amplifier stages that may be implemented according to the present invention in the buffer cards shown in FIGS. 22 and 23;

FIGS. 79A, 79B, 79C, and 79D are cross-sectional side views of an optical bio-disc showing a method of detecting investigational features in a test sample.

Figure 82:
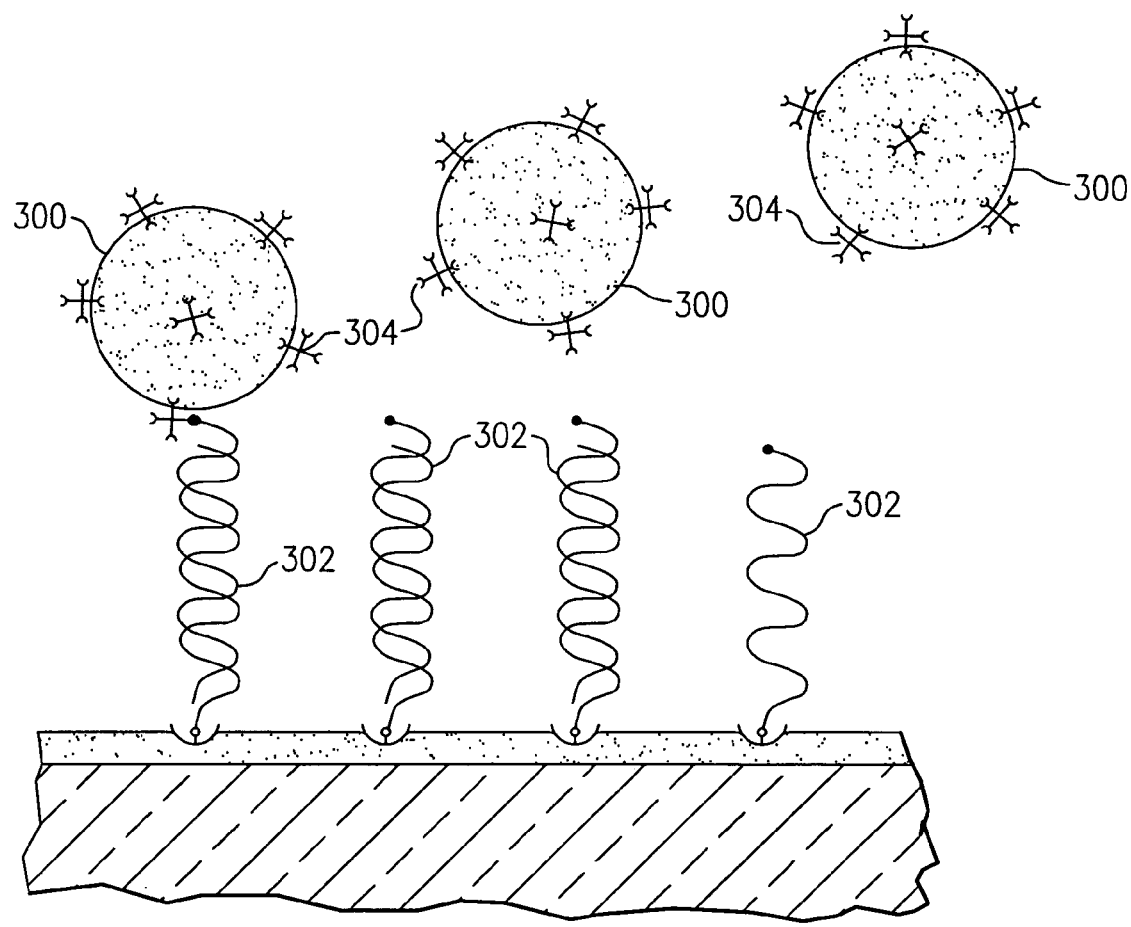
Figure 83A:
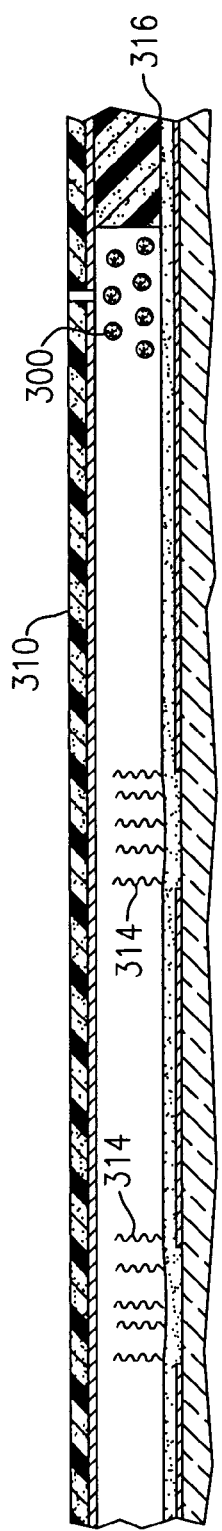
Figure 83B:
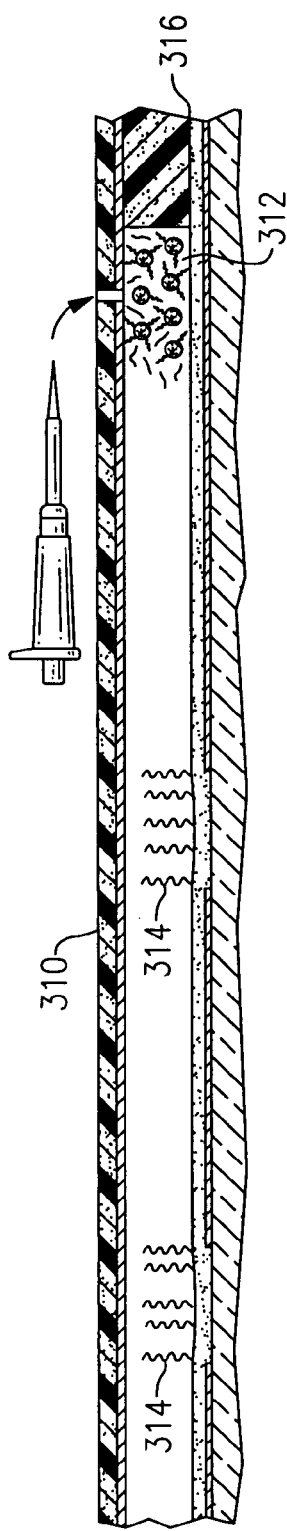
Figure 83C:
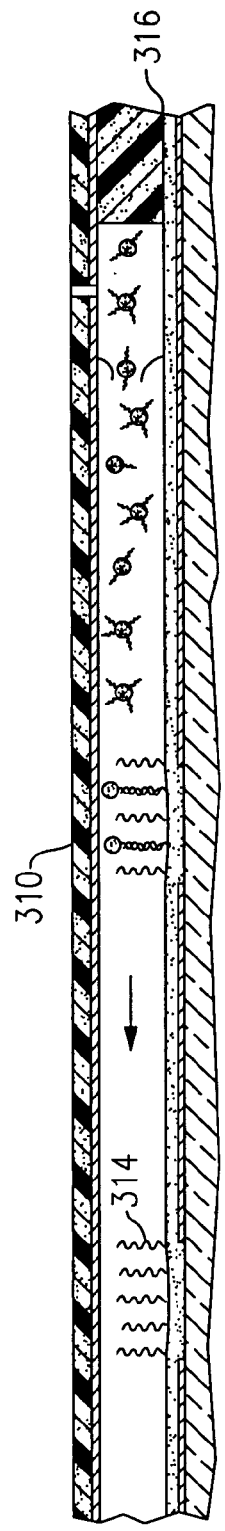
Figure 83D:
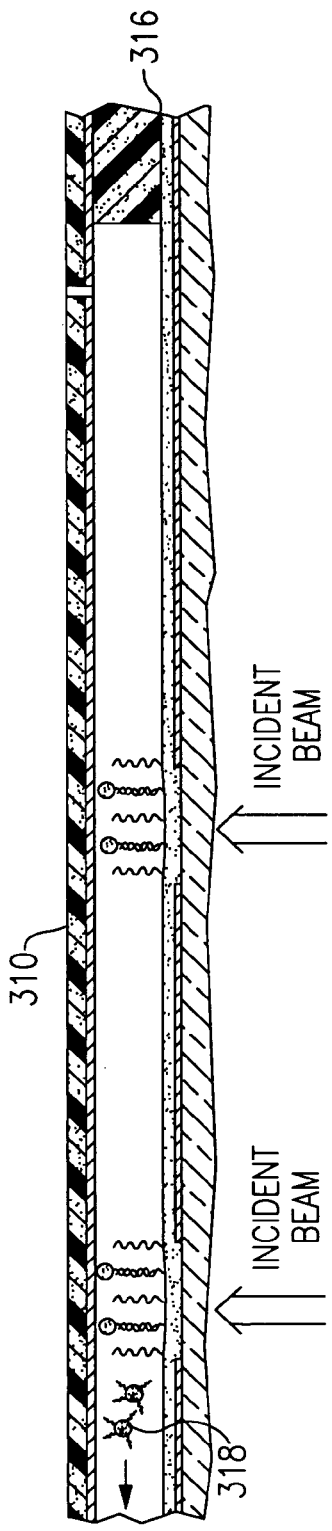
Figure 84:
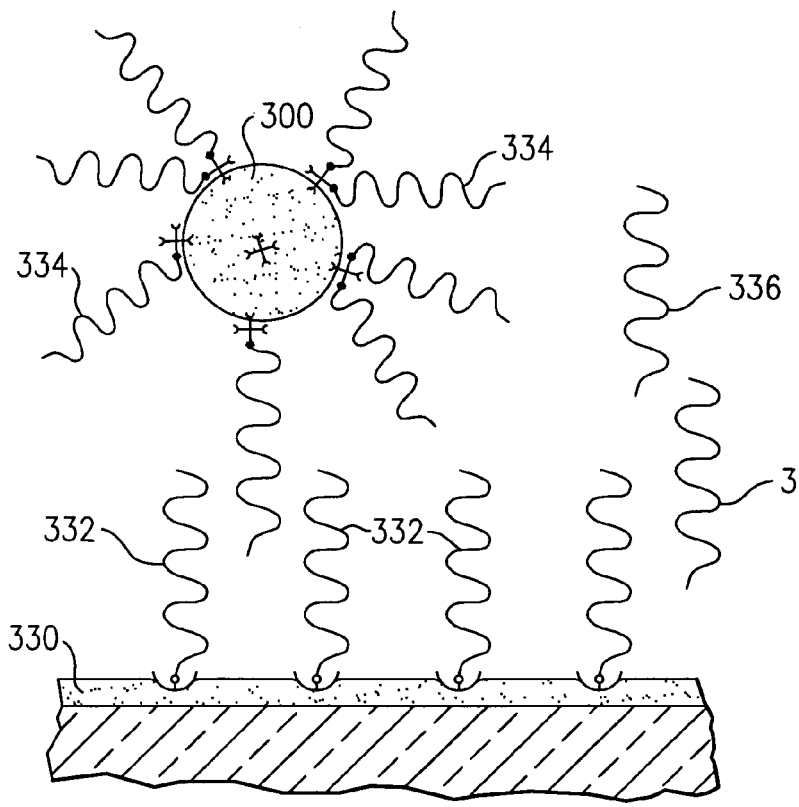
Figure 85:
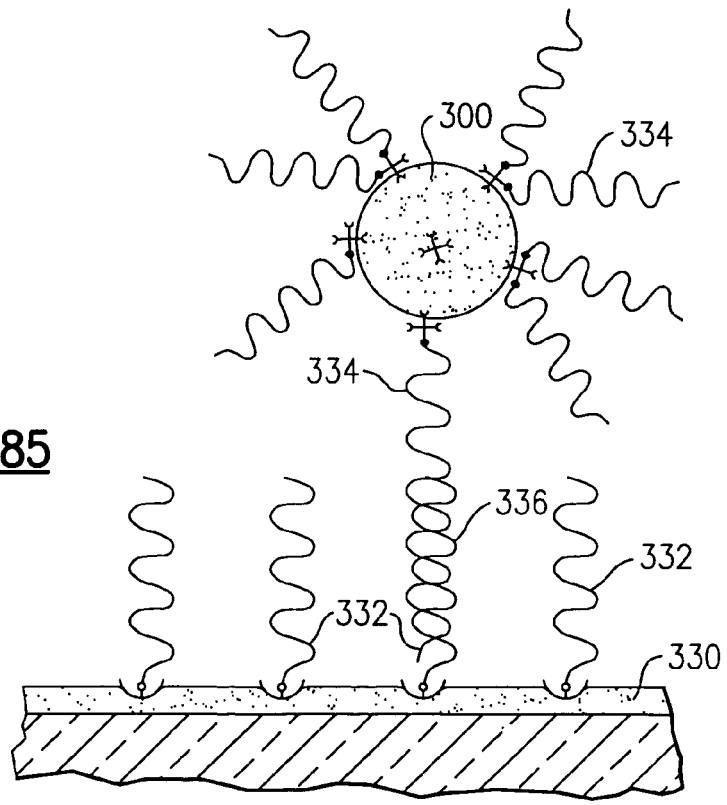
Figure 86:
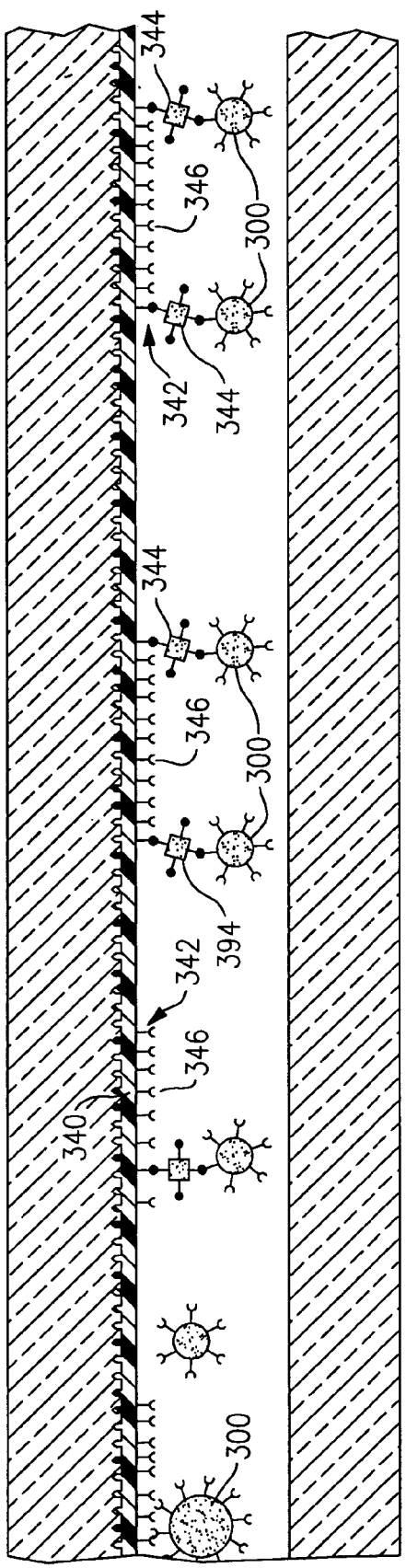

FIGS. 80A, 80B, 80C, and 80D are cross-sectional side views of an optical bio-disc used in a mixed phase assay to detect investigational features in a test sample;

FIGS. 81A, 81B, 81C, 81D, 81E, and 81F are cross-sectional side views of an optical bio-disc showing a method of detecting investigational features in a test sample using ELISA;

FIG. 82 is a detailed partial cross-sectional view of the surface of a bio-disc showing reporter beads having specific affinity for antigens bound to the surface;

FIGS. 83A, 83B, 83C, and 83D are cross-sectional side views of an optical bio-disc showing a method of using reporter beads to detect investigational features in a test sample;

FIG. 84 is a detailed partial cross-sectional view of the surface of a bio-disc showing use of reporter beads, capture probes, and signal probes to detect in-vestigational features in a test sample;

FIG. 85 is view similar to FIG. 84, showing hybridization of the investi-gational feature to the capture and signal probes; and FIG. 86 is a cross-sectional side view of a bio-disc showing use of antibody-coated capture zones to detect analytes of interest in a test sample.

DETAILED DESCRIPTION OF PREFERRED EMBODIMENTS

The present invention provides methods and an apparatus for detecting operational and investigational structures or features on an optical disc assembly without having to physically modify the processing circuitry and using a conventional disc drive. According to one embodiment of the present invention, one or more signal processing circuits within the conventional disc drive is programmably configured to function as an analog-to-digital (A/D) converter. The A/D converter is used to detect an electronic profile associated with investigational features and structures disposed on a surface of the optical disc assembly. The profiles may be used to determine the relative size, composition, and location of the detected structures. Many different signals from the drive may be utilized to render the desired electronic profiles. Different electronic signals available within the drive may result in different electronic profiles, perturbations, or "signatures" for the same investigational feature. It should be understood, however, that each such signature or signal perturbation is unique and thus may be used as a separate and distinct indicator of the respective investigational feature under consideration. The conventional disc drive may then be programmably returned to its original operating configuration. Processing and imaging software both internal and external to the drive are discussed as related aspects of this embodiment of the present invention.

In accordance with another embodiment of this invention, and as an alternative to programmably configuring one or more signal processing circuits within the disc drive to function as an analog-to-digital (A/D) converter, an external AND converter with or without an external buffer card is employed. In these embodiments of the present invention, many different signals from the drive may also be employed to render the desired electronic profiles. As in the prior embodiment, different electronic signals available within the drive may result in different electronic profiles, signal perturbations, or "signatures" for the same investigational feature. It is also understood relative to this embodiment of the present invention, that each such signature is unique and thus may be used as a separate and distinct indicator of the respective investigational feature or attribute thereof under consideration. Processing and imaging software are also related aspects of this embodiment of the present invention.

The electrical characterization of light as it enters an objective assembly of an optical disc drive can be utilized to create multi-dimensional images of investigational features on an optical disc. An optical bio-disc can be designed to facilitate the gathering of data and the creation of the image.

An optical disc drive may be utilized as an optical disc imaging device to produce multi-dimensional images from a signal element (i.e., a specimen to be imaged) in an optical disc assembly. The energy reflected from the surface of an optical disc or optical disc assembly is gathered on the photo detector in an objective assembly and utilized to reproduce a multi-dimensional image. The optical disc properties (mechanical, logical, and optical) and the optical device properties may be optimized to produce high-resolution multi-dimensional images that in some ways distinctly characterize the signal element.

The objective assembly and the optical detector of an optical disc drive can be adjusted to facilitate the collection of high-resolution images of investigational features on the surface of an optical disc. The quad detector inside the objective (or within the optical path of the objective lens) is often organized as depicted by 18 in FIG. 4.

Figure 4:
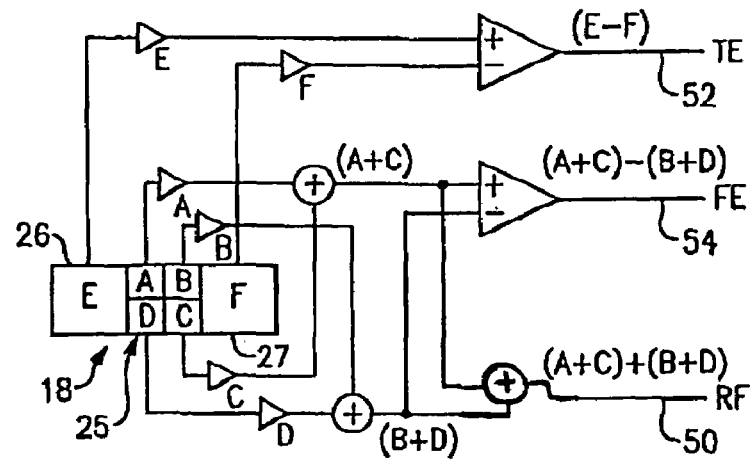
FIG. 4 is a schematic representation of an optical disc detector and associated electronics that use three beams for tracking, focusing, and reading.
Figure 8:
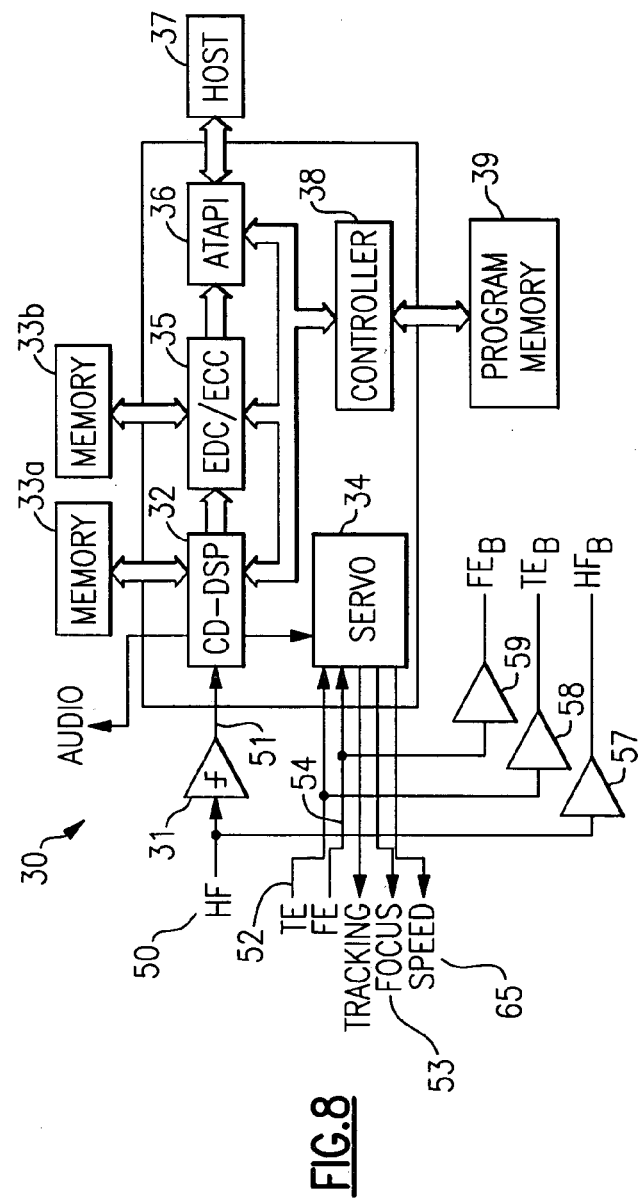
FIG. 8 is a block diagram of a chip set of a generic optical disc reader, modified according to one aspect of the present invention to monitor signals for determining the presence of investigational features or structures on an optical analysis disc.

With reference now to FIG. 8, chip set 30 of FIG. 4 can be supplemented relative to its original configuration by the addition of tap buffers 57, 58, and 59. These tap buffers provide access to unprocessed analog signals such as HF signal 50, TE signal 52, and FE signal 54, respectively, produced by detector 18, thereby permitting external instrumentation to receive these signals without interfering with normal drive operation.

An alternative modification is the addition of tap buffers to allow the unprocessed signals A though F from detector 18 to be processed by external instrumentation or additional circuitry. From these signals, the HF, TE, FE, or any other combination can be formed. Also, any additional detectors available can provide useful signals in this same manner (e.g., G and H detectors in current state-of-the-art drives). Certain drive circuit designs and detector/amplifier devices allow connection of the instrumentation or additional circuitry directly to the detector without the need for the tap buffers.

Referring next to FIG. 9, there is shown an optical disc drive 140 according to the present invention. Optical disc drive 140 has disc tray 168, which is adapted to receive a disc 130 of a type designed to accommodate a wide variety of investigational features. Disc 130 may be an optical bio-disc such as those disclosed in commonly assigned U.S. Provisional Application Nos. 60/252,726 entitled "Bioactive Solid Phase for Specific Cell Capture and Optical Bio-Disc Including Same"; 60/249,391 entitled "Optical Disc Assembly for Performing Microscopy and Spectroscopy Using Optical Disc Drive"; and 60/257,705 entitled "Surface Assembly for Immobilizing DNA Capture Probes and Bead-Based Assay Including Optical Bio-Discs and Methods Relating Thereto."

Known optical disc drives are often packaged within a case that includes both the optical disc drive 140 and one or more processing circuit boards as discussed herein. The basic optical disc drive (e.g., optical disc drive 140) provides a variety of signals derived from the optical disc. For example, most optical disc drives provide an HF signal 50 as a basic information signal. Such drives also provide a tracking error signal (TE signal) 52, a focus error signal (FE signal) 54, and basic signals from the sensing or laser photo detectors often referred to simply as the A, B, C, D, E, and F signals. In a known type of optical disc drive, these signals are processed in a processing circuit board to provide any correcting signals that may be needed to operate the optical disc drive or derive information signals from the optical disc. Such a processing circuit board is frequently packaged within the optical disc drive and may include, for example, a programmable signal processor, as discussed herein.

FIG. 9A shows five implementations of the present invention. These are identified as implementations I, II, III, IV, and V, respectively as illustrated. It should be understood that each implementation might have several embodiments, all of which accomplish the objects of the present invention.

In an embodiment of implementation V of the present invention, the unprocessed HF signal 50 is tapped from the optical disc drive 140 and directed to a modified personal computer or PC 142. Persons skilled in the art will appreciate in light of these teachings that modified PC 142 may be any suitably adapted and programmed processor, microprocessor, application specific integrated circuit (ASIC) or the like. The modified PC 142 includes software and hardware for processing the HF signal generated from the read beam of the optical drive 140 which is modulated as a function of encountering one or more investigational features on or in any one or more of a number of different layers, substrates, or surfaces forming disc 130. The same read beam is also modulated in a conventional manner by encountering or reading operational features in disc 130. Such operational features typically include pits and lands as in a pre-recorded CD-like disc or marks and spaces formed by dyed and undyed areas in a recordable disc such as a CD-R. The pits and lands, or marks and spaces, embody encoded information in the nature of data, program, video, and/or audio according to any one of a number of schemes for encoding such information.

With modified PC 142, the optical disc drive 140 preferably includes a buffer amplifier (not shown for clarity) to provide an amplified replica of the HF signal so that the actual HF signal is not distorted by being excessively loaded. The amplified replica of the HF signal (or the actual HF signal itself, if need be) is coupled to modified PC 142 by a cable. The software and hardware for processing the HF signal in the modified PC 142 includes an analog-to-digital converter (ADC) as part of modified PC 142, preferably a data acquisition board or module that includes a suitable ADC (e.g., with sample rates from 8 MHz to 40 MHz). The ADC digitized sampled data is stored in the PC's RAM, and processed by the PC under control of the PC's software.

Modified PC 142 may advantageously include a keyboard 144, a monitor 146, and speakers 148. After the modified PC 142 processes the raw HF signal in a desired manner, characteristic aspects of the investigational feature (as discussed below) may be displayed on the monitor 146. The monitor 146 and speakers 148 may also be employed to display conventional video or audio encoded on disc 130. Implementation V of the present invention will be hereinafter referred to as the "modified PC implementation" for purposes of convenience and clarity.

In an embodiment of implementation III of the present invention illustrated in FIG. 9A, the optical disc drive 140 is packaged with a processing circuit board that includes a programmable DSP 32 (similar to the DSP in FIG. 8) and an analyzer 154 that operates in combination with a PC 158. PC 158 includes software, and hardware controlled by the software, implemented to accommodate analysis of investigational features. Analyzer 154 may include another programmable DSP, a programmable microprocessor, application specific integrated circuit (ASIC) or the like implemented to perform functions in support of a biological, chemical, or biochemical investigation. Programmable DSP 32 includes an ADC to digitize the HF signal (or other signal). Analyzer 154 may simply provide a count of the number of times a voltage level exceeds a threshold. Alternatively, analyzer 154 may identify voltage variations (e.g., double peaks, etc.) or other waveforms that are characteristic of investigational features. In any event, programmable DSP 32 performs the highest bandwidth functions, PC 158 performs the lowest bandwidth functions, and analyzer 154 performs functions of intermediate bandwidth. Persons skilled in the art will appreciate in light of these teachings that functions of analyzer 154 may be subsumed into the capabilities of programmable DSP 32, PC 158 or both. Persons skilled in the art will also appreciate in light of these teachings that PC 158 may be any suitably adapted and programmed processor, microprocessor, application specific integrated circuit (ASIC) or the like. Aspects of this alternative implementation are described in further detail herein below. For purposes of convenience and clarity, implementation III of the present invention will hereinafter be referred to as the "DSP implementation."

According to an embodiment of implementation I of this invention, a tap-off of the HF signal, as buffered by the tap buffer 57 shown in FIG. 8, from drive 140 may be directed to an external analog-to-digital converter 150 (ADC 150) as shown in FIG. 9A. As with the modified PC embodiment, the optical disc drive 140 preferably includes buffer amplifier 152 to provide an amplified replica of the actual HF signal so that the actual HF signal is not distorted by being excessively loaded. The amplified replica of the actual HF signal (or the HF signal itself, if need be) is coupled to ADC 150. Alternatively, any one of a variety of different signals or signal combinations (e.g., the TE and FE signals or the A, B, C, D, E and F signals) may be tapped off of the drive 140 as illustrated. Aspects of this alternative implementation are also described in further detail herein below. For purposes of convenience and clarity, this embodiment of the present invention will hereinafter be referred to as the "A to D embodiment" of implementation 1. The A to D embodiment may be modified to include external buffer amplifier card 152 illustrated as implementation 11 in FIG. 9A.

With continuing reference to FIG. 9A, implementation IV of the present invention illustrates that the audio output of the optical disc drive 140 (i.e., the audio signal) may be utilized, modified, or augmented to produce a sound when the interrogation beam of the drive encounters an investigational feature or attribute. For example, a disc may be pre-recorded with digital silence yet a sound is produced when the read beam "reads" or detects an investigational feature. In this manner, different investigational features may produce discernibly different sounds or tones. Alternatively, the disc may include a sound track that would be interrupted by the formation or presence of an investigational feature blocking the encoded sound information. These embodiments of the present invention may be generally grouped into three different categories, approaches, or techniques. The first includes using the existing sound card that is currently available and usually packaged in many drive assemblies, for example, an audio CD player. Such a sound card generally produces an analog sound signal, but may also give access to a digital signal representative of the sound. The second approach is directed to internally modifying the audio circuitry that exists in such current drive assemblies to provide the analog or digital signal. The third alternative approach or technique according to the present invention, is to provide an external sound module (depicted as audio processing 156 in FIG. 9A) that interfaces with the disc drive assembly 140, processing software, and an audio output device such as the pair of speakers 148. Implementation IV of the present may generally be referred to as the "audio" implementation.

All of the different implementations illustrated in FIG. 9A, except the modified PC implementation (V), would typically include a conventional PC 158 for functionality described in further detail below. The modified PC implementation would inherently include a PC, and would be modified as to its inputs. However, persons skilled in the art will appreciate in light of these teachings that PC 158 may be any suitably adapted and programmed processor, microprocessor, application specific integrated circuit (ASIC) or the like.

Commonly assigned U.S. patent application Ser. No. 09/421,870 entitled "Trackable Optical Discs with Concurrently Readable Analytic Material" (hereinafter the '870 application) discloses coupling an oscilloscope to the HF or RF signal for detecting the dual peak profiles associated with investigational structures while acquiring the encoded information needed to operate the disc drive. These peaks appear as a result of changes in reflectance as the light beam traverses investigational structures or reporters on the optical disc surface. Such electronic profiles may be advantageously used to detect and discriminate among structures under investigation.

An embodiment of implementation 11 shows an analog-to-digital (A/D) converter 150 (ADC) connected to the HF signal through buffer 152. Implementation II may, for example, determine the number of dual peaks encountered (and thus the number of investigational structures or reporters) on any portion of the optical disc. ADC 150 forms digitized samples of the analog HF signal (or other suitable signal), and forms the samples at a sample rate fast enough to capture the characteristics of the peak profiles that are associated with the investigational structure. The magnitude and/or duration of the digitized peak signals may be interpreted by an associated application program to determine the relative size, composition, and location of the detected structures.

Operational Functions

Figure 6:
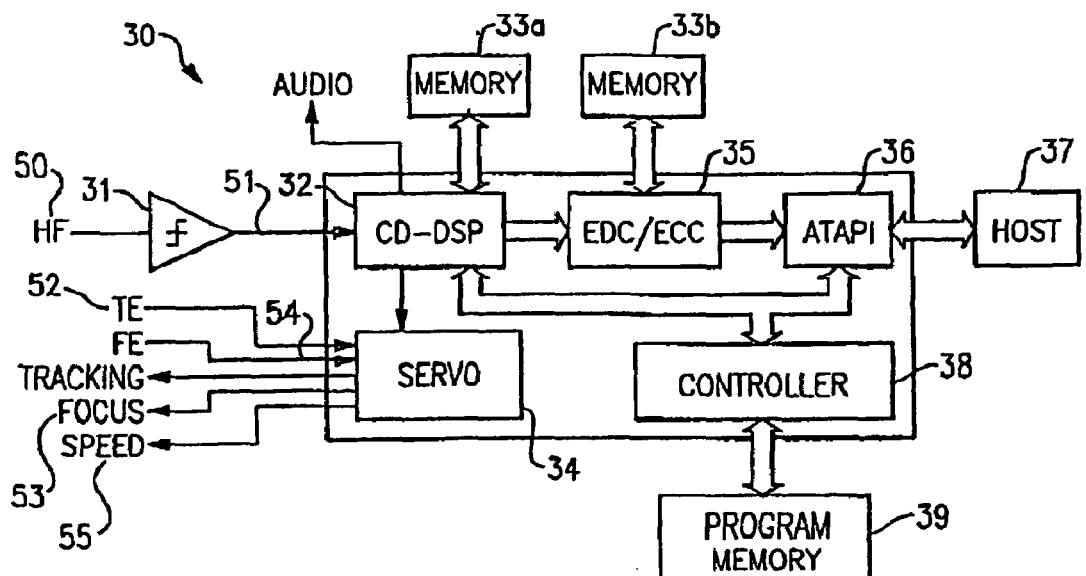
FIG. 6 is a block diagram of a known optical disc reader.
Figure 7:
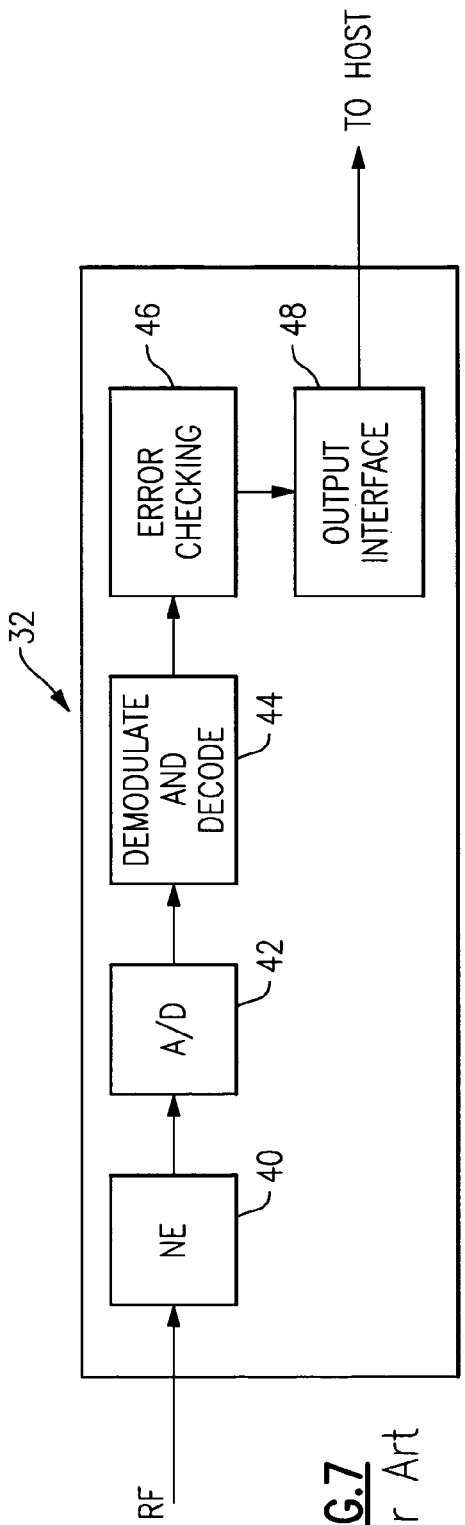
FIG. 7 is a functional block diagram of a conventional digital signal processing circuit.

Light gathered, reflected, or generated from operational features on disc 130 (FIGS. 9A and 12) and processed by components in objective assembly 10 (FIG. 1) are projected onto detector 18 and create electrical signals that are used by servo circuitry 34 (FIG. 6) to provide operational function to the drive. These patterns provide information that allows objective assembly 10 to focus above a focal plane in disc 130 and track operational features (e.g., pits, grooves, lands) that allow objective assembly 10 to be moved along the information tracks associated with the operational surface of the disc assembly.

The operational functions of a drive and the signal that directs the drive to perform those operational functions may be utilized to reproduce a multi-dimensional image. These operational functions include, but are not limited to, focusing, tracking, and synchronization. The sum of all of the energy reflected and/or created from the interaction of the signal element with the light emitted from the objective assembly is often referred to as the HF (high frequency) or RF signal. If the photo detector in the objective assembly is organized in a quadrant (as depicted by 18 in FIG. 4), then the signal is referred to as the quad sum signal. This summed signal contains most of the information necessary to reproduce the image through algorithmic manipulation. The other components of the photo detector will produce signals that may be independently measured to produce additional information or operational signals. For example, the energy gathered in the quad detector of an optical disc drive may be organized to produce operational functions as follows:

$A+B+C+D$=HF or Quad Sum (provides sync. for pits)

$A+D-(B+C)$=Tracking (push-pull technique) (sync. for grooves)

$A+C-(B+D)$=Focusing (astigmatic technique)

$E-F$=Tracking (outrigger technique)

These photo detector component signals may be used independently or in any combination to produce characteristic information about the signal element or signal elements. In most embodiments an algorithmic interaction is necessary in software to reproduce characteristic imaging. The quad detector is the most common in the current market, however a detector distribution that contains more than 4 to 6 components may also be used to enhance characterization. Also, the optical path may be configured in the device to provide signal characterization with coherent, partially coherent, or non-coherent light.

Signal responses may be gathered directly or indirectly from the operational signals in the optical disc drive. In one embodiment of the imaging aspects of this invention, an operational signal is directly amplified, digitized, or sampled (bit resolution, sampling rate) and then algorithmically adjusted through software to produce a characteristic image of the signal element. The operational signals may also be electrically manipulated before or after they are digitized. An operational signal may be filtered, amplified, or summed with another signal component before it is digitized in order to produce a characteristic, non-random, or correlative response. For example, a signal may be measured or characterized by an external electrical manipulation such as a signal analyzer. A signal may show a non-random, correlated event when its response is filtered, amplified, or mathematically combined with other signals (e.g., asymmetry, push pull, cross-talk, radial noise, etc.).

Signals produced from investigational or non-operational features may also be utilized independently or in combination to produce characteristic images of the investigational feature under study. The signal and logical responses produced by the optical disc drive may also be used to reproduce a characteristic of a signal element or investigational feature. This is somewhat different than the utilization of the signals performing the necessary operational characteristics. A digital signal, analog signal, logical response, optical response, or mechanical response may be gathered from an optical disc drive to characterize the signal element or investigational feature. For example, a signal element with a specific optical or physical property will interact with light in such a way that a characteristic energy pattern or energy distribution is created. This characteristic distribution or pattern on the photo detector may be monitored and measured as a response without adversely affecting the operational functions of the drive.

Figure 9B:
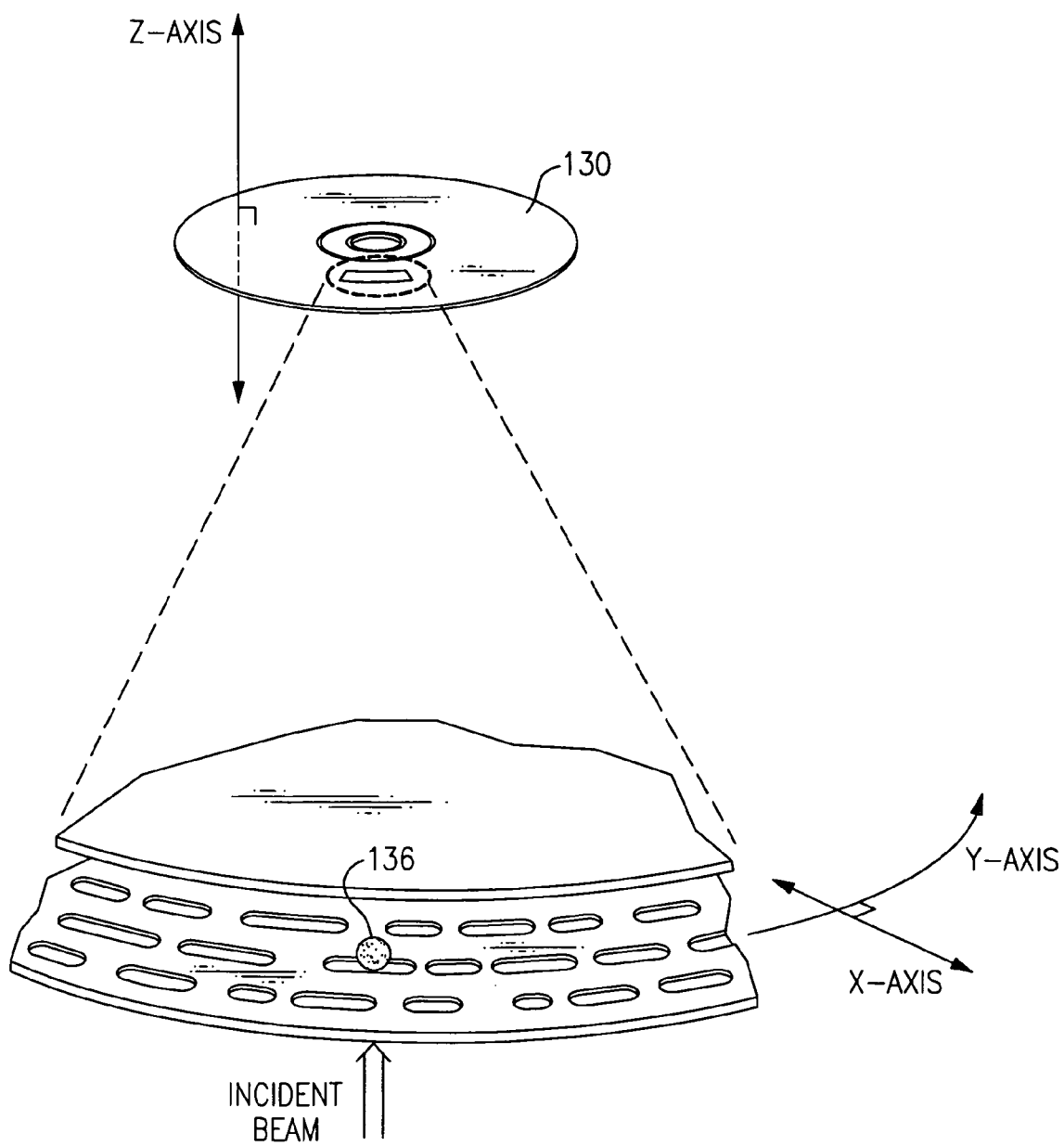
FIG. 9B is an enlarged detailed perspective view of the section indicated in FIG. 9A showing a coordinate reference system used for purposes of 3 dimensional orientation.

In one exemplary embodiment, an objective assembly in an optical disc drive will interface with the operational features on a surface of an optical disc assembly. This interaction may include the support of all of the operational functions or it may include the suspension of one or more of the operational functions in a predefined "Zone" of the disc. The interaction of the incident beam from the objective assembly with the operational surface and investigational features will produce signal responses in the HF signal, the tracking signal, and the focusing signal. The focusing signal including operational information and information about characteristics of an investigational feature, may be used with an electrical servo circuit to support a response to the movement of the objective assembly within a direction that we will refer to as the "Z" direction, as shown in FIG. 9B. The tracking or push-pull signal may be used with an electrical servo circuit to support a response to the movement of the objective assembly in a direction that we will refer to as the "X" direction illustrated in FIG. 9B. The HF signal, DPD signal, or quad sum components may be used to support a response to the movement of the objective assembly in a direction that we will refer to as the "Y" direction. In this way we can gather a 3-dimensional (XYZ) response from the interaction of the incident beam with a signal element or investigational feature 136 by using standard operational responses of the objective assembly.

The signal element or investigational feature 136 covers an area in the disc that interacts directly or indirectly with an operational feature that provides a tracking signal. The signal element may be distal relative to the operational features such as, for example, in a transmissive or semi-reflective disc as described below in further detail. Alternatively, the signal element may be removed from areas having full operational functionality such as in a separate "Zone" or "mirror band" formed in or on the disc wherein at least some of the operational functionality has been removed. The signal element may be on a focal plane that is physically removed from an interference pattern producing other operational signals (focus and/or tracking and/or sync.) The signal element should provide a measurable contrast or energy distribution. This contrast may be provided by the difference between the reflective properties of the operational structure (focal plane) and the reflective properties of the signal element.

The signal element or investigational feature may be less reflective than the operational plane thus providing a decreasing energy sum to the photo detector. The signal element may have the same or similar reflective properties as the operational plane (or focal plane) but provide a diffractive or phase cancellation, or phase enhancement, response that provides a decreasing signal level in the photo detector. The signal element may be more reflective than the operational plane thus providing an increasing signal level in the photo detector sum signal. The design of the optical disc drive and the design of the optical disc assembly operational features may be enhanced to optimize imaging capabilities.

The operational plane that provides a focal plane can be designed to provide maximum contrast or enhancement to the laser/signal element interaction. As would be understood by one of ordinary skill in the art, focal plane includes the point of greatest reflectively at any particular time during laser focusing. If the focal plane is more reflective than the signal element or investigational feature, then it is desirable to enhance the interference or phase contrast characteristics of the design. If the focal plane is less reflective than the signal element, then it is desirable to enhance the reflectivity and linear signal response of the signal. The focal resolution is dependent on the wavelength of the laser in the objective assembly, the numerical aperture of the focal lens, the bandwidth of the focusing servo loop, and the optical properties of the optical disc assembly.

In the design of the disc system according to the present invention, it is important to create strong signal recognition patterns that differentiate operational function from signal element characterization. The light reflected, absorbed, or transmitted through the disc should characterize the signal element with as much detail and magnitude as possible.

The response in the reflected or transmitted light can be influenced by the signal element in many ways. The signal element itself can also be designed with the operational characteristics of the disc to provide a high degree of contrast in the transmitted or reflected light. The energy level, energy distribution, and polarization state of the light can be influenced by the design of the signal element and its relationship to the optical properties of the focal plane in the disc.

One embodiment directed to signal element selection and design, is to create a signal element that has a reflectivity that is vastly different from the reflectivity of the focal plane of the disc. The reflectivity of the signal element is thus designed to be very high or very low in comparison to the reflectivity of the disc. This will produce a high amount of signal contrast and a strong characteristic signal.

The difference in reflectivity between the focal plane and the signal element can be generated in many ways. These include, but are not limited to, the following:

1. The material in the signal element can have a lower or higher reflectivity and thus produce a lower or higher signal level than the surrounding plane of the disc.

2. If the signal element is smaller than the beam size, an interference pattern is created and the size of the signal element can create a destructive or additive component to the signal.

3. The signal element may be activated by an energy source that creates a state condition that results in a lower or higher reflectivity than the surrounding area (phase change materials).

An alternative embodiment directed to signal element selection and design involves the use of materials and states that interfere with the polarization state of the light transmitted or reflected through the disc. The signal element can be designed to have an optical or magnetic property that has a contrasting effect on the polarization state of the light interacting with the disc assembly. There are many ways that this embodiment can be created in the disc. These include, but are not limited to, the following:

1. A signal element can be designed that is transparent but birefringent or diChroic in nature. The optical components of the detector will transmit, reflect, or absorb the resulting signal based on its state.

2. A signal element may be designed to produce a magnetic orientation that provides a contrasting polarization state in the light.

A third group of embodiments directed to signal element selection and design involves the use of optical or interference properties that interfere with the energy distribution of light that is transmitted or reflected through the disc. The signal element can be designed to diffract the light in such a way that it creates a higher energy response from a non-intrinsic detector. A measurable or detectable contrast is provided in the resulting signal by the area of light on the surface of the detector.

A fourth group of embodiments directed to signal element selection and design involves the use of chemical luminescence. The signal element or surface of the disc can be designed to emit energy in a secondary active state. This involves, for example, the use of fluorescent or phosphorescent markers or dyes applied to the signal element and/or an appropriate disc surface. Suitable signal elements for this group of embodiments include, but are not limited to, beads and cells such as blood cells, for example. The state is activated by the incident energy on the disc assembly. A contrasting energy is thereby created and exists in the transmitted or reflected return signal.

The present invention is thus directed to an optical analysis disc for detection of a signal element. The disc preferably includes a substrate layer and an operational layer associated with the substrate layer. The operational layer has operational information encoded therein. According to this aspect of the present invention, the analysis disc further includes a signal element positioned relative to the operational layer. The signal element and the operational layer have optical or magnetic characteristics selected to provide a predetermined contrast therebetween to thereby provide a return signal indicative of distinctions between information associated with the operation layer and characteristics of the signal element.

Incident Light

Figure 1:
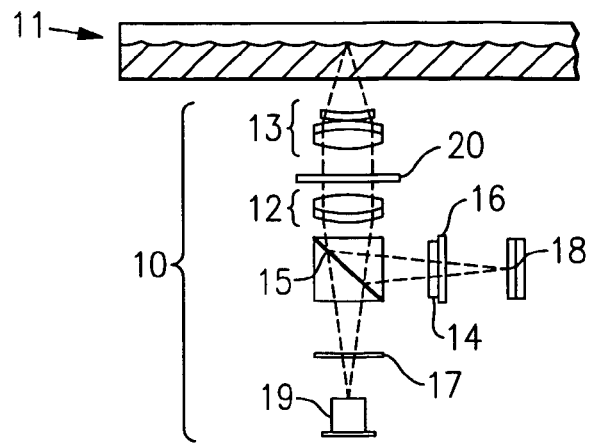
FIG. 1 is a cross-sectional view of typical single-layer CD or CD-like disc and a schematic representation of a reader associated therewith.
Figure 2:
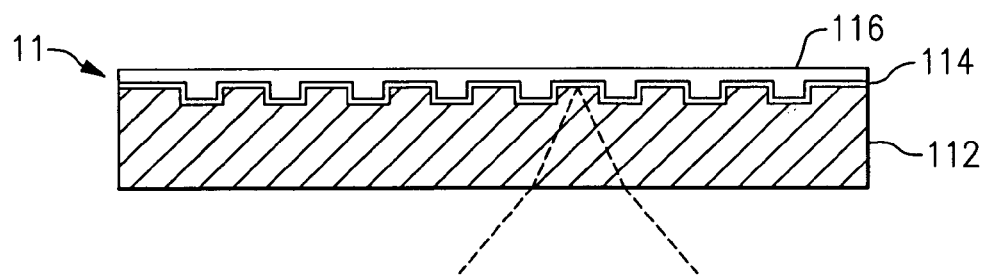
FIG. 2 is a side cross-sectional view of the disc shown in FIG. 1 at greater magnification.

The wavelength of light emitted by laser (i.e., light source 19 FIGS. 1 and 12) utilized in objective assembly 10, FIG. 1, of the optical disc drive will have an effect on the resolution of the optical disc system. In theory, the smallest signal element or investigational feature that may be detected by an objective assembly (at the element/laser interface) with a wavelength $\lambda$ will be $\lambda/2NA$, where NA is the numerical aperture of the objective lens. At any instant in time, the investigational feature or signal element, at the laser/plane interface may be larger or smaller than the field that is covered by the beam at or near the focal point. A signal element that is larger than the laser beam coverage at the laser/signal element interface will produce more characteristic signals than a signal element that is smaller than the laser coverage.

The wavelength of the laser should be as small as possible to enhance the resolution of the signal response. This will result in greater detail and characterization capabilities for smaller signal elements and investigational features. Shorter wavelengths produce smaller focal spots on the focal plane of the optical disc assembly. Therefore, a shorter wavelength will produce a higher spatial resolution in the imaging device. An objective assembly with a high numerical aperture will provide less focal distance and greater diffraction capability.

The drive should have very little mechanical or electrical influence on the signal response or signal consistency of the laser/signal element interface. In certain circumstances, the drive operation may have an influence if designed to do so (e.g., electrical coupling, sync enhancement, signal gain control settings AGC, signal power level setting).

Extracting Information from an Optical Disc

Figure 10:
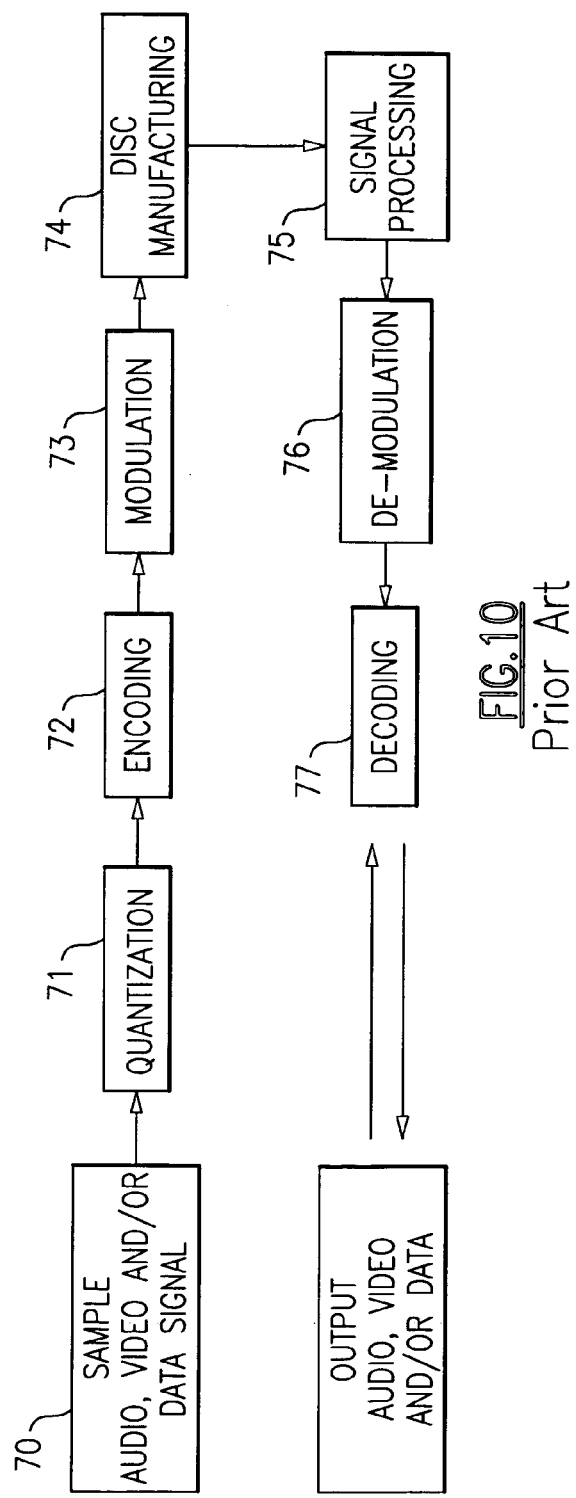
FIG. 10 is a flow chart depicting a known process for fabricating optical discs and then later reading the optical discs.

Referring now to FIG. 10, the conventional process of encoding video, data, or audio information such as music on a disc and then later decoding signals from the disc to recover the audio, video, or data is illustrated. The audio, video, or data signal is sampled at block 70, quantized at block 71, encoded into a standard format at block 72, and modulated onto a master disc at block 73. Replicated discs are then mass manufactured at block 74. In a disc reader, signals derived from a manufactured disc are processed through a signal processor at block 75, demodulated at block 76, then decoded at block 77 to recover the original audio, video, and/or data. This output is then displayed on a monitor and/or played on a pair of speakers for a user's use and enjoyment.

Figure 11:
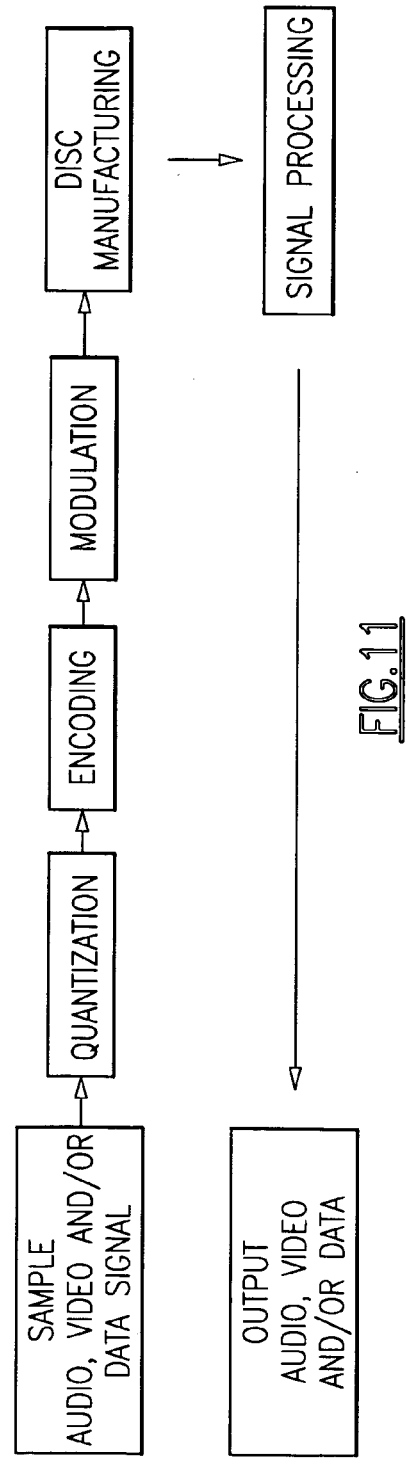
FIG. 11 is a modified path for decoding optical discs according to the present invention.

With reference next to FIG. 11, an optical disc decoding system is shown modified in such a way that some functionality in the system is removed. The path is modified to remove the Demodulation and Decoding operations (blocks 76 and 77 of FIG. 10) and provide a raw digitized signal to a computer to effectively characterize a group of signal elements of investigational features on a surface of the optical disc assembly.

In addition to pre-recorded optical discs, a variety of recordable optical discs are currently available. A recordable master includes a variety of operational features that are designed for use during the recording operation and not the reading operation. Table 1 below summarizes these operational differences.

TABLE 1

| Disc Type | Function | Recording Properties | Reading or Playback Properties |
|---|---|---|---|
| CD-R CD-RW | Focus | Surface Properties | Surface Properties |
| | Tracking | 22.05 KHz Wobble Groove | Pits or Marks |
| | Synchronization (speed control) | 22.05 KHz Wobble Groove | Pit Patterns (Marks) |
| DVD-R DVD-RW DVD-RAM DVD + RW | Focus | Surface Properties | Surface Properties |
| | Tracking | 140 or 160 KHz Wobble Groove | Pits or Marks |
| | Synchronization (speed control) | 140 or 160 KHz Wobble Groove | Pit Patterns (Marks) |

As indicated above, the decoder or servo system of a CD, CD-R, or DVD player can be used to provide a count, correlation, or characterization of a chemical response in the focal or operational feature plane of a disc. Other responses or raw signals from the drive chip set that quantify the signal magnitudes from an investigational feature or signal producing element include the high frequency signal (HF) (AC or DC coupled), the tracking error signal (TE), the focus error signal (FE), the Automatic Gain Control Setting (AGC), the push-pull tracking signal ((B+C)−(A+D)), the CD tracking signal (E−F), the CD-R tracking signal ((A+D)−(B+C)), the focus signal ((A+C)−(B+D)), the differential phase detector signal (DPD) ((A+B)−(C+D)), the power monitor signal from the back of the laser, and the audio signal. Additional signals, which may be employed with the present invention, include the individual signals from the quad detector, A, B, C, and D, or side detectors E and F.

A trend in current conventional drives is to use a high-density photo detector array in place of the typical quad detector. The methods of the present invention may also be advantageously utilized in conjunction with such array detectors currently becoming available in the market. These arrays include, for example, individual signals A, B, C, D, E, F, G . . . . Z. Each of these signals, or combinations thereof, may be advantageously employed according to different embodiments of this invention to obtain the desired electronic profiles, signatures, or signal perturbations that uniquely characterize the signal element, investigational feature, or attribute of interest.

Imaging Techniques and Operational Features

The operational features and layout of the optical bio-disc assembly can be designed to optimize the imaging operation. The optical disc assembly may be further designed in specific areas or "zones" to enhance the detection and characterization of signal elements or investigational features and to provide higher signal resolution with specific laser interface properties.

The operational features most often provide tracking signals that allow the objective assembly to move from the inner to the outer area of the optical disc assembly. A smaller track pitch, or spacing between the operational features, will yield a greater resolution because of the corresponding increase in the number of responses associated with the investigational feature. By providing an operational feature that is smaller than the signal element and a track pitch that is comparable to the signal element, multiple electrical scans can be gathered from the laser/signal element interaction. The number of potential scans of a signal element at a fixed position on or near the operational plane (focal plane) is increased as the track pitch is decreased. The accuracy with which the location or position of the investigational feature or signal element on the disc can be resolved, is increased as the operational features are made smaller given a fixed signal element size. This location accuracy is herein generally referred to as "positional resolution". This holds true with a consistent objective assembly/operational feature interface. The typical track pitch for a CD is 1.5–1.7 µm, for a DVD is 0.73–0.75 µm, and for a DVD-RAM is 0.35 µm.

The operational features also provide synchronization information that affects the speed of rotation of the disc and thus the duration during which the laser interacts with the signal element. Lower speeds produce higher quantized resolution in the digitization of the signal by the A/D converter. This increases the sampling resolution of the system. As the rotational speed is increased, the sampling frequency and bit resolution must be increased in a corresponding manner to achieve a consistent sampling resolution. The typical track speed for a CD is 1.2 m/sec, and for a DVD is 3.49 m/sec.

The optical disc assembly or a section of the optical disc assembly may be designed specifically for imaging. A disc with a slow rotational speed, a tight track pitch, and an optimized focal plane will provide an exceptional response for imaging purposes. An optimal disc or disc component design would also include logic to provide random access to preaddressed investigational locations of positions on the disc. The logic may be encoded in the operational features of the disc or alternatively formed by physical markings on the disc assembly. The logic may be designed to accommodate the investigational protocols for specific assays assigned to different zones on the disc. Such investigational protocols include, but are not limited to, sampling rate, bit resolution, rotational speed, focus and tracking off-set, laser power, laser light wavelength, rotational direction, acceleration, deceleration, and any other system interactions required by a particular assay.

An optical disc system can be created with (1) operational features or tracking features having a very tight track pitch to facilitate the tangential resolution of the data gathered (e.g., DVD-0.74 µm); (2) logic and hardware that provide for land/groove or land/pit tracking, enhancing the tangential resolution (e.g., DVD-RAM or MO); (3) logic or operational features that provide for slower disc revolution speed (shorter pits or wobbled grooves) to provide higher signal detail; (4) disc or lens component thickness' that may be made to promote a smaller or larger spot on the focal plane of the disc assembly (the components to be imaged may be slightly out of the exact focal plane or they may provide a new focal position for the objective assembly); (5) hardware providing a lower wavelength laser to enhance resolution (e.g., DVD 635–650 nm, HD-DVD approximately 400 nm); (6) a sampling system that provides a higher sampling frequency or higher sample bit resolution to enhance the imaging; (7) software to provide the processing functionality of mathematical transforms or operational functions to derive approximations to the imaging; and (8) the disc or lens component positioned laser proximal to the feature that enhances the interaction of the light with the feature (e.g., an SIL-type component for manipulating the evenescent field).

In the imaging of an investigational feature as situated on an optical bio-disc, it is desired to produce any measurable contrast between the investigational feature or signal element and the focal plane. This desired contrast can be achieved by use of reflective signal elements or investigational features in combination with a less reflective focal or operational plane. Alternatively, the desired contrast can also be achieved by use of non-reflective signal elements or investigational features in combination with a more reflective focal or operational plane.

Optical Disc Drive and Related Disc Formats

The optical bio-disc may be implemented on an optical disc including a format such as CD, CD-R, or DVD or a modified version thereof. The bio-disc may include encoded information for performing, controlling, and post-processing the test or assay. For example, such encoded information may be directed to controlling the rotation rate of the disc. Depending on the test, assay, or investigational protocol, the rotation rate may be variable with intervening or consecutive sessions of acceleration, constant speed, and deceleration. These sessions may be closely controlled both as to speed, direction, and time of rotation to provide, for example, predetermined mixing, agitation, or separation of fluids and suspensions with agents, reagents, or antibodies. A disc drive assembly is employed to rotate the disc, read and process any encoded information stored on the disc, and analyze the liquid, chemical, biological, or biochemical component in any assay zone of the disc. The disc drive assembly may also be utilized to write information to the bio-disc. The recording may occur either before or after performing the assay or test.

According to another embodiment of the present invention, an optical disc drive chip set is employed as an A/D converter to sample a read beam and thereafter to identify investigational features and structures, and thereafter to characterize such features and structures as unique signal perturbations or electronic signatures. An optical disc decoding system may be modified in such a way that some functionality in the system is removed. The removal of specific features from the decoding path of an optical disc decoder will provide a raw digital signal that effectively characterizes and uniquely identifies investigational features positioned on the surface of the optical bio-disc, on a substrate within the disc, or residing within a chamber or channel formed as a fluidic element of the disc assembly.

According to another embodiment of the present invention, a conventional disc drive is employed to identify investigational features and structures. In this case, firmware modifications enable the user to monitor known signals within the disc drive, without the need to modify the electronics or hardware. The value of the AGC signal can be useful as a measuring tool. The AGC functionality tries to ensure that the analog output signal has a consistent range. If the disc drive is used to read binary data, only a high value and a low value are needed. In the case of investigational features, however, values may be desirable over a continuum of ranges. The AGC is high where the signal level is low, and vice versa. The AGC can thus be used as a signal that is representative of the light that is received by the detector, and therefore can be used for measurement and detecting changes in an investigational feature.

A CD-R player/recorder of this embodiment adds an adjustment lens to the objective assembly of a commercial optical disc player. A player/recorder that is designed for use in the consumer market for the recording of recordable CD discs can be utilized to detect microscopic structures. The drive is modified at the exit position of the objective assembly. A small refractive optical lens is added to the optical path of a CD-Recordable drive. This optical adjustment lens provides the necessary focusing and polarization characteristics to provide for standard operation of the CD-Recordable drive. The adjustment lens will adjust the focusing path and provide the necessary reflection to the diode laser to provide the desired spot size and energy distribution on the surface of the optical disc. The adjustment lens will provide a polarizing phase shift similar to the polarizing shift provided by the 1.2 mm polycarbonate layer in the construction of the optical disc. The characteristics of the adjustment lens can be changed to provide an optimal situation for the detection of bio-bits such as beads, cells, colloidal gold, carbon, or other microscopic markers and reporters associated with an optical disc. The adjustment lens is designed in such a way as to optimize the operational characteristics of each component in the optical path of an optical disc player/recorder.

A sampling system is designed and optimized to detect and characterize the electrical responses from the investigational structures and signal elements on the surface of the optical analysis disc. The sampling system monitors and delivers information from the servo control signals discussed previously. The information delivered will include qualitative and quantitative information.

The objective assembly of an optical disc player or recorder will send out a modulated or continuous wave laser pulse from a laser diode. It will record the reflected information from the surface of an optical disc on a combination photo detector and will generate four servo signals that provide for the operational requirements (i.e., tracking, focusing, synchronization, and power control). The microscopic structures can be detected and characterized from each, or a combination, of the electrical signals that are generated from the electrical servos. This includes, but is not limited to, the use of all tracking spots on a 3-beam outrigger system to detect and characterize features.

The focusing servo signal may be generated from at least 3 focusing techniques: critical angle focusing, Focault or knife-edge focusing, or astigmatic focusing. The tracking servo signal may be generated from at least 4 types of tracking techniques: one beam push-pull tracking, 3 beam outrigger tracking, Differential Phase Detection (DVD), or one beam high frequency wobble tracking. Synchronization is generated from at least three differing methods: bit clock synchronization or bit pattern sync, zoned clocking method (DVD-RAM), or wobbling groove synchronization. Power control is generated from more than 4 methods: power monitoring signal in PCA or CD-R disc, running power control method or real time power control of pulse diode, power or strategy adjustment, or optimum power encoded in wobble groove information. Logic is generated from over 40 known optical disc formats. Logic can perform position sensing, power control, radial and tangential location, layer sensing, density detection, multi-session usage as well as a wide variety of other functions.

The optical disc drive servos can be used to detect sizes of investigational features, signal elements, or various structures thereof. The movement of the laser across the bio-bit will result in a signal deflection in the optical disc tracking system servo signal and/or the optical disc focus system servo signal. The deflection in the electrical signal associated with a closed loop signal beam push-pull tracking system or 3-beam outrigger tracking system is used to characterize the bio-bit and can be processed as a quantifiable piece of digital or analog information. The deflection in the electrical signal associated with a closed loop 3-beam astigmatic or closed loop 1-beam Focault focusing system can be used to characterize the bio-bit and can be processed as a quantifiable piece of analog or digital information.

As the push-pull tracking system interacts with a spherical bio-bit, the optical assembly is moved in both the horizontal and vertical planes. The movement of the optical assembly in the horizontal plane will be toward the outer or inner radial direction. This will result in a positive or negative deflection of the electrical signal applied to the push pull tracking servo circuit. A low pass or band pass electrical filter may be used to determine the presence and characteristics of the bio-bit.

As the 3-beam outrigger tracking system interacts with a spherical bio-bit, the optical assembly will be moved in both the horizontal and vertical planes. The movements of the optical assembly in the horizontal plane will be toward the outer or inner radial direction. This will result in a positive or negative deflection or the electrical signal applied to the differential tracking servo circuit. A low pass or band pass electrical filter may be used to determine the presence and characteristics of the bio-bit.

An electrical circuit that is electrically isolated from the tracking servo loop can determine differences in the characteristics of the bio-bits. This electrical circuit may be a series of low pass or band pass filters that are used to isolate and characterize the frequency and magnitude of the deflections in the closed loop tracking system that are caused by the movement of the laser over the bio-bits. The size of the bio-bits can be characterized by the magnitude of deflection of the electrical tracking signal in the push-pull tracking system or the outrigger differential. tracking system. The size and shape of the bio-bits may also be characterized by the frequency of the deflection of the electrical tracking signal in the push-pull or differential tracking system.

Controlling Drive Functions

In order for the optical disc system to correctly operate it must: (1) accurately focus above the operational plane of the optical disc assembly; (2) accurately follow the spiral disc track or utilize some form of uniform radial movement across the disc surface; (3) recover enough information to facilitate a form of speed control (CAV, CLV, or VBR); (4) maintain the proper power control by logical information gathered from the disc or by signal patterns detected in the operational plane of the disc; and (5) respond to logic information that is used to control the position of the objective assembly, speed of rotation, or focusing position of the laser responsible for providing operational requirements.

An optical disc objective assembly performs three principal operational requirements by utilizing electrical and logical servos. An objective assembly thus provides an electrical signal to: (1) the focusing servo circuitry, (2) the tracking servo circuitry, and (3) the information processing circuitry. In the case of a CD recordable system, a fourth requirement is necessary to provide power control. In these systems, the objective assembly also provides an electrical signal to the laser power control circuitry ("Signal Monitor").

When a CD-Recordable (CD-R) disc is played back on a CD-Recordable player, it utilizes a "continuous wobbled groove" and a reflective disc surface to provide information to the focusing servo, tracking servo, and power control servo. No features are detected on the surface of the optical disc until a recordable disc is written and contrasting marks have been provided. The quad sum detector will detect light-contrasting structures that are placed on the air-incident surface of a reverse imaged CD recordable disc. These structures will provide characteristic signals that can be detected by electrical monitoring of the quad sum detector.

Figure 12:
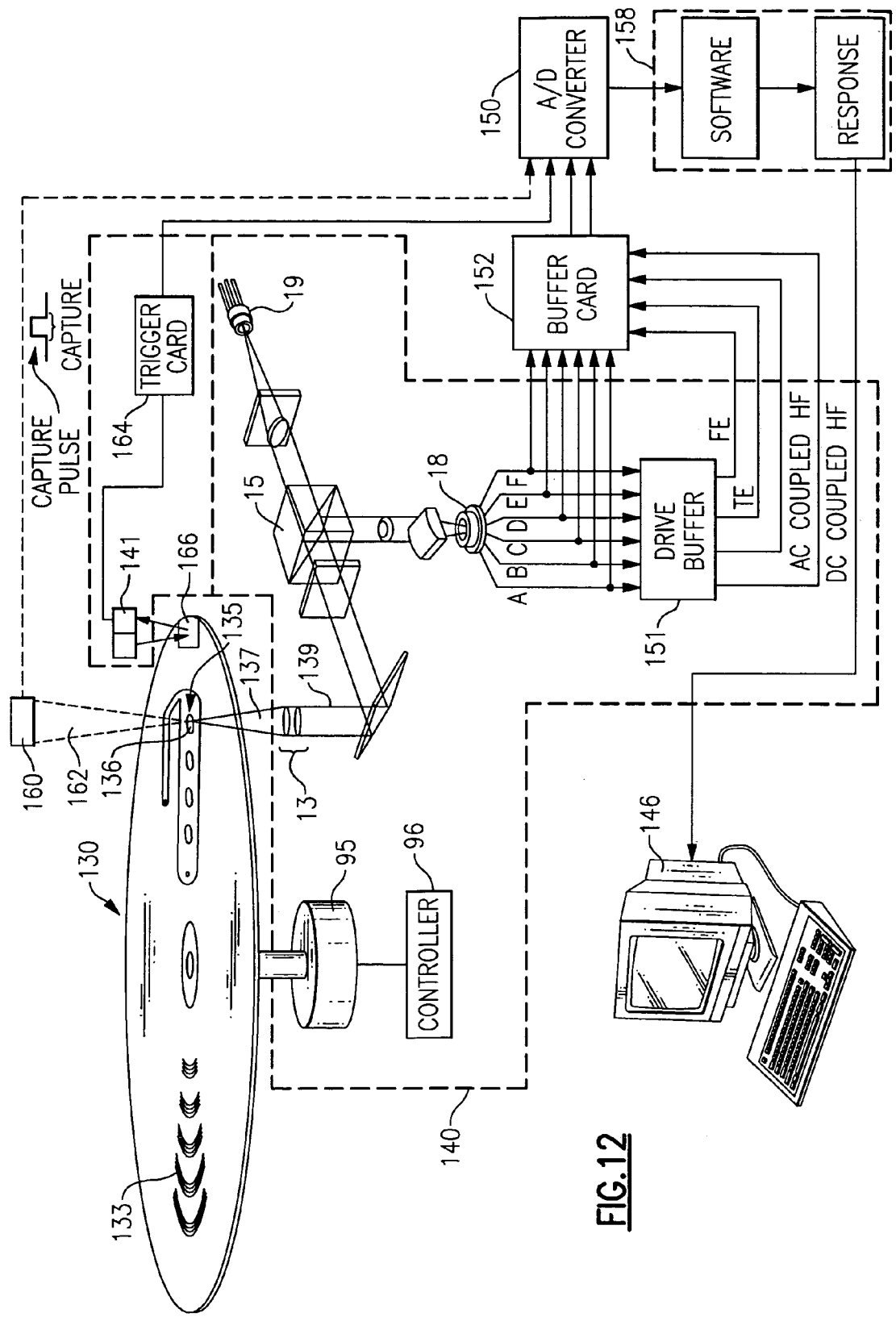
FIG. 12 is a view similar to FIG. 9A showing the optical disc assembly and investigational features in conjunction with the optical components and return beam of an optical disc reader and drive implemented according to a first embodiment of the present invention.

With reference now to FIG. 12, there is shown an expanded view of implementation 11 (FIG. 9A) showing the optical disc assembly 130 with bio-bits, signal elements, or investigational features 136 in conjunction with optical disc drive 140, buffer amplifier card 152, ADC 150, PC 158, and display 146 implemented according to the present invention. In one embodiment, raw detected signals (A, B, C, D, E, and F) are tapped off and fed directly into external buffer amplifier card 152. In another embodiment, detected signals A, B, C, D, E, and F are processed in the optical disc drive's drive buffer 151 prior to entering external buffer amplifier card 152. In yet another embodiment, both tapped off raw signals and signals processed by drive buffer 151 are fed into external buffer amplifier card 152. Signals exiting external buffer amplifier card 152 enter ADC 150 for further processing according to implementation II (FIG. 9A) of the invention.

With continuing reference to FIG. 12, a drive motor 95 and a controller 96 are provided for controlling the rotation of disc 130. A hardware trigger sensor 141 may be used. Trigger sensor 141 provides a signal to ADC 150 that allows for the collection of data only when incident beam 137 is on a target zone 135. Optical bio-disc 130 includes a trigger mark 166 that is read by trigger sensor 141, which feeds the trigger signal to capture trigger card 167. Capture trigger card 167 is preferably, but not necessarily, implemented on buffer card 152. Trigger sensor 141 may be located on the bottom side of disc assembly 130. The system may also include a top detector 160 for detecting transmitted light 162. This light could pass through a semi-reflective disc, or through an area where portions of the reflective layer of the disc have been removed. Further aspects of the types of discs suitable for use with the present invention are discussed below in further detail.

Figure 13:
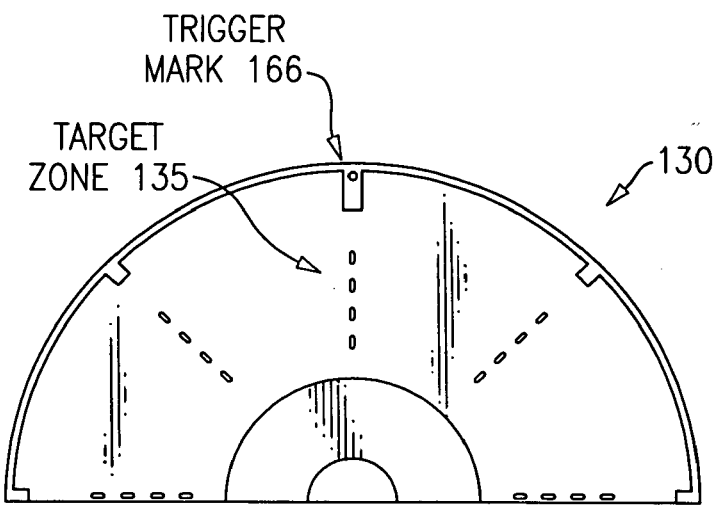
FIG. 13 is a plan view of a disc showing target zones and a hardware trigger.

FIG. 13 shows a plan view of disc 130 with target zones 135 and trigger marks 166. Hardware trigger mark 166 is preferably disposed at an outer periphery of the disc, and preferably is in a radial line with target zones 135.

Capture trigger card 167 provides a signal indicating when trigger mark 166 has reached a predetermined position with respect to investigational features 136. This signal is processed through ADC 150 and into PC 158 to synchronize processing that takes place in PC 158 with the location of trigger mark 166. For example, trigger mark 166 is placed just prior to a sector in bio-disc 130 containing investigational structures. When PC 158 detects trigger mark 166, PC 158 waits a short predetermined time, and then begins processing the signal extracted from the HF signal as data indicative of the presence of an investigational feature. At the same time, when trigger mark 166 is detected by PC 158, PC 158 sets a timer for a longer predetermined time after which PC 158 again processes the signal extracted from the HF signal as operation information used to operate the optical disc drive.

Figure 14:
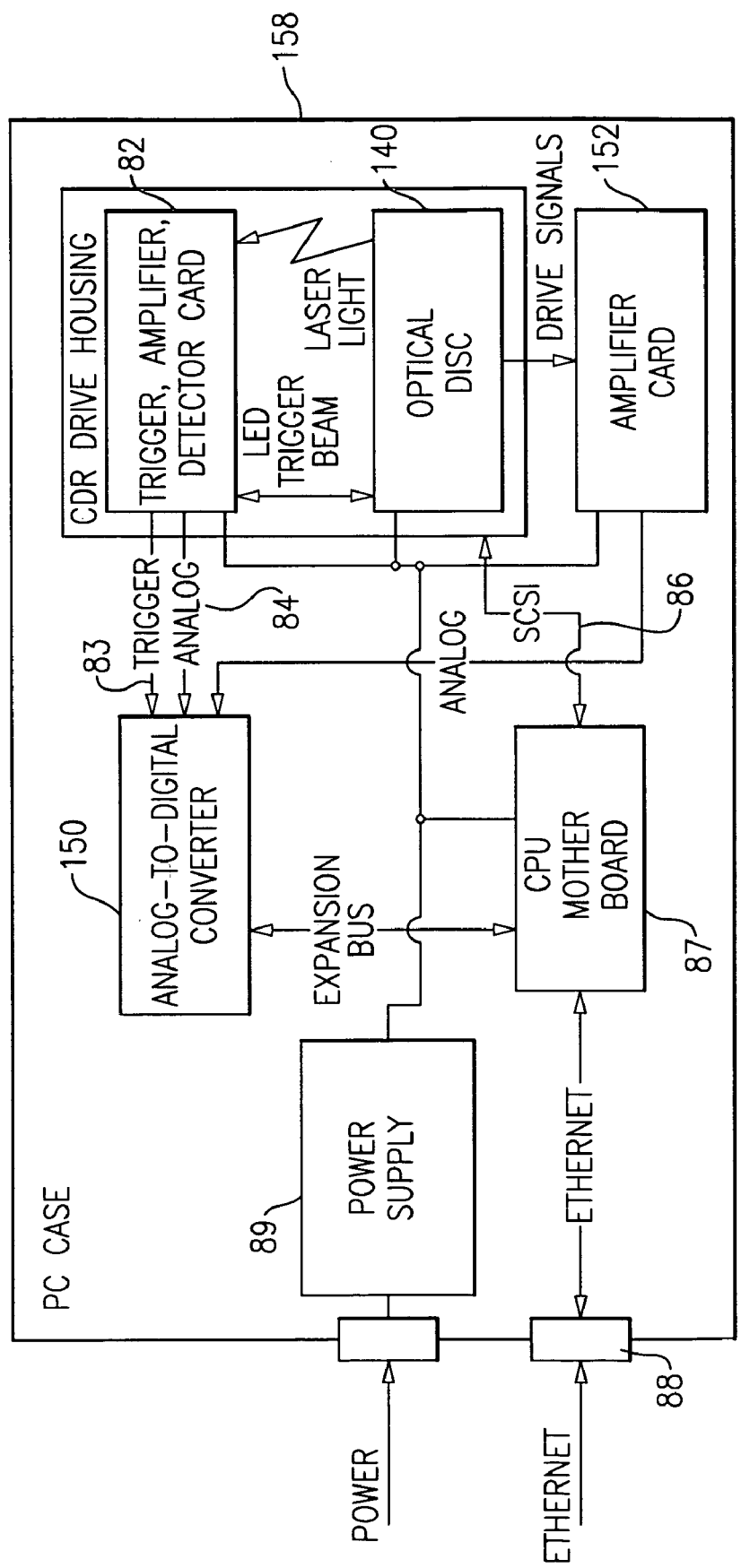
FIG. 14 is a block diagram of an overall drive system according to an embodiment of the present invention.

FIG. 14 is a block diagram showing the relationship of PC 158 with optical disc drive 140. According to an embodiment of implementation 11 (FIG. 9A) of the present invention, additional drive functionality, including top detector 160, trigger sensor 141, and processing circuitry, is preferably located on a single printed circuit board (TAD) 82. This functionality thus detects transmitted light and trigger marks, and then amplifies an analog data signal based on the detected transmitted light. These additions are preferably made so that no change is needed to existing optical disc drive electronics. Therefore, a conventional optical disc drive may be modified prior to initial shipment, or retrofitted with the additional functionality without the need to alter existing hardware.

According to another embodiment of the invention, and as an alternative to trigger mark 166, the trigger signal 83 could be provided in the operational data, such that encoded information on the disc indicates the location of the investigational features. In yet another embodiment, the entire disc is read, but only the data following a predefined set of data is maintained. In this way, all of the data on the disc is initially read into memory, and the data preceding the software trigger is later discarded. Optionally, a second trigger mark can be provided. This second mark can be useful to distinguish from among multiple target zones, while enabling the user to look at a particular zone of interest. If multiple trigger marks, with corresponding trigger detectors, are used, then each trigger mark must be located at a different radius.

ADC 150 may also receive analog drive signals via buffer amplifier card 152, which receives its input signals from optical drive 140. Within PC 158, CPU motherboard 87 communicates with optical disc drive 140 over a small computer systems interface (SCSI) 88 and receives data through an expansion bus from ADC 150. CPU motherboard 87 has an Ethernet connection 88 that allows this data to be offloaded for further processing. A power supply 89 receives a power input and provides the power to CPU motherboard 87 as well as to the other components in the optical disc drive housing and in PC 158.

The data can be processed as it is collected in a real-time manner, or may be stored and post processed by other computers, potentially reducing the complexity of the system.

The trigger, amplifier, detector card TAD 82 is preferably constructed in such a manner that it can be mounted within a conventional optical disc drive of the type that can be used in a drive bay in a computer. One suitable drive used particularly for development purposes is the Plextor model 8220 CD-R drive. While a CD or DVD can be used, a CD-R drive has several useful aspects. Because the CD-R drive allows reading and writing functions, the laser can operate over a higher range of power levels. This functionality of using higher power can be useful for certain types of investigational features. Another useful aspect of a CD-R is that it has the ability to write onto a disc and therefore can be used to write results back onto a disc. This allows results to be saved back onto the disc for later use and to remain with the disc.

Figure 15:
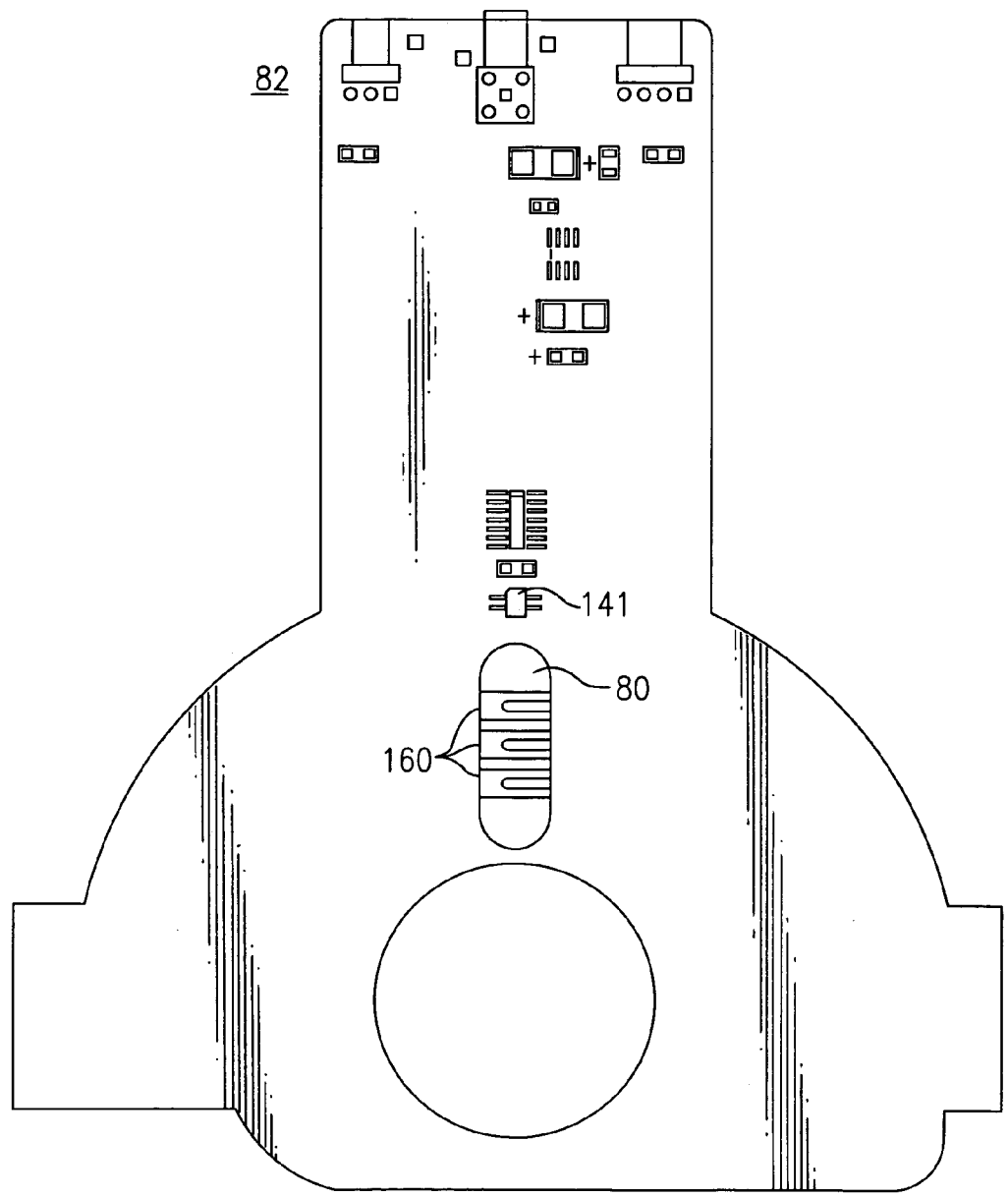
FIG. 15 is a top view of a circuit board including a triggering detection assembly according to another aspect of the present invention.

FIG. 15 is a top view of TAD 82 including a triggering detection assembly according to another aspect of the present invention. The circuit board includes an opening or pass-through port 80 which is needed when implemented in a top detector drive arrangement utilizing a transmissive disc such as those disclosed in commonly assigned U.S. Pat. No. 5,892,577 entitled "Apparatus and Method for Carrying Out Analysis of Samples," incorporated herein by reference, and U.S. Provisional Application No. 60/247,465 entitled "Disc Drive for Optical Bio-Disc." When employed with conventional drives using reflective discs and a typically positioned proximal or bottom detector, the pass-through port 80 is not required. As discussed in conjunction with FIG. 12, the TAD 82 includes trigger sensor 141 and the detector 160. In this particular embodiment, three detectors 160 are used.

Figure 16:
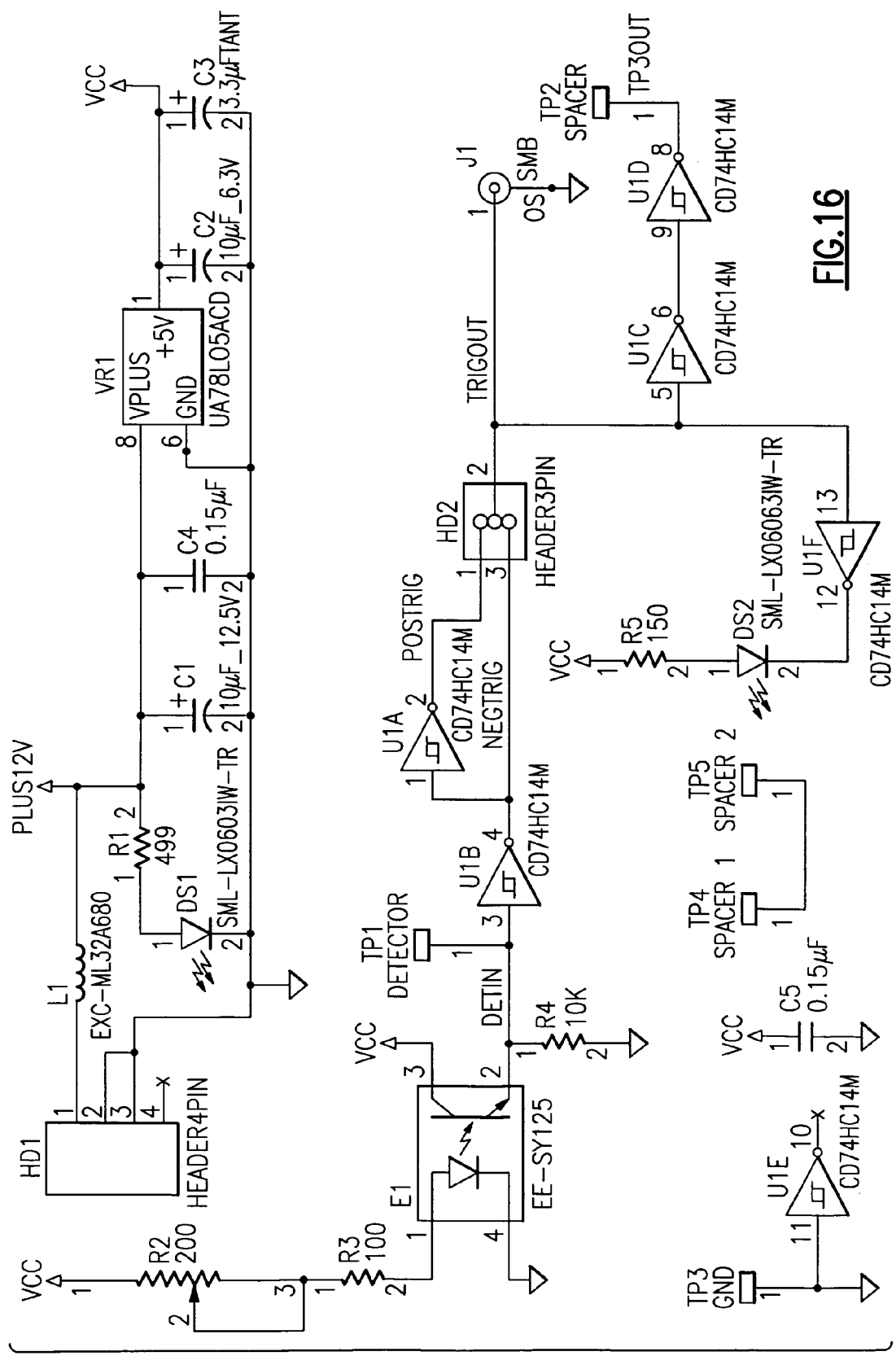
FIG. 16 is an electrical schematic of the triggering circuit shown in FIG. 15.

FIG. 16 is an electrical schematic of the triggering circuit shown in FIG. 15. To acquire information concerning the investigational structures, the optical disc drive according to the present embodiment is provided with suitable triggering circuitry implemented to trigger when detection of the unprocessed HF signal 50 (FIG. 4) is needed. This is necessary because the type of signal processing performed by DSP 32 (FIG. 8), which typically includes demodulation, decoding, and error checking, is intended to convert EFM-encoded information on HF signal 50 to a specific digital format. Although the portion of the disc that provides operational information produces digital formatted data, the investigational features of the present invention do not produce EFM-encoded information. HF signals processed in a manner to decode EFM-encoded information cannot be easily used to detect the dual peaks associated with investigational structures. Thus, the signal or signals of interest are tapped-off before reaching the optical drive's DSP, and trigger mark 166 and trigger circuitry shown in FIGS. 14 and 26 are implemented as discussed above.

Figure 17:
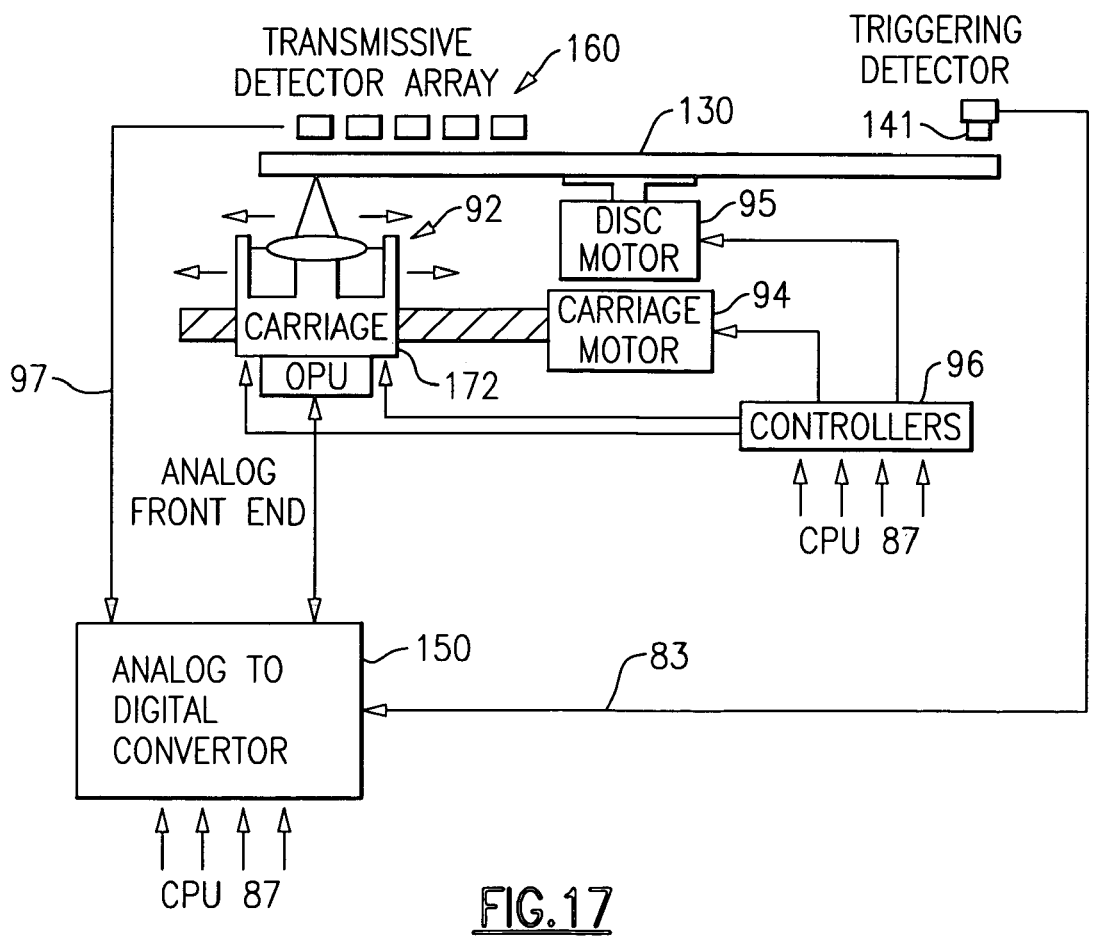
FIG. 17 is a part pictorial, part block diagram showing a disc and a reading system as implemented according to certain aspects of the present invention.

FIG. 17 is a block diagram that illustrates in more detail the inter-relationship between TAD 82 and the disc drive mechanisms. As it is shown here, optical components 92 are mounted on a carriage assembly 172 that is driven by a carriage motor 94, and the disc is driven by the disc motor 95. The carriage assembly 172 includes an optical pick-up unit (OPU). Controllers 96, which receive signals from CPU 87, drive the two motors. Data from the optical components 92, triggering detector signal 83, and signals 83 from transmissive (top) detector 160 or detector array are all provided to TAD 82. The detector for processing the signal from the transmitted or reflected beam of light may be a single detector element or an array of multiple elements arranged radially or circumferentially, and may be placed on the opposite side of the disc from the laser, and may be mounted directly on the TAD or separately.

ADC 150 may optionally be located on a sampling card that allows for very high-speed conversion. One usable card is the Ultrad AD 1280 DX, which has two 12-bit A/D converters sampling up to forty million samples per second.

There are advantages to making changes to the disc drive that provide the least amount of disruption to conventional drives. For this reason, it can be desirable to use a disc that is transmissive. In other words, the disc is reflective enough for the operational data to be seen by the active electronics and normal drive functioning to occur. Yet, still partially transmissive to allow some of the incident light to pass through the disc to a top detector. In this manner, the investigational features can be detected without it being necessary to alter the detection circuitry for reflected light. The reflected light may still be used to read encoded data.

Figure 18:
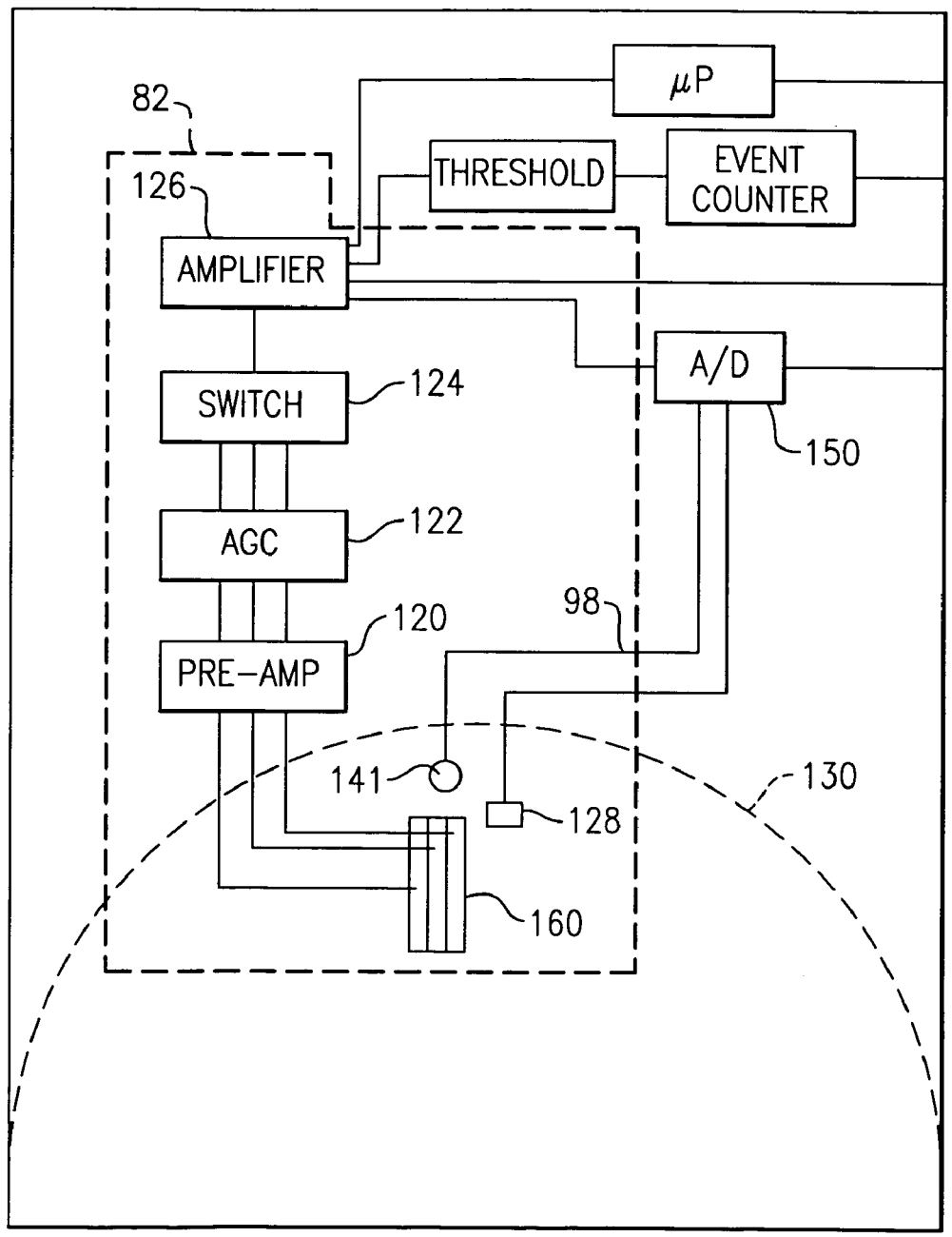
FIG. 18 is a block diagram of a board with functionality including a trigger, an amplifier, and detection circuitry for use in various embodiments of the present invention.

Referring next to FIG. 18, TAD 82 illustrated by functional blocks can include transmissive or top detectors 160 located over the viewing regions or pass through port 80 as illustrated. This detector can be a single detector, an array arranged with different segments oriented radially, or an array with multiple segments oriented circumferentially with multiple detectors arranged along different radii. The detector unit 160 receives signals and provides them to a preamplifier 120, automatic gain control 122, switch 124, and amplifier 126 to produce a signal on the order of 3 volts.

Triggering light source and detector 141 can be provided on TAD 82. This hardware would include a light source and a detector positioned to detect trigger marks, preferably at the periphery of disc 130. In this particular embodiment, a second trigger light source and detector 128 is provided to help distinguish from among a plurality of trigger marks. In this case, both trigger signals are provided to a trigger control circuit. The trigger control circuit passes trigger signals to collect and retain data from the desired sample areas on to ADC 150.

Analog switch 124 can be used when the data detector is an array with multiple elements. There can be multiple detector elements that perform some of the types of refracted light combinations. For example, sums and differences can be used. If desirable, the switch can also be coupled to the detection elements that are under the disc for detecting reflected light. This could allow the system to obtain a differential between the top and bottom detection.

Additional processing and counting functionality can be provided on TAD 82 in order to remove the processing from ADC 150, or to effectively replace ADC 150 and PC 158 (FIG. 9A) to allow more processing to occur on TAD 82. In the case of the test for CD4/CD8, for example, one methodology that is used is to count white blood cells in a target region. Such methods are disclosed in commonly assigned U.S. patent application Ser. No. 09/988,728 entitled "Methods and Apparatus for Detecting and Quantifying Lymphocytes with Optical Biodiscs" filed Nov. 16, 2001. As the laser light is scanned over the assay region, the detector will detect no light at the edge of a blood cell, and will detect full light when centered on a blood cell. As the beam is scanned, it therefore creates a series of high and low signals indicating where a cell is detected. Processing functionality can be added to the card to include threshold crossing circuitry and a counter. Such processing is less complex than that which may be used for other tests. Each of these types of circuits is generally known. Depending on the type of test that is used (the CD4/CD8 being one example), the processing system may need to count hundreds or up to tens of thousands of features in the assay region or target zone. In addition, a microprocessor could also be added to the card.

By providing additional processing and/or counting functionality onto the card, the results from scanning the sample can be provided directly from the card via a USB port or through an Ethernet port. By using Ethernet, data can be provided from a web server so that users can access data with a web browser.

TAD 82 can also include a temperature sensor (not shown) as well as other sensors that may be useful for testing. In the case of temperature, a test may use relative temperature to indicate the presence of some material. Another detector that can be provided is a simple barcode reader that can be used if barcodes are provided on the disc for identification purposes.

The automatic gain control (AGC) 122 and automatic level control (not shown) make sure that the full dynamic range is used, and thus the signals may range, for example, from 0 to 3 volts. The automatic level control (ALC) is used to define a center of the signal, such as 1.5 volts if, for example, the range is 0 to 3 volts. The result of the amplification, ACG, and ALC is that the output can be processed through a threshold circuit and provide consistent results.

As a concrete example of the embodiments depicted in FIGS. 9A and 12, an inventive drive of the present invention includes a known optical disc drive that has been modified to include capture trigger card 164, buffer 152 and ADC 150. The inventive drive and a setup optical disc are sold, for example, to a research laboratory. The setup optical disc contains drive software and is of a known type of optical disc. The research laboratory connects the inventive drive to a known PC (e.g., PC 158) and runs the setup optical disc to install drive control software that enables PC 158 and the inventive drive to operate as a research instrument. Then, diverse types of optical bio-discs 130, that include trigger mark 166 and target zones 135, are sold to the research laboratory to enable diverse investigations and assays to be conducted. Bio-disc 130 may include target zones 135 and related microfluidics in one sector and encoded information in another. The encoded information includes operational information used to operate the optical disc drive and includes data about the type of tests that may be performed by the particular optical analysis disc. Different tests may require different discs and the encoded information on the disc then provides PC 158 with information about the particular test being run.

Figure 19:
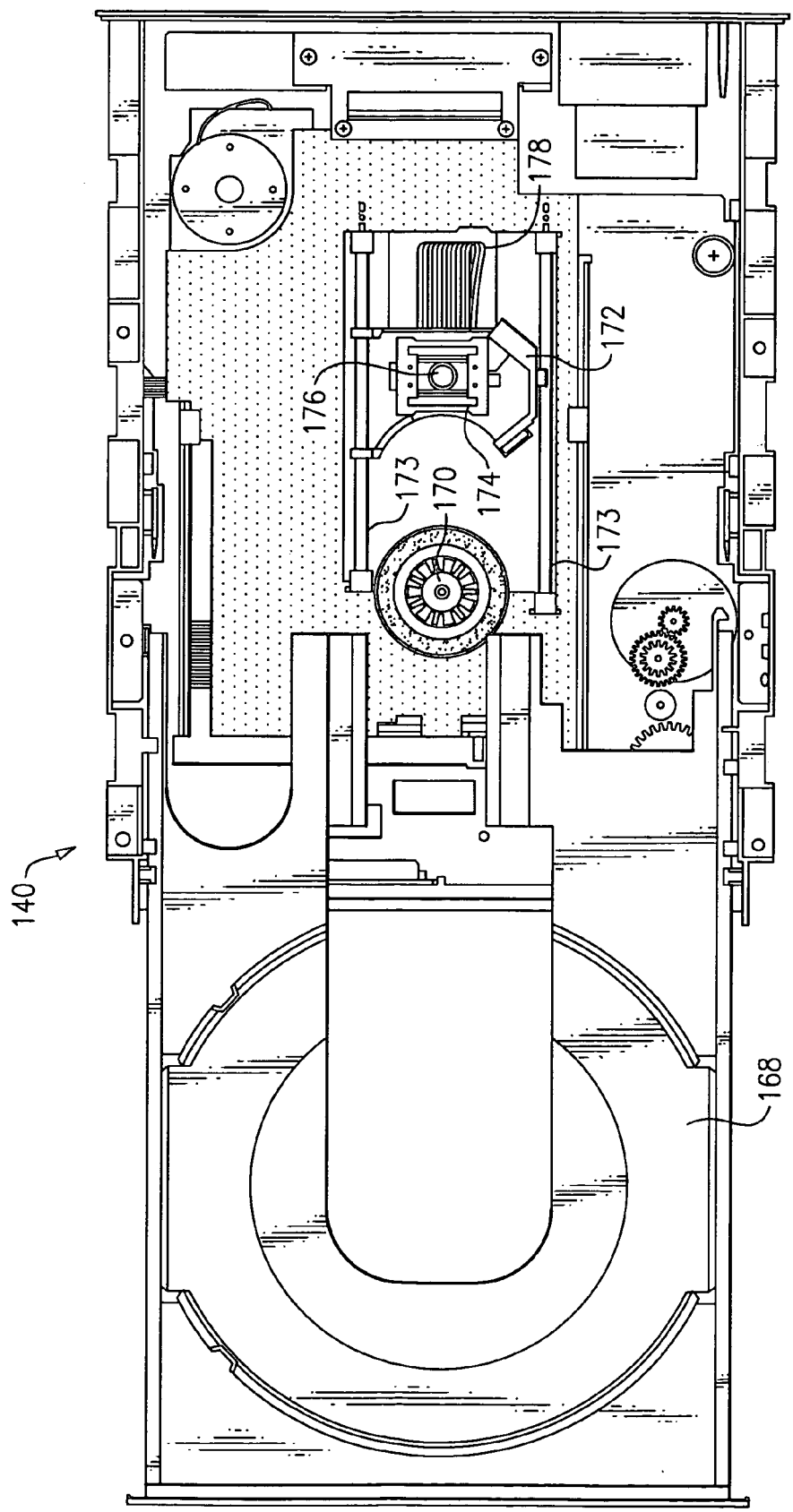
FIG. 19 is a top plan view of an optical disc drive assembly with the housing removed to show the spindle, the carriage assembly, the optical head assembly, and the ribbon cable or connector which transmits signals to and from the optical head assembly.

FIG. 19 is a top plan view of an optical disc drive assembly with the housing removed to show the disc tray 168, the spindle 170, the carriage assembly 172, the optical head assembly 174, and the ribbon cable 178, which transmits signals to and from the optical head assembly. The carriage assembly 172 provides linear movement to optical head assembly 174 along rails 173. Optical head assembly 174 contains lens assembly 176 for focal adjustments of incident and reflected light.

Figure 20:
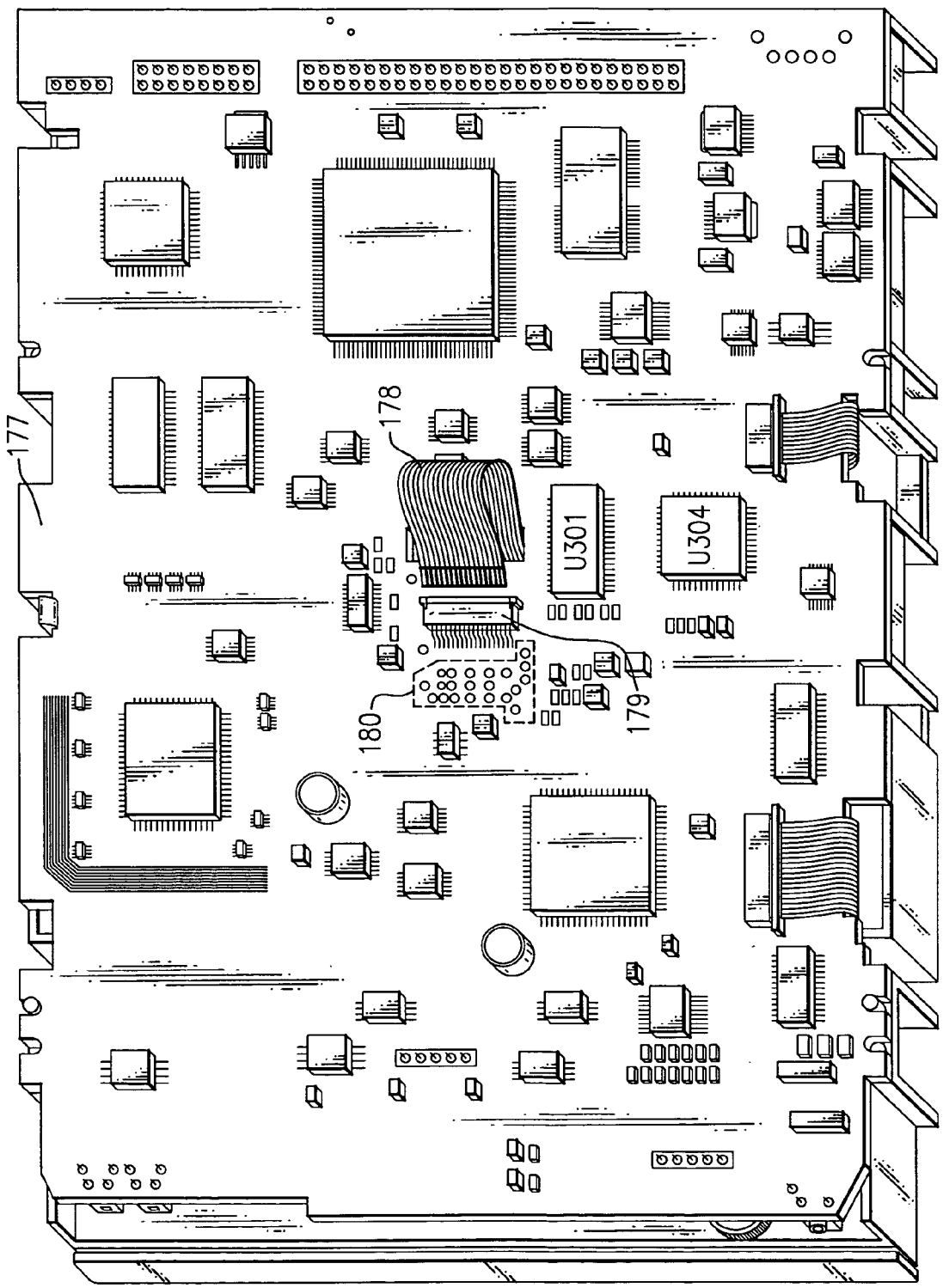
FIG. 20 is a bottom perspective view of the optical disc drive assembly of FIG. 19, illustrating the physical layout of the chip set, related electronic circuitry, and the ribbon connector from the head assembly as unplugged from the circuitry.

FIG. 20 is a bottom perspective view of the optical disc drive assembly of FIG. 19, illustrating the physical layout of the chip set, related electronic circuitry, and ribbon cable 178 from head assembly 174 (FIG. 19) as unplugged from ribbon cable connector 179 on circuit board 177. Signals transmitted to and from optical head assembly 174 may be acquired either directly from ribbon cable 178, at the leads connecting ribbon cable connector 179 to circuit board 177, or at particular solder points 180 on circuit board 177.

Figure 21:
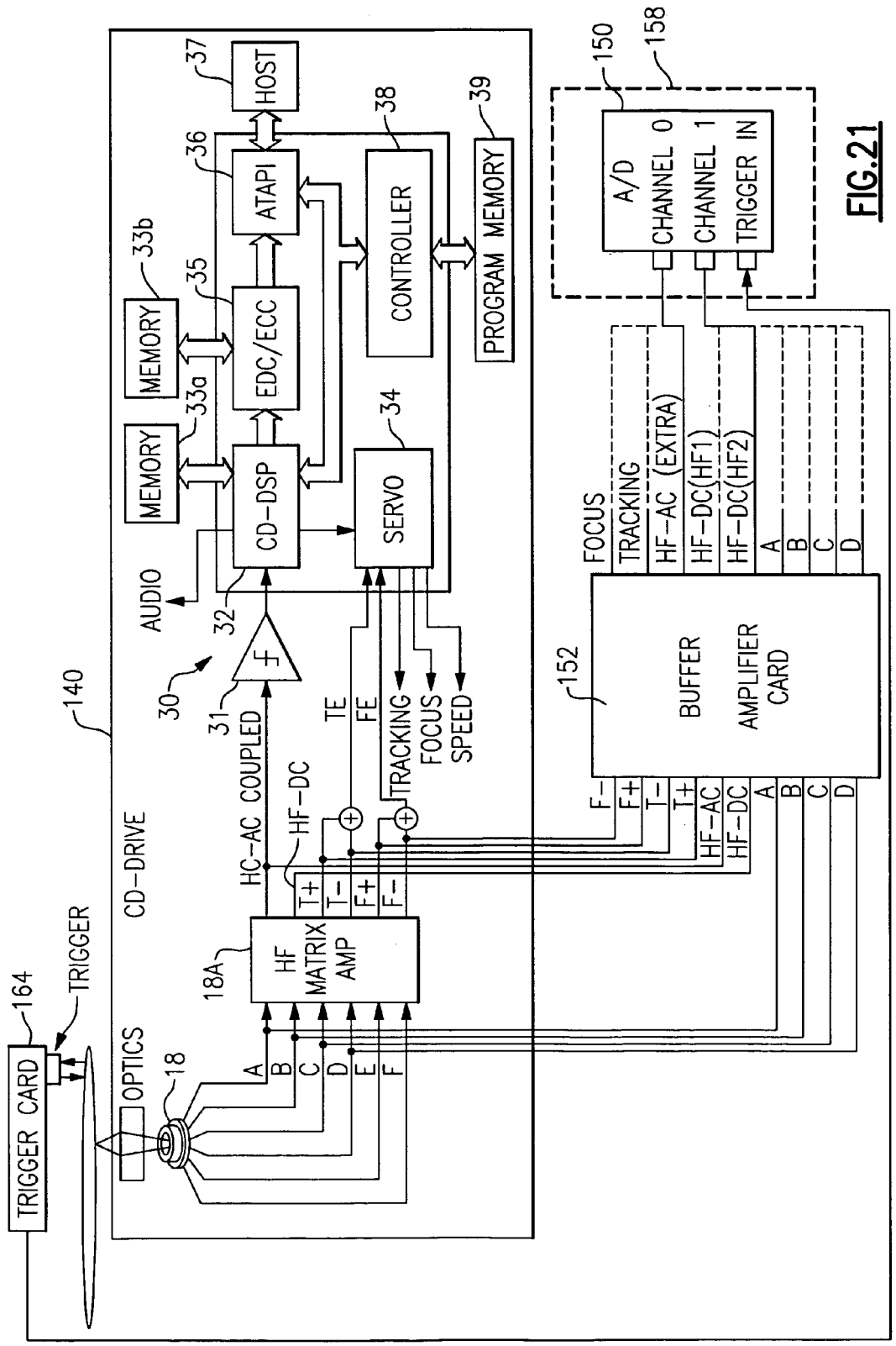
FIG. 21 is a block diagram illustrating the known optical disc reader of FIG. 6 as connected to a buffer card according to different embodiments of this invention.

FIG. 21 is a block diagram depicting interconnections between prior art optical disc reader 140 and buffer amplifier card 152 according to an embodiment of implementation 11 (FIG. 9A) of this invention. A chip set 30 (FIG. 8) according to the present invention is shown to include taps from the A, B, C, and D outputs of detector 18. FIG. 21 further illustrates that the F−, F+, T−, T+, HF-AC coupled, and HF-DC coupled signals may also be tapped off of the HF matrix amplifier 18A of optical disc drive 140. These tapped signals provide access to raw, unprocessed analog signals produced by detector 18 and by the HF matrix amplifier 18A. This permits external instrumentation to receive the signals without interfering with normal drive operation. Such external instrumentation may alternatively include the modified PC 142, the audio processing module 156, the external ADC 150, or the external buffer amplifier card 152 and external ADC 150 as shown in FIG. 9A. As indicated above, FIG. 21 is directed to implementation 11 of the invention as generally illustrated in FIG. 9A.

FIG. 22 is a top perspective view of one physical embodiment of the external buffer amplifier card 152 (FIGS. 9A and 21) adapted to receive signals from optical head assembly 174 (FIG. 19) and drive buffer 151 (FIG. 12) according to the A to D embodiment of the present invention. This electrical device outputs and buffers the operational signals of an optical disc drive. Signals from optical head assembly 174 enter buffer amplifier card 152 at the pins of connector 155. The signals are amplified and buffered via independent groups of resistors, capacitors, and op amps, then directed to output section 157. This embodiment of buffer amplifier card 152 provides 9 to 11 output signals, including Quadrant A, Quadrant B, Quadrant C, Quadrant D, Detector E, Detector F, Un-Equalized HF, Equalized HF, AC coupled HF, Tracking servo response, and Focus servo response.

FIG. 23 is a perspective view of an alternative embodiment of external buffer amplifier card 152 illustrated in FIG. 22. The input signals from the optical head assembly enter at connector 155. The signals directed to the optical disc drive's internal drive buffer 151 (FIG. 12) exit through output section 157, while processed signals are directed through connector 159 to external buffer amplifier card 152 (FIG. 12).

FIG. 24 is a graphical representation illustrating the relationship between FIGS. 24A, 24B, and 24C. FIGS. 24A, 24B and 24C are electrical schematics of the amplifier stages according to a first embodiment of the buffer cards shown in FIGS. 22 and 23.

FIG. 24A is a partial electrical schematic of the buffer amplifier. The analog HF signal 50 (FIG. 4) from optical head assembly 174 (FIG. 19) is taken from pins 1 and 2 of connector 155 (FIGS. 22 and 23). The input signal travels across an input load resistor and a voltage stabilization capacitor to equalize background noise between the positive and negative leads. The positive signal is then fed into an op amp, which is buffered with a variable feedback loop. The amplified signal is directed across an output load resistor and stabilization capacitor before becoming the HF1 signal output at connector J5 of output section 157 (FIG. 22).

The analog F+ signal from optical head assembly 174 is taken from pins 3 and 4 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the FC+ signal.

The analog F− signal from optical head assembly 174 is taken from pins 5 and 6 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the FC− signal.

The analog T+ signal from optical head assembly 174 is taken from pins 7 and 8 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the TC+ signal.

The analog T− signal from optical head assembly 174 is taken from pins 9 and 10 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the TC− signal.

FIG. 24B is another partial electrical schematic of the buffer amplifier. The analog HF-AC signal from optical head assembly 174 (FIG. 19) is taken from pins 11 and 12 of connector 155 (FIGS. 22 and 23). The input signal travels through an input load capacitor, then across an input load resistor and a voltage stabilization capacitor to equalize background noise between the positive and negative leads. The positive signal is then fed into an op amp, which is buffered with a variable feedback loop. The amplified signal is directed across an output load resistor and stabilization capacitor before becoming the HF-AC signal output at connector J3 of output section 157 (FIG. 22).

The analog HF-A signal from optical head assembly 174 is taken from pins 19 and 14 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the HF-A signal output at connector J8 of output section 157. The signal is also tapped at the output lead prior to the stabilization capacitor to feed an HF-A signal into the A to D circuit of the HF2(DC) output at connector J7 (FIG. 24C).

The analog HF-B signal from optical head assembly 174 is taken from pins 17 and 16 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the HF-B signal output at connector J9 of output section 157 (FIG. 22). The signal is also tapped at the output lead prior to the stabilization capacitor to feed an HF-B signal into the A to D circuit of the HF2(DC) output at connector J7 (See FIG. 24C).

The analog HF-C signal from optical head assembly 174 is taken from pins 15 and 18 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the HF-C signal output at connector J10 of output section 157 (FIG. 22). The signal is also tapped at the output lead prior to the stabilization capacitor to feed an HF-C signal into the A to D circuit of the HF2(DC) output at connector J7 (See FIG. 24C).

The analog HF-D signal from optical head assembly 174 is taken from pins 13 and 20 of connector 155. The input signal travels across an input load resistor and a voltage stabilization capacitor to equalize background noise between the positive and negative leads. The positive signal is then fed into an op amp, which is buffered with a fixed feedback loop. The amplified signal is directed across an output load resistor and stabilization capacitor before becoming the HF-D signal output at connector J11 of output section 157 (FIG. 22). The signal is also tapped at the output lead prior to the stabilization capacitor to feed an HF-D signal into the A to D circuit of the HF2(DC) output at connector J7 (See FIG. 24C).

FIG. 24C is yet another partial electrical schematic of the buffer amplifier. The FC+ and FC− signals from FIG. 24A are directed through independent input resistors and then combined. The combined signal is fed into the negative input of an op amp, with a variable positive voltage feeding the positive input. The amplified signal is buffered with a fixed feedback loop and directed through a variable resistor into the negative input of a second op amp. The amplified signal from the second op amp is buffered with a second fixed feedback loop and directed across an output resistor and stabilization capacitor before becoming the FOCUS output at connector J2 of output section 157 (FIG. 22).

The TC+ and TC− signals from FIG. 24A are directed through independent input resistors and then combined. The combined signal is fed into the negative input of an op amp, with a variable positive voltage feeding the positive input. The amplified signal is buffered with a fixed feedback loop and directed through a variable resistor into the negative input of a second op amp. The amplified signal from the second op amp is buffered with a second fixed feedback loop and directed across an output resistor and stabilization capacitor before becoming the TRACKING output at connector J6 of output section 157 (FIG. 22).

The tapped HF-A, HF-B, HF-C, and HF-D signals from FIG. 24B are individually directed through input resistors and then combined as illustrated. The combined signal is fed into the negative input of an op amp, with a variable positive voltage feeding the positive input. The amplified signal is buffered with a fixed feedback loop and directed through a variable resistor into the negative input of a second op amp. The amplified signal from the second op amp is buffered with a second fixed feedback loop and directed across an output resistor and stabilization capacitor before becoming the HF2(DC) output at connector J7 of output section 157 (FIG. 22).

Modifying an Optical Disc Drive—Software

In accordance with other principles of the present invention, it is possible to programmably reconfigure chip set 30 (FIG. 8) so that physical modification of the optical disc drive is not necessary. One way this may be accomplished is by programming DSP 32 (FIG. 8) to operate simply as an A/D converter rather than as, inter alia, a demodulator/decoder. In such a configuration, the DSP chip takes the place of external ADC 150 and supplies the digitized HF signals directly to a host data bus. Investigational structures may be detected by analyzing the resulting digitized HF signal. Alternatively, investigational structures could be detected by routing an unprocessed HF signal through the chip set 30 to an output terminal of optical disc drive 140 (FIG. 9A), connecting the signal to a personal computer (e.g., PC 158), and using hardware and/or software within the personal computer to perform the A/D conversion.

It is possible to programmably configure DSP 32 as an A/D converter without additional demodulation and error correction in multiple ways. For example, a configuration routine stored in program memory 39 (FIG. 8) may operate via controller 38 (FIG. 8) to reconfigure DSP 32. Alternatively, an application program may be able to selectively reconfigure DSP 32 through interface circuitry 36 (FIG. 8) as required. DSP 32 may also configure itself as an A/D converter when it receives a certain type of HF signal. These methods are merely illustrative, and any other suitable software or firmware based reconfiguration methods or path may be used if desired.

FIG. 25 is a functional block diagram of a digital signal processing circuit programmably configured as an analog-to-digital converter in accordance with the principles of an embodiment of implementation III the present invention as represented in FIG. 9A. FIG. 25 illustrates some of the ways in which the processing resources within DSP 32 may be reconfigured to produce a suitable A/D converter according to the present invention. In one possible arrangement, for example, A/D block 42 may be disconnected from path 45 and connected directly to output interface 48 through path 43. In this case, the digitized HF signals completely bypass blocks 44 and 46 and travel to output interface 48. In another arrangement, digitized signals from A/D block 42 travel on path 45, but pass through blocks 44 and 46 without being processed. In some embodiments, it may be desirable to temporarily discontinue power supply to blocks 44 and 46 or place them in a low-power operating mode to reduce power consumption (e.g., in battery operated disc drives). Although the foregoing illustrates several possible A/D converter arrangements, any other suitable arrangement of resources within DSP 32 may be used if desired.

If the bypassing of unneeded functionality can be accomplished through programming, no change to existing hardware is needed, although a modification may be needed to drive firmware.

FIG. 26 is a flow chart illustrating some of the steps involved in detecting investigational elements in accordance with the DSP embodiment of the present invention illustrated in FIG. 25. As shown in FIG. 26, when it is desired to enter detection mode (step 100), a portion of a signal processing system within the drive is configured to operate as an analog-to-digital converter (step 101). This may include programmably reconfiguring one or more chips in chip set 30 (e.g., DSP 32) by employing a remote application program or by using a routine stored in a local program memory 39, FIG. 6. This conversion eliminates the need to physically modify the disc drive electronics, and it allows the invention to take advantage of the configurable processing resources within chip set 30.

At step 102, a plurality of analog data signals are acquired from disc 130 (FIG. 12), which preferably includes investigational structures 136 (FIG. 12), using objective assembly 10 (FIG. 1). Next, at step 103 the analog data signals are combined to produce a sum (HF) signal 50 (FIG. 4) and a tracking error (TE) signal 52 (FIG. 4). Both signals are provided to the signal processing system at step 104. At step 105, the basic information required to operate the disc drive (such as tracking, focus, and speed control) is extracted from TE signal 52. Simultaneously, the signal processing system converts the HF signal 50 into a digitized signal, which is provided to output interface 36 (FIG. 8) at step 105. The digitized sum signal is subsequently used to characterize the investigational features or structures 136 present on disc 130. Once the scanning process is complete, disc drive 140 may be directed to exit the detection mode (step 106). At this point, the portion of chip set 30 (e.g., DSP 32) previously configured as an A/D converter may be returned to its original configuration and normal CD, CD-R, or DVD operation may resume (step 107).

In a variant of the trigger mark 166 (FIG. 13) and trigger circuit 167 arrangement, a registration mark on optical disc assembly 130 itself may be encoded and recorded. Certain digital binary autocorrelation codes (i.e., a sequence of binary bits) may be used to encode the registration mark. For example, the known Barker code is a series of bits (varying in number up to thirteen bits) that has a sharp autocorrelation function with a peak equal to the number of bits (when registered or correlated) and side lobes (when not registered or correlated) equal to one. See Barker, R. H., "Group Synchronization of Binary Digital Systems," as it appears in Jackson, W. (ed.), *Communications Theory*, Academic Press, New York, 1953, pp. 273–287, incorporated herein by reference.

In a concrete example, one thirteen bit Barker code is known to be 1111100110101. When a digital bit stream containing this 13 bit long code is correlated with a receiver searching for this 13 bit long code as a reference, a perfect registration will produce a correlation with 13 identical bits. However, if the bit stream were to be slid forward or back by up to 12 bits, the peak correlation side lobe would be only 1 bit.

Other autocorrelation functions are known with low side lobe out of correlation values and high in correlation values. See Lindner, J., "Binary Sequences Up To Length 40 With Best Possible Autocorrelation Function," *Electron. Letters*, vol. 11, p. 507, October 1975. For example, there are two known codes of length 25 bits, one of which, expressed in octal, is 163402511. An octal digit varies from 0 to 7 and represents, in order, binary 000, 001, 010, 011, 100, 101, 110, and 111. This code has a maximum peak side lobe of 2 and a correlation peak of 25. There are 114 known codes of length 40, one of which, expressed in octal, is 14727057244044. This code has a maximum peak side lobe of 3 and a correlation peak of 40.

Long autocorrelation codes are also characterized by low correlation values with random bits received in a sequence, and high correlation values when the exact code is detected and registered in the bit stream. A bit stream recorded on an optical disc assembly might be constructed to include an autocorrelation code within the data bit stream. A signal processor that analyzes the bit stream would then correlate the bit stream with the autocorrelation code being sought within the incoming bit stream. When the correlation processor encounters the autocorrelation code in the bit stream, the correlation function spikes up very high in relation to normal correlation values with random bit stream data. This provides a registration mark in the same sense that trigger mark 166 provides a registration mark.

Referring again to FIG. 12, optical disc assembly 130 is divided into a sector with investigational features or signal elements 136 situated within target zones 135 and a sector 133 containing operational information used to operate the optical disc system. In this variant, the operational information advantageously includes data, at least some of which includes an autocorrelation code. This data is stored on a sector of optical disc assembly 130 in known ways (e.g., CD ROM, DVD, etc.). When the autocorrelation code is detected and registered in the data stream from the optical disc assembly, two timers are set in PC 158 (or equivalent circuitry). The beginning of the sector containing the investigational features is marked by an expiration of the first timer, and the ending of the sector containing the investigational features is marked by an expiration of the second timer. The duration of the two timers is advantageously included in the data stored on optical disc assembly 130 so that a common disc drive system can be used for different types of bio-discs with different size sectors in which the investigational features are stored.

A conventional optical disc reader generally allows a user to play a disc, while giving the user little ability to control the parameters of the reading, rotating, and data processing. For the most part, users of commercial CD and DVD players would not need such abilities. These firmware-based modifications can generally be made using aftermarket software. In other words, the programming could be provided on a disc or could be available by download via the Internet.

Additional modifications suitable for use in the invention include, but are not limited to, one or more of the following capabilities:

1. Wobble groove playback and random access on a wobble groove, rather than needing to start from the beginning of a disc. This allows the drive to go to an LBA (or an address by some other mode) and play forward from there.

2. Poll the laser monitor value, which allows reading of the value of the laser power detected by the laser power monitor detector in the optical pickup unit.

3. Poll and set the laser power read/play value, which allows a user to monitor and set the power command value to the laser.

4. Poll the automatic gain control (AGC) to get the value of the AGC. The gain is controlled to make sure that the detected signals have consistent amplitude. The amount of gain therefore is an inverse indicator of the signal intensity. Consequently, the signal can be used for detection and measurement.

5. Poll the tracking automatic gain control value.

6. Monitor the C1 and/or P1 decoder activity at a port to monitor types of errors and attain error counts. This is useful because the errors could be useful information for detecting the location of an investigational feature. A conventional drive detects gaps in the encoded data as an error.

7. Monitor the C2 and/or PO decoder activity at a port. See. No. 6 above.

8. Initialize and track operational features on an analysis disc independent of encoded logic. This refers to the ability to control the laser position and control the speed of the disc independent of the data. This functionality allows a user to send a command to keep the drive motor spinning without its operational functions of focus, tracking, and synchronization.

9. Initialize the drive with a specific speed and laser read power. A drive typically has a fixed start-up speed and laser power. This change allows these values to be set and changed by the user. In a typical disc drive system, however, the disc immediately starts to spin to get a focal point, get synchronization information, and find a table of contents. If the information is not found, the disc drive will open up and shut down. In certain circumstances, it may be desirable not to spin the disc as soon as it is inserted into the disc drive. For example, it may be desirable to prevent the drive from automatically spinning when a liquid sample is added to the disc. This change also relates to the change set out in No. 15 below.

10. Stream the main and sub-channel data in all areas of the disc including lead-in and lead-out, which allows more portions of the disc to have data.

11. Push raw-EFM (eight-fourteen modulation) value to a port or secondary port, which allows the user to see 14-bit data before it is translated to 8-bit values. This functionality enables the user to more clearly know exactly what is on the disc. Like No. 10 above, this change allows additional areas on the disc to be used.

12. Push buffered, DC coupled signals, such as TE, FE, and HF, to an external port. This relates to the ability to provide these signals to an external port for additional processing, whereas they are generally used for internal purposes (see FIGS. 4 and 8).

13. Decode and poll values collected from the power calibration area (PCA) and program memory area (PMA) at initialization. This allows additional information to be collected.

14. Pause playback of a disc and open the tracking servo to monitor the open loop tracking signal, which allows the user to monitor the eccentricity of the disc. A disc generally has some eccentricity and therefore, the tracking signal will have a periodic form as the disc is rotated. The eccentricity of the disc arises from imperfect processing of the disc. The tracking signal is thus a reflection of the eccentricity that produces a periodic signal, which is a reflection of the eccentricity. If there is a change in reflectivity in one area, such as due to the presence of an investigational feature, the tracking signal will reflect this change in reflectivity.

15. Set Ghost initialization logic. As indicated in No. 9 above, when a disc is put into a disc drive, it typically starts spinning. One of the initial functions is to find a table of contents. Accordingly, this change allows the user to provide a table of contents to the disc drive controller effectively tricking the disc drive into thinking that it has read the table of contents from the disc.

16. Interactively turn off tracking function.

17. Control and monitor the focusing offset with or without the tracking function. The focus offset changes the size of the laser spot, and thereby changes the amount of energy incident upon the disc. In certain circumstances, it may be desirable to provide heat to the disc or a region of the disc for optimal assay conditions. Therefore, the ability to control the focus offset can allow the user to control heat distribution.

18. Switch layers on a DVD.

19. Monitor value changes at the switching port.

20. Read a CD or CD-RW with a DVD laser. The DVD laser is at a lower wavelength, which can be useful for imaging and for fluorescent detection. Devices that have the ability to read CD and DVD are generally provided with two lasers, one for each mode.

21. Track a wobble groove (1.2 mm) at any frequency with a DVD laser.

22. Monitor the value of a buffered differential phase detection (DPD) signal. The DPD signal is a DVD signal used for tracking, and thus corresponds to the previously discussed ability to monitor the tracking signal.

DVD Technology

The use of DVD technology provides a dramatic increase in the operational margin that is offered by the lower wavelength in the laser diode, and by the drastic increase in density and operational information that is included in the disc format. The bio-bits or signal elements including beads, cells, colloidal gold, carbon, or other microscopic markers and reporters associated with an optical disc, can be located on layer 0 or layer 1 of a DVD disc assembly. Disc designs relating to this aspect of the present invention are more fully described in commonly assigned U.S. patent application Ser. No. 10/006,620 entitled "Multiple Data Layer Optical Discs for Detecting Analytes", filed Dec. 10, 2001, which is herein incorporated by reference.

Layer 0 of a DVD disc is manufactured as a second surface disc. This disc can be manufactured with very little information at the inner diameter so that it will not interfere optically with the detection of bio-bits on the outer diameter of layer 1. Layer 0 may be utilized as an adaptable optical spacer that is placed on layer 1 after processing a bio-bit application. Layer 1 is manufactured as a first surface layer. Normally, it is glued onto layer 0 with special glue that has similar refractive properties to the molded plastic layers (e.g., between 1.54 and 1.58). This maintains optical efficiency and very little loss of signal in the reflected or return path. The specified thickness of this layer is 40–60 microns. The transmissive properties of the outer layer, or layer 0, are preferably then designed to make up for a significant loss of signal resulting from a tiny air interface.

The DVD system is designed to provide automatic signal gain and recover information from surfaces with a reflectivity as low as 30% (only defined for dual layer formats). Automated tilt control may be necessary for this method. The use of multiple lasers will be utilized in this technological application. Layer 0 may become an operational layer that will contain information to provide for the operational requirements of the system. A second layer will be used on layer 1 that will detect the bio-bits, signal elements, or investigational features. Layer 1 may or may not contain pits, lands, or grooves. In one particular embodiment, the bio-bits, signal elements, or investigational features are applied to a DVD-R, DVD-RW, or DVD-RAM application with zoned clocking or pitted wobble groove applications.

A "hybrid" disc in a DVD system is employed as a stepping-stone for this bio-bit detection technique. The word "hybrid" entails the use of multiple densities. For example, layer 0=DVD density and layer 1=CD density.

Increasing Resolution

The power-monitoring signal in a CD or DVD recording system provides a response similar to that of a spectrophotometer. The power control signal or monitor signal of a recording laser diode can be controlled through logical information on the disc or through software. It may also include an analysis of the monitor signal as the focused incident beam is moved across an area of the disc.

An alternative embodiment measures the birefringent properties of an area on an optical disc. This would involve a modified player with a second additional optical path that is currently not available in the consumer market. This optical path involves the use of prisms instead of a rotating polarimeter.

In the areas of mathematics that are used in the decoding processor of a player, the lookup table (that is used to perform modulation or the movement of information from the data bits to the channel bits) can be replaced with a table to optimize detection of bio-bits, signal elements, or investigational features. The mathematics that is adjusted to run length (RLL 2,10) in the Reed Soloman encoding and decoding scheme can be optimized for detection of bio-bits. These adjustments provide information that is used for detection or statistical evaluation of bio-bits. The information is available using standard software detection of C1 or C2 errors on CD decoder interfaces. The information is also available utilizing standard software detection of PI or PO errors on DVD decoder interfaces. The PI/PO data from the DVD decoder may be used to characterize the sizes of bio-bits, signal elements, and investigational features. In one particular embodiment, the EFM or ESM patterns generated by the lookup table are replaced with simple 8-bit patterns that characterize the run length of the item under study. Changes to the decoding system of a player may be performed through a program that is contained in the information stored on the optical disc. The information is loaded into "Flash" EPROM or similar technology.

Another alternative embodiment uses a Solid Immersion Lens (SIL) in the detection of bio-bit technology. A SIL player increases operational resolution significantly.

Yet another alternate embodiment uses a CD-Recordable player that is optimized to read microscopic structures on the surface of an optical disc. The player is adjusted optically to detect the structures in the air interface on the surface of an optical disc. The disc is designed to utilize the CD-Recordable system to provide a platform for quantifiable measurement of microscopic structures.

Optical Bio-Discs

FIG. 27 is an exploded perspective view of the principle structural elements of one embodiment of a particular optical bio-disc 410. FIG. 27 is an example of a reflective zone optical bio-disc 410 (hereinafter "reflective disc") that may be used in the present invention. The principle structural elements include a cap portion 416, an adhesive member 418, and a substrate 420. Cap portion 416 includes an inlet port 422 and a vent port 424. Cap portion 416 may be formed from polycarbonate and is preferably coated with a reflective surface 446 (see FIG. 29) on the bottom thereof as viewed from the perspective of FIG. 27. In the preferred embodiment, trigger marks 166 (FIG. 12) are included on the surface of the reflective layer 442 (see FIG. 29). Trigger marks 166 may include a clear window in all three layers of the bio-disc, an opaque area, or a reflective or semi-reflective area encoded with information that sends data to a processor (e.g., ADC 150 as shown in FIG. 12), that in turn interacts with the operative functions of the interrogation or incident beam 137 (FIG. 12). The second element shown in FIG. 27 is adhesive or channel layer member 418 having fluidic circuits 428 or U-channels formed therein. The fluidic circuits 428 are formed by stamping or cutting the membrane to remove plastic film and form the shapes as indicated. Each of the fluidic circuits 428 may include a flow channel 430 and a return channel 432. Some of the fluidic circuits 428 illustrated in FIG. 27 include a mixing chamber 434. Two different types of mixing chambers 434 are illustrated. The first is a symmetric mixing chamber 436 that is symmetrically formed relative to the flow channel 430. The second is an off-set mixing chamber 438. The off-set mixing chamber 438 is formed to one side of the flow channel 430 as indicated. The third element illustrated in FIG. 27 is substrate 420 including target or capture zones 135. Substrate 420 is preferably made of polycarbonate and has a reflective layer 442 deposited on the top thereof (see FIG. 29). Target zones 135 are formed by removing reflective layer 442 in the indicated shape or alternatively in any desired shape. Alternatively, target zones 135 may be formed by a masking technique that includes masking the target zone 135 areas before applying the reflective layer 442. Reflective layer 442 may be formed from a metal such as aluminum or gold.

FIG. 28 is a top plan view of the optical bio-disc 410 illustrated in FIG. 27 with the reflective layer 442 on the cap portion 416 shown as transparent to reveal the fluidic circuits 428, the target zones 135, the inlet ports 422, the vent ports 424, and trigger marks 166 situated within the disc.

With reference next to FIG. 29, there is shown an enlarged perspective view of the reflective zone type optical bio-disc 410 according to one embodiment of the present invention. This view includes a portion of the various layers thereof, cut away to illustrate a partial sectional view of each principle, layer, substrate, coating, or membrane. FIG. 29 shows the substrate 420 that is coated with the reflective layer 442. An active layer 444 is applied over reflective layer 442. In a preferred embodiment, the active layer 444 may be formed from polystyrene. Alternatively, polycarbonate, gold, activated glass, modified glass, or modified polystyrene such as polystyrene-co-maleic anhydride, may be used. In addition hydrogels can be used. Alternatively, as illustrated in this embodiment, adhesive layer 418 is applied over active layer 444. The exposed section of the adhesive layer 418 illustrates the cut out or stamped U-shaped form that creates the fluidic circuits 428. The final principle structural layer in this reflective zone embodiment of the present bio-disc is cap portion 416. Cap portion 416 includes the reflective surface 446 on the bottom thereof. Reflective surface 446 may be made from a metal such as aluminum or gold. Use of the type of disc illustrated in FIG. 29 with genetic assays is disclosed in commonly assigned co-pending U.S. patent application Ser. No. 10/035,836 entitled "Surface Assembly for Immobilizing DNA Capture Probes and Bead-Based Assay Including Optical Bio-Discs and Methods Relating Thereto" filed Dec. 21, 2001, which is herein incorporated by reference.

Referring now to FIG. 30, there is shown an exploded perspective view of the principle structural elements of a transmissive type of optical bio-disc 410 according to the present invention. The principle structural elements of the transmissive type of optical bio-disc 410 similarly include cap portion 416, adhesive layer 418, and substrate 420. Cap portion 416 includes inlet ports 422 and vent ports 424. Cap portion 416 may be formed from a polycarbonate layer. Optional trigger marks 166 may be included on the surface of a thin semi-reflective layer 443, as best illustrated in FIG. 33. Trigger marks 166 may include a clear window in all three layers of the bio-disc, an opaque area, or a reflective or semi-reflective area encoded with information that sends data to a processor (e.g., ADC 150 as shown in FIG. 12), which in turn interacts with the operative functions of interrogation beam 137 (FIG. 12).

The second element shown in FIG. 30 is an adhesive or channel layer member 418 having fluidic circuits 428 or U-channels formed therein. The fluidic circuits 428 are formed by stamping or cutting the membrane to remove plastic film and form the shapes as indicated. Each of the fluidic circuits 428 may include flow channel 430 and return channel 432. Some of fluidic circuits 428 illustrated in FIG. 30 include mixing chamber 434. Two different types of mixing chambers 434 are illustrated. The first is the symmetric mixing chamber 436 that is symmetrically formed relative to flow channel 430. The second is the off-set mixing chamber 438. Off-set mixing chamber 438 is formed to one side of flow channel 430 as indicated.

The third element illustrated in FIG. 30 is substrate 420 which may include target or capture zones 135. Substrate 420 is preferably made of polycarbonate and has the thin semi-reflective layer 443 (shown in FIG. 34) deposited on the top thereof. Semi-reflective layer 443 associated with substrate 420 of disc 410 illustrated in FIGS. 31 and 34 is significantly thinner than the reflective layer 442 on substrate 420 of the reflective disc 410 illustrated in FIGS. 27, 28 and 29. Thinner semi-reflective layer 443 allows for some transmission of interrogation beam 137 through the structural layers of the transmissive disc as shown in FIG. 12. Thin semi-reflective layer 443 may be formed from a metal such as aluminum or gold.

FIG. 31 is an enlarged perspective view of substrate 420 and semi-reflective layer 443 of the transmissive embodiment of optical bio-disc 410 illustrated in FIG. 30. In a preferred embodiment, thin semi-reflective layer 443 of the transmissive disc illustrated in FIGS. 30, 33, and 34 is approximately 100–300 Å thick and does not exceed 400 Å. This thinner semi-reflective layer 443 allows a portion of incident or interrogation beam 137 (FIG. 12) to penetrate and pass through the semi-reflective layer 443 be detected by a top detector 160 (FIG. 12) while some of the light is reflected or returned back along the incident path. As indicated below, Table 2 presents the reflective and transmissive characteristics of a gold film relative to the thickness of the film. The gold film layer is fully reflective at a thickness greater than 800 Å. While the threshold density for transmission of light through the gold film is approximately 400 Å.

TABLE 2

Au film Reflection and Transmission (Absolute Values)

| Thickness (Angstroms) | Thickness (nm) | Reflectance | Transmittance |
| --- | --- | --- | --- |
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |
| 450 | 45 | 0.9222 | 0.0244 |
| 500 | 50 | 0.9328 | 0.0163 |

TABLE 2-continued

Au film Reflection and Transmission (Absolute Values)

| Thickness (Angstroms) | Thickness (nm) | Reflectance | Transmittance |
| --- | --- | --- | --- |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

In addition to Table 2, FIG. 32 provides a graphical representation of the inverse proportion of the reflective and transmissive nature of the thin semi-reflective layer 443 based upon the thickness of the gold. Reflective and transmissive values used in the graph illustrated in FIG. 32 are absolute values.

FIG. 33 is a top plan view of the transmissive type optical bio-disc 410 illustrated in FIGS. 30 and 31 with the transparent cap portion 416 revealing fluidic channels 428, inlet ports 422, vent ports 424, trigger marks 166, and target zones 135 as situated within the disc.

FIG. 34 is an enlarged perspective view of optical bio-disc 410 according to the transmissive disc embodiment of the present invention. Disc 410 is illustrated with a portion of the various layers thereof cut away to illustrate a partial sectional view of each principle, layer, substrate, coating, or membrane. FIG. 34 illustrates a transmissive disc format with the clear cap portion 416, the thin semi-reflective layer 443 on the substrate 420, and trigger marks 166. Trigger marks 166 include opaque material placed on the top portion of the cap. Alternatively, trigger marks 166 may be formed by clear, non-reflective windows etched on the thin reflective layer 443 of the disc, or any mark that absorbs or does not reflect the signal coming from the trigger detector 160 (FIG. 12). FIG. 34 also shows, the target zones 135 formed by marking the designated area in the indicated shape or alternatively in any desired shape. Markings to indicate target zones 135 may be made on the thin semi-reflective layer 443, on substrate 420, or on the bottom portion of the substrate 420 (under the disc). Alternatively, target zones 135 may be formed by a masking technique that includes masking the entire thin semi-reflective layer 443 except the target zones 135. In this embodiment, target zones 135 may be created by silk screening ink onto the thin semi-reflective layer 443. An active layer 444 is applied over the thin semi-reflective layer 443. In one preferred embodiment, active layer 444 is a thick layer of 2% polystyrene. Alternatively, polycarbonate, gold, activated glass, modified glass, or modified polystyrene such as polystyrene-co-maleic anhydride, may be used. In addition hydrogels can be used. As illustrated in this embodiment, adhesive or channel layer 418 is applied over active layer 444. The exposed section of the adhesive layer 418 illustrates the cut out or stamped U-shaped form that creates fluidic circuits 428. The final principle structural layer in this transmissive embodiment of the present bio-disc 410 is the clear, non-reflective cap portion 416 that includes inlet ports 422 and vent ports 424.

Referring back to FIG. 12, in the case of the reflective bio-disc illustrated in FIG. 29, the return beam 139 is reflected from the reflective surface 446 (see FIG. 35) of cap portion 416 of the optical bio-disc 410. In this reflective embodiment of the present optical bio-disc 410, the return beam 139 is detected and analyzed, for the presence of signal elements or agents, by a bottom detector 18 such as that illustrated in FIG. 1. This reflected return beam either alternately or simultaneously carries both operational information and information characteristic of the bio-bit, signal element, or investigational feature. In the transmissive bio-disc format, on the other hand, the transmitted beam 162 is detected, by a top detector 160, and is also analyzed for the presence of signal agents. In the transmissive embodiment, a photo detector may be used as top detector 160. The hardware triggering mechanism may be used in both reflective bio-discs (FIG. 29) and transmissive bio-discs (FIG. 34).

FIG. 35 is a partial cross sectional view of the reflective disc embodiment of optical bio-disc 410 according to the present invention. FIG. 35 illustrates substrate 420 and reflective layer 442. As indicated above, reflective layer 442 may be made from a material such as aluminum, gold or other suitable reflective material. In this embodiment, the top surface of substrate 420 is smooth. FIG. 35 also shows active layer 444 applied over reflective layer 442. Target zone 135 is formed by removing an area or portion of reflective layer 442 at a desired location or, alternatively, by masking the desired area prior to applying reflective layer 442. As further illustrated in FIG. 35, adhesive layer 418 is applied over active layer 444. FIG. 35 also shows cap portion 416 and reflective surface 446 associated therewith. Thus when cap portion 416 is applied to adhesive layer 418, which includes the desired cut-out shapes, flow channels 430 are thereby formed. Incident beam 137 is initially directed toward substrate 420 from below disc 410, and then focused at a point proximate to reflective layer 442. Since this focusing takes place in target zone 135 where a portion of reflective layer 442 is absent, incident beam 137 continues along a path through active layer 444 and into flow channel 430. Incident beam 137 then continues upwardly traversing through flow channel 430 to eventually fall incident onto reflective surface 446. At this point, incident beam 137 is returned or reflected back along the incident path and thereby forms the return beam 139.

FIG. 36 is a partial cross sectional view of the transmissive embodiment of bio-disc 410 according to the present invention. FIG. 36 illustrates a transmissive disc format with clear cap portion 416 and thin semi-reflective layer 443 on substrate 420. FIG. 36 also shows active layer 444 applied over thin semi-reflective layer 443. In a preferred embodiment, the transmissive disc has thin semi-reflective layer 443 made from a metal such as aluminum or gold approximately 100–300 Angstroms thick and does not exceed 400 Angstroms. This thin semi-reflective layer 443 allows a portion of incident or interrogation beam 137, from light source 19 (FIG. 1), to penetrate and pass upwardly through the disc to be detected by top detector 160 (FIG. 12), while some of the light is reflected back along the same path as the incident beam but in the opposite direction. In this arrangement, the return or reflected beam 139 is reflected from semi-reflective layer 443. Thus in this manner, return beam 139 does not enter into flow channel 430. The reflected light or return beam 139 may be used for tracking incident beam 137 on pre-recorded information tracks formed in or on the semi-reflective layer 443 as described in more detail in conjunction with FIGS. 37 and 38. In the disc embodiment illustrated in FIG. 36, a defined target zone 135 may or may not be present. Target zone 135 may be created by direct markings made on thin semi-reflective layer 443, or on substrate 420. These markings may be created using silk screening or any equivalent method. In the alternative embodiment where no physical indicia are employed to define a target zone, flow channel 430 is utilized as a confined target area in which inspection of an investigational feature is conducted.

Figure 3:
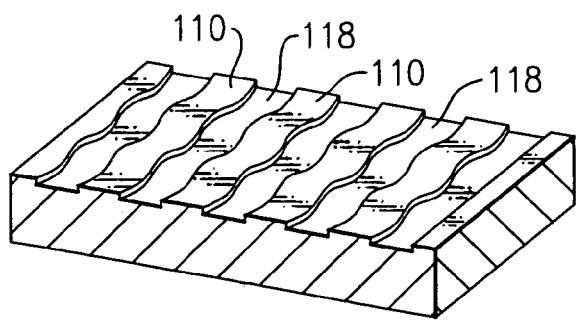
FIG. 3 is a perspective view of the surface of a CD-R disc with wobble grooves.

FIG. 37 is a cross sectional view taken perpendicular to the tracks of the reflective disc embodiment of bio-disc 410 according to the present invention. This view is also taken longitudinally along a radius of a flow channel 430 of the disc. FIG. 37 includes substrate 420 and reflective layer 442. In this embodiment, substrate 420 includes a series of grooves 118, as best illustrated in FIG. 3. Grooves 118 are in the form of a spiral extending from near the center of the disc toward the outer edge. Grooves 118 are implemented so that interrogation beam 137 may track along the spiral grooves 118 on the disc. A raised or elevated portion 110 (FIG. 3) separates adjacent grooves 170 in the spiral. The reflective layer 442 applied over grooves 118 in this embodiment is, as illustrated, conformal in nature. FIG. 37 also shows active layer 444 applied over reflective layer 442. Target zone 135 is formed by removing an area or portion of reflective layer 442 at a desired location or, alternatively, by masking the desired area prior to applying reflective layer 442. As further illustrated in FIG. 37, adhesive layer 418 is applied over active layer 444. FIG. 37 also shows cap portion 416 and the reflective surface 446 associated therewith. Thus, when cap portion 416 is applied to adhesive layer 418, which includes the desired cut-out shapes, flow channel 430 is thereby formed.

FIG. 38 is a cross sectional view taken perpendicular to the tracks of the transmissive disc embodiment of bio-disc 410 according to the present invention. This view is also taken longitudinally along a radius of a flow channel 430 of the disc. FIG. 38 illustrates the substrate 420 and the thin semi-reflective layer 443. Thin semi-reflective layer 443 allows a portion of the incident or interrogation beam 137, from light source 19 (FIGS. 1 and 12), to penetrate and pass through the disc to be detected by top detector 160, while some of the light is reflected back in the form of return beam 139. The thickness of thin semi-reflective layer 443 is determined by the minimum amount of reflected light required by the disc reader to maintain its tracking ability. In this embodiment, substrate 420, like that discussed in FIG. 37, includes the series of grooves 118. Grooves 118 in this embodiment are also preferably in the form of a spiral extending from near the center of the disc toward the outer edge. Grooves 118 are implemented so that interrogation beam 137 may track along the spiral. FIG. 38 also shows active layer 444 applied over thin semi-reflective layer 443 with adhesive layer 418 applied over active layer 444. FIG. 38 also shows cap portion 416 without a reflective surface 446. Thus, when cap portion 416 is applied to adhesive layer 418, which includes the desired cut-out shapes, flow channel 430 is thereby formed and a part of incident beam 137 is allowed to pass therethrough substantially unreflected.

FIG. 39 is a view similar to FIG. 35 showing the entire thickness of the reflective disc and the initial refractive property thereof. FIG. 40 is a view similar to FIG. 36 showing the entire thickness of the transmissive disc and the initial refractive property thereof. Grooves 118 are not shown in FIGS. 39 and 40 since the sections are cut along grooves 118. FIGS. 39 and 40 show narrow flow channel 430 situated perpendicular to the grooves 118 in these embodiments. FIGS. 37, 38, 39, and 40 show the entire thickness of the respective reflective and transmissive discs. In these figures, incident beam 137 is illustrated initially interacting with substrate 420 which has refractive properties that change the path of the incident beam as illustrated to provide focusing of beam 137 onto the reflective layer 442 or the thin semi-reflective layer 443.

Optimizing the Optical Bio-Disc

A disc is optimized to provide a surface for detection of microscopic structures in an optical disc system. An optical disc is created for use in the optically corrected player previously discussed. The disc is manufactured as the "reverse image" or the forward image of a CD-Recordable disc, for example. Such optical discs and related manufacturing methods are further disclosed in commonly assigned U.S. patent application Ser. No. 10/005,313 entitled "Optical Discs for Measuring Analytes" filed Dec. 7, 2001, which is herein incorporated by reference. One such disc is the disc 130 illustrated in FIG. 41 implemented as a "reverse wobble" disc. This embodiment of the disc 130, includes the disc substrate 132 "reversed" as illustrated to form the cap or most distal layer. The disc further includes grooves 118 with bio-bits, signal elements, or investigation features 136 preferably situated therein. A non-integral cover 138 is then utilized as a proximal cap as shown relative to the incident beam 137.

In the Compact Disc Recordable (CD-R) System, a laser is focused through a 1.2 mm polycarbonate (or similar refractive material) and is focused on a groove-like structure filled with dye materials that have absorption-effective properties. The disc manufactured for use in this detection system is manufactured as the "reverse image" of a CD-R disc. The reverse image allows the optical disc reader to interface with the first surface or air-interface of a continuous groove. The air-interface allows for a process that places microscopic structures on the surface that can be read.

The disc is manufactured using an electroforming or "Nickel Stamper" production method referred to as "Matrixing." Once a nickel image has been created from the surface of an optical disc "Master," it can be placed in an electroforming process (or similar process) and a reverse image can be created. The "Master" is often called the "Father" part. The "reverse image part" is often called the "Mother" part. In many CD manufacturing processes, the "Mother" part is used to produce another reverse image that is called the "Son" part. "Father" parts and "Son" parts have the same forward image. "Mother" parts have the reverse image. This process allows a master made from a normal CD-Recordable mastering process to be used for this application. It is technically feasible and possible to create "Father" parts with the correct forward image for this disc. The reverse image part is made of nickel and is utilized in an optical disc molding machine to create a plastic part representing the opposing image.

The reverse image part is more difficult to utilize in a CD manufacturing process because of its geometry. The edge of a forward image part is open and the edge of a reverse image part is closed. A mold must be designed for the CD molding process. This mold is provided with additional vents that allow the movement of polycarbonate or other remoldable refractive material to move properly across the surface of the nickel part. The venting design added to the mold will allow the desired optical discs to be created in a fashion similar to compact discs or CD-R discs.

The desired optical disc is designed with an optimized shape and form of the structure of a continuous groove that originates at the inner diameter and ends at the outer diameter of the disc. The groove depth is optimized to provide a very strong tracking magnitude (push-pull signal). The depth of the manufactured groove is very close to $\frac{1}{8}$ of the wavelength $\lambda$ of the laser light incident on the air interface of the optical disc. The depth of the manufactured groove can also be odd multiples of these values (e.g., $\frac{1}{8}\lambda$, $\frac{3}{8}\lambda$, $\frac{5}{8}\lambda$, etc.). The width of the optical disc groove is optimized to facilitate placement or size detection of the structures that will be placed on the surface of the optical disc. Thus in one preferred embodiment, a $\frac{1}{8}$ wave push-pull tracking derivation is employed. The slope of the groove structure is optimized to provide for an optimal focusing position in the groove and for an optimized tracking signal response. Optimization of the land areas within the continuous groove is performed to reduce signal cross-talk and to optimize structure detection.

The air-incident surface of the optical disc is manufactured to provide light contrast to the microscopic structures that will be placed on the surface of the disc. If the structures absorb light, a reflective material (such as gold) is placed on the air-incident surface. If the structures reflect light, a non-reflective material will be placed on the air-incident surface. The discs are manufactured to provide optimal mechanical performance in a CD recordable player.

The air-incident surface of the reverse image disc provides the required operational requirements of the optically corrected player discussed previously. The adjustment lens will allow the reverse image disc to perform similarly to a non-recorded CD-R disc. This test mode is available through the software interface of a consumer CD-R drive. The player can be placed in a test mode and will track the "wobbled" groove through the information area. The location of a component on the surface of the wobbled groove can be detected to $\frac{1}{75}$ of a second by utilizing the consumer CD-R wobbled groove format. The locational information in the consumer CD-R format is contained in the mastered "wobble" signal and can be secured through the software interface to a consumer drive. Microscopic structures placed on the surface of the reverse image disc will not have an effect on the operational requirements of a wobble groove system until they reach a very high concentration (point of data gathering). In effect, the wobble groove allows for placement of microscopic structures on the surface of the optical disc without having an adverse effect on the operational requirements of the CD-R system.

The characteristics of the structures placed on the surface of the reverse image disc can now be detected by monitoring the quad sum signal of the CD-R objective assembly. The electrical response of these microscopic structures can also be detected in the electrical signal applied to the focusing servo, the tracking servo, and the power control monitoring system. The characteristics of the head movement in the radial and tangential plane parallel to the surface of the reverse image disc can be detected in the electrical signal applied to the tracking servo circuitry. The characteristics of the head movement in the vertical plane perpendicular to the surface of the reverse image disc can be detected on the electrical signal applied to the focusing servo circuitry. These signals can be cross-referenced to the information gathered by the quad sum signal and the power-monitoring signal. The information for each of these responses can be analyzed in a mathematical format to relate dimensional characteristics of the microscopic structure detected on the surface in the reverse image disc. An application of Differential Mathematics or Vector analysis can be applied to extract the characteristics of each microscopic structure.

Structures on the surface of the reverse image disc can be designed for maximum detection resolution by designing a placement and dimensional requirement to remain within the focal position of the laser spot. The microscopic structures should be designed for maximal optical contrast with the surface of the reverse image disc to provide for strong signal detection and low electrical CNR. Microscopic structures applied to the surface of the reverse image disc should be small enough to remain within the focusing plane of the laser spot. As the dimensional characteristics overcome the focal position, a smaller portion of the signal is detected in the quad sum detector, while a larger portion of the signal is detected in the other operational servos.

The disc may be designed with a specialty groove that would accommodate the dimensional aspects of the microscopic structures. The microscopic structures can be designed for placement inside the grooves of the reverse image disc. This would be used to further optimize the quantifiable detection characteristics of the system. The microscopic structures are created in a "spherical shape." These spheres, when placed on the surface of the reverse image disc, generate a very characteristic electrical response in the servo and operational signals in the drive. The land areas of the disc (the areas between the grooves) are created with a smooth round surface, which will allow the spheres to fall into a holding position within the groove that is easily detected by the electrical signals.

The reporter spheres or bio-bits may be created with a diameter that is smaller than the width of the groove as discussed above. This allows the spheres to enter the groove and facilitates detection as represented in FIG. 41. The spheres can also be formed out of a compressible material and have a diameter that is slightly larger than the width of the groove. In one embodiment, an adaptable plate is used to compress the spheres and drive them into the groove.

Having described certain embodiments, it should become apparent that modifications could be made without departing from the scope of the claims as set out below. For example, the terms over and under are used for reference purposes and not absolute positioning.

Investigational Features

The structures, features, characteristics, and attributes that are investigated according to the present invention may include biological, chemical, or organic specimens, test samples, investigational objects such as parts of insects or organic material, and similar test objects or target samples. Such structures, features, and attributes may also include specific chemical reactions and the products and/or by-products resulting therefrom such as, for example, any one of a variety of different colorimetric assays. In the case of an optical bio-disc, the material applied to the disc for investigation and analysis may include biological particulate suspensions and organic material such as blood, urine, saliva, amniotic fluid, skin cells, cerebrospinal fluid, serum, synovial fluid, semen, single-stranded and double-stranded DNA, pleural fluid, cells from selected body organs to tissue pericardial fluid, feces, peritoneal fluid, and calculi. In the case of some of these materials, a reporter may be employed for detection purposes. Reporters useful in the invention described herein include, but are not limited to, plastic micro-spheres or beads made of, for example, latex, polystyrene, or colloidal gold particles with coatings of biomolecules that have an affinity for a given material such as a biotin molecule in a strand of DNA. Appropriate coatings include those made from streptavidin or neutravidin, for example. In this manner, objects too small to be detected by the read beam of the drive may still be detected by association with the reporter.

An optical disc playback device can be used to detect features and surface characteristics in the focusing plane of an optical disc. Microscopic structures, cells, reporters, or "bio-bits" are added to a focusing plane in the optical disc assembly so that they can be detected in the electrical signals that are generated when the laser light reflected or transmitted from the surface of the optical disc is collected by the objective assembly and/or a top detector. The microscopic structures and the optical disc platform are designed to promote accurate detection and to have a minimal effect on the operational requirements of the system.

Small biological and/or spherical structures are measured on the surface or within the focusing planes described as follows. These structures are physically larger than one-half the wavelength of the light used to detect them (the light incident on the structures).

When these microscopic structures or bio-bits exist on the surface of the optical disc focal plane, the structures will appear on the surface of the land areas. Signal elements, bio-bits, or investigational features may also exist on a plane that is not within the immediate field of focus but is very near. In this case, the structures are close enough to the field of focus to be detectable by the reflected laser light. Investigational features such as bio-bits can also exist on multiple planes that are separated from the laser that is fulfilling the operational requirements of characterization of the structures. The bio-bits and other reporters may also be inserted into the groove or pits and cause enough optical interference in the reflected signal to generate a confident detection signal. Bio-bits can also exist within areas that are logically zoned or organized by the manufacturing of the disc. These areas may be land-level or pit-level, and may be very large (e.g., DVD-RAM).

Detecting Investigational Features Investigational features, such as reporters or blood cells, produce a signal level or density change relative to a signal produced by reading information encoded on the disc. Commonly assigned and co-pending U.S. patent application Ser. No. 09/421,870 entitled "Trackable Optical Discs with Concurrently Readable Non-operational Features" filed Oct. 26, 1999, herein incorporated by reference, teaches that micron-sized investigational or "non-operational" structures may be disposed upon a surface of an optical disc in a number of ways. One suitable embodiment for accomplishing this is depicted in FIG. 41 as discussed above. As shown in FIG. 41, light beam 137 is incident upon the disc assembly 130 from below. Disc 130 includes disc substrate 132 and reflective layer 134, upon which investigational structures or features 136 are disposed. Wobble grooves 118, impressed in substrate 132 and coated by reflective layer 134, are indicated in FIG. 41. Also shown is the non-integral cover 138. Investigational structures 136 may be detected, measured, and characterized by the optical disc reader according to the present invention. The operational structures of the disc, including tracking features, may be detected concurrently (or non-concurrently) with, and readily discriminated from, investigational structures using a single optical pickup.

Figure 5:
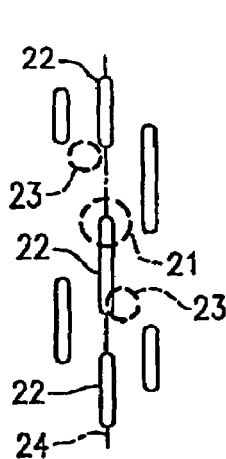
FIG. 5 is a plan view that illustrates the position of beams from a typical three-beam pickup relative to a track on an optical disc.

With reference next to FIG. 42, a view similar to FIG. 5 discussed above, there is shown three light spots that are produced by a typical three-beam optical design incident on an optical disc assembly having pits 60. Laser beam spots 62, 64, and 66 are illustrated as dashed lines on the surface of the optical disc. These beams can be focused on the same surface of the disc as pits 60, or on any other outer surface or inner surface of the disc. These beams can also be focused on different layers of the disc, a "layer" referring to any portion of the disc that has a finite thickness such as in the multi-layer discs disclosed in U.S. patent application Ser. No. 10/006,620 referenced above.

In a three-beam optical disc system, detectors A, B, C, and D, as shown in FIG. 4, are configured to detect light reflected from beam spot 62, as shown in FIG. 42. Also, detectors E and F are independently configured to detect the reflected light from beam spots 64 and 66, respectively. As mentioned above, this configuration has been implemented such that focus and synchronization information are provided by light reflected at beam spot 62 and the tracking information is provided by light reflected at beam spots 64 and 66.

FIG. 43 shows an investigational feature 68 disposed on a surface of an exemplary optical disc assembly. In this arrangement, beam spot 62 can be used to detect operational structures (e.g., pits) for tracking, focus, and synchronization and beam spot 66 can be used simultaneously to detect one or more investigational features 68. Alternatively, beam spot 64 may be used to detect investigational feature 68, depending on the size and location of investigational feature 68.

Also, if investigational feature 68 is sufficiently large, beam spots 64 and 66 can be used in combination (though not necessarily simultaneously) for detecting investigational feature 68. It will be appreciated that a combination of patterns from each of the beam spots can be used to detect the size and position of investigational feature 68. Also, patterns from detectors A, B, C, and D can be combined with patterns from one or both of detectors E and F to determine the size and position of the investigational features. Thus, a single objective assembly can detect different optical paths of operational structures and investigational features. It will be appreciated that the invention disclosed herein relates to the detection of operational and investigational features and is not limited to an optical disc assembly having a pits and lands format. Rather, the invention can be used with any other format such as those discussed above.

FIG. 44 is a graph illustrating a representative relative displacement of the data signal (or density) when the read beam of the drive encounters such an investigational feature on or in the disc. The data signal may be the HF signal, the tacking error signal, the focus error signal, or one or more of a variety of other different signals such as those identified above.

In FIGS. 45 and 46, a change in an "operational" feature such as a groove, pit or land, produces a change in signal level, signal jitter, or error rate. In FIG. 45, a section view of a pit, the pit produces a change in signals A and B from the detector of the disc reader, and, when added, an unusual fluctuation is produced. In FIG. 46, a plan view of a pit, a lateral displacement produces a net displacement in the tracking error signal (TE signal).

An increase or decrease in reflectivity is produced when the incident beam interacts with the disc. This change in reflectivity can be monitored by a corresponding change in the Automatic Gain Control ("AGC") setting, which is output at the drive port. Thus, in accordance with the present invention, when the read or "interrogation" beam of the drive encounters an investigational feature, a change in return light is monitored.

The structure of an optical disc can be anything from a surface with pits and lands, a surface with a continuous wobbled groove, a surface containing a phase contrast hologram, a surface with a combination of pits/grooves or a surface with nothing on it. As discussed previously, reporters, bio-bits, or cellular structures can be measured in many different focusing planes. Bio-bits can also be detected and characterized by multiple lasers, multiple objective assemblies, and multiple laser wavelengths.

Reporters, bio-bits, and cellular structures could be located on the primary surface of a holographic disc. Further details relating to this use of holograms is disclosed in U.S. patent application Ser. No. 10/005,313. The information gathered from the hologram is used for operational characteristics. Bio-bits can be put as close to or as far away from the operational plane as needed. The refractive layer (polycarbonate, polymethyl acrylic or glass) can be adjusted to optimize the desired optical properties of the detection laser:

Alternatively, investigational features may include a chemical reaction, taking place in a flow channel, such as flow channel 430 shown in FIG. 27, formed on or in the disc as illustrated in FIG. 47. In this embodiment, the reflectivity, operational features, or interference patterns on an optical disc are affected by a chemical deposition or reaction. The disc is manufactured with a very low error rate or a known error rate that acts as a data "mask." The data pattern on the disc is designed to produce a logical or physical enhancement to the errors produced by investigational features or groupings of a specific size range.

For example, the interleaving distance can be adjusted in the mastering logic to enhance the burst error response to a specific feature, size, or density distribution. A data pattern is written on the disc to produce as a response to specific feature sizes or density distribution. These may include, but are not limited to, the following:
1. a non-pause;
2. a sound signal (response to digital silence encoding);
3. a specific error correction pattern or distribution (e.g., E11, E21, E31, burst, E12, E22, E32, E42);
4. an uncorrectable error;
5. an ECC/EDC count;
6. an inner or outer parity error;
7. a CRC error in the wobble signal decoder;
8. a sector error (75/sec); or
9. a block error (7350/sec).

In an exemplary embodiment, a fluidic channel is placed within a disc. The disc can have up to 99 tracks with grooves, pits, or a combination of operational features for CD, CD-R, DVD, DVD-RAM, DVD-R, DVD-RW. A specific chemical reaction or deposition of "non-ops" (spheres, metallics, etc.) will enhance or remove material from the metallic reflective layer or the operational or focal plane. Spots or zones are placed on the disc in different bands or tracks. Logic in each band determines the position of the objective assembly. Logic can also determine the "software servo response." Starting with low-density distribution or effect, spots are placed in increasing density and increasing radius positions in each bank or track. On a DVD-RAM disc or similar, the spots are placed within the Zones (Zoned CLF system). The reaction will produce physical changes in the "ops features," inducing errors or error sites on the disc at each location. The digital, analog, optical, mechanical, and logical responses may be evaluated to characterize the effect.

In this embodiment, each site has increasing error rates and an attempt is made to correlate to the error distributions: E11, E21, E31, Burst, E12, E22, E32, E42, Uncorrectable, Unrecoverable, ECC/EDC, or BLER. In a preferred embodiment, the process is started with low-density distributions and moved to higher distributions until a correlation is discovered between the analyte concentration and the error distribution. The disc is advantageously mastered to enhance the correlation. For example, interleaving is modified or changed to enhance the Burst and C2 response.

Reaction with the surface, operational plane, or focal plane of the disc creates and increases or decreases analog signal level or density. The reaction will produce a change in reflectivity or signal density, either a reduction or increase in reflective layer, or a change in shape and/or size of phase/interference features (pits or lands).

As a general proposition, the reflectivity of a metal layer is a function of the thickness of the layer up to a certain threshold thickness as discussed above in connection with FIG. 32. For a variety of different metals such as nickel, aluminum, silver, or gold, as represented in FIG. 48, reflectivity is unchanging and remains essentially constant at between about 80% and nearly 100% for a metal thickness equal to or greater than a threshold thickness. This reflectivity also depends on metal purity and surface conditions. As a general matter relating to certain specific aspects of the present invention, a metal film thickness and surface condition can be altered when a metal film such as reflective layer 443 (as best illustrated in FIG. 34) reacts with a fluid contained in flow channels of the disc.

In FIG. 49, the chemical reaction occurring in the flow channel 430 of the disc illustrated in FIG. 47 causes fluctuations in signals being monitored, for example, the HF or TE signal. When the interrogation beam 137 of a disc drive traverses across a chemical reaction occurring in or on the disc, the envelope of the signal fluctuations increases or decreases with reaction time.

According to another aspect of the present invention, pits, marks, or grooves on a disc can be made of a chemically interactive material. The level of degradation in the material can determine some assay characteristics by providing a change in signal response. Chemistry or assay material can react with the reflective layer and reduce or enhance light transmitted, reflected, refracted, or absorbed according to the change in reflectivity of the reflective or metal layer 443 shown in FIG. 47. For example, operational structures may be made of a nitrated cellulose material. Chemical interactions may change the shape and/or thickness of operational structures, and thus, reduce signal response. Also the pH of the solution may cause a deposition of metal on the surface of a zone in the disc and produce an increase in localized reflectivity. In another implementation, localized reactions may cause the removal of metallic material from the reflective surface. The removal of the material will cause a point of contrast in the signal. The response may be an analog signal characterization or an error rate distribution. Additionally, zones may be designed into the disc for differing concentrations and reactions. In these embodiments, the material is designed in such a way as to degrade at a specific concentration or reaction level.

FIG. 50 generally represents these aspects of the present invention. The disc in FIG. 50 includes zones A, B, and C that are formed, for example, on a DVD-RAM disc with Zoned Constant Linear Velocity, (ZCLV). Zone C included a reaction according to this aspect of the present invention where the reflective layer was removed, while in zones A and B no such metal-removing reaction occurred. The resulting signal traces of, for example, the HF or TE signals are also shown. The signal traces reveal that traces across the zones with the reflective material intact generated a detectable signal, while the scan across the zone without reflective material did not.

With reference now to FIG. 51, there is shown a cross-sectional side view of an optical bio-disc 200 that includes bead reporters 210 as utilized in conjunction with the present invention. Bio-disc 200 includes substrate 202, metal film layer 204, an adhesive or channel layer 206, and cover disc 208. Substrate 202 includes pits or groves or other means on which information may be encoded in known ways. Substrate 202 is generally covered with metal film layer 204 in areas over which information is encoded. However, bio-disc 200 differs from known information discs (e.g., music, DVD, etc.) in that the bio-disc includes an investigational structure (in this case bead reporters) over a part of the disc. Chemical layer 214 (e.g., antibodies) is deposited in a desired target area of the disc. Each bead reporter 210 also has a surface coated with a similar or identical chemical layer 212. The bead reporters 210 are small plastic spheres (or other material spheres) that are coated with a chemical agent to interact with biological chemicals in a solution.

As a specific example of one aspect of the present invention, FIG. 52A presents a graphical representation of two 6.8 µm blue beads positioned relative to several tracks (labeled A through H) of an optical bio-disc according to this invention. These beads were located on and adhered to a disc similar to the disc shown in FIG. 51. Scan traces A through H are depicted, several of which pass over the bead reporters.

FIG. 52B is a series of signature traces including distinctive signal perturbations derived from the bead reporters of FIG. 52A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 52B reveals that a scan over two 6.8 µm reporter beads results in distinct perturbations of the HF signal that can be detected.

As another particular example, FIG. 53A presents a graphical representation of two 6.42 µm red beads positioned relative to the tracks of an optical bio-disc according to the present invention. These beads were located on a disc similar to the disc shown in FIG. 51.

FIG. 53B is a series of signature traces derived from the beads of FIG. 53A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to an ADC 150 and is processed by PC 158 and imaged by display 146 (FIGS. 9A and 12). As described above, modified PC 142 may substitute one or more of the processing devices described herein. FIG. 53B reveals that a scan over two 6.42 µm reporter beads results in distinct perturbations of the HF signal that can be detected.

As yet another example according to the present invention, FIG. 54A presents a graphical representation of two 6.33 µm polystyrene beads positioned relative to the tracks of an optical bio-disc according to the present invention. These beads were located on a disc similar to the disc shown in FIG. 51.

FIG. 54B is a series of signature traces and related signal perturbations derived from the beads of FIG. 54A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (see FIGS. 22 and 23). The signal is amplified and conditioned (FIG. 24B) then directed to output connector J3 of output section 157 (FIG. 22). From buffer amplifier card 152, the signal is sent to an ADC 150 and is processed by PC 158 and imaged by monitor 146 (see FIGS. 9A and 12). As described above, modified PC 142 may substitute one or more of the processing devices described herein. FIG. 54B reveals that a scan over two 6.33 μm polystyrene reporter beads results in distinct perturbations of the HF signal that can be detected.

As yet still another example of certain aspects of the present invention, FIG. 55A presents a graphical representation of a 5.5 μm glass reporter bead positioned relative to the tracks of an optical bio-disc according to this invention. This bead was located on a disc similar to the disc shown in FIG. 51.

FIG. 55B is a series of signature traces derived from the bead illustrated in FIG. 55A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 55B reveals that a scan over a 5.5 μm glass reporter bead results in a perturbation of the HF signal that can be detected.

Another example of this invention is presented in FIG. 56A which shows a graphical representation of a 4.5 μm magnetic bead positioned relative to the tracks of an optical bio-disc according to the present invention. This bead was located on a disc similar to the disc shown in FIG. 51.

FIG. 56B is a series of signature traces derived from the bead illustrated in FIG. 56A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 56B reveals that a scan over a 4.5 μm magnetic reporter bead results in a perturbation of the HF signal that can be detected.

FIG. 57A is a graphical representation of two actual 4.0 μm blue beads positioned relative to the tracks of an optical bio-disc according to another example of certain aspects of the present invention. These beads were located on a disc similar to the disc shown in FIG. 51.

FIG. 57B is a series of signature traces and related signal perturbations derived from the beads of FIG. 57A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 57B reveals that a scan over two 4.0 μm reporter beads results in a perturbation of the HF signal that can be detected.

As yet a further example hereof, FIG. 58A shows a graphical representation of a 2.986 μm polystyrene bead positioned relative to the tracks of an optical bio-disc according to the present invention. This bead was located on a disc similar to the disc shown in FIG. 51.

FIG. 58B is a series of signature traces derived from the bead illustrated in FIG. 58A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 58B reveals that a scan over a 2.986 μm polystyrene reporter bead results in a perturbation of the HF signal that can be detected.

An yet still as a further example of this invention, FIG. 59A presents a graphical representation of two 2.9 μm white beads positioned relative to the tracks of an optical bio-disc according to the present invention. These beads were located on a disc similar to the disc shown in FIG. 51.

FIG. 59B is a series of signature traces derived from the beads of FIG. 59A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 59B reveals that a scan over two 2.9 μm reporter beads results in distinct signal perturbations of the HF signal that can be detected.

FIG. 60A is a graphical representation of four 2.8 μm magnetic beads positioned relative to the tracks of an optical bio-disc according to another specific example of certain aspects of this invention. These beads were located on a disc similar to the disc shown in FIG. 51.

FIG. 60B is a series of signature traces derived from the beads of FIG. 60A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 60B reveals that a scan over four 2.8 μm magnetic reporter beads results in distinct perturbations of the HF signal that can be detected.

As another example, FIG. 61A presents a graphical representation of a mixture of beads including 2.8 μm magnetic beads, 4.0 and 6.8 μm blue polystyrene beads, and different sized silica beads positioned relative to the tracks of an optical bio-disc according to the present invention. These beads were located on a disc similar to the disc shown in FIG. 51.

FIG. 61B is a series of signature traces and related signal perturbations derived from the beads of FIG. 61A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 61B reveals that a scan over the mixture of reporter beads results in distinct perturbations of the HF signal that can be detected.

FIG. 62A is a graphical representation of two 2.9 μm white fluorescent polystyrene beads positioned relative to the tracks of an optical bio-disc according to the present invention. These beads were located on a disc similar to the disc shown in FIG. 51 and in this example a DC coupled signal is utilized rather than the AC coupled signal discussed in connection with the example traces illustrated in FIGS. 52B through 61B.

FIG. 62B is a series of signature traces derived from the beads of FIG. 62A utilizing a DC coupled and buffered HF signal from the optical drive according to the present invention. The HF-DC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24A) then directed to output connector J5 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 62B reveals that a scan over two 2.9 μm white fluorescent polystyrene beads results in distinct perturbations of the HF-DC signal that can be detected.

FIG. 63A is a graphical representation of two 2.9 μm white fluorescent polystyrene beads, as illustrated in FIG. 62A, positioned relative to the tracks of an optical bio-disc according to the present invention. These beads were located on a disc similar to the disc shown in FIG. 51. In this example, a DC coupled and buffered "A" signal is employed to obtain the desired signal traces as discussed in further detail immediately below.

FIG. 63B is a series of signature traces derived from the beads of FIG. 63A utilizing the DC coupled and buffered "A" signal from the optical drive according to the present invention. The HF-A coupled signal (FIG. 22) from optical head assembly 174 (FIG. 19) is directed to buffer amplifier card 152 (FIGS. 22 and 23). The signal is amplified and conditioned (FIGS. 24B and 24C) then directed to output connector J7 of output section 157 (FIG. 22). From buffer amplifier card 152, the signal is sent to ADC 150 and is processed by PC 158 and imaged by monitor 146 (see FIGS. 9A and 12). As described above, modified PC 142 may substitute one or more of the processing devices described herein. FIG. 63B reveals that a scan over two 2.9 μm white fluorescent polystyrene beads results in distinct perturbations of the HF-A signal that can be detected.

FIGS. 64A and 64B are the same cross-sectional side view of optical bio-disc 200 (FIG. 51) showing the biochemical interaction between the bio-disc and the reporter beads in greater detail.

FIG. 64A shows greater detail of chemical layer 214 disposed over metal film over metal film layer 204. Chemical layer 212 is also shown coated over reporter beads 210. In FIG. 64B, the beads are mixed with the biological solution containing investigational feature 216, and injected into or otherwise applied to bio-disc 200 between substrate 202 and cover 208. Both the chemical layer 212 on the surface of the bead reporters 210 and chemical layer 214 attract and adhere to investigational feature 216. In this way, if the chemical under investigation (i.e., investigational feature) is present in the biological solution, the chemical under investigation becomes a bonding agent to bond the bead reporters 210 to substrate 202. When bio-disc 200 is spun up, it acts like a centrifuge. Bead reporters that are not bonded will be forced to an outer periphery of the disc, and bonded bead reporters will remain uniformly distributed over the area of the disc coated with chemical layer 204. It then remains only to decide whether the bead reporters have been swept to an outer periphery of the disc. Examples of such bead-based assay discs and methods of use are described in commonly assigned U.S. Provisional Applications: No. 60/257,705, titled "Surface Assembly for Immobilizing DNA Capture Probes and Bead-Based Assay Including Optical Bio-Discs and Methods Relating Thereto," filed Dec. 22, 2000; No. 60/292,110, titled "Surface Assembly for Immobilizing DNA Capture Probes using Pellets as Reporters in Genetic Assays Including Optical Bio-Discs and Methods Relating Thereto," filed May 18, 2001; and No. 60/302,757, titled "Clinical Diagnostic Optical Bio-Disc and Related Methods for Selection and Detection of Lymphocytes Including Helper-Inducer/Suppressor-Cytotoxic Cells," filed Jul. 3, 2001. By the above examples, the inventors have illustrated that discernable signals of investigational features may be readily detected using reporter beads as described herein.

FIG. 65 is a cross-sectional side view of an optical bio-disc 190 including a proximally positioned red blood cell 199 as the investigational feature interrogated by the read beam 191 of the optical disc drive assembly according to the present invention.

Bio-disc 190 includes substrate 192, metal film layer 194, adhesive or channel layer 196, and cover disc 198. Substrate 192 includes pits, groves, or other means on which information may be encoded in ways known in the art. Substrate 192 is generally covered with metal film layer 194 in areas over which information is encoded. However, bio-disc 190 differs from known information discs (e.g., music, DVD, etc.) in that the bio-disc includes an investigational structure (in this case, a blood cell 199) over a part of the disc. Metal film layer 194 is removed from areas to be used for investigational structures. Capture agent 195 (e.g., antibodies) is deposited in the area of the removed metal film layer. Blood cell 199 may include a biological chemical under investigation (e.g., a chemical unique for blood type A or type B) that has an affinity for capture agent 195. In this way, if the chemical under investigation is present in the biological specimen, the chemical under investigation becomes a binding agent to bind blood cell 199 to substrate 192. When bio-disc 190 is spun in an optical disc drive, the resulting centrifugal force sends blood cells that are not bound to an outer periphery of the disc, while bound blood cells remain distributed over the area of the disc coated with capture agent 195. The bound cells are then detected and quantified using an optical disc reader. Further details relating to this type of on-disc blood typing assays are disclosed in commonly assigned, co-pending U.S. patent application Ser. No. 09/988,850 entitled "Methods and Apparatus for Blood Typing with Optical Bio-Discs" filed Nov. 19, 2001, which is herein incorporated by reference.

As an example of detection of a cell reporter according to certain aspects of the present invention, FIG. 66A presents a graphical representation of proximally positioned red blood cell 199, approximately 6.0 µm in diameter, positioned relative to the tracks of the optical bio-disc 190 illustrated in FIG. 65.

FIG. 66B is a series of signature traces derived from the red blood cell of FIG. 66A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 66B reveals that a scan over a proximally positioned red blood cell results in a perturbation of the HF-AC coupled signal that can be detected.

FIG. 67A is a graphical representation of a proximally positioned red blood cell approximately 6.0 µm in diameter positioned relative to the tracks of an optical bio-disc according to the present invention. For this example, the red blood cell illustrated in FIG. 67A was located on the type of the disc shown in FIG. 65.

FIG. 67B is a series of signature traces derived from the red blood cell of FIG. 67A utilizing a DC coupled and buffered HF signal from the optical drive according to the present invention. The HF-DC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24A) then directed to output connector J5 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 67B reveals that a scan over a proximally positioned red blood cell results in a perturbation of the HF-DC signal that can be detected.

FIG. 68 is a cross-sectional side view of an optical bio-disc 190 similar to the disc shown in FIG. 65, including a distally positioned red blood cell 199 as the investigational feature interrogated by read beam 191 of the optical disc drive assembly according to the present invention.

Bio-disc 190 includes substrate 192, metal film layer 194, adhesive or channel layer 196, and cover disc 198. Substrate 192 generally includes pits or groves or other means on which information may be encoded in known ways except over areas in which investigational structures are to be located. Substrate 192 is generally covered with metal film layer 194 in areas over which information is encoded but not in areas in which investigational structures are to be located. Bio-disc 190 differs from known information discs (e.g., music, DVD, etc.) in that the bio-disc includes an investigational structure (in this case, a blood cell 199) over a part of the disc. Metal film layer 194 is removed from areas to be used for investigational structures. Capture agent 195 (e.g., antibodies) is deposited in the area on cover disc 198 opposite the removed metal film layer. Blood cell 199 may include a biological chemical under investigation (e.g., a chemical unique for blood type A or type B) that is attracted to and adheres to capture agent 195. In this way, if the chemical under investigation is present in the biological specimen, the chemical under investigation becomes a binding agent to bind blood cell 199 to disc cover 198. When bio-disc 190 is spun in an optical disc drive, the resulting centrifugal force sends unbound blood cells to an outer periphery of the disc, while bound blood cells remain distributed over the area of the disc coated with capture agent 195. The bound cells can be detected and quantified using an optical disc reader as further described in U.S. patent application Ser. No. 09/988,850 referenced above.

FIG. 69A is a graphical representation of two distally positioned red blood cells approximately 6.0 µm in diameter positioned relative to the tracks of an optical bio-disc according to this example of these aspects of the present invention. The red blood cells illustrated in FIG. 69A were located on the type of the disc shown in FIG. 68.

FIG. 69B is a series of signature traces derived from the red blood cells of FIG. 69A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to connector output J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 69B reveals that a scan over two distally positioned red blood cells results in distinct perturbations of the HF-AC coupled signal that can be detected.

FIG. 70A is a graphical representation of the two distally positioned red blood cells illustrated in FIG. 69A. The red blood cells illustrated in FIG. 70A were located on the type of the disc shown in FIG. 68.

As yet a further example of certain aspects of this invention, FIG. 70B presents a series of signature traces derived from the red blood cells of FIG. 70A utilizing a DC coupled and buffered HF signal from the optical drive according to the present invention. The HF-DC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24A) then directed to output connector J5 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 70B reveals that a scan over two distally positioned red blood cell results in distinct perturbations of the HF-DC signal that can be detected.

FIG. 71 is a top perspective view of an optical inspection disc 220 with the top cap removed to illustrate a gnat's wing 222 positioned in an inspection channel 224 according to the present invention. Optical inspection disc 220 illustrated in FIG. 71 also includes a trigger mark 166. Trigger mark 166 provides the same function as the trigger mark 166 discussed in detail in conjunction with FIGS. 12 and 13.

FIG. 71A is an enlarged top view of the indicated portion of FIG. 71 showing in greater detail gnat's wing 222, inspection channel 224, and information storage tracks 226 of the optical inspection disc 220 according to this embodiment of the present invention. FIG. 71A also shows a focused spot 227 of the incident beam directed toward the gnats wing 222.

FIG. 72 is a cross-sectional side view taken perpendicular to a radius of optical inspection disc 220 of FIG. 71 including gnat's wing 222 as the investigational feature located within inspection channel 224. Gnat's wing 222 is interrogated according to the present invention by read beam 225 of an optical disc drive assembly.

FIG. 73A is a graphical representation of a lateral section of the gnat's wing 222 of FIG. 71 as positioned in inspection channel 224 relative to tracks 226 of optical inspection disc 220 according to the present invention.

FIG. 73B is a single signature trace derived from the section of the gnat's wing of FIG. 73A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 73B reveals that a scan over an investigational feature such as gnat's wing 222 results in a perturbation of the HF signal that can be detected.

FIG. 74A is a similar graphical representation of a lateral section of gnat's wing 222 of FIG. 71 as positioned in inspection channel 224 relative to tracks 226 of optical inspection disc 220 according to the present invention.

FIG. 74B is a series of four consecutive signature traces derived from the section of the gnat's wing of FIG. 74A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (see FIGS. 9A and 12). As described above, modified PC 142 may substitute one or more of the processing devices described herein. FIG. 74B reveals that consecutive traces, scanned over an investigational feature such as gnat's wing 222, result in distinct perturbations of the HF signal that can be detected.

FIG. 75A is a similar graphical representation of a lateral section of gnat's wing 222 of FIG. 71 as positioned in inspection channel 224 relative to tracks 226 of optical inspection disc 220 according to the present invention.

FIG. 75B is a series of consecutive signature traces at moderate density derived from the section of the gnat's wing of FIG. 75A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (FIGS. 9A and 12). As described above, modified PC 142 may substitute one or more of the processing devices described herein. FIG. 75B reveals that consecutive traces at moderate density, scanned over an investigational feature such as gnat's wing 222, result in distinct perturbations of the HF-AC signal that can be detected.

FIG. 76A is a similar graphical representation of a lateral section of gnat's wing 222 of FIG. 71 as positioned in inspection channel 224 relative to tracks 226 of optical inspection disc 220 according to the present invention.

FIG. 76B is a series of consecutive signature traces at higher density derived from the section of the gnat's wing of FIG. 76A utilizing an AC coupled and buffered HF signal from the optical drive according to the present invention. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22). From buffer amplifier card 152, the signal is sent to ADC 150 and is processed by PC 158 and imaged by monitor 146 (see FIGS. 9A and 12). As described above, modified PC 142 may substitute one or more of the processing devices described herein. FIG. 76B reveals that consecutive traces at higher density, scanned over an investigational feature such as gnat's wing 222, result in distinct perturbations of the HF signal that can be detected and imaged.

FIGS. 77A, 77B, and 77C are pictorial representations of the gnat's wing of FIG. 71 as rendered by imaging methods according to the present invention respectively utilizing either an AC coupled and buffered HF signal, a DC coupled and buffered "A" signal, or a DC coupled and buffered HF signal from an optical drive assembly. The HF-AC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24B) then directed to output connector J3 of output section 157 (FIG. 22).

The HF-A coupled signal (FIG. 21) from optical head assembly 174 (FIG. 19) is directed to buffer amplifier card 152 (FIGS. 22 and 23). The signal is amplified and conditioned (FIGS. 24B and 24C) then directed to output connector J7 of output section 157 (FIG. 22).

The HF-DC coupled signal from HF Matrix Amp 18A (FIG. 21) of optical head assembly 174 (FIG. 19) is directed to buffer amplifier card 152 (FIGS. 22 and 23). The signal is amplified and conditioned (FIG. 24A) then directed to output connector J5 of output section 157 (FIG. 22). From buffer amplifier card 152, the signals are sent to ADC 150 and are processed by PC 158 and imaged by monitor 146 (FIGS. 9A and 12). As described above, modified PC 142 may substitute one or more of the processing devices described herein. FIGS. 77A, 77B, and 77C reveal that scans utilizing different signals produced by the optical head assembly of the disc drive render pictorial representations of the investigational feature that are detectable.

FIG. 78 is a graphical representation illustrating the relationship between FIGS. 78A and 78B.

FIGS. 78A and 78B are electrical schematics of a second embodiment of the amplifier stages that may be implemented according to the present invention in the buffer cards shown in FIGS. 22 and 23.

FIG. 78A is a partial electrical schematic of the buffer amplifier. The analog HF-A signal from the optical head assembly 174 (FIG. 19) is taken from pins 19 and 14 of connector 155 (FIGS. 22 and 23). The input signal travels across an input load resistor and a voltage stabilization capacitor to equalize background noise between the positive and negative leads. The positive signal is then fed into an op amp, which is buffered with a feedback loop. The amplified signal is directed across an output load resistor.

The analog HF-B signal from the optical head assembly 174 is taken from pins 17 and 16 of connector 155 (FIGS. 22 and 23). As above, the signal is amplified and buffered.

The analog HF-C signal from the optical head assembly 174 is taken from pins 15 and 18 of connector 155 (FIGS. 22 and 23). As above, the signal is amplified and buffered.

The analog HF-D signal from the optical head assembly 174 is taken from pins 13 and 20 of connector 155 (FIGS. 22 and 23). As above, the signal is amplified and buffered.

FIG. 78B is a partial electrical schematic of the buffer amplifier. Amplified signals HF-A, HF-B, HF-C, and HF-D pass through independent load resistors and are combined. The combined signal is fed into the negative input of an op amp, which is fed a variable positive signal. The amplified signal is buffered by a feedback loop, and directed across a variable load resistor before being fed into the negative input of another op amp. The amplified signal is buffered by a feedback loop and conditioned by an array of capacitors with a coil. The conditioned signal is then fed into the positive input of an op amp, which is buffered by a feedback loop. The amplified signal is then directed across an output load resistor and stabilization capacitor and is output at connector J6 of output section 157 (FIG. 22).

Optical Bio-Discs for Biological and Chemical Assays

The following discussion is directed to the biological and chemical applications for which the invention is useful. In sequencing applications, a sequence of nucleotide bases within the DNA sample can be determined by detecting which probes have the DNA sample bound thereto. In diagnostic applications, a genomic sample from an individual is screened against a predetermined set of probes to determine if the individual has a disease or a genetic disposition to a disease.

This invention combines microfluidic technology with genomics and proteomics on an optical bio-disc to detect investigational features in a test sample. Referring to FIGS. 79A, 79B, 79C, and 79D, an aqueous test sample 252 is placed on or within an optical bio-disc 250 and is driven through micro-channels 254 across a specially prepared surface 256 to effectuate the desired tests. Capillary action, pressure applied with an external applicator, and/or centrifugal force (i.e., the force on a body in curvilinear motion directed away from the center or curvature or axis of rotation) act upon the test sample to achieve contact with capture probes 258. Nucleic acid probe technology has application in detection of genetic mutations and related mechanisms, cancer screening, determining drug toxicity levels, detection of genetic disorders, detection of infectious disease, and genetic fingerprinting.

Additionally, the invention is adapted for use in a mixed phase system to perform hybridization assays. Referring to FIGS. 80A, 80B, 80C, and 80D, a mixed phase assay involves performing hybridizations on a solid phase such as a thin nylon or nitrocellulose membrane 262. For example, the assays usually involve spin-coating a thin layer of nitrocellulose 262 onto the substrate 264 of a bio-disc 260, using a pipette 266 or similar device to load the membrane with a sample 268, denaturing the DNA or creating single stranded molecules 270, fixing the DNA or RNA to the membrane, and saturating the remaining membrane attachment sites with heterologous nucleic acids and/or proteins 272 to prevent the analytes and reporters from adhering to the membrane in a non-specific manner. All of these steps must be carried out before performing the actual hybridization. Subsequent steps are then performed to achieve hybridization and locate reporter beads in the capture areas or target zones. The incident beam is then utilized to detect the reporters as discussed in reference to FIG. 79.

Optical bio-discs are useful for experimental analysis and assays in the areas of genetics and proteomics in applications as diverse as pharmaco-genomics, gene expression, compound screening, toxicology, forensic investigation, Single Nucleotide Polymorphism (SNPs) analysis, Short Tandem Repeats (STRs), and clinical/molecular diagnostics.

Reporters

Many chemical, biochemical, and biological assays rely upon inducing a change in the optical properties of the particular sample being tested. Such a change may occur upon detection of the investigational feature itself (e.g., blood cells), or upon detection of a reporter. In the case where investigational features are too small to be detected by the read beam of the optical disc drive, reporters having a selective affinity (i.e., a tendency to react or combine with atoms or compounds of different chemical constitution for the investigational features within the test sample) for the investigational feature to facilitate detection. The reporter will react, combine, or otherwise bind to the investigational feature, thereby causing a detectable color, chemiluminescent, luminescent, or other identifiable label into the investigational feature.

Luminescence is formally divided into two categories, fluorescence and phosphorescence, depending on the nature of the excited state. A luminescent molecule has the ability to absorb photons of energy at one wavelength and subsequently emit the energy at another wavelength. Luminescence is caused by incident radiation impinging upon or exciting an electron of a molecule. The electron absorbs the incident radiation and is raised from a lower quantum energy level to a higher one. The excess energy is released as photons of light as the electron returns to the lower, ground-state energy level. Since each reporter has its own luminescent character, more than one labeled molecule, each tagged with a different reporter, can be used at the same time to detect two or more investigational features within the same test sample.

In addition to luminescence, techniques such as color staining using an enzyme-linked immunosorbent assay (ELISA) and gold labeling can be used to alter the optical properties of biological antigen material. For example, in order to test for the presence of an antibody in a blood sample, possibly indicating a viral infection, an ELISA can be carried out which produces a visible colored deposit if the antibody is present. Referring to FIGS. 81A, 81B, 81C, 81D, 81E, and 81F, an ELISA makes use of a surface 280 that is coated with an antigen 282 specific to the antibody 284 to be tested for. Upon exposure of the surface to the blood sample 286, antibodies in the sample bind to the antigens. Subsequent staining of the surface with specific enzyme-conjugated antibodies 288 and reaction of the enzyme with a substrate produces a precipitate 290 that correlates with the level of antigen binding and hence allows the presence of antibodies in the sample to be identified by the optical disc drive. This precipitate is then detected by the incident beam. Further details relating to use of precipitates as a reporting mechanism are disclosed in U.S. Provisional Application No. 60/292,110 entitled "Surface Assembly for Immobilizing DNA Capture Probes Using Pellets as Reporters in Genetic Assays Including Optical Bio-Discs and Methods Relating Thereto" filed May 18, 2001 and U.S. Provisional Application No. 60/313,917 entitled "Surface Assembly for Immobilizing DNA Capture Probes in Genetic Assays Using Enzymatic Reactions to Generate Signal in Optical Bio-Discs and Methods Relating Thereto" filed Aug. 21, 2001, both of which are herein incorporated by reference.

Referring to FIG. 82, bead-based assays involve use of spherical micro-particles, or beads 300 to alter the optical properties of biological antigen material 302. The beads 300 are coated with a chemical layer 304 having a specific affinity for the investigational feature in a test sample. Referring to FIGS. 83A, 83B, 83C, and 83D, when a test sample is loaded into or onto an optical disc 310 containing reporter beads 300 (FIG. 82), the investigational feature 312, if present, binds to the reporter beads 300. Investigational feature 312 further binds to specific capture agents 314 on the surface 316 of the optical disc 310. In this way, if the investigational feature is present in the biological solution, it becomes a binding agent to bind bead reporters 300 to capture agents 314 on the surface 316 of the bio-disc 310. When the bio-disc is spun in the optical disc drive, the resulting centrifugal force sends unbound bead reporters 318 to an outer periphery of the disc, while bound bead reporters remain distributed over the area of the disc coated with the capture agent. The bound beads can be detected and quantified using an optical disc reader. Related dual bead assays are further disclosed in commonly assigned, co-pending U.S. patent application Ser. No. 09/997,741 entitled "Dual Bead Assays Including Optical Biodiscs and Methods Relating Thereto" filed Nov. 27, 2001, which is incorporated herein by reference.

Reporters useful in the invention include, but are not limited to, synthetic or biologically produced nucleic acid sequences, synthetic or biologically produced ligand-binding amino acids sequences, products of enzymatic reactions, and plastic micro-spheres or beads made of, for example, latex, polystyrene or colloidal gold particles with coatings of bio-molecules that have an affinity for a given material such as a biotin molecule in a strand of DNA. Appropriate coatings include those made from streptavidin or neutravidin, for example. These beads are selected in size so that the read or interrogation beam of the optical disc drive can "see" or detect a change of surface reflectivity caused by the particles.

In some embodiments associated with the present invention, reporter beads are bound to the disc surface through DNA hybridization. Referring to FIGS. 84 and 85, a capture probe 332 is attached to the disc surface 330, while a signal probe 334 is attached to reporter beads 300 (FIG. 82). In the case of a hybridization assay, both of the probes are complementary to the target sequence 336. In the presence of target sequence 336, both capture and signal probes hybridize with the target. In this manner, beads 300 are attached to disc surface 330. In a subsequent centrifugation (or wash) step, all unbound beads are removed. Alternatively, the target itself is directly bound or linked to the beads without the presence of an extra signaling probe.

Referring to FIG. 86, in the case of an immunoassay, the disc surface 340 is coated with a receptor 342 (e.g., antibody), which specifically binds to the analyte of interest 344 (e.g., investigational feature). The capture zones 346 for each specific analyte to be assayed could be separated in the analysis field of the disc. If an analyte 344 (antigen or antibody) is captured by the receptor 342 (antibody or antigen, respectively), present on the capture zone 346, then a signal generation combination specific for the analyte can be used to quantify the presence of the analyte.

Alternatively, an investigational feature, if of adequate size for detection by the incident beam of an optical disc drive, may not require a reporter. Certain chemical reactions and the products and by-products resulting therefrom (i.e., precipitates), induce a sufficient change in the optical properties of the biological sample being tested. Such a change may also occur upon detection of the investigation feature itself, such as is the case when the invention is used to create an image of a microscopic structure. The optical disc drive detects changes in the optical properties of the surface of the bio-disc and creates images based thereon.

In a particular embodiment of the invention, an optical disc system (e.g., FIGS. 9A and 12) includes a signal processing system (e.g., 142, or 158 and 156, or 158 and 32 with or without 154, or 158 and 150 with or without 152 of FIG. 9A) and a photo detector circuit (e.g., 18 of FIG. 1) of an optical disc drive configured to generate at least one information-carrying signal (e.g., the HF, TE, or FE signals) from an optical disc assembly (e.g., disc 130 of FIG. 12). The signal processing system is coupled to the photo detector 18 to obtain from the at least one information-carrying signal both operational information (e.g., tracking, focusing and speed signals of FIG. 8) used to operate the optical disc system and indicia data (e.g., traces in FIG. 61B) indicative of a presence of an investigational feature (e.g., investigational feature 68 of FIG. 43) associated with the optical disc assembly.

In a variant of the invention, the signal processing system of the optical disc system includes a PC and an analog-to-digital converter to provide a digitized signal to the PC. The analog-to-digital converter is coupled between the at least one information carrying signal and the PC. The PC includes a program module to detect and characterize peaks (e.g., see traces in FIG. 61B) in the digitized signal. Preferably, the PC further includes another program module to detect and count double peaks (e.g., see traces D and E in FIG. 61B) in the digitized signal.

In another variant of the invention, the signal processing system of the optical disc system includes a PC, an analog-to-digital converter to provide a digitized signal to the PC, and an analyzer 154 (implementation III of FIG. 9A) coupled between the analog-to-digital converter (e.g., the converter in 32 of FIG. 8) and the PC. The analog-to-digital converter is coupled between the at least one information carrying signal and the PC. The analyzer includes logic to detect and characterize peaks in the digitized signal. Preferably, the analyzer further includes logic to detect and count double peaks in the digitized signal.

In still another variant of the invention, the signal processing system of the optical disc system includes a PC and an analog-to-digital converter to provide a digitized signal to the PC (implementation IV of FIG. 9A). The analog-to-digital converter is coupled between the at least one information carrying signal and the PC. The signal processing system further includes an audio processing module (e.g., 156 of FIG. 9A) coupled between the at least one information-carrying signal and the analog-to-digital converter. Preferably, the optical disc assembly is pre-recorded with a predetermined sound, and the PC includes a program module to detect the indicia data in a deviation of the at least one information carrying signal from the predetermined sound when the investigational feature is present. In an alternative variant, the predetermined sound is encoded silence.

In still yet another variant of the invention, the signal processing system of the optical disc system includes a PC and an analog-to-digital converter to provide a digitized signal to the PC (implementation 11 of FIG. 9A). The analog-to-digital converter is coupled between the at least one information carrying signal and the PC. The signal processing system further includes an external buffer amplifier (e.g., 152 of FIG. 9A) coupled between the at least one information-carrying signal and the analog-to-digital converter.

In a further variant of the invention, the signal processing system of the optical disc system includes a PC and an analog-to-digital converter to provide a digitized signal to the PC. The analog-to-digital converter is coupled between the at least one information carrying signal and the PC. The signal processing system further includes a trigger detection circuit (e.g., 164 of FIG. 12) coupled to the analog-to-digital converter. The trigger detection circuit is operative to detect a particular time in relation to a time when the indicia data is present in the at least one information-carrying signal.

In an alternative embodiment, the signal processing system includes a programmable digital signal processor selectively configurable to either (1) extract the operational information from the at least one information-carrying signal while in a first configuration or (2) operate as an analog-to-digital converter to provide the indicia data while in a second configuration. For example, see FIG. 25 and implementation III of FIG. 9A.

In another alternative embodiment, the signal processing system of the optical disc system includes a PC (e.g., 158 of FIG. 9A), a programmable digital signal processor (e.g., 32 of FIG. 9A) coupled to the at least one information-carrying signal, and an analyzer (e.g., 154 of FIG. 9A) coupled between the programmable digital signal processor and the PC. The analyzer provides the indicia data as depicted in implementation III of FIG. 9A.

In yet another alternative embodiment, the signal processing system of the optical disc system includes a trigger detection circuit (e.g., 164 of FIG. 12) that detects a time period during which the investigational feature associated with the optical disc assembly is scanned by the photo detector circuit.

In a further alternative embodiment, the signal processing system of the optical disc system includes a trigger detection circuit (e.g., 164 of FIG. 12) that detects a particular time in relation to a time when the indicia data is present in the at least one information-carrying signal. The time when the indicia data is present in the at least one information-carrying signal occurs periodically. The particular time is either (1) a predetermined time in advance of, (2) a time at, or (3) a predetermined time after each time the indicia data either begins to be present or ends in the at least one information-carrying signal.

In still yet another alternative embodiment, the signal processing system of the optical disc system includes a PC (e.g., 158 of FIG. 9A), and an audio processing module (e.g., 156 of FIG. 9A) coupled between the PC and the at least one information-carrying signal. Preferably, the sound processing module is either an external module independent of the optical disc drive, a drive module that is a part of the optical disc drive, or a modified drive module that is a part of the optical disc drive. In a variant of this embodiment, the PC includes a processor coupled to the sound module, and a software module stored in a memory to control the processor to extract the indicia data from sound data (e.g., see implementation IV of FIG. 9A).

In yet a further alternative embodiment, the photo detector circuit of the optical disc system includes circuitry to generate an analog signal as the at least one information-carrying signal. The analog signal includes either a high frequency signal from a photo detector, a tracking error signal, a focus error signal, an automatic gain control setting, a push-pull tracking signal, a CD tracking signal, a CD-R tracking signal, a focus signal, a differential phase detector signal, a laser power monitor signal or a sound signal.

In another embodiment, the optical disc system further includes the optical disc assembly (e.g., 130 of FIG. 12). The optical disc assembly has the associated investigational feature (e.g., 136 of FIG. 12) disposed on the assembly in a first disc sector and has the operational information (e.g., 133 of FIG. 12) used to operate the optical disc drive encoded on the assembly in a remaining disc sector.

In a variant, the optical disc assembly includes a trigger mark (e.g., 166 of FIG. 12) that is disposed on the optical disc assembly in a predetermined position relative to the first disc sector. The signal processing system further includes a trigger detection circuit (e.g., 164 of FIG. 12) that detects the trigger mark. Preferably, the trigger detection circuit detects the trigger mark periodically and detects the trigger mark either (1) a predetermined time in advance of, (2) a time at, or (3) a predetermined time after a time when the associated investigational feature is read by the photo detector circuit based on the predetermined position of the trigger mark relative to the first disc sector.

In a variant, the associated investigational feature of the optical disc assembly includes either plastic micro-spheres with a bio-molecule coating, colloidal gold beads with a bio-molecule coating, silica beads, glass beads, magnetic beads, or fluorescent beads.

In another embodiment of the invention, there is provided a method that includes the steps of depositing a test sample, spinning the optical disc, directing an incident beam, detecting a return beam, processing the detected return beam, and processing the detected return beam. The step of depositing a test sample includes depositing the sample at a predetermined location on an optical disc assembly. The step of spinning the optical disc includes spinning the assembly in an optical disc drive. The step of directing an incident beam includes directing the beam onto the optical disc assembly. The step of detecting a return beam includes detecting the return beam formed as a result of the incident beam interacting with the test sample. The step of processing the detected return beam processes the detected return beam to acquire information about an investigational feature associated with the test sample.

In a variant of this embodiment, the step of detecting a return beam forms a plurality of analog signals. The step of processing the detected return beam includes summing a first subset of the plurality of analog signals to produce a sum signal, combining either the first subset or a second subset of the plurality of analog signals to produce a tracking error signal, obtaining information used to operate an optical disc drive from the tracking error signal, and converting the sum signal to a digitized signal.

In another embodiment of the invention, the invention is a method that includes steps of acquiring a plurality of analog signals, summing a first subset, combining a second subset, obtaining information, and converting the sum signal to a digitized signal. The step of acquiring a plurality of analog signals acquires analog signals from an optical disc assembly using a plurality of photo detectors. The step of summing a first subset sums a first subset of the plurality of analog signals to produce a sum signal. The step of combining a second subset combines a second subset of the plurality of analog signals to produce a tracking error signal. The step of obtaining information obtains information used to operate an optical disc drive from the tracking error signal.

In a variant, the steps of acquiring and summing produce the sum signal that includes perturbations indicative of an investigational feature located at a location of the optical disc assembly.

In another variant, the method further includes a step of characterizing the investigational feature based on the digitized signal.

In another variant of the method, the step of converting includes configuring a portion of an optical disc drive chip set to operate as an analog-to-digital converter. Preferably, the step of configuring includes programming a digital signal processing chip within the optical disc drive chip set to operate as an analog-to-digital converter. Preferably, the digital signal processing chip includes a normalization function, an analog-to-digital converter function, a demodulation/decode function, and an output interface function. Preferably, the step of configuring further includes passing the sum signal around the demodulation/decode function by creating a path from the analog-to-digital converter function to the output interface function. Preferably, the step of configuring further includes deactivating the demodulation/decode function.

In another variant of the method, the step of converting includes configuring a digital signal processing chip that includes a normalization function, an analog-to-digital converter function, a demodulation/decode function, and an output interface function, and the step of configuring includes creating a path from the analog-to-digital converter function to the output interface function so that the sum signal is unprocessed by the demodulation/decode function. Preferably, the step of configuring includes deactivating the demodulation/decode function.

In yet another embodiment of the invention, a method includes steps of adapting a portion of a signal processing system, acquiring a plurality on analog signals, converting the analog signals, and characterizing investigational features based on a digitized signal. The step of adapting a portion of a signal processing system includes adapting the portion to operate as an analog-to-digital converter. The step of acquiring a plurality on analog signals acquires the analog signals from a photo detector circuit of an optical disc drive. The plurality of analog signals includes information that is indicative of investigational features on an optical disc assembly. The step of converting the analog signals converts the analog signals into a digitized signal with the signal processing system. Preferably, the step of adapting includes programming a digital signal processing chip within the signal processing system to operate as the analog-to-digital converter.

In another alternative embodiment of the invention, a method includes steps of receiving and converting. The step of receiving includes receiving each of at least one analog signal at a corresponding input of signal processing circuitry. The at least one analog signal has been provided by at least one corresponding photo detector element that detects light returned from a surface of an optical disc assembly. The step of converting includes converting each of the at least one analog signal into a corresponding digitized signal. Each digitized signal is substantially proportional to an intensity of the returned light detected by a corresponding one of the at least one photo detector element.

In a variant of this embodiment, the step of converting includes operating the signal processing circuitry to bypass any demodulation of a first digitized signal. Preferably, the step of converting further includes operating the signal processing circuitry to bypass any decoding of the first digitized signal, and operating the signal processing circuitry to bypass any checking for errors in the first digitized signal.

In another variant of this embodiment, the step of converting includes operating the signal processing circuitry to bypass any decoding of a first digitized signal.

In yet another variant of this embodiment, the step of converting includes operating the signal processing circuitry to bypass any checking for errors in a first digitized signal.

In still another variant of this embodiment, the method further includes a step of combining at least two of the at least one analog signal. Preferably, the step of combining is a step selected from a group consisting of adding, subtracting, dividing, multiplying, and a combination thereof. Preferably, the step of combining is performed before the step of converting. Alternatively, the step of combining may be performed after the step of converting.

In a further variant, the method further includes a step of supplying a first digitized signal of the at least one digitized signal at an output interface of the signal processing circuitry after the step of converting without substantially modifying the first digitized signal between the steps of converting and supplying. Preferably, the signal processing circuitry includes a digital signal processor. Preferably, the signal processing circuitry consists of a digital signal processor.

The materials for use in the method of the invention are ideally suited for the preparation of a kit. Such a kit may include a carrier member being compartmentalized to receive in close confinement an optical bio-disc and one or more containers such as vials, tubes, and the like, each of the containers including a separate element to be used in the method. For example, one of the containers may include a reporter and/or protein-specific binding reagent, such as an antibody. Another container may include isolated nucleic acids, antibodies, proteins, and/or reagents described herein, known in the art or developed in the future. The constituents may be present in liquid or lyophilized form, as desired. The antibodies used in the assay kits of the present invention may be monoclonal or polyclonal antibodies. For convenience, one may also provide the reporter affixed to the substrate of the bio-disc. Additionally, the reporters may further be combined with an indicator, (e.g., a radioactive label or an enzyme) useful in assays developed in the future. A typical kit also includes a set of instructions for any or all of the methods described herein.

In a variant of this embodiment, the carrier may be further compartmentalized to include a setup optical disc containing software for configuring a computer for use with the bio-disc. Optionally, the kit may be packaged with a modified optical disc drive. For example, the kit may be sold for educational purposes as an alternative to the common microscope.

While this invention has been described in detail with reference to a certain preferred embodiments, it should be appreciated that the present invention is not limited to those precise embodiments. Rather, in view of the present disclosure which describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Having thus described the invention with the details and particularity required by the patent laws, what is claimed and desired protected by Letters Patent is set forth in the appended claims.

What we claim is:

1. A method of acquiring information regarding one or more investigational features related to a biological sample on an optical bio-disc, the method comprising:
   acquiring a plurality of analog signals from an optical disc assembly using one or more photo detectors;
   summing a first subset of the plurality of analog signals to produce a sum signal, wherein the sum signal is indicative of one or more investigational features related to the biological sample;
   combining a second subset of the plurality of analog signals to produce a tracking error signal;
   obtaining information used to operate an optical disc drive from the tracking error signal; and
   configuring a portion of an optical disc drive chip set to perform an analog-to-digital converter function, a demodulation/decode function, and an output interface function, wherein said step of configuring further comprises by-passing said sum signal around said demodulation/decode function.

2. The method of claim 1 wherein the steps of acquiring and summing produce the sum signal, and the sum signal includes perturbations indicative of the one or more investigational feature related to the sample.

3. The method of claim 1 wherein the step of processing the sum signal comprising digitizing the sum signal and characterizing the one or more investigational feature based on the digitized signal.

4. The method of claim 1, further comprising configuring a portion of an optical disc drive chip set to operate as an analog-to-digital converter.

5. The method of claim 4 wherein the step of configuring comprises programming a digital signal processing chip within said optical disc drive chip set to operate as an analog-to-digital converter.

6. The method of claim 5 wherein said digital signal processing chip includes a normalization function, an analog-to-digital converter function, a demodulation/decode function, and an output interface function.

7. The method of claim 1, wherein the biological sample comprises at least one of: blood, urine, saliva, amniotic fluid, skin cells, cerebrospinal fluid, serum, synovial fluid, semen, single-stranded and double-stranded DNA, pleural fluid, cells from selected body organs, pericardial fluid, feces, peritoneal fluid, and calculi.

8. The method of claim 1, wherein each of the one or more investigational features comprises at least one of: a bio-bit, a reporter, a blood cell, and a chemical reaction.

9. The method of claim 1, wherein the optical bio-disc includes one or more reporters having an affinity for the investigational features related to the biological sample.

10. The method of claim 9, wherein the one or more reporters includes at least one of: plastic micro-spheres, colloidal gold beads, silica beads, glass beads, latex beads, polystyrene beads, magnetic beads, and fluorescent beads.

11. A method comprising:
    acquiring a plurality of analog signals from an optical disc assembly using one or more photo detectors;
    summing a first subset of the plurality of analog signals to produce a sum signal;
    combining a second subset of the plurality of analog signals to produce a tracking error signal;
    obtaining information used to operate an optical disc drive from the tracking error signal; and
    configuring a portion of an optical disc drive chip set to perform an analog-to-digital converter function, a demodulation/decode function, and an output interface function, wherein said step of configuring further comprises by-passing said sum signal around said demodulation/decode function by creating a path from said analog-to-digital converter function to said output interface function.

12. The method of claim 11 wherein said step of configuring further comprises deactivating said demodulation/decode function.

13. A method comprising:
    acquiring a plurality of analog signals from an optical disc assembly using one or more photo detectors;
    summing a first subset of the plurality of analog signals to produce a sum signal;
    combining a second subset of the plurality of analog signals to produce a tracking error signal;
    obtaining information used to operate an optical disc drive from the tracking error signal; and
    converting the sum signal to a digitized signal;
    wherein said step of converting includes configuring a digital signal processing chip that includes a normalization function, an analog-to-digital converter function, a demodulation/decode function, and an output interface function; and said step of configuring comprises creating a path from said analog-to-digital converter function to said output interface function so that said sum signal is unprocessed by said demodulation/decode function.

14. The method of claim 13 wherein said step of configuring comprises deactivating said demodulation/decode function.

15. A system of acquiring information regarding one or more investigational features related to a biological sample on an optical bio-disc, the system comprising:
    means for acquiring a plurality of analog signals from an optical disc assembly using one or more photo detectors;
    means for summing a first subset of the plurality of analog signals to produce a sum signal, wherein the sum signal is indicative of one or more investigational features related to the sample;
    means for combining a second subset of the plurality of analog signals to produce a tracking error signal;
    means for obtaining information used to operate an optical disc drive from the tracking error signal; and
    a demodulation means for performing a demodulation function; and
    means for processing the sum signal to acquire information regarding the one or more investigational features related to the sample, wherein said sum signal bypasses said demodulation means via one or more electrical paths from said summing means directly to said processing means.

16. A system of acquiring information regarding one or more investigational of a biological sample on an optical bio-disc, the system comprising:
    a light source for emitting light so that at least a portion of the light is incident on the optical bio-disc;
    one or more photo detectors for sensing portions of the light reflected from the optical bio-disc, wherein the one or more photo detectors output a plurality of analog signals corresponding to the sensed reflected light;

at least one electronic device for summing a first subset of the plurality of analog signals to produce a sum signal, wherein the sum signal is indicative of one or more investigational features of the sample, and for producing a tracking error signal based at least partly on a second subset of the plurality of analog signals;

a demodulator for performing a demodulation function; and a processor for processing the sum signal to acquire information regarding the one or more investigational features of the sample, wherein said sum signal bypasses said demodulator via one or more electrical paths from said electronic device directly to said processor.

17. The system of claim 16, wherein the biological sample comprises at least one of: blood, urine, saliva, amniotic fluid, skin cells, cerebrospinal fluid, serum, synovial fluid, semen, single-stranded and double-stranded DNA, pleural fluid, cells from selected body organs, pericardial fluid, feces, peritoneal fluid, and calculi.

18. The system of Claim 16, wherein the optical bio-disc comprises one or more reporters having an affinity for one or more of the investigational features of the biological sample.

19. The system of Claim 17, wherein the one or more reporters includes at least one of: plastic micro-spheres, colloidal gold beads, silica beads, glass beads, latex beads, polystyrene beads, magnetic beads, and fluorescent beads.

* * * * *

UNITED STATES PATENT AND TRADEMARK OFFICE
CERTIFICATE OF CORRECTION

| | |
|---|---|
| PATENT NO. | : 7,200,088 B2 |
| APPLICATION NO. | : 10/043688 |
| DATED | : April 3, 2007 |
| INVENTOR(S) | : Mark Oscar Worthington et al. |

It is certified that error appears in the above-identified patent and that said Letters Patent is hereby corrected as shown below:

On The Title Page Item (63), under Related U.S. Application Data, after "2001" please insert -- now Patent No. 7,061,594--.

On Sheet 8 of 76 of Drawings, at marker 150 of Figure 17, please delete "CONVERTOR" and insert therefore, --CONVERTER--.

At column 1, line 10, after "2001" please insert -- now Patent No. 7,061,594--.

At column 1, line 32, after "bio-discs" please delete "discs".

At column 6, line 60, please delete "investi-gational" and insert therefore --investigational--.

At column 14, line 47, after "kit" please delete "of".

At column 17, line 15, please delete "bio-discs" and insert therefore, --bio-disc--.

At column 19, line 23, please delete "bio-discs" and insert therefore, --bio-disc--.

At column 20, line 63, please delete "in-vestigational" and insert therefore, --investigational--.

At column 20, line 66, please delete "investi-gational" and insert therefore, --investigational--.

At column 21, line 37, please delete "AND" and insert therefore, --A/D--.

At column 23, line 49, please delete "biochenical" and insert therefore, --biochemical--.

At column 24, line 20, please delete "1" and insert therefore, --I--.

At column 24, line 22, please delete "11" and insert therefore, --II--.

At column 25, line 8, please delete "11" and insert therefore, --II--.

At column 28, line 27, please delete "diChroic" and insert therefore, --dichroic--.

At column 30, line 41, after "G" please insert --,--.

At column 31, line 60, please delete "evenescent" and insert therefore, --evanescent--.

At column 34, line 65, please delete "11" and insert therefore, --II--.

At column 35, line 53, please delete "11" and insert therefore, --II--.

At column 39, line 25, please delete "11" and insert therefore, --II--.

At column 39, line 40, please delete "11" and insert therefore, --II--.

At column 49, line 42, after "443" please insert --to--.

At column 56, line 38, please delete "Non-operational" and inser t therefore, --Nonoperational--.

At column 58, line 9, please delete "laser:" and insert therefore, --laser.--.

UNITED STATES PATENT AND TRADEMARK OFFICE
CERTIFICATE OF CORRECTION

PATENT NO. : 7,200,088 B2
APPLICATION NO. : 10/043688
DATED : April 3, 2007
INVENTOR(S) : Mark Oscar Worthington et al.

It is certified that error appears in the above-identified patent and that said Letters Patent is hereby corrected as shown below:

At column 72, line 65, please delete "11" and insert therefore, --II--.

Signed and Sealed this

Thirtieth Day of October, 2007

JON W. DUDAS
*Director of the United States Patent and Trademark Office*